(12) United States Patent
Kolakowski et al.

(10) Patent No.: US 11,970,485 B2
(45) Date of Patent: *Apr. 30, 2024

(54) RET KINASE INHIBITORS

(71) Applicant: Eli Lilly and Company, Indianapolis, IN (US)

(72) Inventors: Gabrielle R. Kolakowski, Longmont, CO (US); Erin D. Anderson, Boulder, CO (US); Steven W. Andrews, Longmont, CO (US); Christopher Pierre Albert Jean Boldron, Toulouse (FR); Kevin R. Condroski, Lafayette, CO (US); Thomas C. Irvin, Erie, CO (US); Manoj Kumar, Broomfield, CO (US); Elizabeth A. McFaddin, Nederland, CO (US); Megan L. McKenney, Boulder, CO (US); Johnathan Alexander McLean, Arvada, CO (US); Tiphaine Mouret, Toulouse (FR); Michael J. Munchhof, Corvallis, MT (US); Thomas Pierre Dino Pancaldi, Toulouse (FR); Michael Alexander Pilkington-Miksa, Toulouse (FR); Marta Pinto, Toulouse (FR)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/047,794

(22) Filed: Oct. 19, 2022

(65) Prior Publication Data

US 2023/0265085 A1 Aug. 24, 2023

Related U.S. Application Data

(62) Division of application No. 17/519,878, filed on Nov. 5, 2021, now Pat. No. 11,697,647.

(60) Provisional application No. 63/110,643, filed on Nov. 6, 2020.

(51) Int. Cl.
| | |
|---|---|
| C07D 413/12 | (2006.01) |
| A61P 35/00 | (2006.01) |
| C07D 231/38 | (2006.01) |
| C07D 401/04 | (2006.01) |
| C07D 401/12 | (2006.01) |
| C07D 403/12 | (2006.01) |
| C07D 413/14 | (2006.01) |
| C07D 417/12 | (2006.01) |
| C07D 417/14 | (2006.01) |

(52) U.S. Cl.
CPC ............ *C07D 413/12* (2013.01); *A61P 35/00* (2018.01); *C07D 231/38* (2013.01); *C07D 401/04* (2013.01); *C07D 401/12* (2013.01); *C07D 403/12* (2013.01); *C07D 413/14* (2013.01); *C07D 417/12* (2013.01); *C07D 417/14* (2013.01)

(58) Field of Classification Search
CPC ... C07D 413/14; C07D 231/38; C07D 413/12
USPC ....................................................... 514/236.5
See application file for complete search history.

(56) References Cited

U.S. PATENT DOCUMENTS

| | | | |
|---|---|---|---|
| 11,697,647 B2* | 7/2023 | Kolakowski | C07D 401/04 514/236.5 |
| 2017/0267661 A1 | 9/2017 | Kim et al. | |
| 2021/0363140 A1 | 11/2021 | Anderson et al. | |

FOREIGN PATENT DOCUMENTS

| | | |
|---|---|---|
| WO | 2014/141187 A1 | 9/2014 |
| WO | 2017/145050 A1 | 8/2017 |
| WO | 2020/035065 A1 | 2/2020 |

OTHER PUBLICATIONS

International Search Report and Written Opinion in International Application No. PCT/US2021/028836, dated Jul. 2, 2021, 6 pages.
International Search Report and Written Opinion in International Application No. PCT/US2021/058206, dated Feb. 2, 2022, 10 pages.

* cited by examiner

*Primary Examiner* — Kahsay Habte
(74) *Attorney, Agent, or Firm* — Bradley W. Crawford

(57) ABSTRACT

Disclosed herein are compounds of formula I:

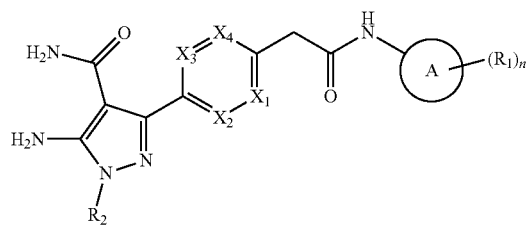

or a pharmaceutically acceptable salt thereof, where the variables are as defined herein. These compounds are useful in treating RET associated cancers. Formulations containing the compounds of formula I and methods of making the compounds of formula I are also disclosed.

24 Claims, No Drawings

Specification includes a Sequence Listing.

RET KINASE INHIBITORS

BACKGROUND

The Rearranged during transfection (RET) kinase is a single-pass transmembrane receptor belonging to the tyrosine kinase superfamily that is required for normal development, maturation, and maintenance of several tissues and cell types. The extracellular portion of the RET kinase contains four calcium-dependent cadherin-like repeats involved in ligand binding and a juxtamembrane cysteine-rich region necessary for the correct folding of the RET extracellular domain, while the cytoplasmic portion of the receptor includes two tyrosine kinase subdomains.

RET signaling is mediated by the binding of a group of 35 soluble proteins of the glial cell line-derived neurotrophic factor (GDNF) family ligands (GFLs), which also includes neurturin (NTRN), artemin (ARTN), and persephin2 (PSPN). Unlike other receptor tyrosine kinases, RET does not directly bind to GFLs and requires an additional co-receptor, which can be one of four GDNF family receptor-α (GFRα) family members that are tethered to the cell surface by a glycosylphosphatidylinositol linkage. GFLs and GFRα family members form binary complexes that in turn bind to RET and recruit it into cholesterol-rich membrane subdomains where RET signaling occurs.

Upon binding of the ligand-co-receptor complex, RET dimerization and autophosphorylation on intracellular tyrosine residues recruits adaptor and signaling proteins to stimulate multiple downstream pathways. Adaptor protein binding to these docking sites leads to activation of Ras-MAPK and PI3K-Akt/mTOR signaling pathways or to recruitment of the CBL family of ubiquitin ligases that functions in RET downregulation of the RET-mediated functions.

Disruptions in normal RET activity due to abnormal RET expression stemming from genetic alterations in the RET kinase, including protein-gene fusions and activating point mutations, lead to overactive RET signaling and uncontrolled cell growth, e.g., various cancer types and certain gastrointestinal disorders such as irritable bowel syndrome (IBS). The ability to inhibit abnormal RET activity in patients with cancer or other disorders related to overactive RET signaling would be of great benefit. Additionally, some RET kinase genetic alterations are altering the conformational structure of a RET kinase to such an extent that a given RET kinase inhibitor may be less effective (or ineffective). In such cases, new RET kinase inhibitors that are effective to the modified RET kinase would greatly benefit patients.

SUMMARY

Disclosed herein are compounds of formula I:

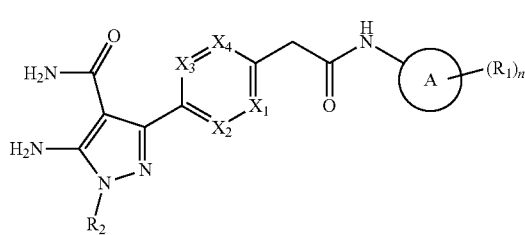

wherein

A is $C_6$-$C_{10}$ aryl or $C_5$-$C_6$ heteroaryl;

each $R_1$ is independently hydrogen, halogen, $C_1$-$C_6$ alkyl, $C_1$-$C_6$ heteroalkyl, —($C_1$-$C_4$ alkyl)($C_5$-$C_6$ heteroalkyl), —($C_0$-$C_4$ alkyl)($C_3$-$C_7$ cycloalkyl), —($C_0$-$C_4$ heteroalkyl)($C_3$-$C_7$ cycloalkyl), —($C_0$-$C_4$ alkyl)($C_3$-$C_7$ cycloheteroalkyl), —($C_0$-$C_4$ heteroalkyl)($C_3$-$C_7$ cycloheteroalkyl), —($C_0$-$C_4$ alkyl)($C_4$-$C_{10}$ bicyclyl), —($C_0$-$C_4$ alkyl)($C_5$-$C_6$ aryl), —($C_0$-$C_4$ alkyl)($C_5$-$C_6$ heteroaryl), —($C_0$-$C_4$ alkyl)($C_4$-$C_{10}$ heterobicyclyl), $C_5$-$C_{12}$ spiranyl, $C_5$-$C_{12}$ heterospiranyl, dimethylphosphoryl, adamantyl, $C_1$-$C_6$ alkoxy, —($C_1$-$C_4$ alkyl)-$SO_2$—($C_1$-$C_4$ alkyl), difluoromethylsulfanyl, or pentafluorosulfanyl, wherein each $R_1$ is unsubstituted or when it is capable of being substituted, it is substituted with one or more substituents that are independently selected from the group consisting of halogen, cyano, hydroxyl, oxo, methyl, methoxy, hydroxymethyl, ethyl, ethoxy, hydroxyethyl, methylamine, N,N-diethylmethylamine, mono-, di, or trihalomethoxy, mono-, di-, or tri-halomethyl, and $C_0$-$C_3$ alkyl-pyrrolidinyl, where the pyrrolidinyl group is unsubstituted or substituted with one, two or 3 independently selected halogen atoms, and wherein two $R_1$ groups can fuse to form a ring structure that includes a portion of A and is optionally aromatic, and n is 1, 2, 3, 4, 5, or 6;

$X_1$, $X_2$, $X_3$, and $X_4$ are each independently N, CH, C—$CH_3$, C—$CH_2$—OH, C—$OCH_3$, C—$CH_2$—$OCH_3$, or C-halogen; and $R_2$ is $C_1$-$C_6$ alkyl, —($C_0$-$C_4$ alkyl)($C_3$-$C_7$ cycloalkyl), —($C_0$-$C_4$ alkyl)($C_4$-$C_7$ heterocycloalkyl), —($C_0$-$C_4$ alkyl)($C_4$-$C_{10}$ bicyclic) each optionally substituted with one or more of halogen, cyano, hydroxyl, oxo, methyl, methoxy, hydroxymethyl, ethyl, ethoxy, hydroxyethyl, cyclopropyl, or mono-, di-, or tri-halomethyl;

or a pharmaceutically acceptable salt thereof.

Further disclosed herein are methods of using the compounds of formula I or pharmaceutically acceptable salts thereof, and pharmaceutical compositions thereof, to treat cancer, in particular for the treatment of cancer with abnormal RET expression (e.g., a RET-associated cancer like medullary thyroid cancer or RET fusion lung cancer) are also provided. The methods include administering a therapeutically effective amount of a compound of formula I or a pharmaceutically acceptable salt thereof, to a patient in need.

Also provided herein are compounds of formula I or pharmaceutically acceptable salts thereof, for use in therapy. Further provided herein, are the compounds of formula I or pharmaceutically acceptable salts thereof, for use in the treatment of cancer, in particular for use in the treatment of cancer with abnormal RET expression (e.g., a RET-associated cancer like medullary thyroid cancer or RET fusion lung cancer). The use of compounds of formula I or pharmaceutically acceptable salts thereof, in the manufacture of a medicament for treating cancer, in particular for use in the treatment of cancer with abnormal RET expression (e.g., a RET-associated cancer like medullary thyroid cancer or RET fusion lung cancer), is also provided.

Incorporated herein by reference is the XML file X22787A.xml, which was created in the ST26 format on Oct. 19, 2022, and has a size of 2.9 KB, i.e., 2900 bytes.

DESCRIPTION

Novel RET kinase inhibitor compounds are described herein. These new compounds could address the need for potent, effective treatment of disorders associated with abnormal RET activity, e.g., IBS or cancer, especially cancer stemming from overactive RET signaling (i.e., RET-associated cancers). More specifically, these new compounds could address the need for potent, effective treatment of RET-associated cancers such as lung cancer (e.g., small cell lung carcinoma or non-small cell lung carcinoma), thyroid cancer (e.g., papillary thyroid cancer, medullary thyroid cancer, differentiated thyroid cancer, recurrent thyroid cancer, or refractory differentiated thyroid cancer), thyroid adenoma, endocrine gland neoplasms, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, or cervical cancer.

Provided herein are compounds of formula I:

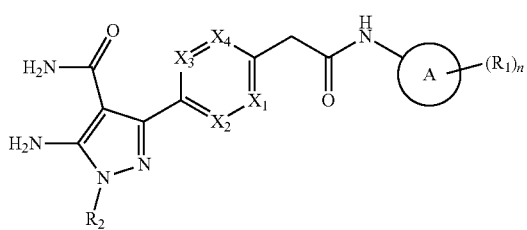

wherein

A is $C_6$-$C_{10}$ aryl or $C_5$-$C_6$ heteroaryl;

each $R_1$ is independently hydrogen, halogen, $C_1$-$C_6$ alkyl, $C_1$-$C_6$ heteroalkyl, —($C_1$-$C_4$ alkyl)($C_5$-$C_6$ heteroalkyl), —($C_0$-$C_4$ alkyl)($C_3$-$C_7$ cycloalkyl), —($C_0$-$C_4$ heteroalkyl)($C_3$-$C_7$ cycloalkyl), —($C_0$-$C_4$ alkyl)($C_3$-$C_7$ cycloheteroalkyl), —($C_0$-$C_4$ heteroalkyl)($C_3$-$C_7$ cycloheteroalkyl), —($C_0$-$C_4$ alkyl)($C_4$-$C_{10}$ bicyclyl), —($C_0$-$C_4$ alkyl)($C_5$-$C_6$ aryl), —($C_0$-$C_4$ alkyl)($C_5$-$C_6$ heteroaryl), —($C_0$-$C_4$ alkyl)($C_4$-$C_{10}$ heterobicyclyl), $C_5$-$C_{12}$ spiranyl, $C_5$-$C_{12}$ heterospiranyl, dimethylphosphoryl, adamantyl, $C_1$-$C_6$ alkoxy, —($C_1$-$C_4$ alkyl)-$SO_2$—($C_1$-$C_4$ alkyl), difluoromethylsulfanyl, or pentafluorosulfanyl, wherein each $R_1$ is unsubstituted or when it is capable of being substituted, it is substituted with one or more substituents that are independently selected from the group consisting of halogen, cyano, hydroxyl, oxo, methyl, methoxy, hydroxymethyl, ethyl, ethoxy, hydroxyethyl, methylamine, N,N-diethylmethylamine, mono-, di, or trihalomethoxy, mono-, di-, or tri-halomethyl, and $C_0$-$C_3$ alkyl-pyrrolidinyl, where the pyrrolidinyl group is unsubstituted or substituted with one, two or 3 independently selected halogen atoms, and wherein two $R_1$ groups can fuse to form a ring structure that includes a portion of A and is optionally aromatic, and n is 1, 2, 3, 4, 5, or 6;

$X_1$, $X_2$, $X_3$, and $X_4$ are each independently N, CH, C—$CH_3$, C—$CH_2$—OH, C—$OCH_3$, C—$CH_2$—$OCH_3$, or C-halogen; and $R_2$ is $C_1$-$C_6$ alkyl, —($C_0$-$C_4$ alkyl)($C_3$-$C_7$ cycloalkyl), —($C_0$-$C_4$ alkyl)($C_4$-$C_7$ heterocycloalkyl), —($C_0$-$C_4$ alkyl)($C_4$-$C_{10}$ bicyclic) each optionally substituted with one or more of halogen, cyano, hydroxyl, oxo, methyl, methoxy, hydroxymethyl, ethyl, ethoxy, hydroxyethyl, cyclopropyl, or mono-, di-, or tri-halomethyl;

or a pharmaceutically acceptable salt thereof.

In some aspects, in the compounds and pharmaceutically acceptable salts of formula I, at least one of $X_1$, $X_2$, $X_3$, and $X_4$ is CH. Sometimes, $X_1$, $X_2$, $X_3$, and $X_4$ are each CH. Alternatively, at least one of $X_1$, $X_2$, $X_3$, and $X_4$ is N. In an embodiment, $X_1$ is N and each of $X_2$, $X_3$, and $X_4$ is CH. In another embodiment, $X_2$ is N and each of $X_1$, $X_3$, and $X_4$ is CH. In some compounds, at least one of $X_1$ and $X_2$ is C—Cl or C—F. In other compounds, $X_1$ and $X_2$ are independently selected from the group consisting of C—Cl and C—F. In still other compounds, $X_1$ and $X_2$ are independently selected from the group consisting of C—Cl and C—F, and $X_3$ and $X_4$ are both CH. Alternatively, $X_1$ and $X_3$ independently selected from the group consisting of C—Cl and C—F. In some compounds, $X_2$ is C—$OCH_3$ or C—$CH_2$—OH.

In some compounds and pharmaceutically acceptable salts of formula I, $X_2$ and $X_3$ are both N. In other compounds, $X_2$ and $X_3$ are both N and $X_1$ and $X_4$ are independently selected from CH, C—Cl, C—F, C—$OCH_3$ and C—$CH_2$—OH. In still other compounds, $X_2$ and $X_3$ are both N and $X_1$ and $X_4$ are both CH. In still other compounds, $X_2$ and $X_3$ are both N and $X_1$ and $X_4$ are independently CH, C—Cl or C—F. In some compounds, $X_1$ and $X_4$ are both N. In other compounds, $X_1$ and $X_4$ are both N and $X_2$ and $X_3$ are independently selected from CH, C—Cl, C—F, C—$OCH_3$ and C—$CH_2$—OH. In still other compounds, $X_1$ and $X_4$ are both N and $X_2$ and $X_3$ are both CH. In still other compounds, $X_1$ and $X_4$ are both N and $X_2$ and $X_3$ are independently CH, C—Cl or C—F.

In some compounds and pharmaceutically acceptable salts of formula I, $X_1$ and $X_3$ are both N and $X_2$ and $X_4$ are independently selected from CH, C—Cl, C—F, C—$OCH_3$ and C—$CH_2$—OH. In other compounds, $X_1$ and $X_3$ are both N and $X_2$ and $X_4$ are both CH. In other compounds, $X_1$ and $X_3$ are both N and $X_2$ and $X_4$ are independently CH, C—Cl or C—F.

In the compounds and pharmaceutically acceptable salts of formula I, or pharmaceutically acceptable salts thereof, A-($R_1$)$_n$ is

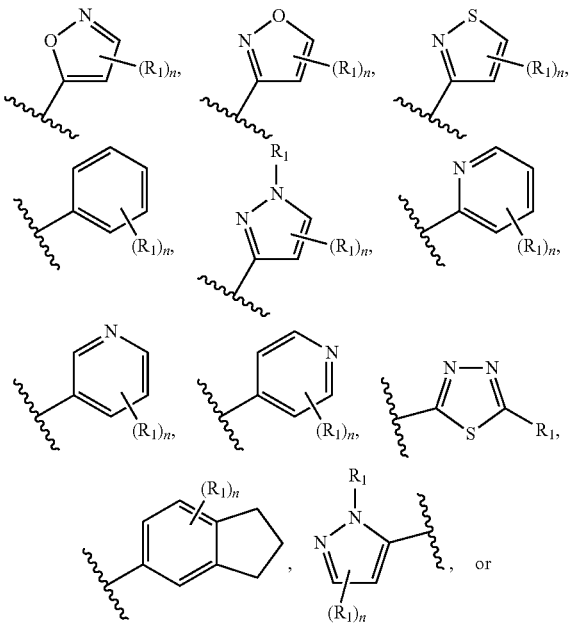

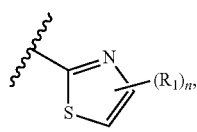

wherein a wavy line indicates connection to the backbone and the maximum value of n depends on the number of substitutable positions on the A-ring.

In one aspect, in the compounds and salts of formula I, $A\text{-}(R_1)_n$ is

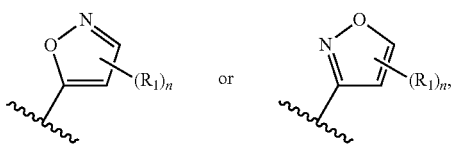

and the maximum value of n depends on the number of substitutable positions on the A-ring.

In an aspect, in the compounds and pharmaceutically acceptable salts of formula I $A\text{-}(R_1)_n$ is:

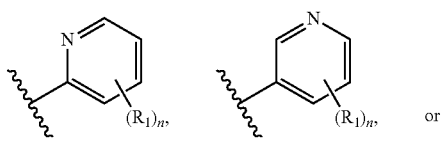

and the maximum value of n depends on the number of substitutable positions on the A-ring.

In another aspect, in the compounds and pharmaceutically acceptable salts of formula I $A\text{-}(R_1)_n$ is

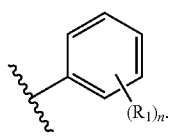

In one embodiment, n is no more than 5. In a further embodiment, n is 1-3 or 1-2. In a further embodiment, when n is three, each $R_1$ group is independently a halogen, methyl, or a methoxy. In another embodiment, when n is 2, at least one $R_1$ is a halogen, while the other $R_1$ is methyl, or a methoxy. In another embodiment, n is 2 and one $R_1$ is $CF_3$. In still another embodiment, n is 2, one $R_1$ is $CF_3$ and the other $R_1$ group is $-CH_2$-piperazinyl, where the piperazinyl is optionally substituted with a $C_1$-$C_4$ alkyl group, such as methyl or ethyl.

In some aspects, in the compounds and pharmaceutically acceptable salts of formula I $A\text{-}(R_1)_n$ is

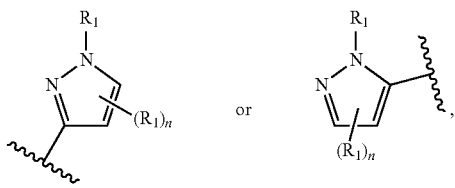

and the maximum value of n depends on the number of substitutable positions on the A-ring.

In some aspects, in the compounds and pharmaceutically acceptable salts of formula I $A\text{-}(R_1)_n$ is

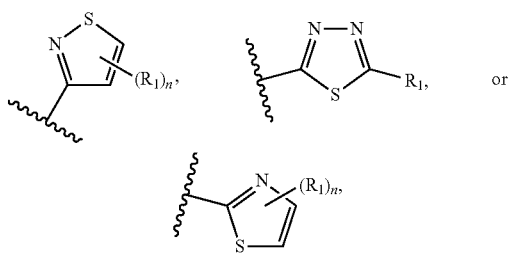

and the maximum value of n depends on the number of substitutable positions on the A-ring.

The compounds and pharmaceutically acceptable salts of formula I encompass the compounds and pharmaceutically acceptable salts of formulas Ia, Ib, Ic, and Id:

Ia

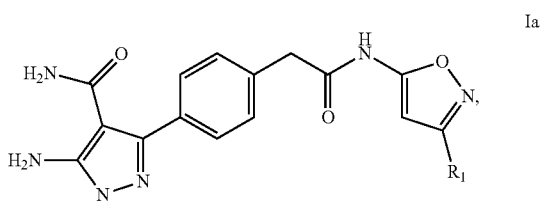

Ib

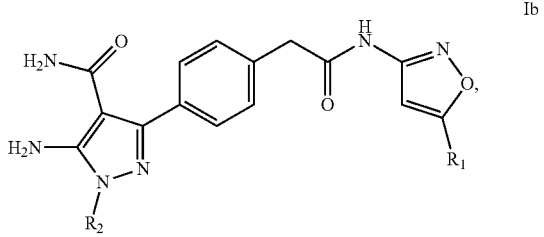

Ic

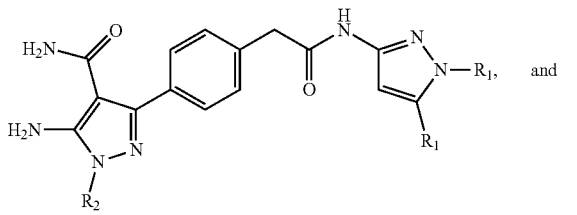

and

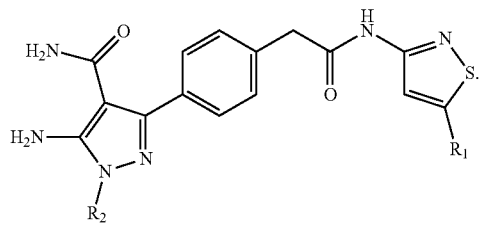

Id

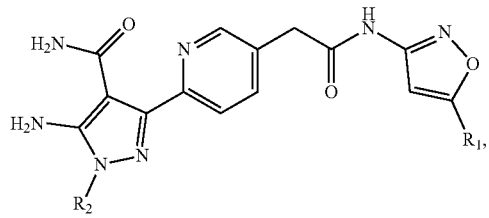

Ij

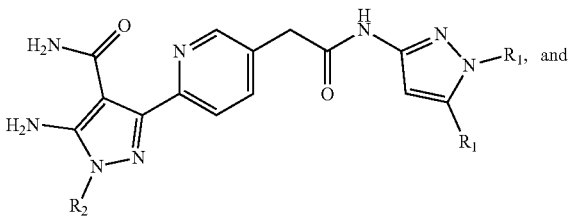

Ik

In the compounds and pharmaceutically acceptable salts of formulas Ia, Ib, Ic, and Id, $X_1$, $X_2$, $X_3$, and $X_4$ of formula I are CH.

The compounds and pharmaceutically acceptable salts of formula I, also encompass the compounds of formula Ie, If, Ig, Ih, Ii, Ij, Ik, Il and pharmaceutically acceptable salts thereof:

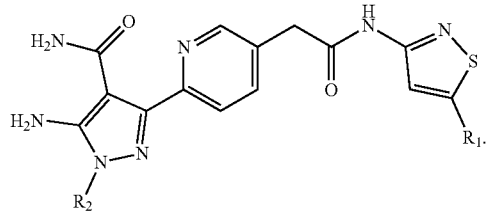

Il

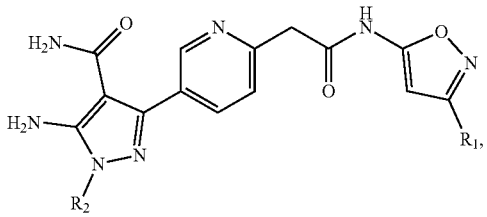

Ie

The compounds and pharmaceutically acceptable salts of formulas Ie to Il, correspond to formula I, wherein one of $X_1$, $X_2$, $X_3$, and $X_4$ is N, while the others are CH.

The compounds and pharmaceutically acceptable salts of formula I, also encompass the compounds of formula Im, In, Io, Ip, Iq, Ir, Is, It, and pharmaceutically acceptable salts thereof:

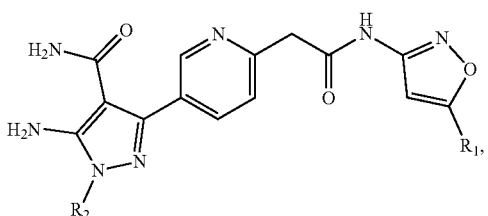

If

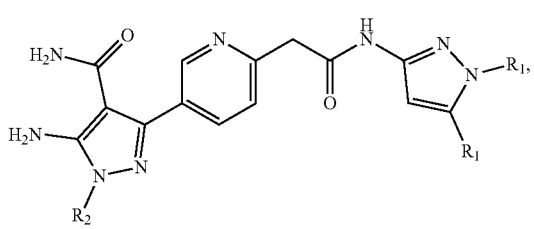

Ig

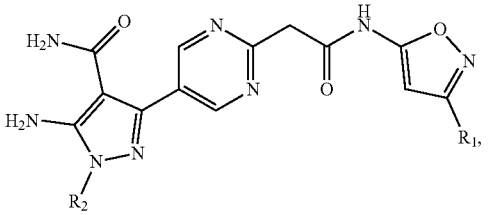

Im

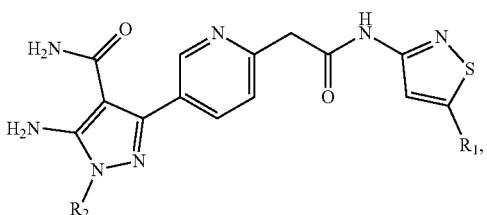

Ih

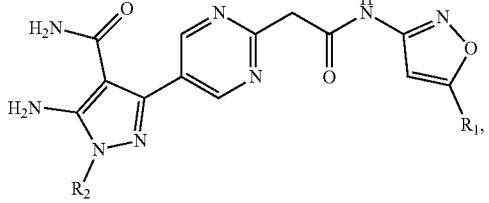

In

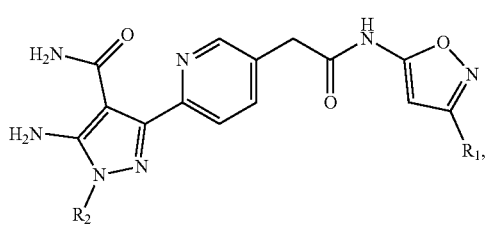

Ii

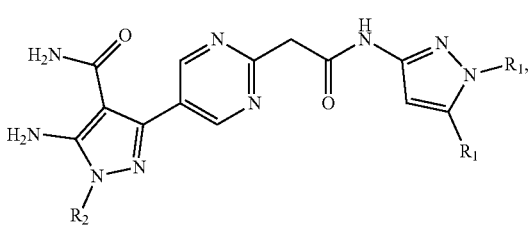

Io

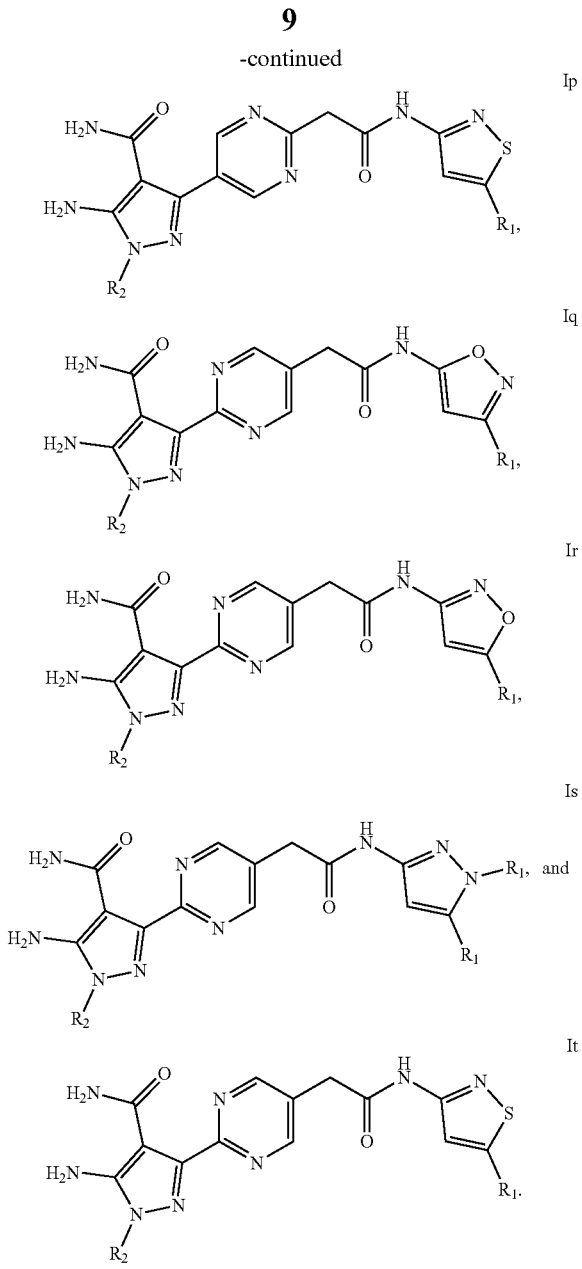

The compounds and pharmaceutically acceptable salts of formulas Im, In, Io, Ip, Iq, Ir, Is, and It correspond to compounds of formula I wherein $X_2$ and $X_3$ are both N, while $X_1$ and $X_4$ are both CH or $X_2$ and $X_3$ are both CH, while $X_1$ and $X_4$ are both N.

The compounds of formula I, also encompass the compounds of formula Iu, Iv, Iw, and Ix:

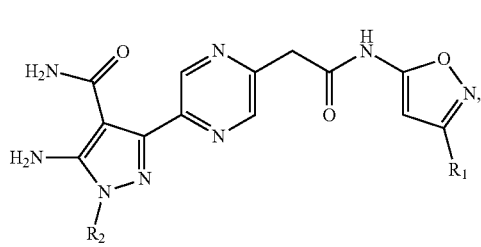

The compounds and pharmaceutically acceptable salts of formulas Iu, Iv, Iw, and Ix, correspond to compounds of formula I wherein $X_1$ and $X_3$ are both N, while $X_2$ and $X_4$ are both CH.

In the compounds and pharmaceutically acceptable salts of formulas I and Ia to Ix, $R_2$ is —$C_1$-$C_6$ alkyl, —$C_1$-$C_4$ alkyl-tetrahydrofuranyl, —$C_1$-$C_6$ hydroxyalkyl, —$C_1$-$C_6$ haloalkyl, —$C_1$-$C_6$ alkyl-O—$C_1$-$C_2$ alkyl, —$C_3$-$C_6$ cycloalkyl, tetrahydrofuranyl, pyranyl, —$C_1$-$C_4$ alkyl-tetrahydropyranyl, —$C_1$-$C_4$ alkyl —$C_3$-$C_6$ cycloalkyl, and azetidinyl, wherein each is unsubstituted or substituted with one or two groups that are independently selected from the group consisting of halogen, cyano, hydroxyl, oxo, methyl, methoxy, hydroxymethyl, ethyl, ethoxy, hydroxyethyl, cyclopropyl, or mono-, di-, or tri-halomethyl. In an embodiment, the —$C_1$-$C_6$ alkyl is an ethyl group.

In an aspect, in the compounds and pharmaceutically acceptable salts of formulas I and Ia to Ix, $R_2$ is tert-butyl, —CH($CH_3$)-cyclopropyl, -2-tetrahydrofuranyl, -3-tetrahydrofuranyl, -3-pyranyl, -4-pyranyl, —CH($CH_3$)$CH_2$OH, —C($CH_3$)$_2$$CH_2$OH, —$CH_2$-(2-tetrahydrofuranyl), —$CH_2$-(3-tetrahydrofuranyl), —($CH_2$)$_3$OH, —C($CH_3$)$_2$$CH_2$O$CH_3$, —CH($CH_3$)$CF_3$, —$CH_2$$CF_3$, —C($CH_3$)$_2$$CH_2$O$CH_3$, cyclopentyl,

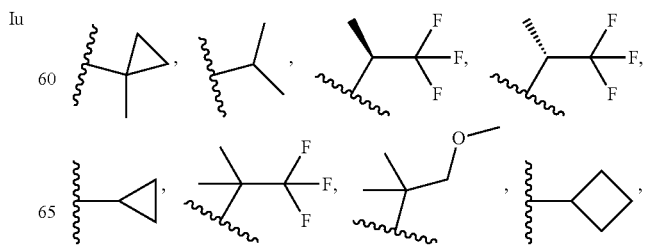

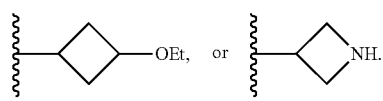

In another aspect, in the compounds and pharmaceutically acceptable salts of formulas I and Ia to Ix, $R_2$ is

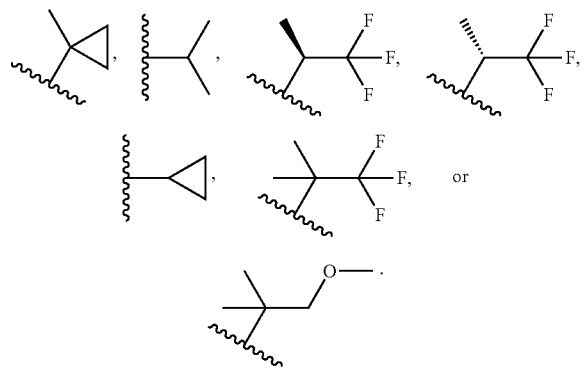

In one aspect, in the compounds and pharmaceutically acceptable salts of formulas I and Ia to Ix, $R_2$ is

In another aspect, in the compounds and pharmaceutically acceptable salts of formulas I and Ia to Ix, $R_2$ is

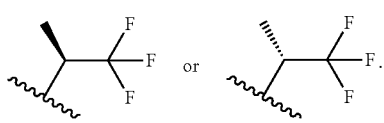

In yet another aspect, in the compounds and pharmaceutically acceptable salts of formulas I and Ia to Ix, $R_2$ is

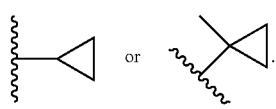

In still another aspect, in the compounds and pharmaceutically acceptable salts of formulas I and Ia to Ix, $R_2$ is

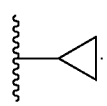

In still another aspect, in the compounds and pharmaceutically acceptable salts of formulas I and Ia to Ix, $R_2$ is

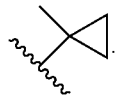

In an aspect, the compounds and pharmaceutically acceptable salts of formula I encompass the compounds and pharmaceutically acceptable salts of formulas IIa to Ix, and IIIa to IIIx:

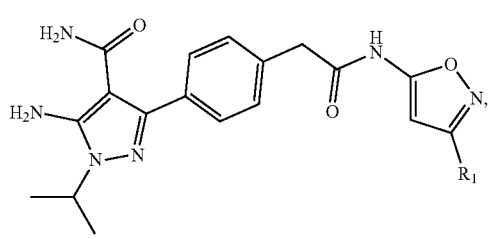

IIa

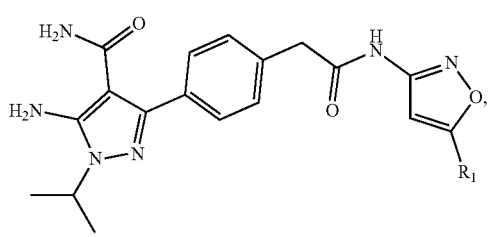

IIb

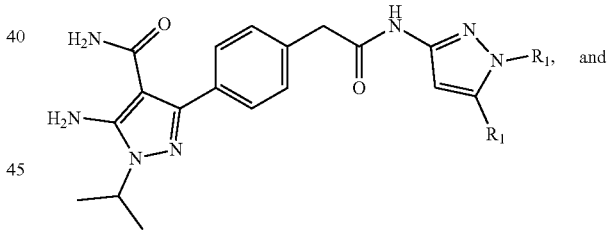

IIc, and

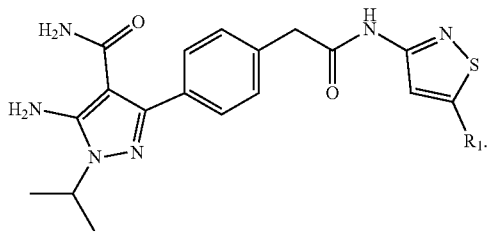

IId

The compounds and pharmaceutically acceptable salts of formulas IIa, IIb, IIc, and IId correspond to compounds of formula I wherein $X_1$, $X_2$, $X_3$, and $X_4$ are CH and $R_2$ is isopropyl.

The compounds and pharmaceutically acceptable salts of formula I, also encompass the compounds of formula IIe, IIf, IIg, IIh, IIi, IIj, IIk, IIl and pharmaceutically acceptable salts thereof.

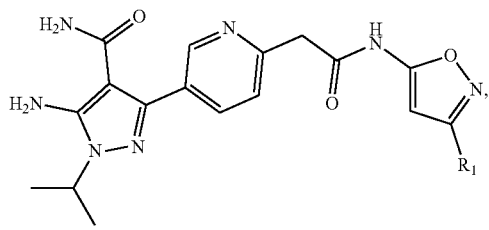

IIe

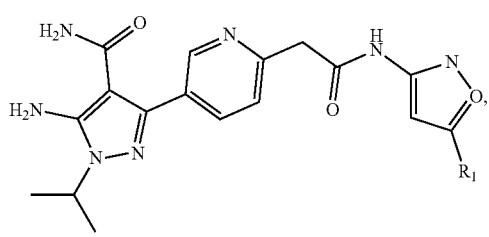

IIf

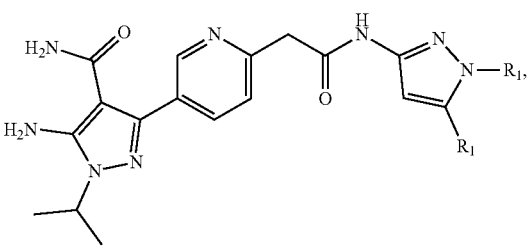

IIg

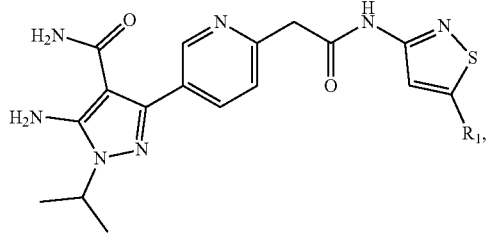

IIh

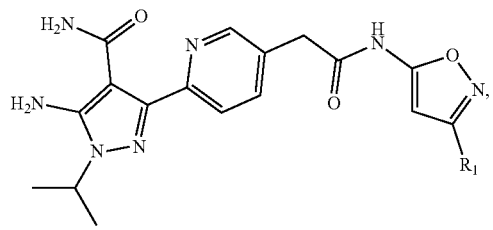

IIi

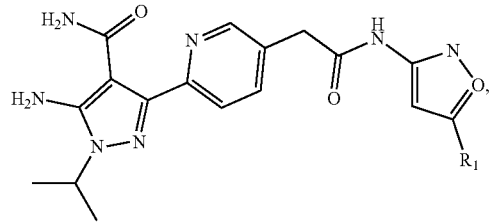

IIj

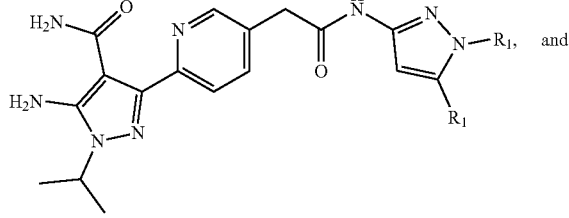

IIk

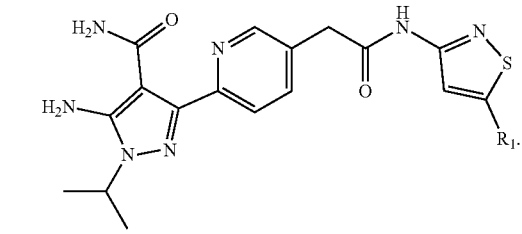

IIl

The compounds and pharmaceutically acceptable salts of formulas IIe to IIl, correspond to compounds of formula I, wherein one of $X_1$, $X_2$, $X_3$, and $X_4$ is N, while the others are CH and $R_2$ is isopropyl.

The compounds and pharmaceutically acceptable salts of formula I, also encompass the compounds of formulas IIm, IIn, IIo, IIp, IIq, IIr, IIs, IIt, and pharmaceutically acceptable salts thereof:

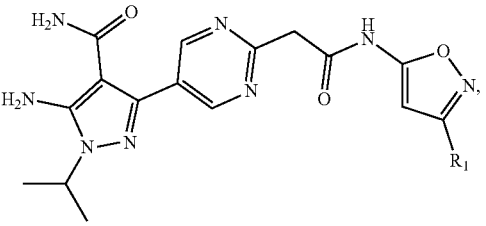

IIm

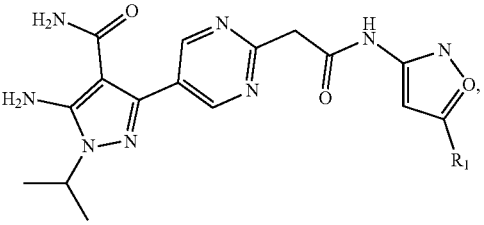

IIn

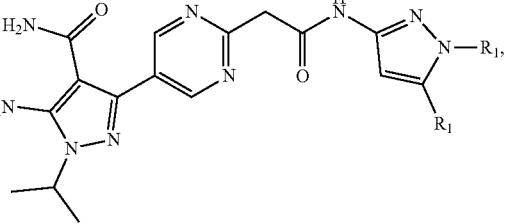

IIo

-continued

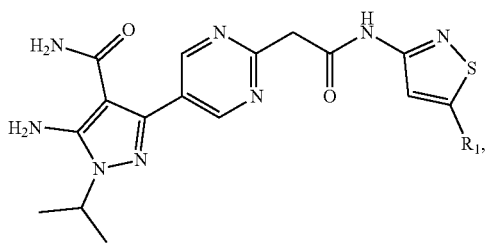
IIp

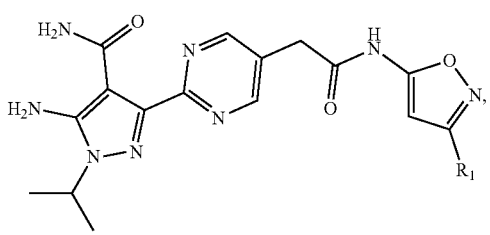
IIq

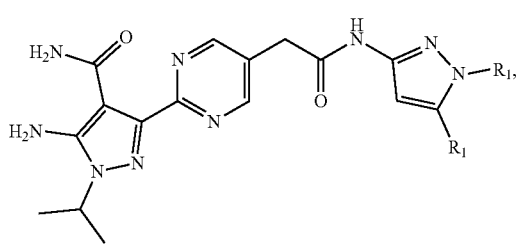
IIr

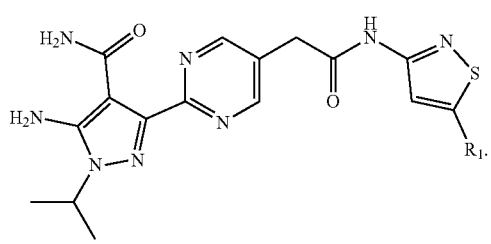
IIs

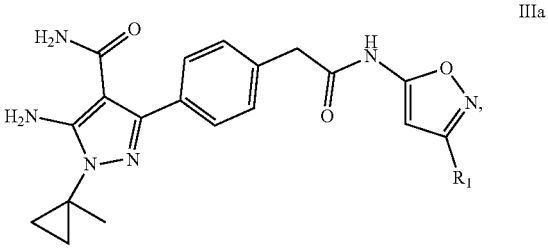
IIt

The compounds and pharmaceutically acceptable salts of formulas IIm, IIn, IIo, IIp, IIq, IIr, IIs, and IIt correspond to compounds of formula I wherein $X_2$ and $X_3$ are both N, while $X_1$ and $X_4$ are both CH or $X_2$ and $X_3$ are both CH, while $X_1$ and $X_4$ are both N and $R_2$ is isopropyl.

The compounds of formula I, also encompass the compounds of formula IIu, Iv, IIw, and IIx:

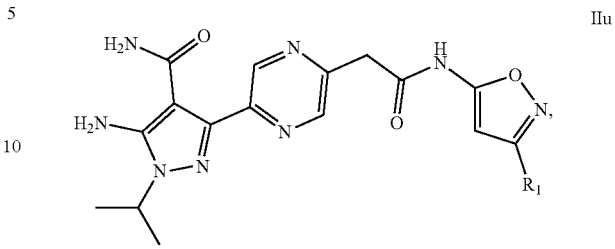
IIu

IIv

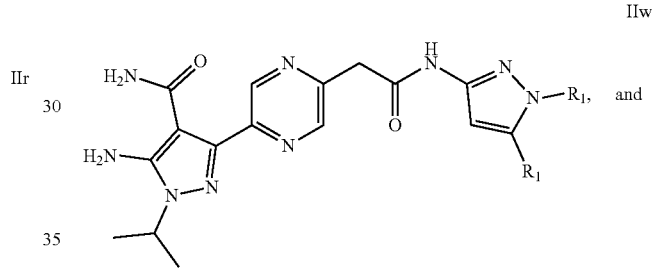
IIw

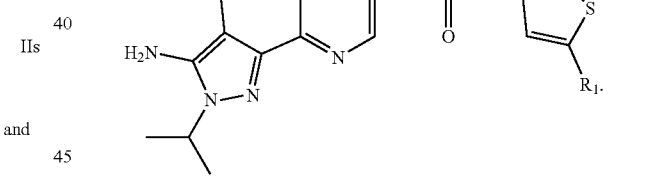
IIx

The compounds and pharmaceutically acceptable salts of formulas IIu, Iv, IIw, and Ix, correspond to compounds of formula I wherein $X_1$ and $X_3$ are both N, while $X_2$ and $X_4$ are both CH, and $R_2$ is isopropyl. The compounds and pharmaceutically acceptable salts of formula I encompass the compounds of formula IIIa, IIIb, IIIc, and IIId, and pharmaceutically acceptable salts thereof.

IIIa

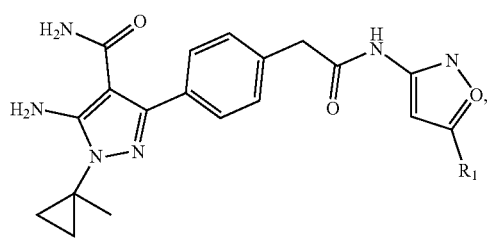

IIIb

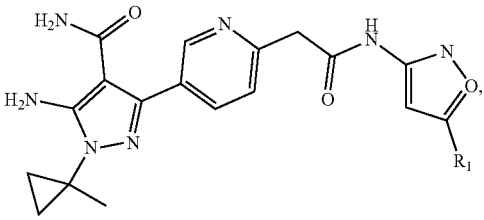

IIIf

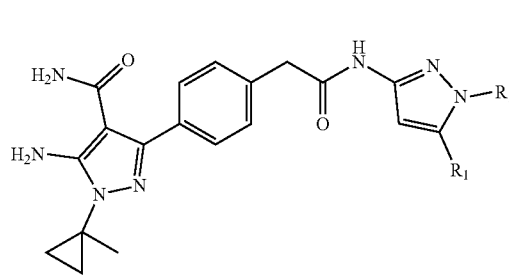

IIIc, and

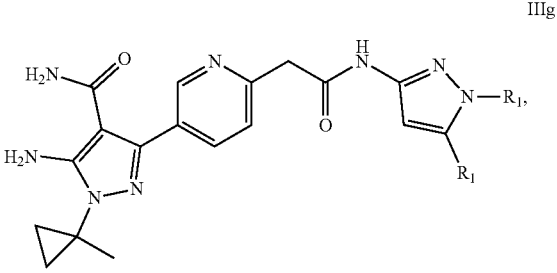

IIIg

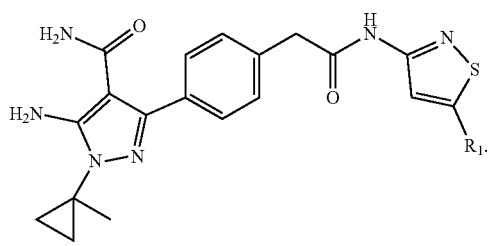

IIId

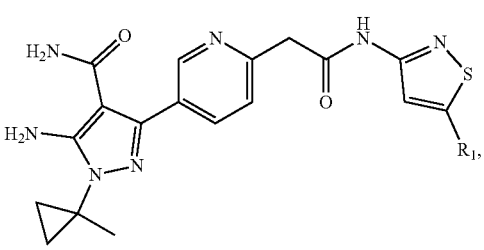

IIIh

The compounds and pharmaceutically acceptable salts of formulas IIIa, IIIb, IIIc, and IIId, correspond to compounds of formula I wherein $X_1$, $X_2$, $X_3$, and $X_4$ are CH, and $R_2$ is

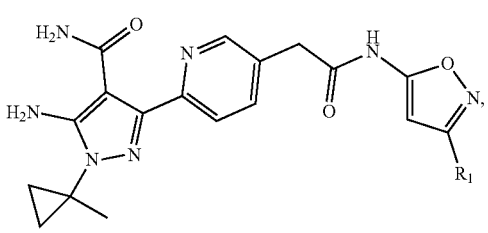

IIIi

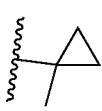

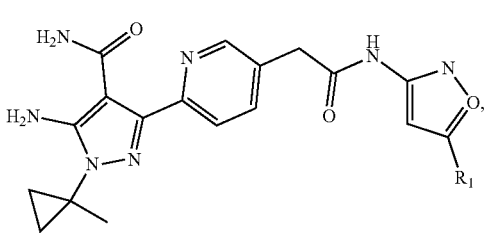

IIIj

The compounds and pharmaceutically acceptable salts of formula I, also encompass the compounds of formula IIIe, IIIf, IIIg, IIIh, IIIi, IIIj, IIIk, IIIl and pharmaceutically acceptable salts thereof:

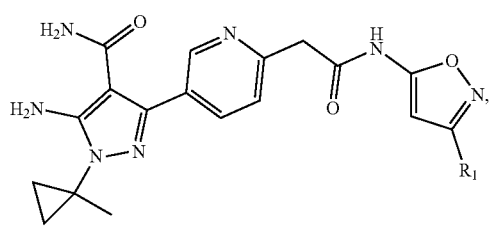

IIIe

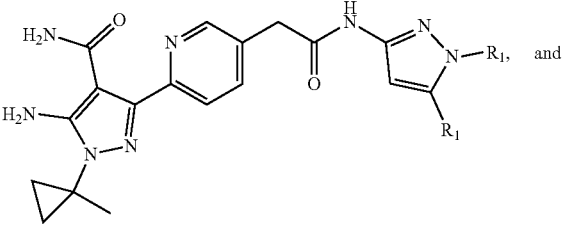

IIIk, and

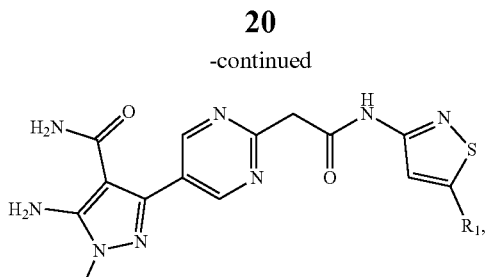
IIIl

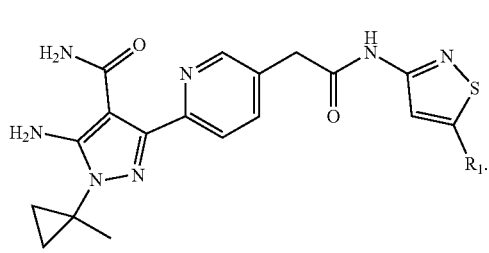

The compounds and pharmaceutically acceptable salts of formulas IIIe to IIIl correspond to compounds of formula I wherein one of $X_1$, $X_2$, $X_3$, and $X_4$ is N, while the others are CH, and $R_2$ is

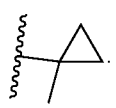 [SMILES: *C1(C)CC1]

The compounds and pharmaceutically acceptable salts of formula I, also encompass the compounds of formula IIIm, IIIn, IIIo, IIIp, IIIq, IIIr, IIIs, IIIt, and pharmaceutically acceptable salts thereof:

IIIm

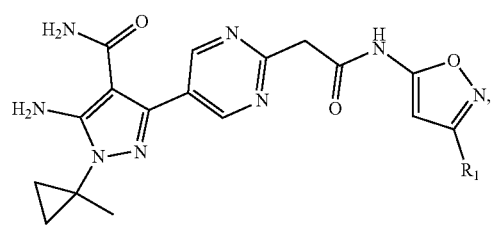

IIIn

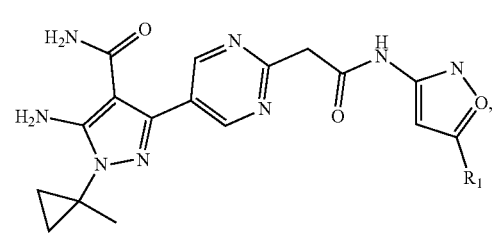

IIIo

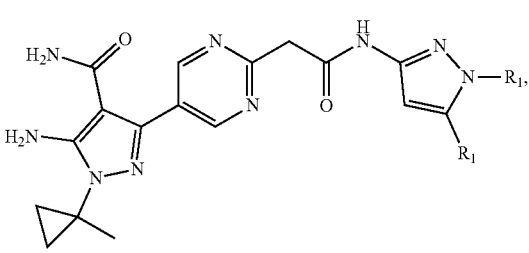

IIIp

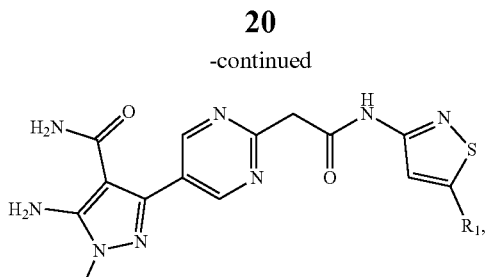

IIIq

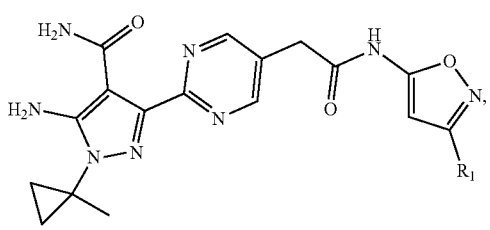

IIIr

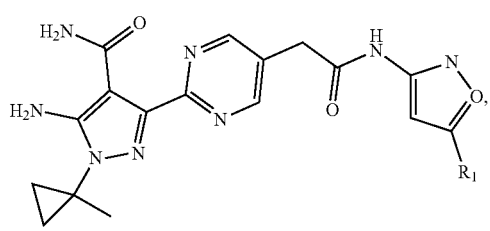

IIIs

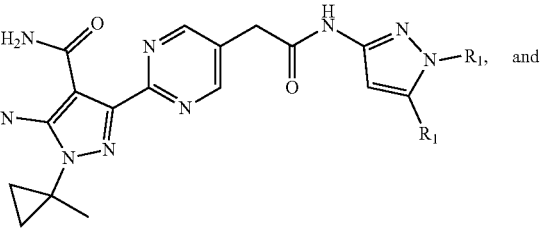

and

IIIt

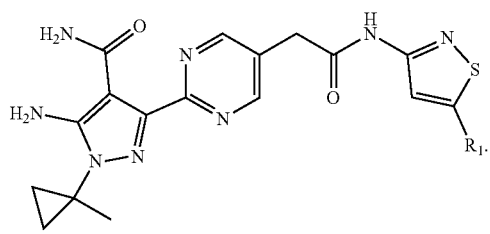

The compounds and pharmaceutically acceptable salts of formulas IIIm, IIIn, IIIo, IIIp, IIIq, IIIr, IIIs, and IIIt correspond to compounds of formula I wherein $X_2$ and $X_3$ are both N, while $X_1$ and $X_4$ are both CH or $X_2$ and $X_3$ are both CH, while $X_1$ and $X_4$ are both N and $R_2$ is

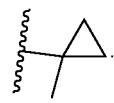 [SMILES: *C1(C)CC1]

The compounds of formula I, also encompass the compounds of formula IIIu, IIIv, IIIw, and IIIx:

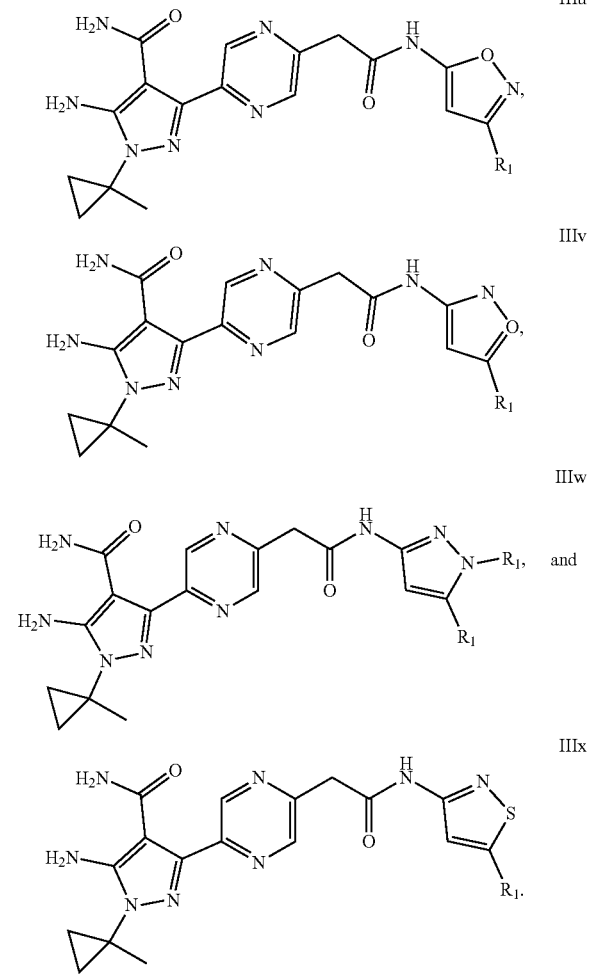

The compounds and pharmaceutically acceptable salts of formulas IIIu, IIIv, IIIw, and IIIx, correspond to compounds of formula I wherein $X_1$ and $X_3$ are both N, while $X_2$ and $X_4$ are both CH or $X_2$ and $X_4$ are both N, while $X_1$ and $X_3$ are both CH, and $R_2$ is

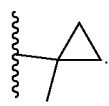 [SMILES: *C1(C)CC1]

In an aspect, in the compounds and pharmaceutically acceptable salts of formulas I, Ia to Ix, IIa to Ix and IIIa to IIIx, each $R_1$ is independently hydrogen, $C_1$-$C_6$ alkyl, $C_4$-$C_8$ bridged bicycloalkyl, $C_5$-$C_{12}$ spirane, wherein each $R_1$ is optionally substituted with one or more of halogen, cyano, hydroxyl, oxo, methyl, methoxy, hydroxymethyl, ethyl, ethoxy, hydroxyethyl, methylamine, N,N-diethylmethylamine, or mono-, di-, or tri-halomethyl.

In another aspect, in the compounds and pharmaceutically acceptable salts of formulas I, Ia to Ix, IIa to Ix and IIIa to IIIx, each $R_1$ is independently 2-chloro-4-methyl-phenyl, 2,4-dichloro-3-fluoro-phenyl, 2-methy-4-chloro-phenyl, 2-chloro-4-methoxy-phenyl, 2-chloro-4-trifluoromethyl-phenyl, 2-methoxy-4-chloro-phenyl, 2,2-dimethylpropyl; 2-chloro-4-fluoro-phenyl; 2,4-dichlorophenyl; 1,1-dimethyl-2,2,2-trifluoroethyl; 1,1-dimethylethyl; 1,1-dimethylpropyl; trifluoromethyl; 1,1-dimethyl-2,2-difluoropropyl; 1,1-dimethyl-3,3,3-trifluoropropyl; 1-methylcyclopropyl; (1-methylcyclopropyl)methyl; 3-methylbicyclo[1.1.1]pentan-1-yl; 3-(trifluoromethyl)bicyclo[1.1.1]pentan-1-yl; or (3,3-dimethylcyclobutyl)methyl.

In a further aspect, in the compounds and pharmaceutically acceptable salts of formulas I, Ia to Ix, IIa to Ix and IIIa to IIIx, each $R_1$ is independently a $C_4$-$C_8$ bridged bicycloalkyl that is unsubstituted or substituted with 1 or 2 groups independently selected from the group consisting of $C_1$-$C_4$ alkyl, $CF_3$, halo, and CN.

In another aspect, in the compounds and pharmaceutically acceptable salts of formulas I, Ia to Ix, IIa to Ix and IIIa to IIIx, each $R_1$ is independently a $C_4$-$C_8$ bridged bicycloalkyl that is unsubstituted or substituted with 1 or 2 groups independently selected from the group consisting of methyl, ethyl, $CF_3$, halo, and CN.

In some aspects, in the compounds and pharmaceutically acceptable salts of formulas I, Ia to Ix, IIa to Ix and IIIa to IIIx, each $R_1$ is independently a bridged $C_4$-$C_8$ bicycloalkyl that is

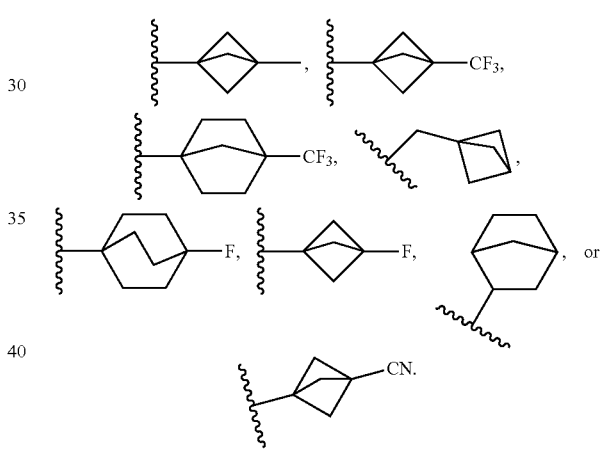

In other aspects, in the compounds and pharmaceutically acceptable salts of formulas I, Ia to Ix, IIa to Ix and IIIa to IIIx, each $R_1$ is independently a $C_5$-$C_{12}$ spirane that is unsubstituted or substituted with 1 or 2 groups that are independently selected from the group consisting of =O, —OH, $C_1$-$C_4$ alkyl, —$CF_3$, and halo each $R_1$ is independently a $C_5$-$C_{12}$ heterospirane that is unsubstituted or substituted with 1 or 2 groups that are independently selected from the group consisting of =O, —OH, $C_1$-$C_4$ alkyl, —$CF_3$, and halo. Examples of $C_5$-$C_{12}$ spiranes or $C_5$-$C_{12}$ heterospiranes include

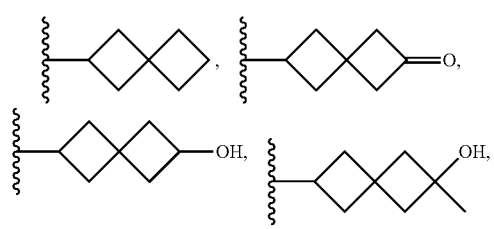

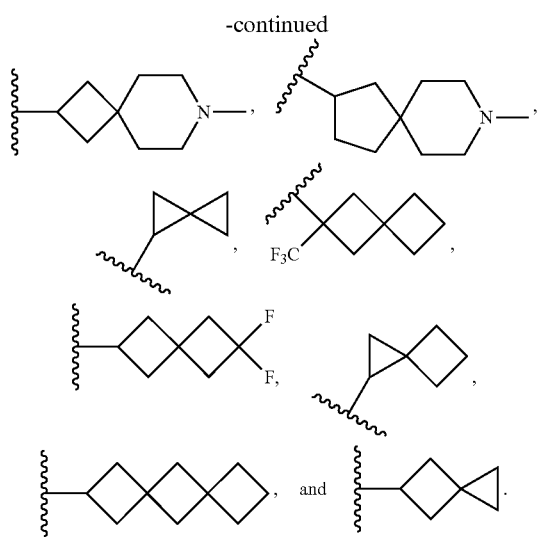

In an aspect, in the compounds and pharmaceutically acceptable salts of formulas I, Ia to Ix, IIa to Ix and IIIa to IIIx, n is 1 and $R_1$ is a $C_5$-$C_{12}$ spirane that is unsubstituted or substituted with 1 or 2 groups that are independently selected from the group consisting of =O, —OH, methyl, ethyl, $CF_3$, and halo.

In yet another aspect, in the compounds and pharmaceutically acceptable salts of formulas I, Ia to Ix, IIa to Ix and IIIa to IIIx, each $R_1$ is independently halogen, $C_1$-$C_6$ alkyl, —($C_0$-$C_4$ alkyl)($C_3$-$C_7$ cycloalkyl), —($C_0$-$C_4$ alkyl)(phenyl), —($C_1$-$C_4$ alkyl)($C_5$-$C_6$ heteroalkyl), —($C_0$-$C_4$ heteroalkyl)($C_3$-$C_7$ cycloheteroalkyl), or —($C_0$-$C_4$ alkyl)($C_5$-$C_6$ heteroaryl), wherein each $R_1$ is optionally substituted with one or more substituents independently selected from the group consisting of halogen, cyano, hydroxyl, oxo, methyl, methoxy, hydroxymethyl, ethyl, ethoxy, hydroxyethyl, methylamine, N,N-dimethylmethylamine, and mono-, di-, or tri-halomethyl.

In an aspect, in the compounds and pharmaceutically acceptable salts of formulas I, Ia to Ix, IIa to Ix and IIIa to IIIx, each $R_1$ is unsubstituted. In an alternate aspect, each $R_1$ is substituted with no more than four groups, or no more than three groups or no more than two groups or only with one group.

In another aspect, in the compounds and pharmaceutically acceptable salts of formulas I, Ia to Ix, IIa to Ix and IIIa to IIIx, each $R_1$ is independently —$CH_2C(CH_3)_3$, —$CH(CH_2CH_3)_2$, —$CF_2CH_3$, —$CH_2CH_2CF_3$, —$C(CH_3)_2F$, —$C(CH_3)_2CF_3$, —$CH_2$-cyclopentyl, —$CH_2$-cyclohexyl, —$CH_2$-cyclopropyl, —$CH_2$-cyclobutyl, —$CH_2$-morpholinyl, —$CH_2$-pyrrolidinyl, phenyl, naphthyl, pyran-4-yl, 4-methylphenyl, 4-methoxyphenyl, 2-fluorophenyl, 2-fluoro-4-chlorophenyl, 3-trifluoromethylphenyl, 3-fluoro-5-trifluoromethylphenyl, cyclopropyl, cyclobutyl, cyclopentyl, cyclohexyl, cycloheptyl, 2,4-dimethylphenyl, 4-chlorophenyl, 2-methylphenyl, 3-fluorophenyl, 3-chlorophenyl, 2-methoxyphenyl, 4-difluoromethoxyphenyl, —$C(CH_3)_2SO_2CH_3$, 4-fluorophenyl, 2,4-difluorophenyl, 2,4-dichlorophenyl, 3-chlorophenyl, methyl, ethyl, tert-butyl, isopropyl, trifluoromethyl, 3-methoxyphenyl, 3-bromophenyl, 4-bromophenyl, 2,4,6-trifluoromethylphenyl, 3-tetrahydrofuranyl, —$C(CH_3)_2CH_2CH_3$, —$C(CH_3)_2OH$, 3,3-dimethylcyclobut-1-yl, 2,3-dichlorobenzyl, 3,3-difluoromethylcyclobutyl, 2,2-dimethylcycloprop-1-yl, 2,2-difluorocyclopropyl, N-methylimidazolyl, 2-methyl-4-chlorophenyl, 2,4-dichloro-3-fluorophenyl, —$CH_2OCH_3$, —$CH_2CF_3$, —$CF_2CH_3$, —$CF_2C(CH_3)_3$, —$CH(CH_3)$cyclopropyl, 2,6-difluorophenyl, pyrid-2-yl, pyrid-3-yl, pyrid-4-yl, 3-chloropyrid-2-yl, 2-methylpyrid-3-yl, 4-methylpyrid-3-yl, 3,5-dichloropyrid-2-yl, 3,3-difluorocyclopentyl, fluoro, chloro, bromo, 2-methoxy-4-chloro-phenyl, 2-fluoro-4-chlorophenyl, 3-fluoro-4-chlorophenyl, benzyl, piperidinyl, 4-methyl-piperidinyl, 4-methoxy-piperidinyl, N-methylpyrazol-3-yl, —C(O)-piperidinyl, —$OCHF_2$,

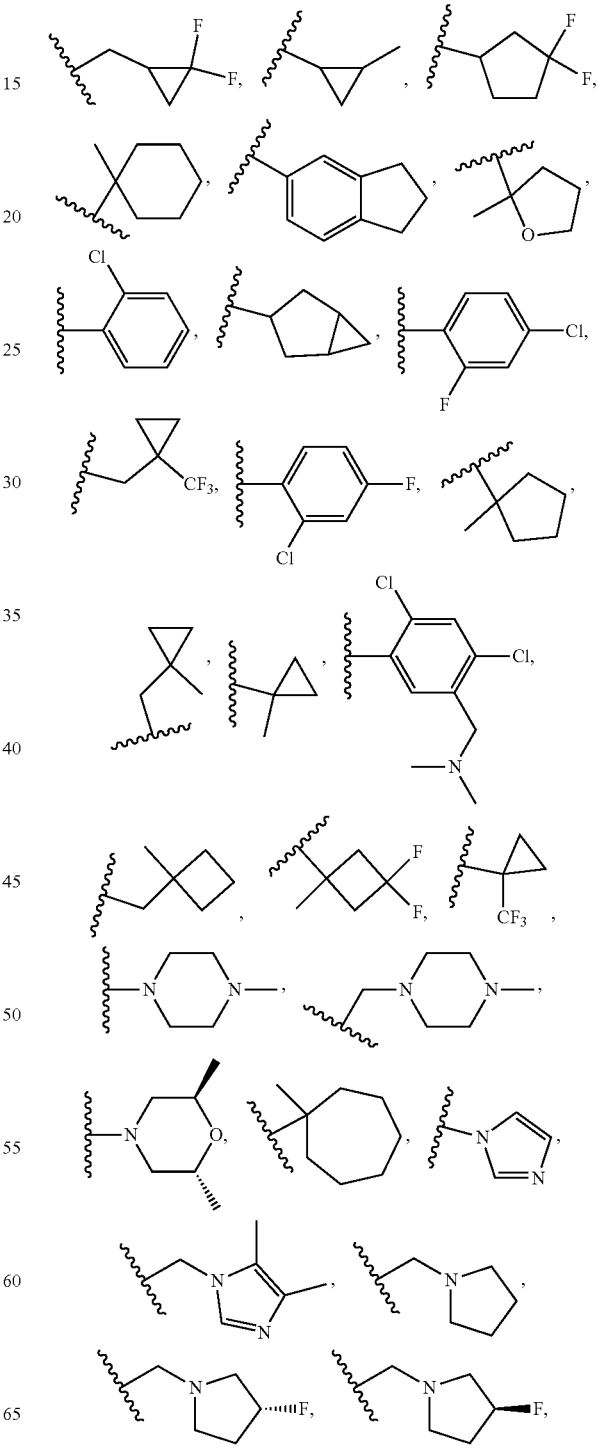

-continued

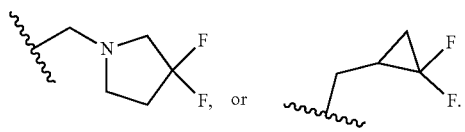 [SMILES: *CN1CCC(F)(F)C1 ; "or" ; *CC1CC1(F)F]

In an aspect, in the compounds and pharmaceutically acceptable salts of formulas I, Ia to Ix, IIa to Ix and IIIa to IIIx, $R_1$ is 2,2-dimethylpropyl or

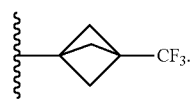 [SMILES: *C12CC(C(F)(F)F)(C1)C2]

In a further aspect, in the compounds and pharmaceutically acceptable salts of formulas I, Ia to Ix, IIa to Ix and IIIa to IIIx, $R_1$ is 2,2-dimethylpropyl.

In a still further aspect, in the compounds and pharmaceutically acceptable salts of formulas I, Ia to Ix, IIa to Ix and IIIa to IIIx, $R_1$ is

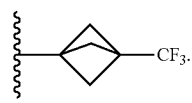 [SMILES: *C12CC(C(F)(F)F)(C1)C2]

In another aspect, in the compounds and pharmaceutically acceptable salts of formulas I, Ia to Ix, IIa to Ix and IIIa to IIIx, each $R_1$ is independently

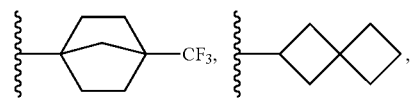

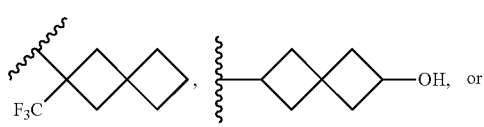

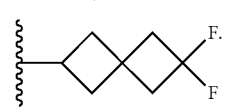

In a different aspect, in the compounds and pharmaceutically acceptable salts of formulas I, Ia to Ix, IIa to Ix and IIIa to IIIx, $R_1$ is $C_1$-$C_6$ alkyl, which is unsubstituted or substituted with one or more substituents that are independently selected from the group consisting of halogen, cyano, hydroxyl, oxo, methyl, methoxy, hydroxymethyl, ethyl, ethoxy, hydroxyethyl, methylamine, N,N-dimethylmethylamine, and mono-, di-, and tri-halomethyl.

In yet another aspect, the compounds and pharmaceutically acceptable salts of formula I are:

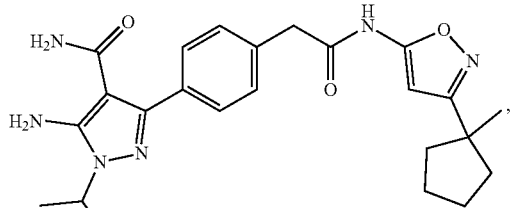

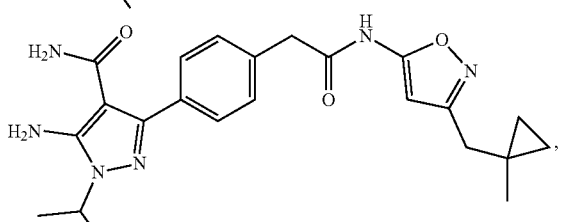

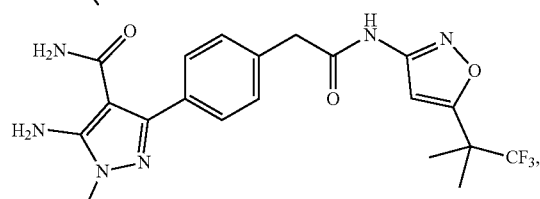

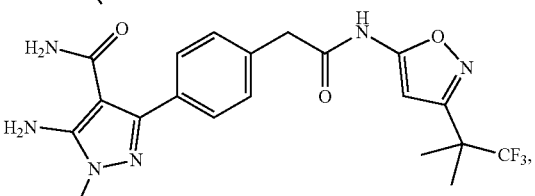

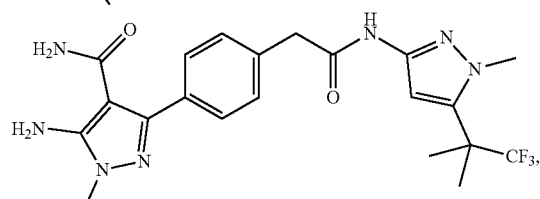

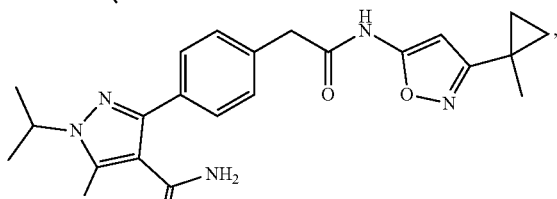

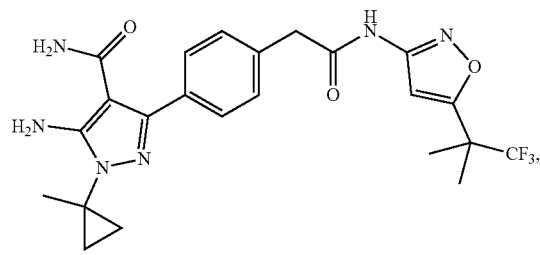

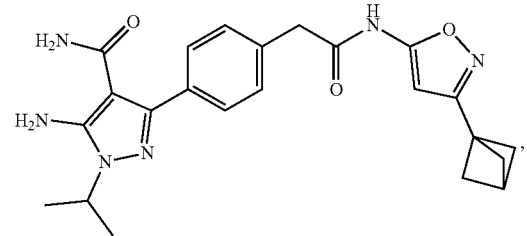
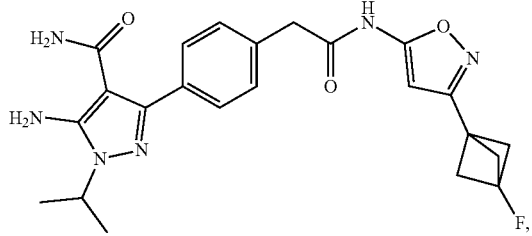
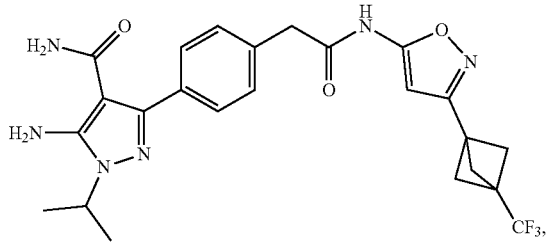
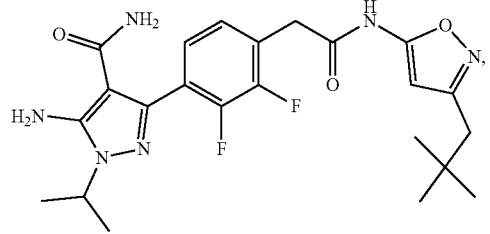
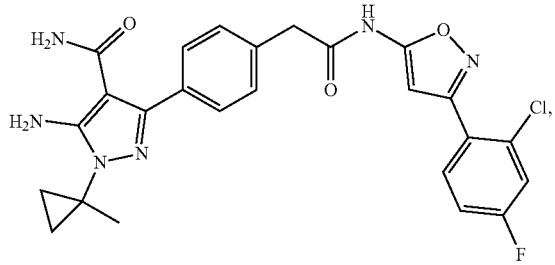
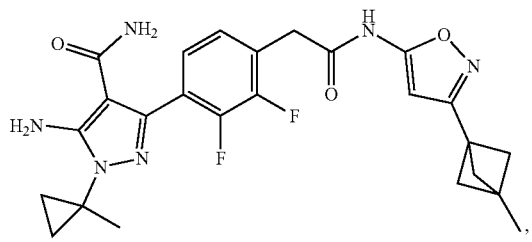
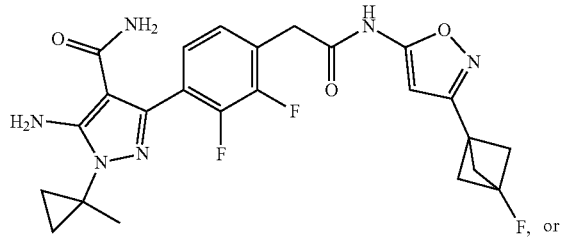
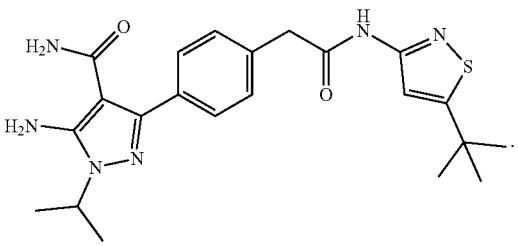
In still yet another aspect, the compounds and pharmaceutically acceptable salts of formula I.
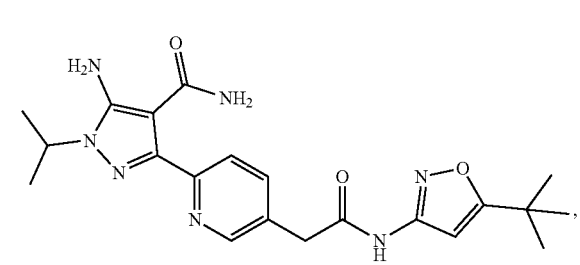
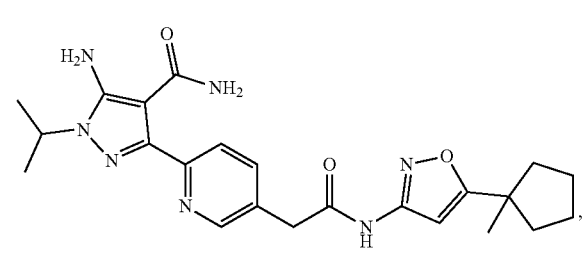
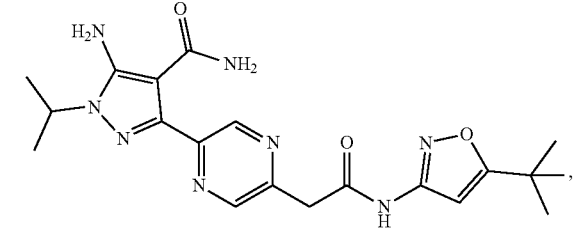
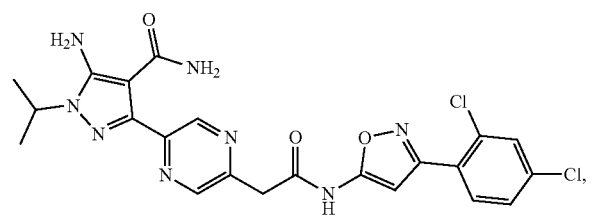
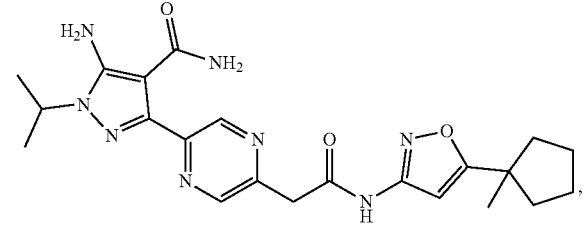

-continued

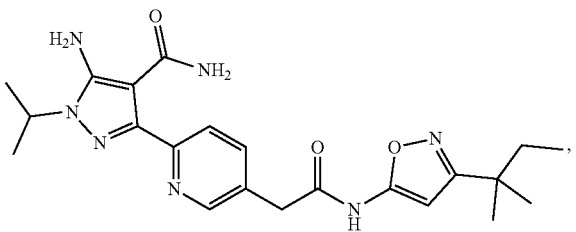

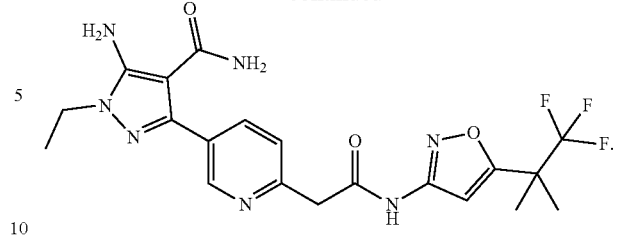

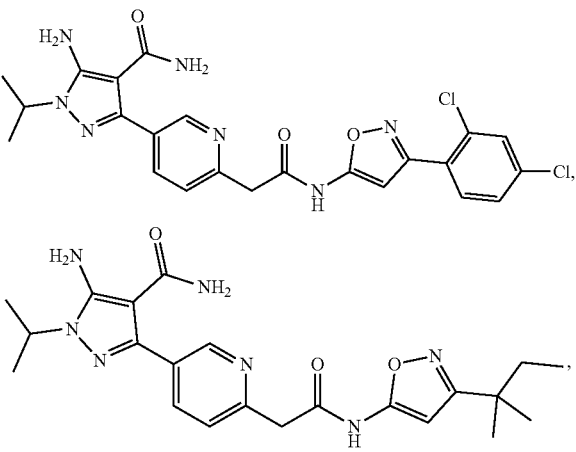

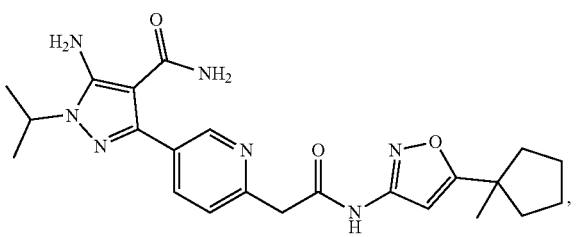

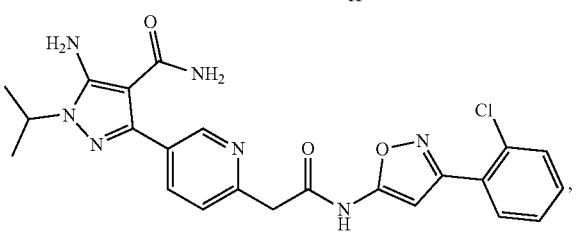

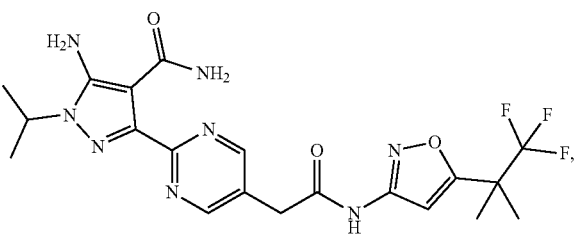

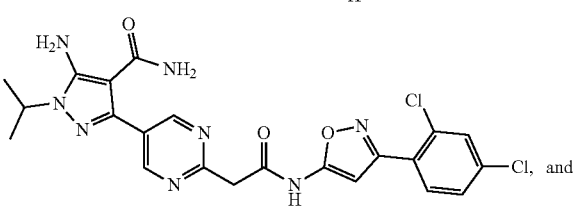

Definitions

The specific chemical naming conventions used herein are intended to be familiar to one of skill in the chemical arts. Some terms are defined specifically for additional clarity.

As used herein, the term alkyl means saturated linear or branched-chain monovalent hydrocarbon radicals of one to six atoms, e.g., "$C_1$-$C_6$ alkyl." In cases where a zero is indicated, e.g., $C_0$-$C_4$ alkyl or $C_0$-$C_3$ alkyl, this component of the substituent group can be absent, thus, if a $C_5$ heterocycloalkyl substituent is at the $R_2$ position in formula (I), the $C_5$ heterocycloalkyl substituent could be described by the —($C_0$-$C_4$ alkyl)($C_3$-$C_7$ heterocycloalkyl) substituent as described for $R_2$ (i.e., the substituent group would be —($C_0$) ($C_5$ heterocycloalkyl)). Examples include, but are not limited to, methyl, ethyl, propyl, 1-propyl, isopropyl, and butyl. Similarly, as used herein, the term heteroalkyl means saturated linear or branched-chain monovalent alkyl molecules as defined herein containing one or more heteroatoms that have replaced carbon(s) in the alkyl chain. Typically, there are no more than four heteroatoms or no more than three heteroatoms in the heteroalkyl group.

As used herein, the term aryl refers to a functional group or substituent derived from an aromatic ring containing six to ten carbon atoms, e.g., $C_6$-$C_{10}$ aryl, or five to six carbon atoms, e.g., $C_5$-$C_6$ aryl, and no heteroatoms. Examples of aryl groups include phenyl and naphthyl. As used herein, the term heteroaryl refers to a functional group or substituent derived from an aromatic ring containing carbon atoms and one or more heteroatoms (e.g., nitrogen, oxygen, or sulfur) as part of the aromatic ring. Examples include rings having five or six atoms, at least one of which is a heteroatom. Examples of heteroaryl groups include, but are not limited to, pyridyl, pyrazinyl, pyrimidinyl, pyridazinyl, furanyl, pyrrolyl, thiophenyl, imidazolyl, pyrazolyl, oxazolyl, isoxazolyl, and thiazolyl.

As used herein, the term $C_3$-$C_7$ cycloalkyl means a cyclic alkyl molecule containing three to seven carbon atoms. Examples of $C_3$-$C_7$ cycloalkyls include, but are not limited to, cyclopropyl, cyclobutyl, and cyclopentyl. Similarly, as used herein, the terms heterocycloalkyl and cycloheteroalkyl mean a cycloalkyl molecule as defined herein, containing three to seven total atoms at least one of which is a heteroatom. Heterocycloalkyl or cycloheteroalkyl groups can be fused to other groups, such as phenyl groups. For example, a piperidine fused to a phenyl can form a tetrahydroisoquinoline or a tetrahydroquinoline.

As used herein, the terms bicyclic, bicyclyl, and bicycloalkyl refer to a group having two or more fused or bridged rings. $C_4$-$C_{10}$ bicyclic, $C_4$-$C_{10}$ bicyclyl, and $C_4$-$C_{10}$ bicycloalkyl contain from four to ten carbon atoms. When the bicyclic group is fused, the two rings share two adjacent atoms. When the bicyclic group is bridged (also referred to as a bridged bicycloalkyl), the two rings share three or more atoms. Bridged bicycloalkyl groups may have four to ten carbon atoms or four to eight carbon atoms. Such groups may be referred to as "$C_4$-$C_{10}$ bridged bicycloalkyl" or "$C_4$-$C_5$ bridged bicycloalkyl," respectively. Bicyclic molecules can be all aliphatic, all aromatic, or mixed aromatic and aliphatic. The term $C_4$-$C_{10}$ heterobicyclic refers to $C_4$-$C_{10}$ bicyclic groups as defined that also include one or more hetero atoms. Examples of bridged bicycloalkyl groups useful with the compounds of formula (I) include, but are not limited to: $CF_3CF_3$

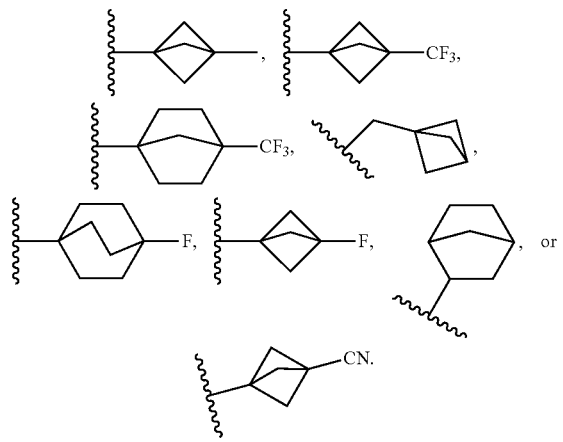

Examples of $C_4$-$C_{10}$ heterobicyclic include, but are not limited to:

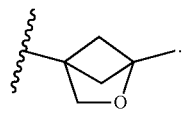 [SMILES: *C12COC(C)(C1)C2]

As used herein, the terms $C_5$-$C_{12}$ spiranyl or spirane or spiranes refers to a spirocyclic ring system. $C_5$-$C_{12}$ spiranyl, $C_5$-$C_{12}$ spirane and $C_5$-$C_{12}$ spiranes refer to spirocyclic rings systems having 5 to 12 ring carbons. The spirocyclic ring system contains at least two and up to four rings, at least two of which must be connected via a spiro attachment. $C_5$-$C_{12}$ spiranes may be unsubstituted or substituted as described herein.

$C_5$-$C_{12}$ heterospiranyl refers to a spirocyclic ring system having 5 to 12 ring atoms, at least one of which is a heteroatom, i.e., not a carbon. The heterospiranyl ring system contains two to four rings, at least two of which must be connected via a spiro attachment. $C_5$-$C_{12}$ heterospiranes may be unsubstituted or substituted as described herein. Examples of substituted and unsubstituted $C_5$-$C_{12}$ spiranes and $C_5$-$C_{12}$ heterospiranes include, but are not limited to:

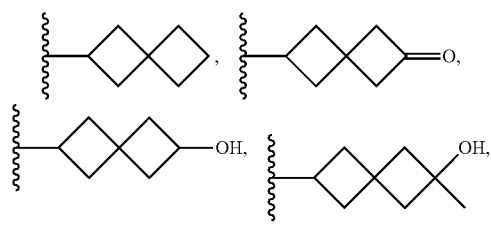

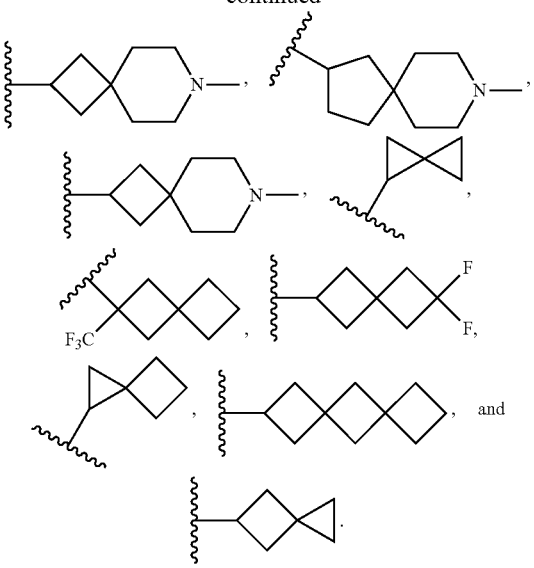

As used herein, the term halogen or halo means fluoro (F), chloro (Cl), bromo (Br), or iodo (I).

As used herein, the term oxo means an oxygen that is double-bonded to a carbon atom, which can be represented as =O.

Compounds of formulas I, Ia to Ix, IIa to Ix, and/or IIIa to IIIx can be deuterated or triturated at one or more positions and such deuterated or triturated forms are part of the invention. Deuterium modification involves replacing one or more hydrogen atoms of a drug with deuterium atoms in an attempt to slow the CYP-mediated metabolism of a drug or to reduce the formation of undesirable metabolites. Tritium modification makes the molecule radioactive and allows researchers to determine where the drug is deposited in the body and how it is metabolized.

The compounds of formulas I, Ia to Ix, IIa to Ix, and/or IIIa to IIIx described herein may form pharmaceutically acceptable salts. Such pharmaceutically acceptable salts of the compounds of formulas I, Ia to Ix, IIa to Ix, and/or IIIa to IIIx are intended to be included. Pharmaceutically acceptable salts and common methodology for preparing them are well known in the art (see, e.g., P. Stahl, et al. *Handbook of Pharmaceutical Salts: Properties, Selection and Use*, 2$^{nd}$ Revised Edition (Wiley-VCH, 2011); S. M. Berge, et al., "Pharmaceutical Salts," *Journal of Pharmaceutical Sciences*, Vol. 66, No. 1, January 1977).

The compounds of formulas I, Ia to Ix, IIa to Ix, and/or IIIa to IIIx as described herein are generally effective over a wide dosage range. For example, dosages per day fall within the range of about 0.01 mg/kg to about 200 mg/kg. Further, the compounds of formulas I, Ia to Ix, IIa to Ix, and/or IIIa to IIIx as described herein can be administered, for example, in an amount of about 0.05 mg/kg to about 150, about 0.1 mg/kg to about 150, about 0.5 mg/kg to about 150 mg/kg, about 1 mg/kg to about 150 mg/kg, about 5 mg/kg to about 150 mg/kg, about 5 mg/kg to about 100 mg/kg, about 20 mg/kg to about 40 mg/kg, about 25 mg/kg to about 35 mg/kg, about 50 mg/kg to about 70 mg/kg, about 55 mg/kg to about 65 mg/kg, about 90 mg/kg to about 110 mg/kg, about 95 mg/kg to about 105 mg/kg, or about 50 mg/kg to about 150 mg/kg.

Alternatively, compounds of formulas I, Ia to Ix, IIa to Ix, and/or IIIa to IIIx as described herein can be administered, for example, in an amount of about 0.1 mg/kg to about 15 mg/kg, or about 0.5 mg/kg to about 10 mg/kg, or 1 mg/kg to about 9 mg/kg, or about 2 mg/to about 8 mg/kg or about 3 mg/kg to 7 mg/kg. Additionally, the compounds of formulas I, Ia to Ix, IIa to Ix, and/or IIIa to IIIx as described herein can be administered, for example, in an amount of about 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4, mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, about 105 mg/kg, about 110 mg/kg, about 115 mg/kg, about 120 mg/kg, about 125 mg/kg, about 130 mg/kg, about 135 mg/kg, about 140 mg/kg, about 145 mg/kg, about 150 mg/kg, about 155 mg/kg, about 160 mg/kg, about 165 mg/kg, about 170 mg/kg, about 175 mg/kg, about 180 mg/kg, about 185 mg/kg, about 190 mg/kg, about 195 mg/kg, or about 200 mg/kg. Daily administration can be once-daily or in multiple doses, e.g., twice-daily (BID) administration. Dosing can be 160 mg orally twice daily for patients weighing >50 kg or 120 mg for patients weighing <50 kg. It will be understood that the amount of a compound actually administered will be determined by a physician, in light of the relevant circumstances, including the condition to be treated, the chosen route of administration, the actual compound or compounds administered, the age, weight, and response of the individual patient, and the severity of the patient's symptoms. Possibly CNS involvement/need for increased CNS exposure is also typically considered.

The compounds of formulas I, Ia to Ix, IIa to IIx, and/or IIIa to IIIx as described herein can be formulated as pharmaceutical compositions that can be administered by a variety of routes. Such pharmaceutical compositions and processes for preparing the same are well known in the art (see, e.g., *Remington: The Science and Practice of Pharmacy* (A. Gennaro, et al., eds., 21st ed., Mack Publishing Co., 2005)). Specifically, the compounds of formulas I, Ia to Ix, IIa to IIx, and/or IIIa to IIIx as described herein, or pharmaceutically acceptable salts thereof, can be combined with one or more pharmaceutically acceptable carriers, diluents, or excipients. More particularly, the compounds described herein by formulas I, Ia to Ix, IIa to IIx, and/or IIIa to IIIx can be formulated as pharmaceutical compositions. Further, the compounds of formulas I, Ia to Ix, IIa to IIx, and/or IIIa to IIIx as described herein, or pharmaceutically acceptable salts thereof, can be combined with one or more other therapeutic agents. For example, the compounds of formulas I, Ia to Ix, IIa to IIx, and/or IIIa to IIIx as described herein, or pharmaceutically acceptable salts thereof, can be a component in a pharmaceutical composition for the treatment of cancer in combination with one or more pharmaceutically acceptable carriers, diluents, or excipients, and optionally with one or more additional therapeutic agents. In concomitant therapies, when patients have multiple driver mutations/alterations detected—such as when an EGFR mutation and a clinically significant RET alteration are detected, the compounds of formulas I, Ia to Ix, IIa to Ix, and/or IIIa to IIIx can be administered in combination with a second therapeutic agent. Examples of combinations include, but are not limited to compounds of formulas I, Ia to Ix, IIa to Ix, and/or IIIa to IIIx and osimertinib. Other examples of combinations include compounds of formulas I, Ia to Ix, IIa to Ix, and/or IIIa to IIIx combined with one or more of platinum based chemotherapeutic acids, and/or non-platinum based chemotherapeutic agents. Pharmaceutical compositions containing the compounds of formulas I, Ia to Ix, IIa to IIx, and/or IIIa to IIIx as described herein, or pharmaceutically acceptable salts thereof, can be used in the methods described herein.

The term "treating" (or "treat" or "treatment") as used herein refers to restraining, slowing, stopping, or reversing the progression or severity of an existing symptom, condition or disorder.

As used herein, the term "irritable bowel syndrome" or "IBS" means gastrointestinal disorders including, but not limited to, diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, and inflammatory bowel disease.

As used herein, the terms "cancer" and "cancerous" refer to or describe the physiological condition in patients that is typically characterized by unregulated cell proliferation. Included in this definition are benign and malignant cancers. By "early stage cancer" or "early stage tumor" is meant a cancer that is not advanced or metastatic or is classified as a Stage 0, I, or II cancer. Examples of cancer include, but are not limited to, lung cancer (e.g., small cell lung carcinoma or non-small cell lung carcinoma), thyroid cancer (e.g., papillary thyroid cancer, medullary thyroid cancer, differentiated thyroid cancer, recurrent thyroid cancer, or refractory differentiated thyroid cancer), thyroid adenoma, endocrine gland neoplasms, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, and cervical cancer.

The term "RET-associated disease or disorder" as used herein refers to diseases or disorders associated with or having a dysregulation of a RET gene, a RET kinase (also called herein RET kinase protein), or the expression or activity or level of any (e.g., one or more) of the same (e.g., any of the types of dysregulation of a RET gene, a RET kinase, a RET kinase domain, or the expression or activity or level of any of the same described herein).

The term "RET-associated cancer" as used herein refers to cancers associated with or having a dysregulation of a RET gene, a RET kinase (also called herein RET kinase protein), or expression or activity, or level of any of the same. Non-limiting examples of a RET-associated cancer are described herein.

The phrase "dysregulation of a RET gene, a RET kinase, or the expression or activity or level of any of the same" refers to a genetic mutation or alteration. Examples of such genetic mutations causing dysregulation of a RET gene, a RET kinase, or the expression or activity or level of any of the same include, but are not limited to, a RET gene translocation that results in the expression of a fusion protein, a deletion in a RET gene that results in the expression of a RET protein that includes a deletion of at least one amino acid as compared to the wild-type RET protein, a mutation in a RET gene that results in the expression of a RET protein with one or more point mutations, or an alternative spliced version of a RET mRNA that results in a RET protein having a deletion of at least one amino acid in the RET protein as compared to the wild-type RET protein or a RET gene amplification that results in overexpression of a RET protein or an autocrine activity resulting from the overexpression of a RET gene in a cell that results in a pathogenic increase in the activity of a kinase domain of a RET protein (e.g., a constitutively active kinase domain of a RET protein) in a cell. A dysregulation of a RET gene, a RET protein, or expression or activity, or level of any of the same, can be a mutation in a RET gene that encodes a RET protein that is constitutively active or has increased activity as compared to a protein encoded by a RET gene that does not include the mutation. For example, a dysregulation of a RET gene, a RET protein, or expression or activity, or level of any of the same, can be the result of a gene or chromosome translocation which results in the expression of a fusion protein that contains the 2nd half/portion of RET, and the 1st half of some other gene that is not RET. In some examples, dysregulation of a RET gene, a RET protein, or expression or activity or level of any of the same can be a result of a gene translocation of one RET gene with another non-RET gene.

Methods for the treatment of RET-associated diseases or disorders, in particular for the treatment of IBS or cancer with abnormal RET expression, using the compounds of formulas I, Ia to Ix, IIa to Ix, and/or IIIa to IIIx as described herein are provided. Examples of cancers with abnormal RET expression include cancers caused by dysregulation of a RET gene, a RET kinase, or the expression or activity or level of any of the same. One such method of treating RET-associated diseases or disorders such as IBS or cancer includes administering a therapeutically effective amount of a compound of formulas I, Ia to Ix, IIa to Ix, and/or IIIa to IIIx or pharmaceutically acceptable salts thereof to a patient in need thereof. Another method of treating RET-associated diseases or disorders such as IBS or cancer includes a) detecting a dysregulation of a RET gene, a RET kinase, or the expression or activity or level of any of the same in a sample from the patient; and b) administering a therapeutically effective amount of a compound of formulas I, Ia to Ix, IIa to Ix, and/or IIIa to IIIx or a pharmaceutically acceptable salt.

The dysregulation of a RET gene, a RET kinase, or the expression or activity or level of any of the same can be the result of one or more chromosome translocations or inversions resulting in a RET gene fusion (i.e., the genetic translocations result in an expressed protein that is a fusion protein containing residues from a non-RET partner protein, and including a minimum of a functional RET kinase domain). Non-limiting examples of RET fusion partners and their associated cancers include ACBD5 (papillary thyroid cancer); AFAP1 (NSCLC); AFAP1L2 (papillary thyroid cancer); AKAP13 (papillary thyroid cancer); BCR (chronic myelomonocytic leukemia); C10orf118 (papillary thyroid cancer); CCDC6 (also called PTC1, D10S170, or H4) (NSCLC, colon cancer, papillary thyroid cancer, adenocarcinomas, lung adenocarcinoma, metastatic colorectal cancer, adenosquamous carcinomas, breast cancer); CCDC88C (NSCLC); CCDC186-RET, CEP55 (diffuse gastric cancer); CGNL1 (pancreatic cancer); CLIP1 (adenocarcinoma); CUX1 (lung adenocarcinoma); DLG5 (non-anaplastic thyroid cancer); DOCK1 (NSCLC); EML4 (papillary thyroid cancer); ERC1 (also called ELKS) (papillary thyroid cancer, breast cancer); ETV6 (salivary cancer); FGFR1OP (CMML, primary myelofibrosis with secondary acute myeloid leukemia); FKBP15 (papillary thyroid cancer); FOXP4 (lung adenocarcinoma); FRMD4A (NSCLC); GOLGA5 (also called PTC5) (papillary thyroid cancer, spitzoid neoplasms); H4L (various); HOOK3 (papillary thyroid cancer); HRH4-RET (thyroid cancer and/or papillary thyroid cancer); HTIF1 (various); KIAA1217 (also called SKT) (papillary thyroid cancer, lung adenocarcinoma, NSCLC); KIAA1468 (also called PTC9 and RFG9) (papillary thyroid cancer, lung adenocarcinoma); KIF13A (NSCLC); KIF5B (NSCLC, ovarian cancer, spitzoid neoplasms, lung adenocarcinoma, adenosquamous carcinomas); KTN1 (also called PTC8) (papillary thyroid cancer); MBD1 (also known as PCM1) (papillary thyroid cancer); MPRIP (NSCLC); MYH10 (infantile myofibromatosis); MYH13 (medullary thyroid cancer); NCOA4 (also called PTC3, ELE1, and RFG) (papillary thyroid cancer, NSCLC, colon cancer, salivary gland cancer, metastatic colorectal cancer, lung adenocarcinoma, adenosquamous carcinomas diffuse sclerosing variant of papillary thyroid cancer, breast cancer, actinic cell cancer, mammary analog secretory cancer); OLFM4 (Small-bowel cancer); PARD3 (NSCLC); PCM1 (papillary thyroid cancer); PIBF1 (bronchiolus lung cell cancer); PICALM (NSCLC); PPFIBP2 (papillary thyroid cancer); PRKAR1A (also called PTC2) (papillary thyroid cancer); PTClex9 (a novel CCDC6 rearrangement) (metastatic papillary thyroid cancer); PTC4 (a novel NCO4/ELE1 rearrangement) (papillary thyroid cancer); RAB61P2 (papillary thyroid cancer); RASAL2 (Sarcoma); RASGEF1A (breast cancer); RBPMS (NSCLC); RFG8 (papillary thyroid cancer); RRBP1 (colon cancer); RUFY1 (colorectal cancer); RUFY2 (NSCLC; papillary thyroid cancer); RUFY3 (papillary thyroid cancer); SLC12A2 (NSCLC); SORBS2 (papillary thyroid cancer); SPECCIL (papillary thyroid cancer; thyroid gland cancer); SQSTM1 (papillary thyroid cancer); TAF3 (pancreatic cancer); TBL1XR1 (papillary thyroid cancer, thyroid gland cancer); TFG (pancreatic cancer); TIF1G (various); TRIM24 (also called PTC6) (papillary thyroid cancer); TRIM27 (also called RFP) (papillary thyroid cancer); AKAP13 (papillary thyroid cancer); TRIM33 (also called PTC7 and RFG7) (NSCLC, papillary thyroid cancer); and UEVLD (papillary thyroid cancer). The fusion protein can be, for example, KIF5B-RET. Fusions that were identified in single tumors included CCDC186-RET, ERC1-RET, KTN1-RET, and RUFY3-RET. Still other RET fusion proteins may not be included in the listing herein or are not yet known; however, the compounds of formulas I, Ia to Ix, IIa to Ix, and/or IIIa to IIIx and methods for their use as described herein are expected to be effective inhibitors.

The dysregulation of a RET gene, a RET kinase, or expression or activity or level of any of the same, can be caused by one or more point mutations, insertions, or deletions in a RET gene (compared to wildtype RET). For reference, the sequence of mature human RET protein (SEQ ID NO: 1) is provided here:

```
MAKATSGAAG LRLLLLLLLP LLGKVALGLY FSRDAYWEKL

YVDQAAGTPL LYVHALRDAP EEVPSFRLGQ HLYGTYRTRL

HENNWICIQE DTGLLYLNRS LDHSSWEKLS VRNRGFPLLT

VYLKVFLSPT SLREGECQWP GCARVYFSFF NTSFPACSSL

KPRELCFPET RPSFRIRENR PPGTFHQFRL LPVQFLCPNI

SVAYRLLEGE GLPFRCAPDS LEVSTRWALD REQREKYELV

AVCTVHAGAR EEVVMVPFPV TVYDEDDSAP TFPAGVDTAS

AVVEFKRKED TVVATLRVFD ADVVPASGEL VRRYTSTLLP

GDTWAQQTFR VEHWPNETSV QANGSFVRAT VHDYRLVLNR

NLSISENRTM QLAVLVNDSD FQGPGAGVLL LHFNVSVLPV

SLHLPSTYSL SVSRRARRFA QIGKVCVENC QAFSGINVQY

KLHSSGANCS TLGVVTSAED TSGILFVNDT KALRRPKCAE

LHYMVVATDQ QTSRQAQAQL LVTVEGSYVA EEAGCPLSCA

VSKRRLECEE CGGLGSPTGR CEWRQGDGKG ITRNFSTCSP

STKTCPDGHC DVVETQDINI CPQDCLRGSI VGGHEPGEPR

GIKAGYGTCN CFPEEEKCFC EPEDIQDPLC DELCRTVIAA

AVLFSFIVSV LLSAFCIHCY HKFAHKPPIS SAEMTFRRPA

QAFPVSYSSS GARRPSLDSM ENQVSVDAFK ILEDPKWEFP

RKNLVLGKTL GEGEFGKVVK ATAFHLKGRA GYTTVAVKML

KENASPSELR DLLSEFNVLK QVNHPHVIKL YGACSQDGPL

LLIVEYAKYG SLRGFLRESR KVGPGYLGSG GSRNSSSLDH

PDERALTMGD LISFAWQISQ GMQYLAEMKL VHRDLAARNI

LVAEGRKMKI SDFGLSRDVY EEDSYVKRSQ GRIPVKWMAI

ESLFDHIYTT QSDVWSFGVL LWEIVTLGGN PYPGIPPERL

FNLLKTGHRM ERPDNCSEEM YRLMLQCWKQ EPDKRPVFAD

ISKDLEKMMV KRRDYLDLAA STPSDSLIYD DGLSEEETPL

VDCNNAPLPR ALPSTWIENK LYGMSDPNWP GESPVPLTRA

DGTNTGFPRY PNDSVYANWM LSPSAAKLMD TFDS
```

Non-limiting examples of potentially activating RET kinase protein point mutations, insertions, or deletions as compared to wild-type RET kinase can occur at the following amino acid positions: 2, 3, 4, 5, 6, 7, 8, 11, 12, 13, 20, 32 (e.g., S32L), 34 (e.g., D34S), 40 (e.g., L40P), 56 (e.g., L56 M), 64 (e.g., P64L), 67 (e.g., R67H), 114 (e.g., R114H), 136 (e.g., glutamic acid to stop codon), 145 (e.g., V145G), 180 (e.g., arginine to stop codon), 200, 292 (e.g., V292 M), 294, 321 (e.g., G321R), 330 (e.g., R330Q), 338 (e.g., T338I), 360 (e.g., R360W), 373 (e.g., alanine to valine (p.A373V) frameshift), D378-G385delinsE, 393 (e.g., F393L), 423 (e.g., G423R), 432, 446 (e.g., G446R), 505-506 (6-Base Pair In-Frame Germline Deletion in Exon 7), 510 (e.g., A510V), 511 (e.g., E511K), 513 (e.g., G513D), 515 (e.g., C515R, C515S, C515W), 525 (e.g., R525W), 531 (e.g., C531R, or 9 base pair duplication), 532 (e.g., duplication), 533 (e.g., G533C, G533S), 550 (e.g., G550E), 591 (e.g., V591I), 593 (e.g., G593E), 595 (e.g., E595D and E595A), 600 (e.g., R600Q), 602 (e.g., I602V), 603 (e.g., K603Q, K603E), 606 (e.g., Y606C), 609 (e.g., C609Y, C609S, C609G, C609R, C609F, C609W, C609C), 611 (e.g., C611R, C611S, C611G, C611Y, C611F, C611W), 616 (e.g., E616Q), 618 (e.g., C618S, C618Y, C618R, C618T, C618G, C618F, C618W), 620 (e.g., C620S, C620W, C620R, C620G, C620L, C620Y, C620F), 623 (e.g., E623K), 624 (e.g., D624N), 630 (e.g., C630A, C630R, C630S, C630Y, C630F, C630W, C630G), 631 (e.g., D631N, D631Y, D631A, D631G, D631V, D631E), 632 (e.g., E632K, E632G), 632-633 (6-Base Pair In-Frame Germline Deletion in Exon 11), 633 (e.g., 9 base pair duplication), 634 (e.g., C634W, C634Y, C634S, C634R, C634F, C634G, C634L, C634A, or C634T, or an insertion ELCR, or a 12 base pair duplication, or in combination with A640G, A641A, or A641T) (e.g., causing MTC), 634/852 (e.g., C634R/I852 M), 635 (e.g., R635G), 636 (e.g., T636P, T636 M), 648 (e.g., V648I), 649 (e.g., S649L), 664 (e.g., A664D), 665 (e.g., H665Q), 666 (e.g., K666E, K666 M, K666N, K666R), 675 (T675T, silent nucleotide change), 686 (e.g., S686N), 689 (e.g., S689T), 691 (e.g., G691S), 694 (e.g., R694Q), 700 (e.g., M700L), 706 (e.g., V706 M, V706A), 713 splice variant (e.g., E713K), 732 (e.g., E732K), 736 (e.g., G736R), 748 (e.g., G748C), 765 (e.g., S765P), 766 (e.g., P766S, P766 M6), 768 (e.g., E768Q, E768D), 769 (e.g., L769L), 770 (e.g., R770Q), 771 (e.g., D771N), 777 (e.g., N777S), 778 (e.g., V778I), 781 (e.g., Q781R), 788 (e.g., I788I), 790 (e.g., L790F, L790T), 791 (e.g., Y791F, Y791N), 791/852 (e.g., Y791F/I852 M), 802, 804 (e.g., V804L, V804 M, V804E, V804G, V804S) (e.g., causing MTC), 804/918 (e.g., V804 M/M918T, V804L/M918T), 805 (e.g., E805K), 804/805 (e.g., V804 M/E805K), 806 (e.g., Y806F, Y806C, Y806H, Y806Y), 810 (e.g., G810R, G810S, G810A, G810C, G810V), 818 (e.g., E818K), 819 (e.g., S819I), 823 (e.g., G823E), 826 (e.g., Y826 M, Y826S), 833 (e.g., R833C), 841 (e.g., P841L, P841P), 843 (e.g., E843D), 844 (e.g., R844W, R844Q, R844L), 848 (e.g., M848T), 852 (e.g., I852 M), 865 (e.g., L865V), 870 (e.g., L870F), 873 (e.g., R873W), 876 (e.g., A876V), 881 (e.g., L881V), 882, 883 (e.g., A883F, A883P, A883S, A883T, A883Y), 884 (e.g., E884K), 886 (e.g., R886W), 891 (e.g., S891A), 897 (e.g., R897Q), 898 (e.g., D898V), 900 (e.g., Y900F), 901 (e.g., E901K), 904 (e.g., S904F, S904C), 905 (e.g., Y905F), 907 (e.g., K907E, K907 M), 908 (e.g., R908K), 911 (e.g., G911D), 912 (e.g., R912P, R912Q), 918 (e.g., M918T, M918V, M918L, M918R) (e.g., causing MTC), 919 (e.g., A919V), 921 (e.g., E921K), 922 (e.g., S922P, S922Y), 930 (e.g., T930 M), 961 (e.g., F961L), 972 (e.g., R972G), 981 (e.g., Y981F), 982 (e.g., R982C), 1009 (e.g., M1009V), 1015 (e.g., Y1015F), 1017 (e.g., D1017N), 1041 (e.g., V1041G), 1064 (e.g., M1064T), 1096 (e.g., Y1096F), In-Frame Deletion in Exons 6 and 11, 3 bp In-Frame Deletion in Exon 15, Nucleotide position 2136+2 (e.g., 2136+2T>G), del632-636 ins6, and RET-extracellular cysteine mutation (which is defined as a mutation that included at least one of the following cysteine residues: 609, 611, 618, 620, 630, or 634). Other mutations included D631-liter633delinsE, E632-liter633del, A883F, D631-liter633delinsV, L790F, D898-E901del, D898_E901del+D903_S904delinsEP, K666N, T636-V637insCRT, and D378-G385delinsE. Still other mutations include D631-liter633delinsE, E632-liter633del, A883F, D631-liter633delinsV, L790F, D898-E901del, D898_E901del+D903_S904delinsEP, K666N, T636-V637insCRT, and D378-G385delinsE. The RET kinase protein point mutations/insertions/deletions can be, for example, M918T, M918V, C634W, V804L, or V804 M. Other RET kinase protein point mutations/insertions/deletions may not be included in the listing herein or are not yet known; however, the compounds of formulas I, Ia to Ix, IIa to Ix, and/or IIIa to IIIx and methods for their use as described herein are expected to be effective inhibitors.

A dysregulation of a RET gene, a RET kinase, or expression or activity or level of any of the same, can also include a splice variation in a RET mRNA which results in an expressed protein that is an alternatively spliced variant of RET having at least one residue deleted (as compared to the wild-type RET kinase) resulting in a constitutive activity of a RET kinase domain.

A "RET kinase inhibitor" as defined herein refers to compounds that inhibit RET activity using a measurement such as the Biological Assays described below in the examples.

In some cases, a RET kinase containing a mutation, insertion, or deletion is more resistant to inhibition of its phosphotransferase activity by one or more first RET kinase inhibitor(s), as compared to a wildtype RET kinase or a RET kinase not including the same mutation. Such mutations may not decrease the sensitivity of the cancer cell or tumor having the RET kinase to treatment a compound of formulas I, Ia to Ix, IIa to Ix, and/or IIIa to IIIx as described herein (e.g., as compared to a cancer cell or a tumor that does not include the particular RET inhibitor resistance mutation). In these cases, a RET inhibitor resistance mutation can result in a RET kinase that has one or more of an increased $V_{max}$, a decreased $K_m$ for ATP, and an increased $K_D$ for a first RET kinase inhibitor, when in the presence of a first RET kinase inhibitor, as compared to a wildtype RET kinase or a RET kinase not having the same mutation in the presence of the same first RET kinase inhibitor.

In other cases, a RET kinase containing a mutation, insertion, or deletion, has increased resistance to a compound of formulas I, Ia to Ix, IIa to Ix, and/or IIIa to IIIx as described herein, as compared to a wildtype RET kinase or a RET kinase not including the same mutation. In such cases, a RET inhibitor resistance mutation can result in a RET kinase that has one or more of an increased $V_{max}$, a decreased $K_m$, and a decreased $K_D$ in the presence of a compound of formulas I, Ia to Ix, IIa to Ix, and/or IIIa to IIIx as described herein, as compared to a wildtype RET kinase or a RET kinase not having the same mutation in the presence of the same compound of formulas I, Ia to Ix, IIa to Ix, and/or IIIa to IIIx as described herein.

Examples of RET inhibitor resistance mutations can include point mutations, insertions, or deletions in and near the ATP binding site in the tertiary structure of RET kinase, including, but not limited to, the gatekeeper residue, P-loop residues, residues in or near the DFG motif, and ATP cleft solvent front amino acid residues. Additional examples of these types of mutations include changes in residues that may affect enzyme activity and/or drug binding including but are not limited to residues in the activation loop, residues near or interacting with the activation loop, residues contributing to active or inactive enzyme conformations, changes including mutations, deletions, and insertions in the loop proceeding the C-helix and in the C-helix. Specific residues or residue regions that at which mutations are known to create RET inhibitor resistance include but are not limited to the following amino acids (based on the human wildtype RET protein sequence (SEQ ID NO: 1)): 732 (e.g., E732K); 788 (e.g., I788N); 804 (e.g., V804 M, V804L, V804E); 804/805 (e.g., V804 M/E805K); 806 (e.g., Y806C, Y806E, Y806S, Y806H, Y806N); 810 (e.g., G810A, G810C, G810R, G810S, G810V); and 865 (e.g., L865V).

Further examples of RET inhibitor resistance mutation positions include, but are not limited to, the following amino acids (based on the human wildtype RET protein sequence (SEQ ID NO: 1)): L730P, G731V, E732K, G733V, E734K, L760 M, K761E, E762K, N763D, A764V, S765N, P766A, S767C, E768K, L779 M, I788 M, M868R, K869E, L870Q, V871 M, H872R, R873P, D874Y, L881R, L895 M, S896N, R897C, D898Y, V899G, Y900D, E901K, E902K, D903Y, S904C, Y905D, V906 M, K907E, R908P, S909C, Q910R, G911C, and R912P. These mutations (which may also include single or multiple amino acid changes, insertions within or flanking the sequences, and deletions within or flanking the sequences) are thought to induce a steric hindrance and/or an active conformational effect that changes inhibitor binding characteristics.

Compounds of formulas I, Ia to Ix, IIa to Ix, and/or IIIa to IIIx as described herein may be useful in treating patients that develop cancers with certain RET inhibitor resistance mutations. For example, resistance mutations that result in an increased resistance to a RET inhibitor like a substitution at amino acid position 804 (e.g., V804 M, V804L, or V804E), and/or one or more other RET inhibitor resistance mutations like those discussed above may be treated by either dosing in combination or as a follow-up therapy to existing drug treatments. For example, if a patient is treated with a first RET kinase inhibitor and the patient develops a RET inhibitor resistance mutation, the patient could then be subsequently treated with a compound of formulas I, Ia to Ix, IIa to Ix, and/or IIIa to IIIx as described herein, or pharmaceutically acceptable salts thereof (assuming that the compound of formulas I, Ia to Ix, IIa to Ix, and/or IIIa to IIIx as described herein is a suitable inhibitor of the particular RET kinase inhibitor mutation present). As another example, if a patient is known to have a particular RET kinase inhibitor mutation (or multiple mutations), the patient could simultaneously be treated with multiple RET kinase inhibitors including a compound (or compounds) of formulas I, Ia to Ix, IIa to Ix, and/or IIIa to IIIx as described herein, or pharmaceutically acceptable salts thereof that are effective against the RET kinase inhibitor mutation(s) present. Examples of currently known RET kinase inhibitors include pazopanib, sitravatinib, regorafenib, motesanib, RXDX-105, alectinib, BLU6864, cabozantinib, dovitinib, foretinib, lenvatinib, ponatinib, pralsetinib, selpercatinib, sorafenib, sunitinib, and vandetanib.

The types of cancers that can be treated using the compounds of formula I, formula Ia, formula Ib, formula Ic, formula Id and pharmaceutically acceptable salts thereof, include hematological cancer or solid tumor cancer. Examples of the types of cancer that can be treated using a compound of formulas I, Ia to Ix, IIa to Ix, and/or IIIa to IIIx as described herein include lung cancer (e.g., small cell lung carcinoma or non-small cell lung carcinoma), thyroid cancer (e.g., Anaplastic thyroid cancer, Hurthle cell thyroid cancer, follicular thyroid cancer, poorly differentiated thyroid cancer, papillary thyroid cancer, medullary thyroid cancer, differentiated thyroid cancer, recurrent thyroid cancer, or refractory differentiated thyroid cancer), thyroid adenoma, endocrine gland neoplasms, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, and cervical cancer. Specifically, the types of cancer can be lung cancer or thyroid cancer. More specifically, the cancer can be non-small cell lung carcinoma or medullary thyroid cancer. Further examples of the types of cancers that can be treated using the compounds of formulas I, Ia to Ix, IIa to Ix, and/or IIIa to IIIx and the methods as described herein include acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, lung neoplasm, pulmonary cancer, pulmonary neoplasms, pulmonary carcinosarcoma, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromocytoma, pituitary cancer, plasma cell neoplasm, pleuropulmonary blastoma, pregnancy and breast cancer, primary central nervous system lymphoma, primary peritoneal cancer, prostate cancer, rectal cancer, colon cancer, colonic neoplasms, renal cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

Examples of the types of hematological cancers that can be treated using the compounds of formulas I, Ia to Ix, IIa to Ix, and/or IIIa to IIIx and the methods as described herein include leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMIL), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In one embodiment, the hematological cancer (e.g., the hematological cancer that is a RET-associated cancer) is AML or CMML.

Examples of the types of solid tumor cancers that can be treated using the compounds of formulas I, Ia to Ix, IIa to Ix, and/or IIIa to IIIx and the methods as described herein include thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, xanthogranuloma tumor, breast cancer, colon cancer, colorectal cancer, rectal neuroendocrine cancer, prostate cancer, renal cell carcinoma, head and neck tumors, neuroblastoma, and melanoma.

Also provided herein is a compound of formulas I, Ia to Ix, IIa to Ix, and/or IIIa to IIIx as described herein, or pharmaceutically acceptable salts thereof, for use in the treatment of RET-associated diseases or disorders such as IBS or cancer. Cancers that can be treated using a compound of formula I, Ia, Ib, Ic and/or Id, or pharmaceutically acceptable salts thereof, t are described herein above. The treatment of RET-associated diseases or disorders can also include a step of performing an in vitro assay using a biological sample from a patient, determining the presence of a dysregulation of a RET gene, a RET kinase, or expression or activity or level of any of the same, and administering a therapeutically effective amount of the compound of formulas I, Ia to Ix, IIa to Ix, and/or IIIa to IIIx as described herein, to the patient if a dysregulation of a RET gene, a RET kinase, or expression or activity or level of any of the same is present. In these uses, the biological sample can be a tumor sample and the tumor sample can be analyzed using methods known to those of skill in the art such as genomic/DNA sequencing. Additionally, in these uses the sample can be obtained from the patient prior to the first administration of the compound of formulas I, Ia to Ix, IIa to Ix, and/or IIIa to IIIx as described herein. In these uses of the compound of formulas I, Ia to Ix, IIa to Ix, and/or IIIa to IIIx as described herein in a therapy can be based upon a patient being selected for treatment by having at least one dysregulation of a RET gene, a RET kinase, or expression or activity or level of any of the same. Also, in these therapeutic uses a compound of formulas I, Ia to Ix, IIa to Ix, and/or IIIa to IIIx as described herein, or pharmaceutically acceptable salts thereof, may be administered to the patient at a dose of about 1 mg/kg to 200 mg/kg (effective dosage sub-ranges are noted herein above).

Certain stereochemical centers have been left unspecified and certain substituents have been eliminated in the following schemes for the sake of clarity and are not intended to limit the teaching of the schemes in any way. Furthermore, individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). The designations "isomer 1" and "isomer 2" refer to the compounds that elute from chiral chromatography first and second, respectively, under the conditions described herein and if chiral chromatography is initiated early in the synthesis, the same designation is applied to subsequent intermediates and examples. Additionally, the intermediates described in the following schemes may contain a number of nitrogen or oxygen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007). Certain abbreviations are defined as follows: "ACN" refers to acetonitrile; "ATP" refers to adenosine triphosphate; "bis(pinacolato)diboron" refers to 4,4,4',4',5,5,5',5'-octamethyl-2,2'-bi-1,3,2-dioxaborolane; "Boc" refers to tert-butoxycarbonyl; "Boc$_2$O" refers to di-tert-butyl dicarbonate; "BSA" refers to Bovine Serum Albumin; "BTFFH" refers to Fluoro-N,N,N',N'-bis(tetramethylene) formamidinium hexafluorophosphate; "Bu" refers to butyl; "COMU®" refers to (1-cyano-2-ethoxy-2-oxoethylidenaminooxy)dimethylamino-morpholino-carbenium hexafluorophosphate; "DCM" refers to dichloromethane or methylene chloride; "DIPEA" refers to N,N-diisopropylethylamine or N-ethyl-N-isopropyl-propan-2-amine; "DMAP" refers to 4-dimethylaminopyridine; "DMF" refers to N,N-dimethylformamide; "DMSO" refers to dimethyl sulfoxide; "DTT" refers to dithiothreitol; "EtOAc" refers to ethyl acetate; "ee" refers to enantiomeric excess; "Et$_2$O" refers to diethyl ether; "EtOH" refers to ethanol or ethyl alcohol; "FA" refers to formic acid; "GST" refers to glutathione S-transferase; "HATU" refers to 1-[bis(dimethylamino)methylene]-1H-1,2,3-triazolo[4,5-b]pyridinium 3-oxide hexafluorophosphate; "HEK" refers to human embryonic kidney; "hr" or "hrs" refers to hour or hours; "HOAc" refers to acetic acid; "HTRF" refers to homogeneous time resolved fluorescence; "IgG" refers to immunoglobulin G; "IPA" refers to isopropyl alcohol or isopropanol; "IPAm" refers to Isopropylamine; "iPr$_2$O" refers to isopropyl ether; "[Ir(OMe)(1,5-cod)]$_2$" refers to di-mu-methanolatodiiridium(Ir—Ir)-cycloocta-1,5-diene or (1,5-cyclooctadiene)(methoxy)iridium(I) dimer or bis(1,5-cyclooctadiene)di-μ-methoxydiiridium(I); "KOAc" refers to potassium acetate; "LDA" refers to lithium diisopropylamide; "MeI" refers to methyl iodide or iodomethane; "MeOH" refers to methanol or methyl alcohol; "MeTHF" refers to 2-methyltetrahydrofuran; "min" refers to minute or minutes; "Mn(dpm)$_3$" refers to manganese(3+) tris[(3Z)-2,6,6-tetramethyl-5-oxo-3-hepten-3-olate], Mn(TMHD)$_3$, Shenvi hydrogenation catalyst, or tris(dipivaloylmethanato) manganese; "NaOAc" refers to sodium acetate; "NaOMe" refers to sodium methoxide; "NMI" refers to 1-methylimidazole or N-methylimidazole; "Parkins catalyst" refers to hydrido(dimethylphosphinous acid-kP)[hydrogen bis(dimethylphosphinito-kP)]platinum(II) and is CAS #173416-05-2; "PBS-T" refers to Phosphate Buffered Saline+ Tween@20; "Pd(dppf)Cl$_2$)" refers to [1,1' bis(diphenylphosphino)ferrocene]dichloropalladium (II); "Pd (dppf)Cl$_2$)·CH$_2$Cl$_2$" refers to [1,1' bis(diphenylphosphino) ferrocene]dichloropalladium (II), coupled with DCM; "PE" refers to petroleum ether; "PhSiH$_3$" refers to phenylsilane; "RT" refers to room temperature; "SFC" refers to supercritical fluid chromatography; "tert-BuOH" refers to tert butyl alcohol; "TBTU" refers to O-(Benzotriazol-1-yl)-N, N,N',N-tetramethyluronium tetrafluoroborate or N,N,N',N'-Tetramethyl-O-(benzotriazol-1-yl)uronium tetrafluoroborate; "TCFH" refers to N,N,N',N'-tetramethylchloroformamidinium hexafluorophosphate; "TEA" refers to triethylamine; "TFA" refers to trifluoroacetic acid; "THF" refers to tetrahydrofuran; "T3P®" refers to propanephosphonic acid anhydride, 2,4,6-tripropyl-1,3,5, 2,4,6-trioxatriphosphorinane-2,4,6-trioxide, or PPACA; "t$_{(R)}$" refers to retention time and "WT" refers to wild-type.

The compounds of the present invention, or pharmaceutically acceptable salts thereof, may be prepared according to the following Preparations and Examples by methods well known and appreciated in the art. Suitable reaction conditions for the steps of these Preparations and Examples are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. As an illustration, compounds of the preparations and examples can be isolated, for example, by silica gel purification, isolated directly by filtration, or crystallization. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally similar compounds and the procedures described in the Preparations and Examples which follow including any novel procedures. Intermediates and processes useful for the synthesis of the compounds described by formula (I) are intended to be included in this description.

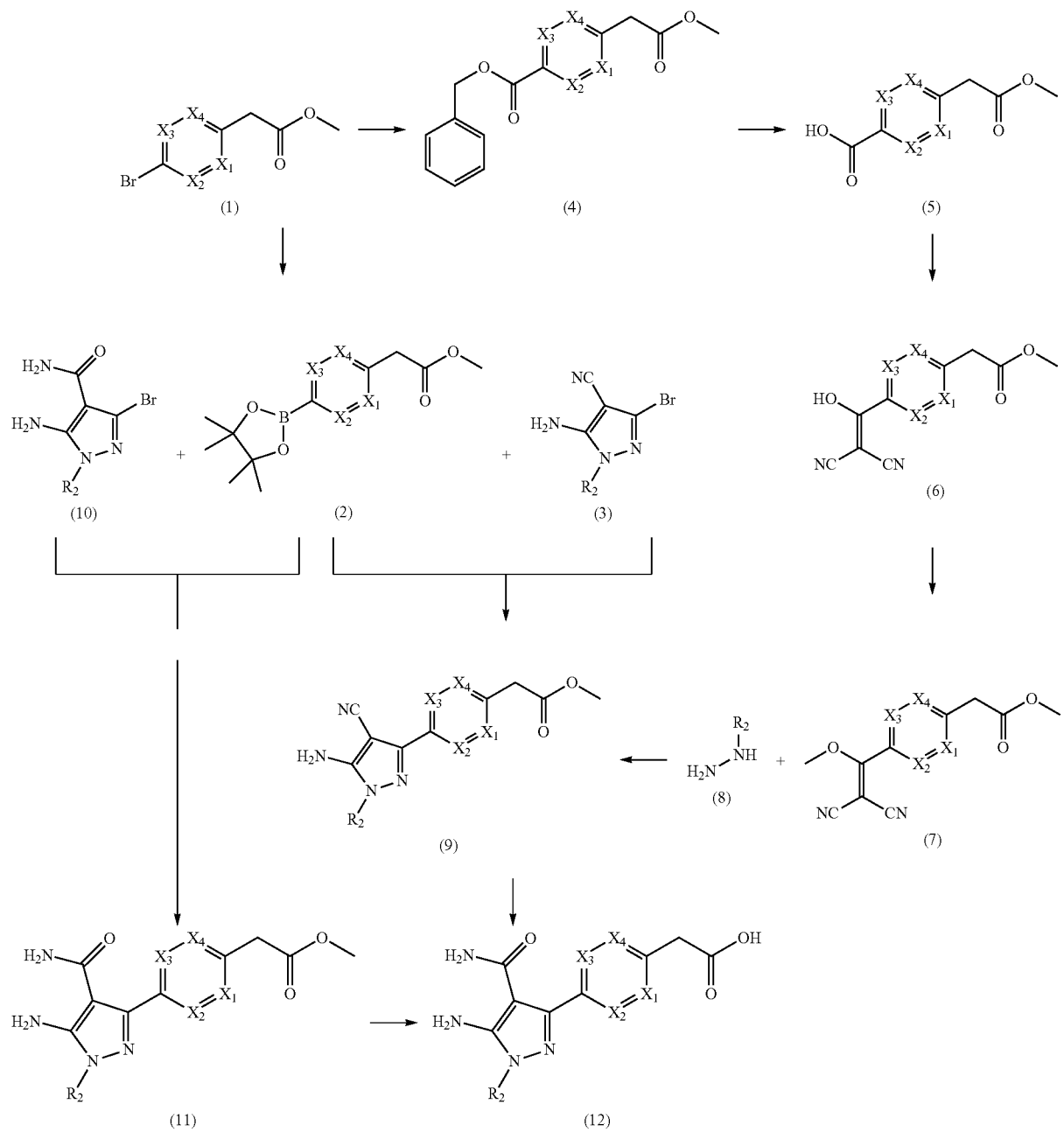

Scheme 1 depicts the preparation of the compounds of (12). A person of ordinary skill in the art will recognize that borylation of aryl bromide (1) under typical Miyaura reaction conditions may provide boronic ester (2). Treatment of boronic ester (2) with the appropriate bromopyrazole (3) and metal catalyst, under Suzuki coupling conditions, may afford amino pyrazole (9).

Alternatively, palladium-catalyzed carbonylation of aryl bromide (1) with carbon monoxide and benzyl alcohol may provide benzyl carboxylate (4). Palladium-catalyzed debenzylation of benzyl carboxylate (4) with hydrogen may provide carboxylic acid (5). Preparation of the acyl chloride of acid (5) and subsequent reaction with malononitrile under basic conditions may afford malononitrile (6). Methylation of vinyl alcohol (6) may be achieved with dimethyl sulfate to provide methoxy (7). Reacting the appropriately substituted hydrazine (8) with the dinitrile Michael acceptor (7) can also afford amino pyrazole (9).

Treatment of boronic ester (2) with the appropriate bromopyrazole (10) and metal catalyst, under Suzuki coupling conditions, may afford amino pyrazole (11). Carboxylic acid (12) may be obtained by saponification of ester (11) with the proper nucleophilic base.

Alternatively, carboxylic acid (12) may also be obtained from the ester (9) in a two-step one pot reaction of oxidation and saponification using peroxide and base.

Scheme 2

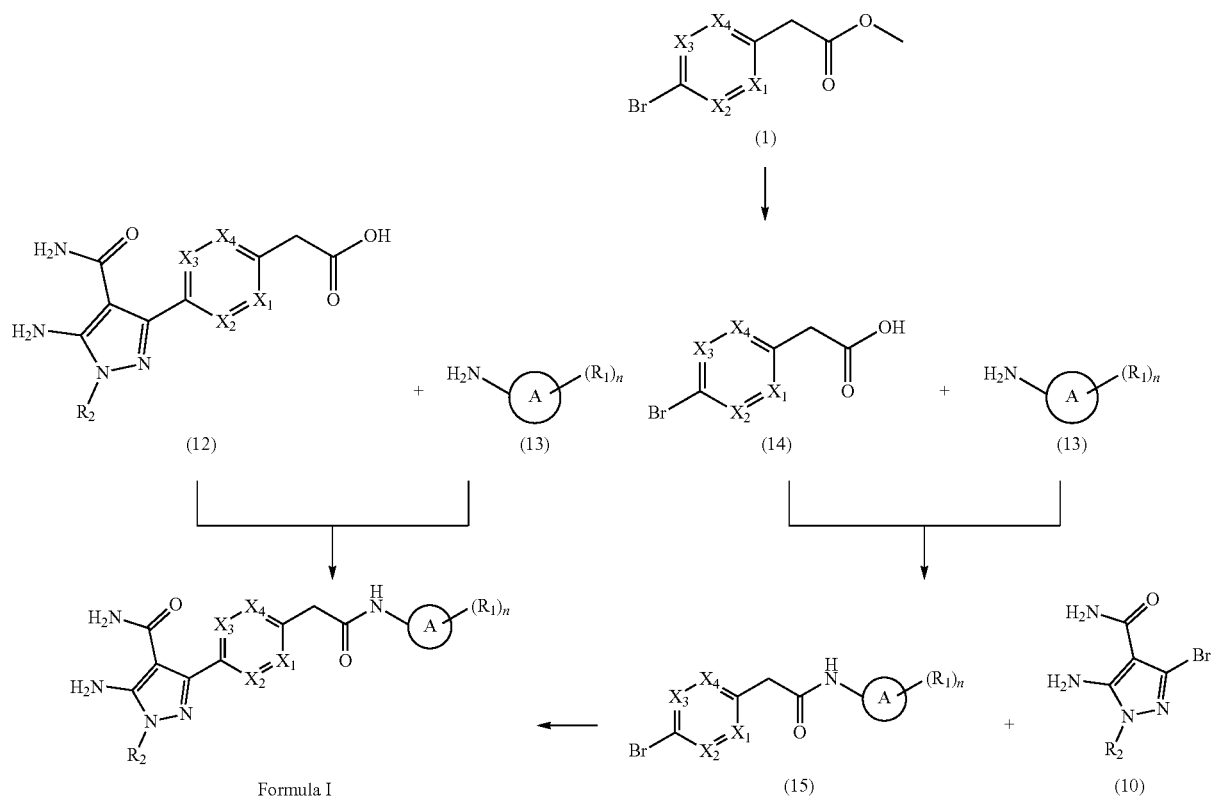

Scheme 2 depicts the preparation of the compounds of formulas I, Ia to Ix, IIa to IIx, and/or IIIa to IIIx as described herein. Saponification of ester (1) may furnish carboxylic acid (14) in essentially the same manner as described for the carboxylic acid (12) in Scheme 1. The skilled artisan will recognize that carboxylic acid (14) and primary amine (13) may be joined by utilizing the appropriate amide coupling reagent under conditions suitable for amide bond formation to provide amide (15). Borylation of aryl bromide (15) under typical Miyaura reaction conditions, followed by treatment of the in-situ boronic ester with bromopyrazole (10) and metal catalyst, under Suzuki coupling conditions, may afford compounds of formulas I, Ia to Ix, IIa to Ix, and/or IIIa to IIIx.

Alternatively, amide coupling of carboxylic acid (12) and primary amine (13) may provide compounds of formulas I, Ia to Ix, IIa to Ix, and/or IIIa to IIIx in essentially the same manner described for amide (15) above.

Scheme 3

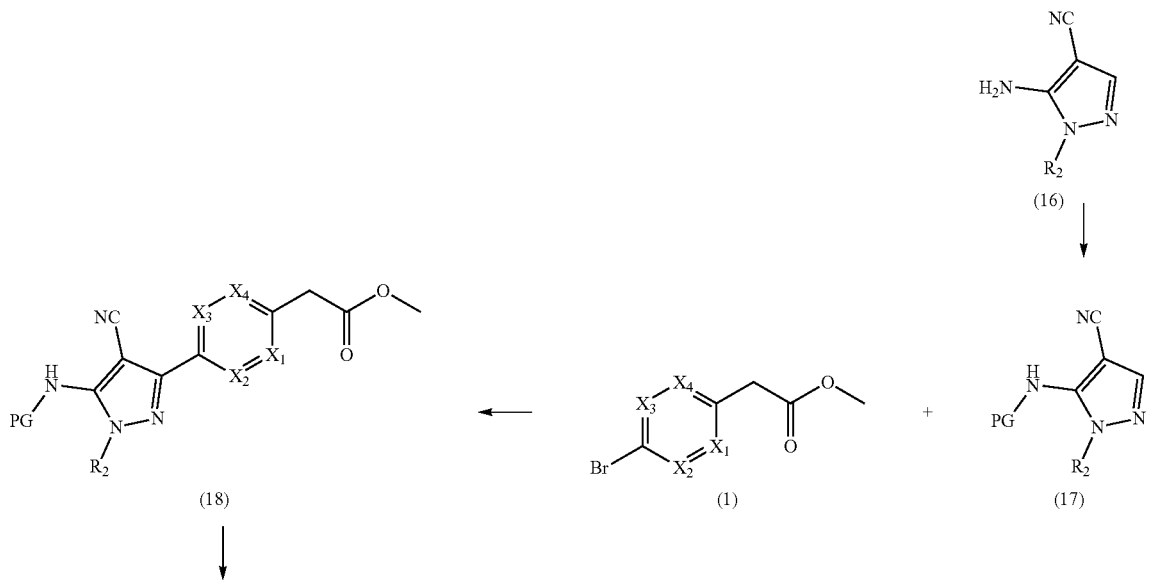

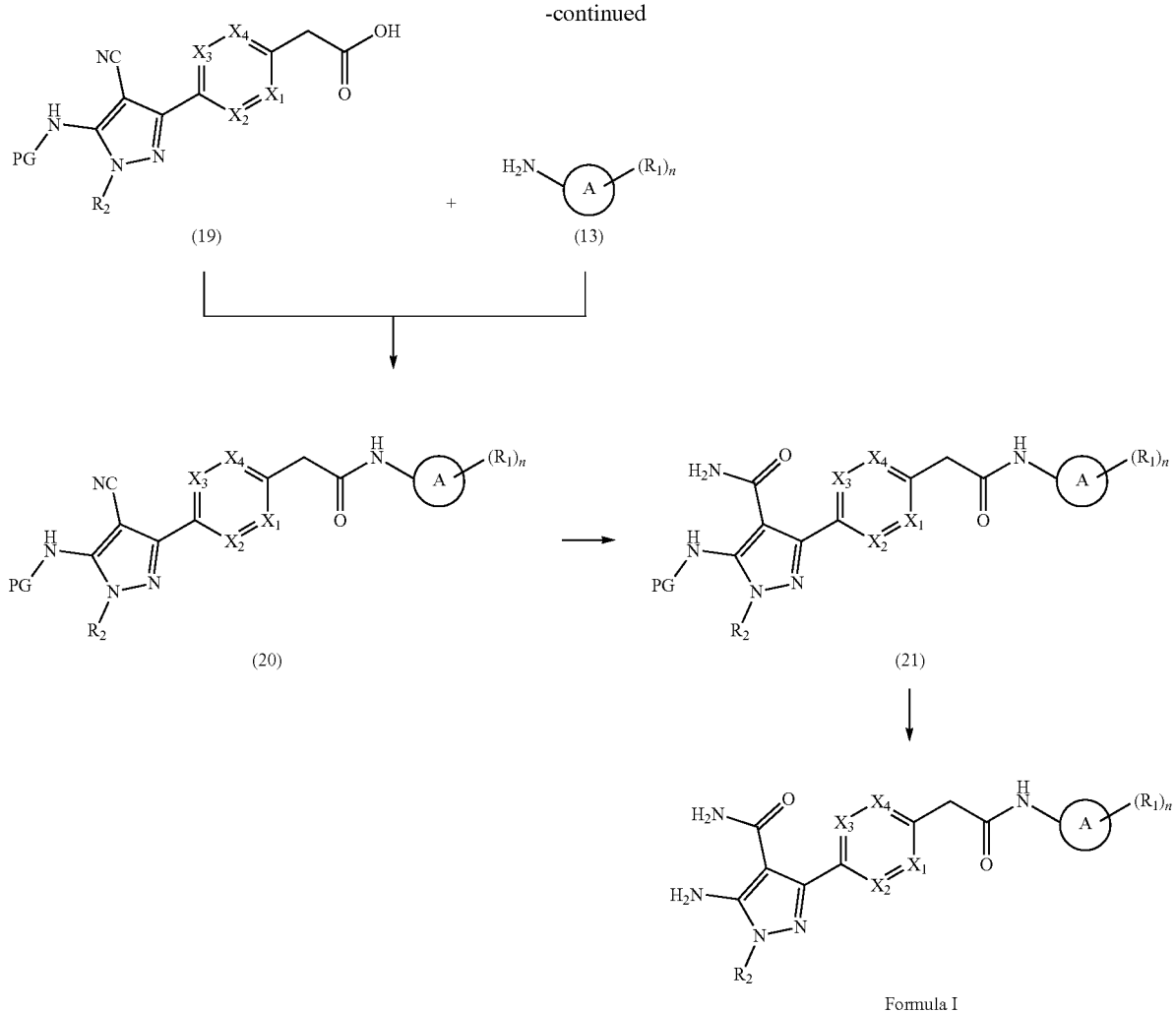

Scheme 3 depicts additional preparations of the compounds of formulas I, Ia to Ix, IIa to IIx, and/or IIIa to IIIx as described herein. Protection of primary amine (16) with an appropriate protecting group may provide the mono- or bis-protected amino pyrazole (17).

Iridium-catalyzed C—H borylation of pyrazole (17), followed by treatment of the in-situ boronic ester with aryl bromide (1) and metal catalyst, under Suzuki coupling conditions, may afford biaryl (18). Saponification of ester (18) may furnish carboxylic acid (19) in essentially the same manner as described for the carboxylic acid (12) in Scheme 1. Amide coupling of carboxylic acid (19) and primary amine (13) may provide amide (20) in essentially the same manner as described for the amide (12) in Scheme 2. The nitrile moiety of amino pyrazole (20) may be converted to carboxamide (21), under a variety of conditions such as metal catalyzed hydration, acidic hydrolysis, and oxidation. Removal of the protecting group from the protected amino pyrazole (21) may provide additional compounds of formulas I, Ia to Ix, IIa to Ix, and/or IIIa to IIIx as described herein.

Scheme 4

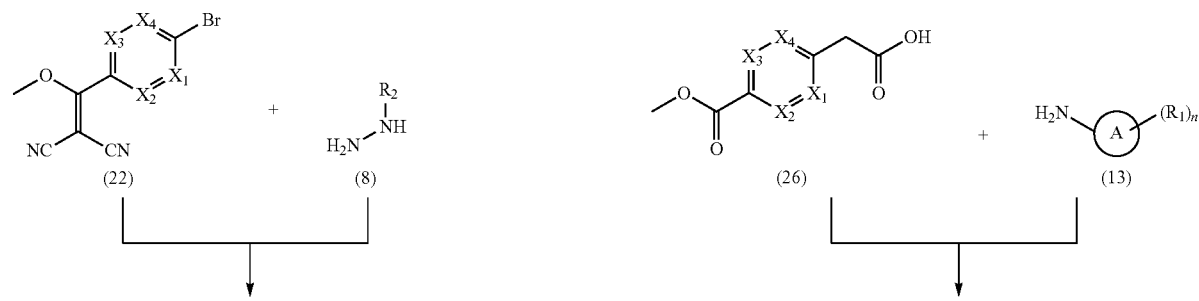

51

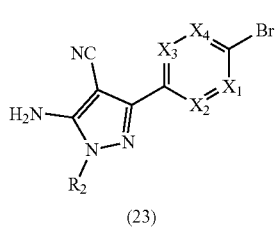

(23)

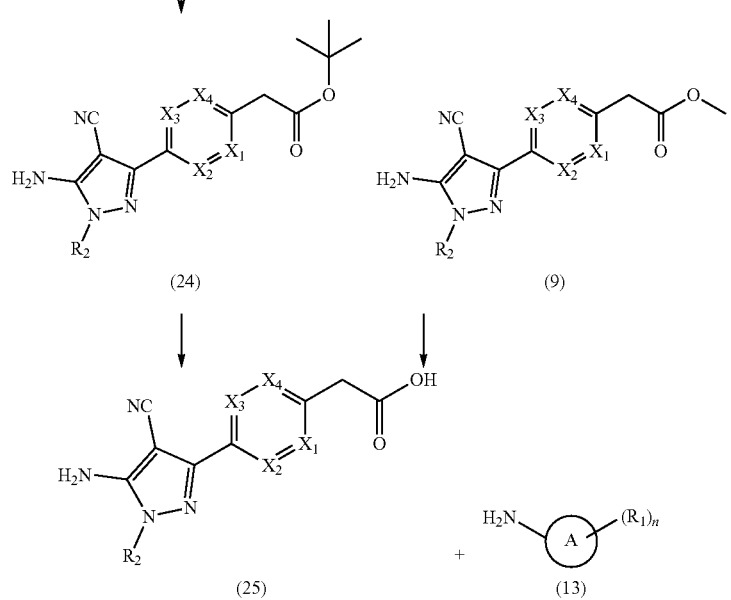

(24)    (9)

(25)    (13)

(31)

Formula I

52

-continued

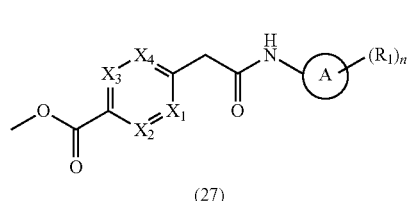

(27)

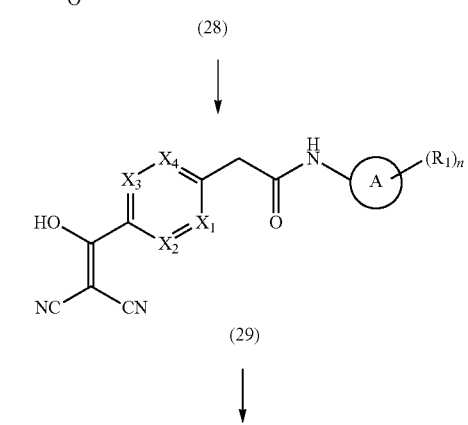

(28)

(29)

(30)

+

(8)

Scheme 4 depicts alternative preparations of the compounds of formulas I, Ia to Ix, IIa to Ix, and/or IIIa to IIIx as described herein. Reacting the appropriately substituted hydrazine (8) with the dinitrile Michael acceptor (22) can afford amino pyrazole (23) in essentially the same manner as described for the amino pyrazole (9) in Scheme 1. Treatment of aryl bromide (23) with the appropriate alkylzinc halide and metal catalyst, under Negishi coupling conditions may afford tert-butyl ester (24). Acidic deprotection of tert-butyl ester (24) may provide carboxylic acid (25).

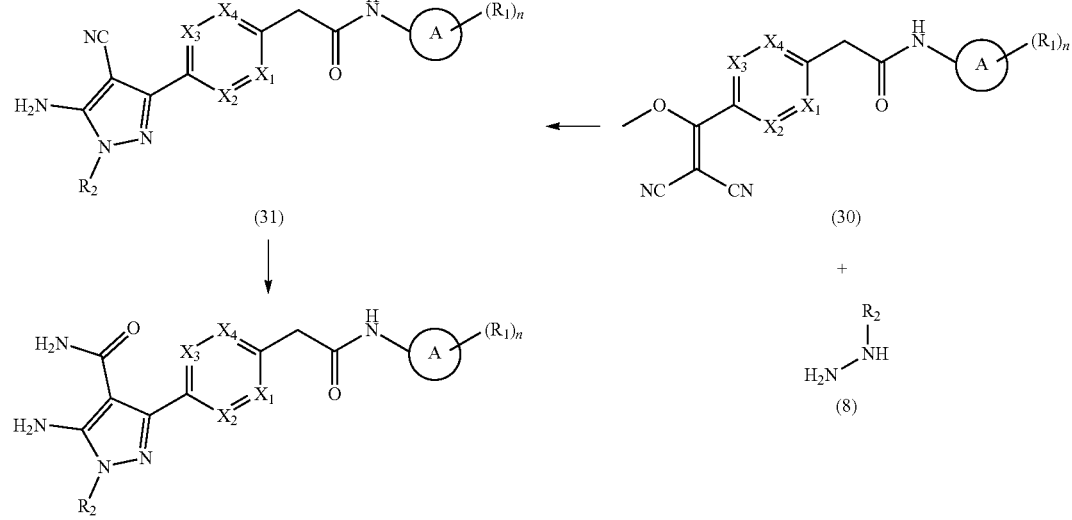

Alternatively, saponification of ester (9) may furnish carboxylic acid (25) in essentially the same manner as described for the carboxylic acid (12) in Scheme 1. Amide coupling of carboxylic acid (25) and primary amine (13) may provide amide (31) in essentially the same manner as described for the amide (12) in Scheme 2.

Alternatively, amide coupling of carboxylic acid (26) and primary amine (13) may provide amide (27) in essentially the same manner as described for the amide (12) in Scheme 2. Saponification of ester (27) may furnish carboxylic acid (28) in essentially the same manner as described for the carboxylic acid (12) in Scheme 1. Preparation of the acyl chloride of acid (28) and subsequent reaction with malononitrile under basic conditions may afford malononitrile (29). Methylation of vinyl alcohol (29) may be achieved with dimethyl sulfate to provide methoxy (30). Reacting the appropriately substituted hydrazine (8) with the dinitrile Michael acceptor (30) can afford amino pyrazole (31) in essentially the same manner as described for the amino pyrazole (9) in Scheme 1.

The nitrile moiety of amino pyrazole (31) may be converted to additional compounds of formulas I, Ia to Ix, IIa to Ix, and/or IIIa to IIIx as described herein, under a variety of conditions such as metal catalyzed hydration, acidic hydrolysis, and oxidation.

In an optional step, a pharmaceutically acceptable salt of a compound of formulas I, Ia to Ix, IIa to Ix, and/or IIIa to IIIx can be formed by reaction of an appropriate free base of formulas I, Ia to Ix, IIa to Ix, and/or IIIa to IIIx with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). "Salt selection for basic drugs," *International Journal of Pharmaceutics*, 33: 201-217 (1986). One of ordinary skill in the art will appreciate that a compound of formulas I, Ia to Ix, IIa to Ix, and/or IIIa to IIIx is readily converted to and may be isolated as a pharmaceutically acceptable salt.

PREPARATIONS AND EXAMPLES

Preparation 1 tert-Butyl N-(tert-butoxycarbonyl)-N-(5-iodo-4-methyl-1,3-thiazol-2-yl)carbamate

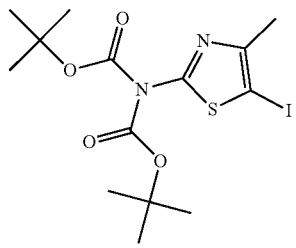 [SMILES: Cc1nc(N(C(=O)OC(C)(C)C)C(=O)OC(C)(C)C)sc1I]

A mixture of 5-iodo-4-methyl-1,3-thiazol-2-amine (16.0 g, 66.7 mmol), Boc$_2$O (32.0 g, 146 mmol) and DMAP (0.81 g, 6.63 mmol) in THF (200 mL) is stirred for 2 hr at RT under N$_2$. The mixture is concentrated under reduced pressure. The residue is purified by silica gel chromatography, eluting with a gradient of 12:1 to 5:1 PE:EtOAc to give the title compound (20.0 g, 68%) as a yellow solid. ES/MS (m/z) 441.0 (M+H).

Preparation 2

5-(2,2-Dimethylpropyl)-4-methyl-1,3-thiazol-2-amine

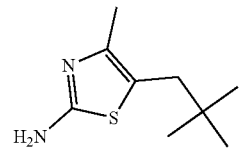

Zinc chloride (5.84 mL, 4.09 mmol, 0.7 M in THF) is added to a solution of bromo(2,2-dimethylpropyl)magnesium (6.50 mL, 3.25 mmol, 0.5 M in THF) at 0° C. and the mixture is stirred for 30 min at 0° C. under N$_2$. To this mixture is added tert-butyl N-(tert-butoxycarbonyl)-N-(5-iodo-4-methyl-1,3-thiazol-2-yl)carbamate (1.20 g, 2.73 mmol) and Pd(t-Bu$_3$P)$_2$ (0.28 g, 0.55 mmol) in portions over 1 min at RT. The mixture is stirred for an additional 2 hr at 100° C. under N$_2$. The reaction is quenched by the addition of saturated aq. NH$_4$Cl (20 mL) at RT. The mixture is extracted with EtOAc (2×50 mL). The combined organic extracts are washed with brine (2×30 mL), dried over anhydrous Na$_2$SO$_4$, filtered, and the filtrate is concentrated under reduced pressure. The residue is purified by reversed-phase chromatography (C18 column), eluting with a gradient of 45% to 52% ACN in H$_2$O (0.1% NH$_4$HCO$_3$) to give the title compound (80 mg, 16%) as a yellow solid. ES/MS (m/z) 185.1 (M+H).

Preparation 3

Methyl 2-[4-bromo-3-(bromomethyl)phenyl]acetate

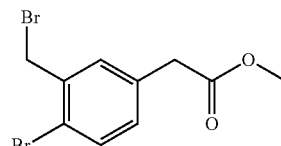

To a stirred solution of methyl 2-(4-bromo-3-methylphenyl)acetate (5.50 g, 22.6 mmol) in CCl$_4$ (200 mL) at RT under N$_2$ is added successively 1-bromopyrrolidine-2,5-dione (4.23 g, 23.8 mmol) and 2-[(E)-(1-cyano-1-methylethyl)azo]-2-methyl-propanenitrile (1.30 g, 7.92 mmol). The reaction mixture is stirred at 80° C. for 5 hr. The mixture is poured in a solution of NaHCO$_3$ and the aqueous layer is extracted with DCM (2×). The combined organic extracts are washed with brine, dried over Na$_2$SO$_4$, filtered, and concentrated under reduced pressure. The material is purified by silica gel chromatography, eluting with a gradient of 2% to 10% EtOAc in cyclohexane to give the title compound as a colorless oil (1.69 g, 23%). ES/MS (m/z) 342 (M+Na).

Preparation 4

Methyl 2-[4-bromo-3-(methoxymethyl)phenyl]acetate

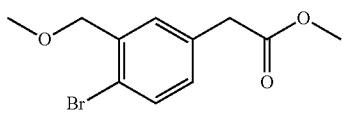

To a stirred solution of methyl 2-[4-bromo-3-(bromomethyl)phenyl]acetate (0.60 g, 1.86 mmol) in MeOH (10 mL) at 5° C. under $N_2$ is added NaOMe (0.41 mL, 2.19 mmol, 30 wt % in MeOH). The reaction mixture is stirred at RT overnight. The reaction mixture is concentrated, $H_2O$ is added to the residue, and the mixture is extracted with EtOAc (2×). The combined organic extracts are washed with brine, dried over $NaSO_4$, filtered, and concentrated under reduced pressure to give the title compound as a pale yellow oil (0.42 g, 83%). ES/MS (m/z) 274 (M+H).

Preparation 5

Methyl 2-(4-bromo-3-chloro-2-fluoro-phenyl)acetate

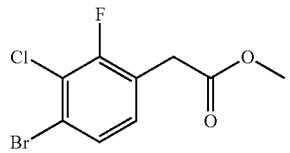

To 2-(4-bromo-3-chloro-2-fluorophenyl)acetic acid (0.50 g, 1.78 mmol) in MeOH (15 mL) at 0° C. under $N_2$ is added dropwise thionyl chloride (0.39 mL, 5.33 mmol). The mixture is allowed to warm to RT and stirred for 16 hr. The mixture is concentrated under reduced pressure and dried under vacuum. The material is purified by silica gel chromatography, eluting with a gradient of 25% to 100% DCM in heptane to give the title compound as a colorless oil (0.50 g, 100%).

The following compound in Table 1 is prepared essentially as described for methyl 2-(4-bromo-3-chloro-2-fluoro-phenyl)acetate, using the appropriate acid, adjusting the reaction time to determine completion of the reaction, and purifying chromatography as appropriate, and substituting EtOH for MeOH to prepare the ethyl ester if desired.

TABLE 1

| Prep No. | Chemical Name | Structure |
|---|---|---|
| 6 | Ethyl 3-methylbicyclo[1.1.1]pentane-1-carboxylate | 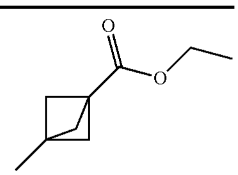 |

Preparation 7

Methyl 2-[4-bromo-3-(tert-butoxymethyl)phenyl]acetate

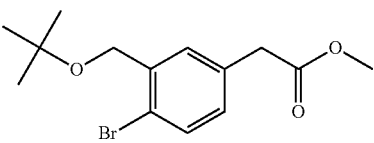 [SMILES: COC(=O)Cc1ccc(Br)c(COC(C)(C)C)c1]

To a suspension of Ag-trifluoromethanesulfonate (0.44 g, 1.71 mmol) in dry tert-BuOH (10 mL) and dry DCM (20 mL), protected from visible light, is added a solution of methyl 2-[4-bromo-3-(bromomethyl)phenyl]acetate (0.50 g, 1.55 mmol) in dry DCM (5 mL) at RT under $N_2$. The reaction mixture is stirred at RT for 16 hr, then poured into saturated aq. $NaHCO_3$. The aqueous layer is extracted with DCM (2×). The combined organic extracts are dried over $Na_2SO_4$, filtered, and concentrated under reduced pressure to give the title compound as a colorless oil (0.51 g, 95%). $^1H$ NMR ($d_6$-DMSO, 400 MHz) δ (ppm) 7.53 (d, J=8.1 Hz, 1H), 7.39 (d, J=2.2 Hz, 1H), 7.12 (dd, J=8.1, 2.3 Hz, 1H), 4.41 (s, 2H), 3.70 (s, 2H), 3.62 (s, 3H), 1.25 (s, 9H).

Preparation 8

2-[(tert-Butoxycarbonyl)[(tert-butoxycarbonyl)amino]amino]-2-methylpropan-1-ol

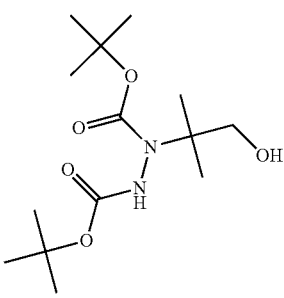 [SMILES: CC(C)(C)OC(=O)NN(C(=O)OC(C)(C)C)C(C)(C)CO]

To a stirred solution of Mn(dpm)$_3$ (0.42 g, 0.69 mmol) in IPA (150 mL) is added methallyl alcohol (5.00 g, 69.3 mmol), di-tert-butyl azodicarboxylate (24.0 g, 103 mmol), and PhSiH$_3$ (7.50 g, 69.3 mmol) dropwise at 0° C. under $N_2$. The mixture is stirred for 1 hr at 0° C. under $N_2$ and for 12 hr at RT under $N_2$. The solvent is removed under reduced pressure and the residue is purified by silica gel chromatography, eluting with a gradient of 10:1 to 4:1 PE:EtOAc to give the title compound (15.0 g, 71%) as a white solid. $^1H$ NMR (CDCl$_3$, 300 MHz) δ 4.30-4.02 (m, 2H), 3.42-3.19 (m, 1H), 1.59-1.42 (m, 24H).

Preparation 9

2-Hydrazinyl-2-methylpropan-1-ol 2HCl

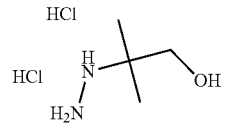

To a solution of 2-[(tert-butoxycarbonyl)[(tert-butoxycarbonyl)amino]amino]-2-methylpropan-1-ol (15.0 g, 49.3 mmol) in 1,4-dioxane (100 mL), HCl (50 mL, 4N in 1,4-dioxane) is added and the mixture is stirred for 2 hr at RT. The reaction is concentrated under reduced pressure. The crude product is triturated with Et$_2$O (30 mL) to give the title compound (4.4 g, 63%) as a white solid. $^1$H NMR (d$_6$-DMSO, 300 MHz) δ 6.41 (s, 5H), 3.40 (s, 2H), 1.14 (s, 6H).

Preparation 10 tert-Butyl N-(1-methylcyclopropyl)-N-nitroso-carbamate

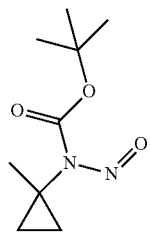

To a stirred solution of tert-butyl N-(1-methylcyclopropyl)carbamate (2.00 g, 11.7 mmol) in DCM (20 mL) is added tert-butyl nitrite (2.40 g, 23.3 mmol) in portions at RT under N$_2$ and the mixture is stirred for 2 hr at RT under N$_2$. The mixture is concentrated under reduced pressure and the residue is purified by silica gel chromatography, eluting with 25:1 to 20:1 PE:EtOAc to give the title compound (1.30 g, 55%) as a brown liquid. $^1$H NMR (d$_6$-DMSO) δ 1.59 (s, 9H), 1.10 (s, 3H), 0.86-0.84 (m, 2H), 0.70-0.65 (m, 2H).

Preparation 11

(1-Methylcyclopropyl)hydrazine hydrochloride

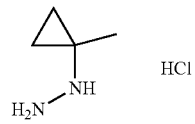

To a stirred solution of tert-butyl N-(1-methylcyclopropyl)-N-nitroso-carbamate (1.20 g, 5.99 mmol) in HCl (8 mL, 4N in 1,4-dioxane) is added Zn (0.78 g, 11.9 mmol) in portions at 0° C. under N$_2$ and the mixture is stirred for 12 hr at RT under N$_2$. The mixture is filtered, the filter cake is washed with H$_2$O (3×10 mL), and the filtrate is concentrated under reduced pressure to give the title compound (2.0 g, crude) as an off-white solid which is used directly without further purification. $^1$H NMR (d$_6$-DMSO) δ 1.30 (s, 3H), 0.77-0.73 (m, 2H), 0.54-0.50 (m, 2H).

Preparation 12

Methyl spiro[2.2]pentane-2-carboxylate

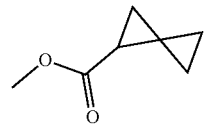

To a stirred solution of spiro[2.2]pentane-1-carboxylic acid (95%, 1.25 g, 10.6 mmol) in Et$_2$O (37.5 mL) and MeOH (7.5 mL) at 0° C. is added 2 M diazomethyl(trimethyl)silane in hexanes (6.9 mL, 13.8 mmol) dropwise. The reaction mixture is stirred at RT overnight. Et$_2$O is removed under reduced pressure and the reaction mixture is diluted with pentane (125 mL). The solution is washed with saturated aq. NaHCO$_3$(2×), H$_2$O (3×), and brine, dried over Na$_2$SO$_4$, filtered, and concentrated under reduced pressure to give the title compound (1.53 g, crude) as a yellow oil which is used directly without further purification.

Preparation 13

2-(Trifluoromethyl)spiro[3.3]heptane-2-carbonyl chloride

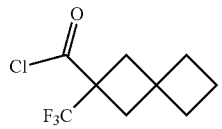

2-(Trifluoromethyl)spiro[3.3]heptane-2-carboxylic acid (1.02 g, 4.90 mmol) is suspended in DCM (40 mL) and DMF (0.10 mL). The slurry is cooled to 0° C. and oxalyl chloride (3.0 mL, 6.00 mmol, 2 M in DCM) is added. The reaction is stirred at 0° C. for 5 min then allowed to warm to RT and stirred for 1 hr. The solvent is removed under reduced pressure to give a yellow residue. The residue is used without further purification.

The following compounds in Table 2 are prepared essentially as described for 2-(trifluoromethyl)spiro[3.3]heptane-2-carbonyl chloride using the appropriate acid, oxalyl chloride (1-1.5 eq) and solvents (DCM, DMF) ranging from 0-50 mL and adjusting reaction time to determine completion of the reaction. The reaction temperature can range from 0° C.-25° C.

TABLE 2

| Prep No. | Chemical Name | Structure |
|---|---|---|
| 14 | 4-(Trifluoromethyl)bicyclo[2.2.1]heptane-1-carbonyl chloride | 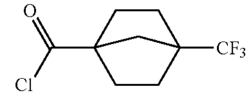 [SMILES: O=C(Cl)C12CCC(C(F)(F)F)(CC1)C2] |

TABLE 2-continued

| Prep No. | Chemical Name | Structure |
|---|---|---|
| 15 | 2-(1-Methylcyclopropyl)acetyl chloride | 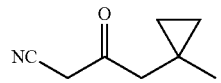 |
| 16 | 4,4,4-Trifluoro-3,3-dimethyl-butanoyl chloride | 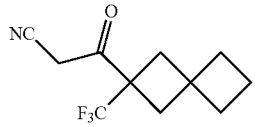 [SMILES: N#CCC(=O)C1(C(F)(F)F)CC2(CCC2)C1] |

Preparation 17

Benzyl 2,2-dimethylcyclobutanecarboxylate

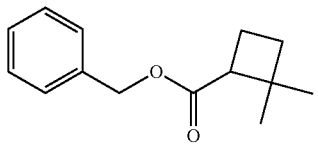 [SMILES: CC1(C)CCC1C(=O)OCc1ccccc1]

To a stirred solution of 2,2-dimethylcyclobutane-1-carboxylic acid (1.50 g, 11.7 mmol) in DCM (20 mL) at 0° C. under $N_2$ is added dropwise oxalyl chloride (1.0 mL, 11.7 mmol) followed by DMF (30 µL). The mixture is slowly allowed to warm to RT and stirred for 5 hr. Benzylalcohol (1.4 mL, 13.5 mmol) is added dropwise at 0° C. and the reaction mixture is slowly allowed to warm to RT and stirred for 20 hr. The mixture is poured into saturated aq. $NaHCO_3$. The aqueous layer is extracted with pentane (2×). The combined organic extracts are washed with brine, dried over $Na_2SO_4$, filtered, and concentrated under reduced pressure. The crude material is purified by silica gel chromatography, eluting with a gradient of 5% to 50% DCM in pentane to give the title compound (2.6 g, 100%) as a colorless oil. ES/MS (m/z) 219 (M+H).

Preparation 18

2-[2-(3,3-Dimethylcyclobutyl)-1,3-dioxolan-2-yl]acetonitrile

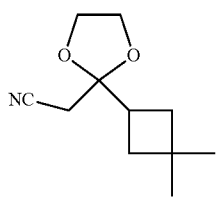

To a stirred solution of 3-(3,3-dimethylcyclobutyl)-3-oxo-propanenitrile (0.60 g, 4.00 mmol) in DCM (8 mL) at 25° C. under $N_2$ is added ethane-1,2-diol (0.67 mL, 12.0 mmol) and chloro(trimethyl)silane (1.5 mL, 12.0 mmol). The reaction mixture is stirred at reflux for 12 hr and cooled to RT. $NaHCO_3$ (aq) is added. The aqueous layer is extracted with DCM. The combined organic extract is washed with brine, dried over $Na_2SO_4$, filtered, and dried under vacuum. The residue is purified by silica gel chromatography, eluting with a gradient of 10% to 30% EtOAc in cyclohexane to give the title compound (0.56 g, 72%) as a colorless oil. $^1$H NMR ($d_6$-DMSO, 400 MHz) δ (ppm) 4.09-3.98 (m, 2H), 4.01-3.90 (m, 2H), 2.79 (s, 2H), 2.61 (s, 2H), 1.79-1.57 (m, 6H), 1.41 (s, 2H), 1.12 (s, 3H), 1.01 (s, 3H).

Preparation 19

4-(1-Methylcyclopropyl)-3-oxo-butanenitrile

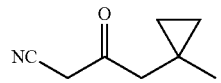

ACN (0.36 mL, 6.89 mmol) and benzyl 2-(1-methylcyclopropyl)acetate (1.27 g, 6.22 mmol) are combined in THF (15 mL) under $N_2$ and cooled to −78° C. LDA (11.0 mL, 22.0 mmol, 2 M in THF) is added dropwise and the reaction is stirred for 10 min at −78° C. The reaction is allowed to warm to 21° C. over 1 hr. The reaction is acidified to pH 1 with conc. HCl and the mixture is extracted with EtOAc (3×100 mL). The combined organic extracts are dried over $Na_2SO_4$, filtered, and concentrated to give the title compound (1.4 g, crude) as an orange oil. The material is used without further purification.

Preparation 20

3-Oxo-3-[2-(trifluoromethyl)spiro[3.3]heptan-2-yl]propanenitrile

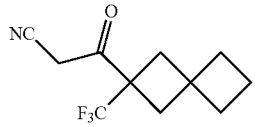 [SMILES: N#CCC(=O)C1(C(F)(F)F)CC2(CCC2)C1]

ACN (0.28 mL, 5.36 mmol) and benzyl 2-(trifluoromethyl)spiro[3.3]heptane-2-carboxylate (1.40 g, 4.69 mmol) are combined in THF (15 mL) under $N_2$ and cooled to −78° C. LDA (2.82 mL, 5.64 mmol, 2 M in THF) is added dropwise and the reaction is stirred for 10 mins at −78° C. The reaction is allowed to warm to 21° C. over 1 hr. The reaction is acidified to pH 1 with conc. HCl and the mixture is extracted with EtOAc (3×100 mL). The combined organic extracts are dried over $Na_2SO_4$, filtered, and concentrated to give the title compound (1.05 g, 97%) as an orange oil. This material is used directly without further purification.

The following compounds in Table 3 are prepared essentially as described for 3-oxo-3-[2-(trifluoromethyl)spiro [3.3]heptan-2-yl]propanenitrile using the appropriate base (LDA or nBuLi in hexanes or THF) from 1.2-4.2 equivalents and adjusting reaction time to determine completion of the reaction.

TABLE 3

| Prep. No. | Chemical Name | Structure |
|---|---|---|
| 21 | 3-Oxo-4-[1-(trifluoromethyl)cyclopropyl]butanenitrile | 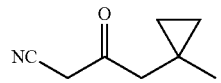 |

TABLE 3-continued

| Prep. No. | Chemical Name | Structure |
|---|---|---|
| 22 | 3-Oxo-3-(4-(trifluoromethyl)bicyclo[2.2.1]heptan-1-yl)propanenitrile | 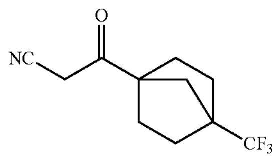 [SMILES: N#CCC(=O)C12CCC(C(F)(F)F)(CC1)C2] |
| [1]23 | 3-(4-Fluorobicyclo[2.2.2]octan-1-yl)-3-oxopropanenitrile | 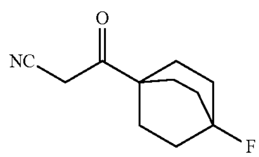 [SMILES: N#CCC(=O)C12CCC(F)(CC1)CC2] |
| 24 | 3-(2,2-Difluorospiro[3.3]heptan-6-yl)-3-oxo-propanenitrile | 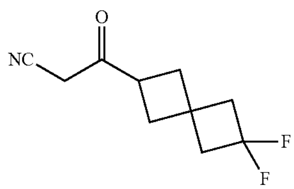 [SMILES: N#CCC(=O)C1CC2(C1)CC(F)(F)C2] |

[1]nBuLi used instead of LDA.

Preparation 25

3-[3-Methylbicyclo[1.1.1]pentan-1-yl]-3-oxopropanenitrile

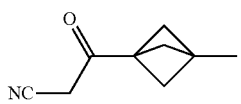

To THF (5 mL) is added n-BuLi (1.71 mL, 4.28 mmol, 2.5 M in THF) at 0° C. under $N_2$. To the mixture is added ACN (0.24 mL, 4.59 mmol) in THF (5 mL) dropwise over 5 min at −78° C. under $N_2$. The mixture is stirred for 1 hr at −78° C. To the mixture is added methyl 3-methylbicyclo[1.1.1]pentane-1-carboxylate (0.40 g, 2.85 mmol) in THF (5 mL) dropwise at −78° C. under $N_2$. The mixture is stirred for 1 hr at RT. The reaction is quenched by the addition of saturated aq. $NH_4Cl$ (20 mL) at 0° C. The mixture is acidified to pH 4 with 1N aq. HCl and extracted with DCM (3×50 mL). The combined organic extracts are washed with brine (2×100 mL), dried over anhydrous $Na_2SO_4$, filtered, and concentrated under reduced pressure to give the title compound (0.36 g, 85%) as a brown liquid. The crude product is used without further purification.

Preparation 26

3-(3-Fluorobicyclo[1.1.1]pentan-1-yl)-3-oxopropanenitrile

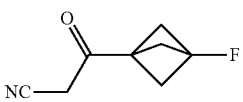 [SMILES: N#CCC(=O)C12CC(F)(C1)C2]

To a stirred solution of n-BuLi (2.0 mL, 2.5 M in n-hexanes, 5.00 mmol) in THF (20 mL) is added a solution of ACN (0.28 mL, 5.36 mmol) in THF (4 mL) dropwise at −78° C. under $N_2$. The mixture is stirred for 30 min at −78° C. To the mixture is added a solution of methyl 3-fluorobicyclo[1.1.1]pentane-1-carboxylate (0.48 g, 3.33 mmol) in THF (4 mL) dropwise over 10 min at −78° C. The mixture is allowed to warm to RT and stirred for an additional 3 hr. The reaction is quenched with saturated aq. $NH_4Cl$, acidified to pH 4 with 2 N aq. HCl, and extracted with DCM (3×50 mL). The combined organic extracts are washed with brine (100 mL), dried over anhydrous $Na_2SO_4$, filtered, and concentrated under reduced pressure to give the title compound (0.50 g, crude) as a brown oil. The crude product is used without further purification. $^1$H NMR (CDCl$_3$, 300 MHz) δ 3.57 (s, 2H), 2.50 (d, 6H).

Preparation 27

3-Oxo-3-[3-(trifluoromethyl)bicyclo[1.1.1]pentan-1-yl]propanenitrile

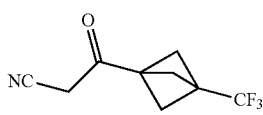 [SMILES: N#CCC(=O)C12CC(C(F)(F)F)(C1)C2]

n-BuLi (0.83 mL, 2.08 mmol, 2.5 M in hexanes) is added to THF (10 mL) at 0° C. under $N_2$. ACN (0.12 mL, 2.30 mmol) in THF (2 mL) is added dropwise over 2 min at −78° C. under $N_2$ and the reaction is stirred for 1 hr at −78° C. Methyl 3-(trifluoromethyl)bicyclo[1.1.1]pentane-1-carboxylate (0.27 g, 1.39 mmol) in THF (2 mL) is added dropwise to the reaction mixture at −78° C. and the reaction is stirred at RT for 12 hr. The reaction is quenched by the addition of saturated aq. $NH_4Cl$ (20 mL), acidified to pH 4 with conc. HCl, and extracted with DCM (3×50 mL). The combined organic extracts are washed with brine, dried over anhydrous $Na_2SO_4$, filtered, and concentrated under reduced pressure to give the title compound (0.29 g, crude). The crude product is used without further purification. $^1$H NMR (CDCl$_3$, 300 MHz) δ 3.54 (s, 2H), 2.39 (s, 6H).

The following compounds in Table 4 are prepared essentially as described for 3-oxo-3-[3-(trifluoromethyl)bicyclo[1.1.1]pentan-1-yl]propanenitrile, adjusting reaction time to determine completion of the reaction, and purification conditions as appropriate. The reaction can be allowed to warm to RT after the carboxylate is added. n-BuLi can be in hexanes or THF.

TABLE 4

| Prep. No. | Chemical name | Structure |
|---|---|---|
| 28 | 3-(2-Cyanoacetyl)bicyclo[1.1.1]pentane-1-carbonitrile | 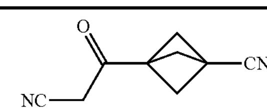 |
| 29 | 3-Oxo-3-[4-(trifluoromethyl)bicyclo[2.2.1]heptan-1-yl]propanenitrile | 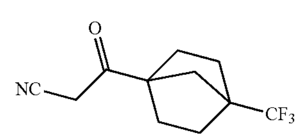 [SMILES: N#CCC(=O)C12CCC(C(F)(F)F)(CC1)C2] |

TABLE 4-continued

| Prep. No. | Chemical name | Structure |
|---|---|---|
| 30 | 3-(3-Chloropyridin-2-yl)-3-oxopropanenitrile | 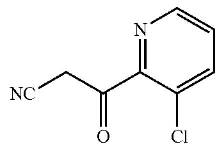 [SMILES: N#CCC(=O)c1ncccc1Cl] |
| 31 | 3-(2,2-Dimethylcyclopropyl)-3-oxo-propanenitrile | 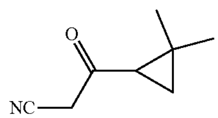 |
| 32 | 4-(1-Methylcyclobutyl)-3-oxo-butanenitrile | 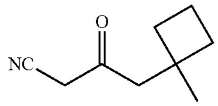 |
| 33 | 3-Oxo-3-spiro[2.2]pentan-2-yl-propanenitrile | 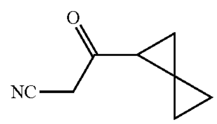 |
| 34 | 4-(2,2-Difluorocyclopropyl)-3-oxo-butanenitrile | 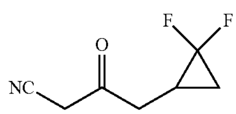 [SMILES: N#CCC(=O)CC1CC1(F)F] |
| 35 | 3-Oxo-3-spiro[2.3]hexan-2-yl-propanenitrile | 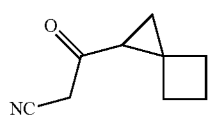 [SMILES: N#CCC(=O)C1CC12CCC2] |
| 36 | 3-(2,2-Dimethylcyclobutyl)-3-oxo-propanenitrile | 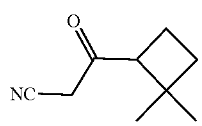 |
| 37 | 3-(3,3-Difluoro-1-methyl-cyclobutyl)-3-oxo-propanenitrile | 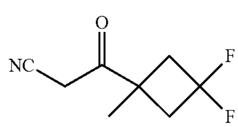 |
| 38 | 4,4-Difluoro-5,5-dimethyl-3-oxo-hexanenitrile | 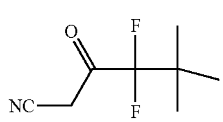 |

Preparation 39

5-(2,5-Dimethyl-1H-pyrrol-1-yl)-3-(1,1,1-trifluoro-2-methylpropan-2-yl)-1H-pyrazole

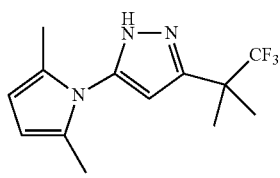 [SMILES: Cc1ccc(C)n1-c1cc(C(C)(C)C(F)(F)F)n[nH]1]

A solution of 3-(1,1,1-trifluoro-2-methylpropan-2-yl)-1H-pyrazol-5-amine (0.50 g, 2.59 mmol), hexane-2,5-dione (0.91 mL, 7.76 mmol) and HOAc (0.015 mL, 0.26 mmol) in toluene (10 mL) is stirred for 2 hr at 100° C. under $N_2$. The mixture is concentrated under reduced pressure. The residue is purified by reversed-phase chromatography (C18 gel column), eluting with a gradient of 30% to 50% ACN in $H_2O$ (0.1% FA) to give the title compound (0.61 g, 87%) as a yellow solid. ES/MS (m/z) 272.1 (M+H).

Preparation 40

3-(2,5-Dimethyl-1H-pyrrol-1-yl)-1-methyl-5-(1,1,1-trifluoro-2-methylpropan-2-yl)-1H-pyrazole

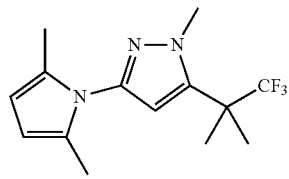 [SMILES: Cc1ccc(C)n1-c1cc(C(C)(C)C(F)(F)F)n(C)n1]

A solution of 5-(2,5-dimethyl-1H-pyrrol-1-yl)-3-(1,1,1-trifluoro-2-methylpropan-2-yl)-1H-pyrazole (0.50 g, 1.84 mmol), MeI (0.46 mL, 7.39 mmol) and $K_2CO_3$ (0.51 g, 3.69 mmol) in ACN (10 mL) is stirred for 4 hr at 80° C. under $N_2$. The mixture is concentrated under reduced pressure. The residue is purified by preparative TLC, eluting with 5:1 PE:EtOAc to give the title compound (95 mg, 18%) as a white solid. ES/MS (m/z) 286.2 (M+H).

Preparation 41

1-Methyl-5-(1,1,1-trifluoro-2-methylpropan-2-yl)-1H-pyrazol-3-amine

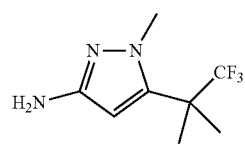

A solution of KOH (53 mg, 0.94 mmol) in EtOH (1 mL) and $H_2O$ (1 mL) is added to a solution of hydroxylamine HCl (0.13 g, 1.87 mmol) in EtOH (2 mL). 3-(2,5-Dimethyl-1H-pyrrol-1-yl)-1-methyl-5-(1,1,1-trifluoro-2-methylpropan-2-yl)-1H-pyrazole (90 mg, 0.32 mmol) is added and the mixture is stirred for 4 hr at 100° C. under $N_2$. The mixture is concentrated under reduced pressure. The residue is purified by reversed-phase chromatography (C18 gel column), eluting with a gradient of 10% to 30% ACN in $H_2O$ (0.1% FA) to give the title compound (45 mg, 68%) as a white solid. ES/MS (m/z) 208.1 (M+H).

Preparation 42

3-[(1-Methylcyclopropyl)methyl]isoxazol-5-amine

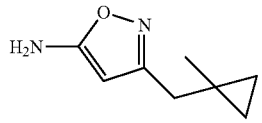

4-(1-Methylcyclopropyl)-3-oxo-butanenitrile (1.40 g, 10.2 mmol) is dissolved in H$_2$O (15 mL). NaOH (0.45 g, 11.3 mmol) is added followed by hydroxylamine sulfate (1.84 g, 11.2 mmol). The pH is adjusted to ~10 with 2 M aq. NaOH (5.0 mL, 10.0 mmol). The mixture is heated to 100° C. for 1.5 hr. Conc. HCl (1 mL) is added and the mixture is stirred for 15 min. The mixture is diluted with H$_2$O (30 mL) and extracted with EtOAc (2×30 mL). The combined organic extracts are dried over anhydrous NH$_2$SO$_4$ and concentrated under reduced pressure. The residue is purified by silica gel chromatography, eluting with a gradient of 10% to 70% EtOAc in hexanes to give the title compound (0.54 g, 35%). ES/MS (m/z) 153.0 (M+H).

Preparation 43

3-(3-Fluorobicyclo[1.1.1]pentan-1-yl)isoxazol-5-amine

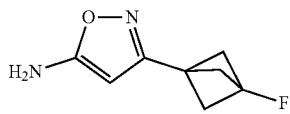

To a stirred solution of 3-(3-fluorobicyclo[1.1.1]pentan-1-yl)-3-oxopropanenitrile (0.50 g, 3.26 mmol) in MeOH (5 mL) is added hydroxylamine HCl (0.68 g, 9.79 mmol) and KOAc (0.96 g, 9.78 mmol) at 0° C. under N$_2$. The mixture is stirred for 5 hr at RT under N$_2$. The mixture is poured into H$_2$O (50 mL) and extracted with DCM (3×50 mL). The combined organic extracts are dried over anhydrous Na$_2$SO$_4$, filtered, and concentrated under reduced pressure. The residue is purified by reversed-phase chromatography (C18 column), eluting with a gradient of 25% to 45% ACN in H$_2$O (0.1% NH$_4$HCO$_3$) to give the title compound (0.22 g, 40%) as a light yellow solid. ES/MS (m/z) 169.1 (M+H).

Preparation 44

3-(Bicyclo[1.1.1]pentan-1-yl)isoxazol-5-amine

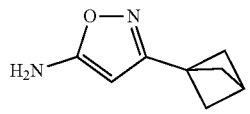

To a stirred solution of 3-(bicyclo[1.1.1]pentan-1-yl)-3-oxopropanenitrile (0.87 g, 6.44 mmol) in MeOH (10 mL) is added hydroxylamine HCl (1.34 g, 19.3 mmol) and KOAc (1.89 g, 19.3 mmol) at 0° C. under N$_2$. The mixture is stirred for 5 hr at RT under N$_2$. The mixture is poured into H$_2$O (50 mL) and extracted with DCM (3×50 mL). The combined organic extracts are dried over anhydrous Na$_2$SO$_4$, filtered, and concentrated under reduced pressure. The residue is washed with hexanes (2×5 mL) to give the title compound (0.73 g, 75%) as a light yellow solid. ES/MS (m/z) 151.3 (M+H).

Preparation 45

3-(3-Methyl-1-bicyclo[1.1.1]pentanyl)isoxazol-5-amine

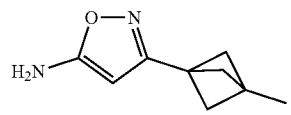

To a stirred mixture of 3-[3-methylbicyclo[1.1.1]pentan-1-yl]-3-oxopropanenitrile (0.35 g, 2.35 mmol) and hydroxylamine HCl (0.18 g, 2.59 mmol) in H$_2$O (8 mL) is added NaOH (0.19 g, 4.75 mmol) in portions at RT under N$_2$. The mixture is stirred for 1 hr at 100° C. under N$_2$. The mixture is allowed to cool to RT. The precipitated solids are collected by filtration and washed with H$_2$O (3×20 mL) to give the title compound (0.30 g, 78%) as a light yellow solid. ES/MS (m/z) 165.1 (M+H).

Preparation 46

3-(3-(Trifluoromethyl)bicyclo[1.1.1]pentan-1-yl)isoxazol-5-amine

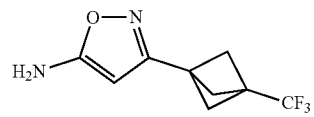

A mixture of 3-oxo-3-[3-(trifluoromethyl)bicyclo[1.1.1]pentan-1-yl]propanenitrile (0.28 g, 1.38 mmol), hydroxylamine HCl (0.11 g, 1.58 mmol) and H$_2$O (10 mL) is added NaOH (0.11 g, 2.75 mmol) in portions at RT under N$_2$. The mixture is heated to 100° C. for 1 hr. The mixture is allowed to cool to RT and is extracted with DCM (3×50 mL). The combined organic extracts are washed with brine, dried over anhydrous Na$_2$SO$_4$, filtered, and concentrated under reduced pressure. The resulting solid is triturated with Et$_2$O (10 mL). The solids are collected by filtration and washed with Et$_2$O to give the title compound (0.22 g, 73%). ES/MS (m/z) 219.2 (M+H).

The following compounds in Table 5 are prepared essentially as described for 3-(3-(trifluoromethyl)bicyclo[1.1.1]pentan-1-yl)isoxazol-5-amine using the appropriate reagents (hydroxylamine sulfate or hydroxylamine HCl) about 1-6 equivalents, bases (NaOH, NaOAc, or KOAc) about 1-6 equivalents in the appropriate solvent (EtOH, MeOH, H$_2$O, or 1,4-dioxane), adjusting the reaction time to determine completion of the reaction and using appropriate chromatography conditions or precipitation for purification. The reaction temperature can range from 0 to 100° C. and the reaction mixture can be acidified in work-up if appropriate. The reagents can be added together at 0° C. in portions or all at once.

TABLE 5

| Prep No. | Chemical Name | Structure | ES/MS m/z (M + H) |
|---|---|---|---|
| 47 | 3-Spiro[3.3]heptan-2-ylisoxazol-5-amine | 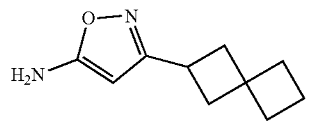 [SMILES: Nc1cc(C2CC3(CCC3)C2)no1] | 179.1 |
| 48 | 3-[2-(Trifluoromethyl)spiro[3.3]heptan-2-yl]isoxazol-5-amine | 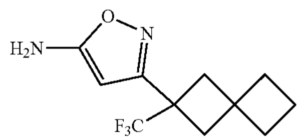 [SMILES: Nc1cc(C2(C(F)(F)F)CC3(CCC3)C2)no1] | 247.1 |
| 49 | 3-[[1-(Trifluoromethyl)cyclopropyl]methyl]isoxazol-5-amine | 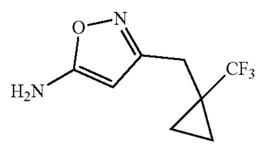 [SMILES: Nc1cc(CC2(C(F)(F)F)CC2)no1] | 207.1 |
| 50 | 3-(4-(Trifluoromethyl)bicyclo[2.2.1]heptan-1-yl)isoxazol-5-amine | 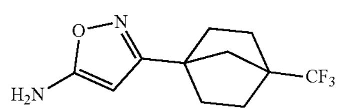 [SMILES: Nc1cc(C23CCC(C(F)(F)F)(CC2)C3)no1] | 247.1 |
| 51 | 3-(3,3,3-Trifluoro-2,2-dimethyl-propyl)isoxazol-5-amine | 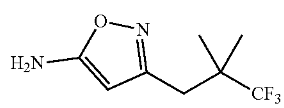 | 209.0 |
| 52 | 3-(3,3-Dimethylcyclobutyl)isoxazol-5-amine | 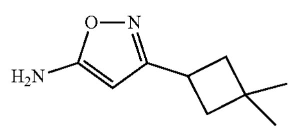 | 167.1 |
| 53 | 3-(4-Fluorobicyclo[2.2.2]octan-1-yl)isoxazol-5-amine | 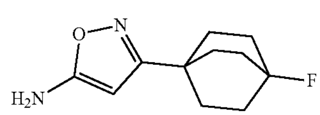 [SMILES: Nc1cc(C23CCC(F)(CC2)CC3)no1] | 211.2 |
| 54 | 3-(2,2-Difluorospiro[3.3]heptan-6-yl)isoxazol-5-amine | 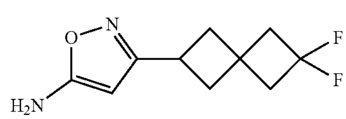 [SMILES: Nc1cc(C2CC3(C2)CC(F)(F)C3)no1] | 215.1 |
| 55 | 3-(3,3-Difluorocyclobutyl)isoxazol-5-amine | 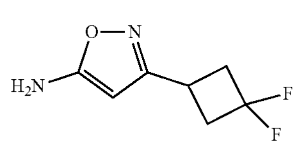 [SMILES: Nc1cc(C2CC(F)(F)C2)no1] | 175.1 |
| 56 | 3-Spiro[2.3]hexan-5-ylisoxazole-5-amine | 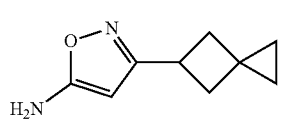 [SMILES: Nc1cc(C2CC3(CC3)C2)no1] | 165.1 |
| 57 | 3-(3-Bicyclo[1.1.1]pentanylmethyl)isoxazol-5-amine | 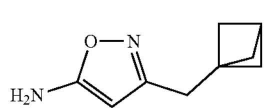 [SMILES: Nc1cc(CC23CC(C2)C3)no1] | 165.1 |

TABLE 5-continued

| Prep No. | Chemical Name | Structure | ES/MS m/z (M + H) |
|---|---|---|---|
| 58 | 3-(3,5-Dichloropyridin-2-yl)-1,2-oxazol-5-amine | 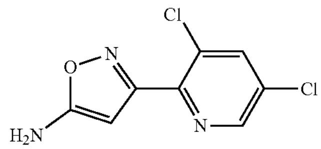 [SMILES: Nc1cc(-c2ncc(Cl)cc2Cl)no1] | 230 |
| 59 | 3-(3-Chloropyridin-2-yl)isoxazol-5-amine | 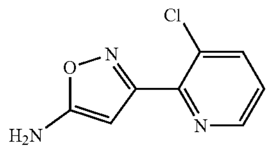 [SMILES: Nc1cc(-c2ncccc2Cl)no1] | 195.0 |
| 60 | 3-(4-Methylpyridin-3-yl)-1,2-oxazol-5-amine | 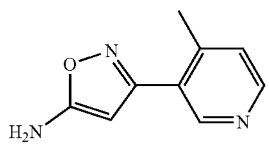 | 176.1 |
| 61 | 3-(2-Methylpyridin-3-yl)-1,2-oxazol-5-amine[1] | | |
| 62 | 3-(2,2-Dimethylcyclopropyl)isoxazol-5-amine | 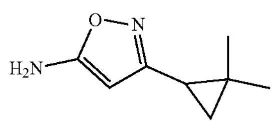 | 152 |
| 63 | 3-Spiro[2.2]pentan-2-ylisoxazol-5-amine | 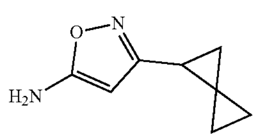 [SMILES: Nc1cc(C2CC23CC3)no1] | 151 |
| 64 | 3-[(2,2-Difluorocyclopropyl)methyl]isoxazol-5-amine | 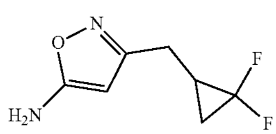 [SMILES: Nc1cc(CC2CC2(F)F)no1] | 175 |
| 65 | 3-Spiro[2.3]hexan-2-ylisoxazol-5-amine | 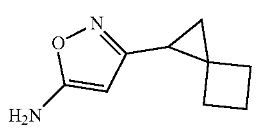 | 165.3 |
| 66 | 5-Spiro[2.3]hexan-2-ylisoxazol-3-amine | 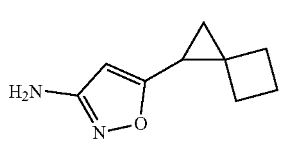 [SMILES: Nc1cc(C2CC23CCC3)on1] | 165.3 |
| 67 | 3-(2,2-Dimethylcyclobutyl)isoxazol-5-amine | 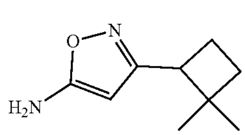 | 167 |
| 68 | 5-(2,2-Dimethylcyclobutyl)isoxazol-3-amine | 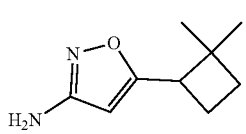 | 167 |

TABLE 5-continued

| Prep No. | Chemical Name | Structure | ES/MS m/z (M + H) |
|---|---|---|---|
| ²69 | 3-[(1-Methylcyclobutyl)methyl]isoxazol-5-amine | | 166 |
| ²70 | 3-(3,3-Difluoro-1-methyl-cyclobutyl)isoxazol-5-amine | | 189 |
| ²71 | 3-(1,1-Difluoro-2,2-dimethyl-propyl)isoxazol-5-amine | | 191 |
| 72 | 3-(5-Amino-1,2-oxazol-3-yl)bicyclo[1.1.1]pentane-1-carbonitrile | | 176.3 |
| 73 | 3-[4-(Trifluoromethyl)bicyclo[2.2.1]heptan-1-yl]-1,2-oxazol-5-amine | | 247.2 |

¹No base is used and after work-up, the product is used without further purification,
²After heating for 2 hr at 70-100° C., c HCl (0.9 equiv) is added and the mixture is heated at 60-100° C. for 30 min-24 hr.
The mixture is cooled to 0° C. and the pH adjusted to 9-11 with 30% aq NaOH or NaHCO₃ and worked up as above.

Preparation 74

3-(3,3-dimethylcyclobutyl)-4-fluoro-isoxazol-5-amine

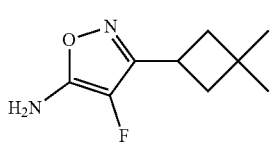

To 1-(chloromethyl)-4-fluoro-1,4-diazoniabicyclo[2.2.2]octane; ditetrafluoroborate (0.46 g, 1.30 mmol) and 3-(3,3-dimethylcyclobutyl)isoxazol-5-amine (0.20 g, 1.20 mmol) in a sealed vial is added ACN (12 mL). The mixture is irradiated at 100° C. for 20 min under microwave conditions. The reaction is cooled to RT and concentrated under reduced pressure. The crude material is purified by reversed-phase chromatography (C18Aq column), eluting with a gradient of 0% to 100% ACN in H₂O (0.1% HOAc). The desired fractions are combined and concentrated to remove ACN. To the remaining aqueous solution is added saturated aq. NaHCO₃ until a pH of 9 is reached. The mixture is extracted with DCM (2×10 mL). The organic extracts are combined, dried over anhydrous Na₂SO₄, diatomaceous earth is added, and the mixture is concentrated under vacuum. The material is further purified by silica gel chromatography, eluting with a gradient of 5% to 40% EtOAc in cyclohexane to give the title compound (48 mg, 22%). ES/MS (m/z) 185.3 (M+H).

The following compounds in Table 6 are prepared essentially as described for 3-(3,3-dimethylcyclobutyl)-4-fluoro-isoxazol-5-amine using the appropriate adjusting reaction time to determine completion of the reaction, and purification conditions as appropriate.

TABLE 6

| Prep No. | Chemical name | Structure | ES/MS m/z (M + H) |
|---|---|---|---|
| 75 | 3-(2,2-Dimethylpropyl)-4-fluoro-isoxazol-5-amine | 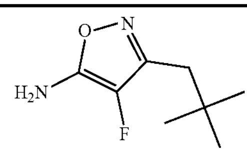 | 173.3 |
| 76 | 4-Fluoro-3-(3-methyl-1-bicyclo[1.1.1]pentanyl)isoxazol-5-amine | 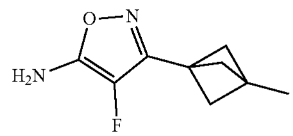 | 183 |

Preparation 77

5-(2-Methylbutan-2-yl)-1,2-oxazol-3-amine

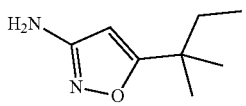

To a stirred mixture of 4,4-dimethyl-3-oxohexanenitrile (3.00 g, 21.6 mmol) and hydroxylamine sulfate (3.89 g, 23.7 mmol) in MeOH (5 mL) and H$_2$O (45 mL) is added NaHCO$_3$ (4.53 g, 53.9 mmol) in portions at RT under N$_2$. The mixture is stirred for 5 hr at 65° C. under N$_2$. The mixture is allowed to cool to RT. The mixture is acidified to pH 1 with conc. HCl and stirred for 20 min at reflux under N$_2$. The mixture is allowed to cool to RT and the pH adjusted to 8 with NaOH. The mixture is extracted with DCM (3×200 mL). The combined organic extracts are washed with brine (2×200 mL), dried over anhydrous Na$_2$SO$_4$, filtered, and concentrated under reduced pressure. The residue is purified by reversed-phase chromatography (C18 column), eluting with a gradient of 30% to 40% ACN in H$_2$O (0.1% NH$_4$HCO$_3$), to give the title compound (1.20 g, 36%) as a light yellow solid. $^1$H NMR (CDCl$_3$) δ 5.53 (s, 1H), 1.66 (q, 2H), 1.27 (s, 6H), 0.82 (t, 3H).

Preparation 78

5-(3,3-Dimethylcyclobutyl)isoxazol-3-amine

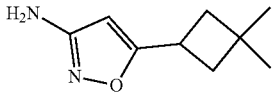

To a sealed vial is added hydroxylamine HCl (0.79 g, 11.4 mmol) in MeOH (0.5 mL) and 7 M NH$_3$ in MeOH (2.0 mL, 14.0 mmol). The suspension is stirred at 25° C. for 30 min. A solution of 2-[2-(3,3-dimethylcyclobutyl)-1,3-dioxolan-2-yl]acetonitrile (0.56 g, 2.87 mmol) in MeOH (0.5 mL) and quinolin-8-ol (42 mg, 0.29 mmol) are added and the mixture is stirred at 65° C. for 12 hr and cooled to RT. The mixture is filtered, the filtrate is concentrated under reduced pressure, and re-concentrated from toluene (3×) to give the intermediate 2-[2-(3,3-dimethylcyclobutyl)-1,3-dioxolan-2-yl]-N'-hydroxy-acetamidine as a yellow solid which is used without further purification. In a sealed vial, 2-[2-(3,3-dimethylcyclobutyl)-1,3-dioxolan-2-yl]-N'-hydroxy-acetamidine is dissolved in EtOH (2 mL) and acidified to pH 1 with conc. HCl. The reaction mixture is stirred at 80° C. for 12 hr. The mixture is concentrated under reduced pressure and the residue is diluted with DCM. Saturated aq. NaHCO$_3$ is added until the solution is basic (pH 11). The organic layer is separated and the aqueous phase is extracted with DCM. The combined organic extracts are washed with brine, dried over Na$_2$SO$_4$, filtered, and concentrated under reduced pressure. The crude material is purified by silica gel chromatography, eluting with a gradient of 0% to 5% MeOH in DCM to give the title compound as a yellow solid (30 mg, 6.3%). ES/MS (m/z) 167 (M+H).

Preparation 79

Methyl 2-[2-methoxy-4-(4,4,5,5-tetramethyl-1,3,2-dioxaborolan-2-yl)phenyl]acetate

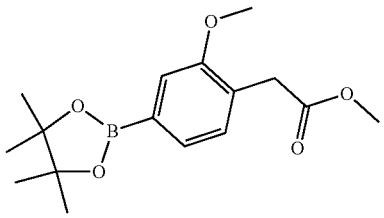

Methyl 2-(4-bromo-2-methoxy-phenyl)acetate (0.15 g, 0.579 mmol), bis(pinacolato)diboron (0.18 g, 0.709 mmol), KOAc (95%, 0.18 g, 1.74 mmol), Pd(dppf)Cl$_2$CH$_2$Cl$_2$) (95%. 22 mg, 0.029 mmol) and 1,4-dioxane (2.7 mL) are added together. The reaction mixture is stirred at 80° C. overnight. The reaction is quenched with H$_2$O and DCM is added. The two layers are separated and the aqueous phase is extracted with DCM (3×10 mL). The combined organic extracts are dried over Na$_2$SO$_4$, filtered, and concentrated under vacuum to give the title compound as a brown oil which is used crude without further purification. ES/MS (m/z) 307.2 (M+H).

The following compound in Table 7 is prepared essentially as described for methyl 2-[2-methoxy-4-(4,4,5,5-tetramethyl-1,3,2-dioxaborolan-2-yl)phenyl]acetate using the appropriate reagents, adjusting reaction time to determine completion of the reaction and purifying by chromatography as appropriate. The reaction temperature can range from about 80-100° C., filtered through talcum powder, and purified as appropriate.

TABLE 7

| Prep No. | Chemical Name | Structure | ES/MS m/z (M + H) |
|---|---|---|---|
| 80 | Methyl 2-[2,6-difluoro-4-(4,4,5,5-tetramethyl-1,3,2-dioxaborolan-2-yl)phenyl]acetate | 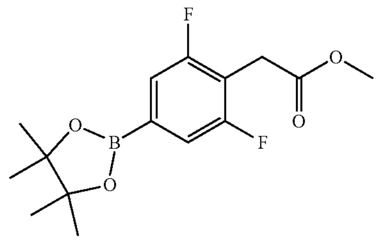 | 313 |

Preparation 81

Methyl 2-[4-(5-amino-4-cyano-1-isopropylpyrazol-3-yl)-3-chlorophenyl]acetate

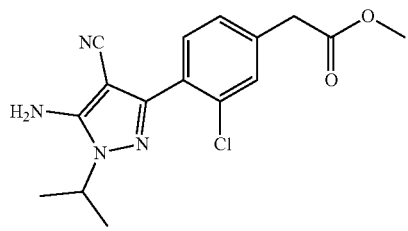 [SMILES: COC(=O)Cc1ccc(-c2nn(C(C)C)c(N)c2C#N)c(Cl)c1]

A solution of methyl 2-(3-chloro-4-(4,4,5,5-tetramethyl-1,3,2-dioxaborolan-2-yl)phenyl)acetate (1.00 g, 3.22 mmol), 5-amino-3-bromo-1-isopropylpyrazole-4-carbonitrile (0.73 g, 3.22 mmol), Pd(dppf)Cl$_2$ (0.47 g, 0.64 mmol), and K$_3$PO$_4$ (2.05 g, 9.66 mmol) in 1,4-dioxane:H$_2$O (12 mL, 5:1) is stirred for 2 hr at 120° C. under N$_2$ and cooled to RT. The solution is filtered through diatomaceous earth and washed with EtOAc (200 mL), filtered, and concentrated under reduced pressure. The residue is purified by reversed-phase chromatography (C18 column), eluting with a gradient of 10% to 50% ACN in H$_2$O, to give the title compound (0.30 g, 28%) as a white solid. ES/MS (m/z) 333.1 (M+H).

The following compound in Table 8 is prepared essentially as described for methyl 2-[4-(5-amino-4-cyano-1-isopropylpyrazol-3-yl)-3-chlorophenyl]acetate, adjusting reaction time to determine completion of the reaction and purifying by titration or chromatography as appropriate. The reaction temperature can range from RT to 120° C.

TABLE 8

| Prep No. | Chemical Name | Structure | ES/MS m/z (M + H) |
|---|---|---|---|
| 82 | Ethyl 2-[4-(5-amino-4-cyano-1-isopropyl-pyrazol-3-yl)-2-fluoro-phenyl]acetate | 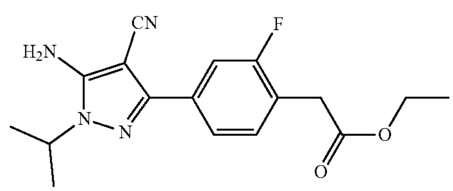 [SMILES: CCOC(=O)Cc1ccc(-c2nn(C(C)C)c(N)c2C#N)cc1F] | 331.1 |

Preparation 83

Methyl 2-[4-(5-amino-4-cyano-1-isopropylpyrazol-3-yl)-2,3-difluorophenyl]acetate

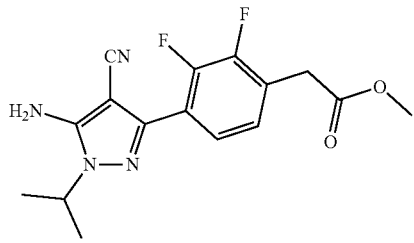 [SMILES: COC(=O)Cc1ccc(-c2nn(C(C)C)c(N)c2C#N)c(F)c1F]

To a stirred mixture of methyl 2-(4-bromo-2,3-difluorophenyl)acetate (5.00 g, 18.9 mmol) and bis(pinacolato)diboron (5.75 g, 22.6 mmol) in 1,4-dioxane (30 mL) is added KOAc (3.70 g, 37.7 mmol) and Pd(dppf)Cl$_2$·CH$_2$Cl$_2$ (1.54 g, 1.88 mmol) at RT. The mixture is stirred for 1 hr at 80° C. under N$_2$, filtered, and the filter cake is washed with 1,4-dioxane (5 mL). To the filtrate is added 5-amino-3-bromo-1-isopropylpyrazole-4-carbonitrile (4.75 g, 20.7 mmol), Pd(dppf)Cl$_2$·CH$_2$Cl$_2$ (1.54 g, 1.88 mmol), K$_2$CO$_3$ (5.21 g, 37.7 mmol) and H$_2$O (7 mL) at RT. The mixture is stirred for 1 hr at 80° C. The mixture is allowed to cool to RT and the residue is purified by silica gel chromatography, eluting with 3:1 to 2:1 PE:EtOAc to give the title compound (4.90 g, 78%) as a yellow solid. ES/MS (m/z) 335.1 (M+H).

Preparation 84

Benzyl 2-fluoro-4-(2-methoxy-2-oxoethyl)benzoate

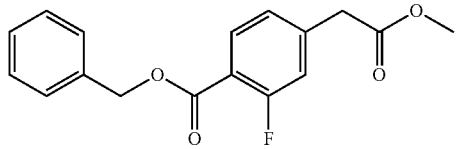 [SMILES: COC(=O)Cc1ccc(C(=O)OCc2ccccc2)c(F)c1]

To a solution of methyl 2-(4-bromo-3-fluorophenyl)acetate (5.45 g, 22.1 mmol), TEA (9.2 mL, 66.0 mmol) and benzyl alcohol (2.5 mL, 24.0 mmol) in toluene (150 mL) is added Pd(dppf)Cl$_2$ (0.32 g, 0.44 mmol) in a pressure tank. The mixture is purged with N$_2$ for 1 min and then is pressurized to 30 atm with CO. The mixture is stirred for 24 hr at 115° C. under a CO atmosphere. The mixture is allowed to cool to RT, filtered, and the filter cake is washed with EtOAc (2×50 mL). The filtrate is concentrated under reduced pressure and the residue is purified by silica gel chromatography, eluting with a gradient of 10:1 to 3:1 PE:EtOAc to give the title compound (2.63 g, 39%) as a colorless oil. ES/MS (m/z) 320.05 (M+NH$_3$+H).

Preparation 85

2-Fluoro-4-(2-methoxy-2-oxoethyl)benzoic acid

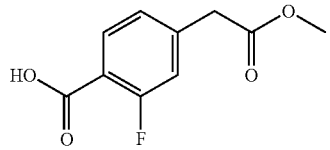

To a solution of benzyl 2-fluoro-4-(2-methoxy-2-oxoethyl)benzoate (2.63 g, 8.70 mmol) in MeOH (25 mL) is added Pd/C (10%, 0.90 g, 0.85 mmol) at RT under N$_2$. The mixture is stirred for 2 hr at RT under H$_2$. The mixture is filtered, the filter cake is washed with MeOH (2×10 mL), and the filtrate is concentrated under reduced pressure to give the title compound (1.51 g, 82%) as a white solid which is used without further purification.

Preparation 86

Methyl 2-[4-(2,2-dicyano-1-methoxyeth-1-en-1-yl)phenyl]acetate

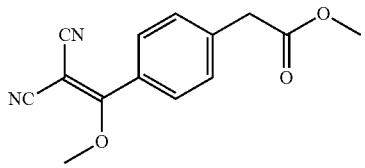 [SMILES: COC(=O)Cc1ccc(C(OC)=C(C#N)C#N)cc1]

To a stirred solution of 4-(2-methoxy-2-oxoethyl)benzoic acid (40.0 g, 206 mmol) and a few drops of DMF in DCM (300 mL) is added oxalyl chloride (21.2 mL, 247 mmol) dropwise at 0° C. The mixture is stirred for 2 hr at RT. The mixture is concentrated under reduced pressure to give the intermediate methyl 2-(4-(chlorocarbonyl)phenyl)acetate. In another vessel, a solution of malononitrile (13.6 g, 206 mmol) in THF (100 mL) is added dropwise to a stirred suspension of NaH (16.5 g, 412 mmol, 60% in mineral oil) in THF (100 mL) at 0-10° C. under N$_2$. The mixture is stirred for 20 min at RT. To this mixture is added methyl 2-(4-(chlorocarbonyl)phenyl)acetate in THF (200 mL) dropwise at 0-10° C. The mixture is stirred for 1 hr at RT. Dimethyl sulfate (23.4 mL, 247 mmol) is added and the mixture is refluxed overnight at 80° C. under N$_2$. H$_2$O (300 mL) is added and the mixture is extracted with EtOAc (3×200 mL). The combined organic extracts are washed with brine, dried over Na$_2$SO$_4$, filtered, and concentrated under reduced pressure. The residue is purified by silica gel chromatography, eluting with a gradient of 4:1 to 1:1 PE:EtOAc to give the title compound (42.0 g, 80%) as a yellow solid. $^1$H NMR (CDCl$_3$, 400 MHz) δ 7.51-7.40 (m, 4H), 3.96 (s, 3H), 3.75 (s, 3H), 3.74 (s, 2H).

Preparation 87

Methyl 2-[4-(5-amino-4-cyano-1-isopropylpyrazol-3-yl)phenyl]acetate

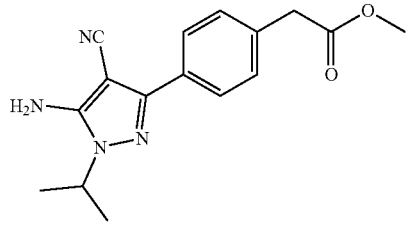 [SMILES: COC(=O)Cc1ccc(-c2nn(C(C)C)c(N)c2C#N)cc1]

A solution of methyl 2-[4-(2,2-dicyano-1-methoxyeth-1-en-1-yl)phenyl]acetate (2.50 g, 9.76 mmol) and isopropylhydrazine HCl (1.29 g, 11.7 mmol) and TEA (4.1 mL, 29.4 mmol) in EtOH (40 mL) is stirred for 1 hr at RT under $N_2$. The mixture is concentrated under reduced pressure and extracted with EtOAc (3×100 mL). The combined organic extracts are washed with brine (2×100 mL), dried over anhydrous $Na_2SO_4$, filtered, and concentrated under reduced pressure. The residue is purified by trituration with $Et_2O$ (50 mL) to give the title compound (2.00 g, 69%) as a yellow solid. ES/MS (m/z) 299.0 (M+H).

Preparation 88

Methyl 2-[4-(5-amino-4-carbamoyl-1-isopropyl-pyrazol-3-yl)-2-methoxy-phenyl]acetate

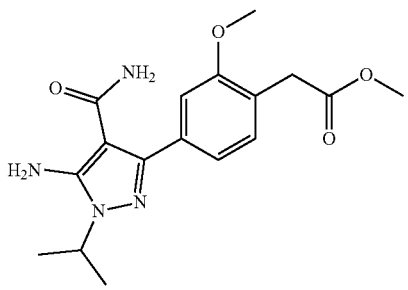 [SMILES: COC(=O)Cc1ccc(-c2nn(C(C)C)c(N)c2C(N)=O)cc1OC]

Methyl 2-[2-methoxy-4-(4,4,5,5-tetramethyl-1,3,2-dioxaborolan-2-yl)phenyl]acetate (67%, 0.21 g, 0.460 mmol), 5-amino-3-bromo-1-isopropyl-pyrazole-4-carboxamide (0.14 g, 0.567 mmol), $K_2CO_3$ (0.13 g, 0.941 mmol) and Pd(dppf)$Cl_2$·$CH_2Cl_2$ (19 mg, 0.0231 mmol) are added together in a mixture of 1,4-dioxane (3.7 mL) and $H_2O$ (0.73 mL). The reaction is heated at 140° C. for 1 hr under microwave irradiation. The reaction mixture is filtered through diatomaceous earth, washed with EtOAc, and evaporated to dryness. The crude material is purified by silica gel chromatography, eluting with a gradient of 0% to 8% MeOH in DCM to give the title compound (0.17 g, quantitative yield). ES/MS (m/z) 347.2 (M+H).

The following compound in Table 9 is prepared essentially as described for methyl 2-[4-(5-amino-4-carbamoyl-1-isopropyl-pyrazol-3-yl)-2-methoxy-phenyl]acetate adjusting the reaction time to determine completion of the reaction and purification as appropriate.

TABLE 9

| Prep. No. | Chemical name | Structure | ES/MS m/z (M + H) |
|---|---|---|---|
| 89 | Methyl 2-[4-(5-amino-4-carbamoyl-1-isopropyl-pyrazol-3-yl)-2,6-difluoro-phenyl]acetate | 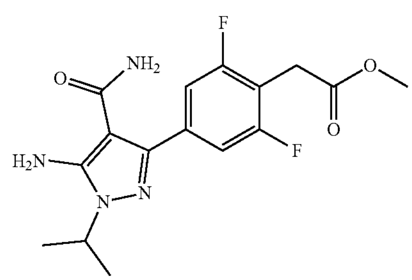 [SMILES: COC(=O)Cc1c(F)cc(-c2nn(C(C)C)c(N)c2C(N)=O)cc1F] | 353 |

Preparation 90 tert-Butyl N-tert-butoxycarbonyl-N-(4-cyano-2-isopropyl-pyrazol-3-yl)carbamate

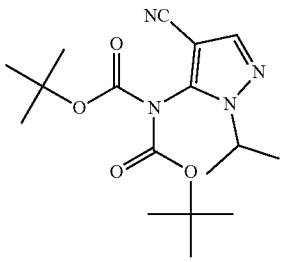 [SMILES: CC(C)n1ncc(C#N)c1N(C(=O)OC(C)(C)C)C(=O)OC(C)(C)C]

Preparation 91 tert-Butyl N-(4-cyano-2-isopropyl-pyrazol-3-yl)carbamate

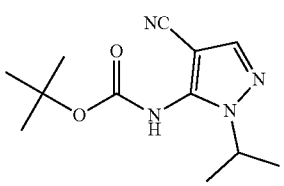 [SMILES: CC(C)n1ncc(C#N)c1NC(=O)OC(C)(C)C]

To a stirred solution of 5-amino-1-isopropyl-pyrazole-4-carbonitrile (4.80 g, 32.0 mmol) in THF (205 mL) is added successively N,N-dimethylpyridin-4-amine (0.38 g, 3.11 mmol), TEA (13 mL, 93.3 mmol) and tert-butoxycarbonyl tert-butyl carbonate (14.7 g, 67.4 mmol). The reaction mixture is stirred at RT overnight. The reaction mixture is quenched with saturated aq. NH$_4$Cl (15 mL) and extracted with EtOAc (3×20 mL). The combined organic extracts are washed with brine, dried over Na$_2$SO$_4$, filtered, and concentrated under reduced pressure. The residue is purified by silica gel chromatography, eluting with a gradient of 2% to 30% EtOAc in cyclohexane to give tert-butyl N-tert-butoxycarbonyl-N-(4-cyano-2-isopropyl-pyrazol-3-yl)carbamate as an off white solid (7.67 g, 68%), ES/MS (m/z) 373 (M+Na) and tert-butyl N-(4-cyano-2-isopropyl-pyrazol-3-yl)carbamate as an off-white solid (1.12 g, 14%), ES/MS (m/z) 251 (M+H).

Preparation 92

Methyl 2-[4-[5-(tert-butoxycarbonylamino)-4-cyano-1-isopropyl-pyrazol-3-yl]-2,3-difluoro-phenyl]acetate

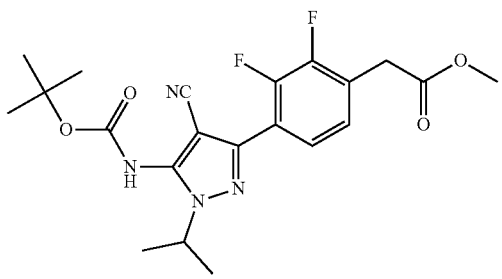 [SMILES: COC(=O)Cc1ccc(-c2nn(C(C)C)c(NC(=O)OC(C)(C)C)c2C#N)c(F)c1F]

THF (4.8 mL) is added to tert-butyl N-tert-butoxycarbonyl-N-(4-cyano-2-isopropyl-pyrazol-3-yl)carbamate (0.79 g, 2.25 mmol), bis(pinacolato)diboron (0.46 g, 1.81 mmol), [Ir(OMe)(1,5-cod)]2 (31 mg, 0.047 mmol) and 4-tert-butyl-2-(4-tert-butyl-2-pyridyl)pyridine (26 mg, 0.093 mmol) under N$_2$. The mixture is stirred at reflux for 4 hr. The reaction mixture is cooled to RT and concentrated under reduced pressure. The residue is dissolved in a mixture of 4:1 DCM:EtOAc (20 mL) and this solution is passed through a pad of silica gel (2 g). The pad is washed with 3:1 DCM:EtOAc (2×10 mL). The filtrates are combined, concentrated under reduced pressure, and dried under vacuum to give a crude residue. To the residue under N$_2$ is added Cs$_2$CO$_3$ (2.14 g, 6.57 mmol) and methyl 2-(4-bromo-2,3-difluoro-phenyl)acetate (0.50 g, 1.89 mmol) in 1,4-dioxane (10 mL). Pd(dppf)Cl$_2$·CH$_2$Cl$_2$ (0.10 g, 0.123 mmol) and 4 Å molecular sieves are then added under Ar. The mixture is heated to 90° C. overnight. The mixture is cooled to RT, diluted with EtOAc, and filtered through diatomaceous earth. The filtrate is diluted with H$_2$O and the aqueous layer is extracted with EtOAc (2×). The combined organic extracts are washed with brine, dried over Na$_2$SO$_4$, filtered, and concentrated under reduced pressure. The crude material is purified by silica gel chromatography, eluting with a gradient of 2% to 80% DCM in EtOAc to give the title compound (0.64 g, 94% purity, 73%) as a beige solid. ES/MS (m/z) 435 (M+H).

Preparation 93

Methyl 2-[4-[5-(tert-butoxycarbonylamino)-4-cyano-1-isopropyl-pyrazol-3-yl]phenyl]acetate

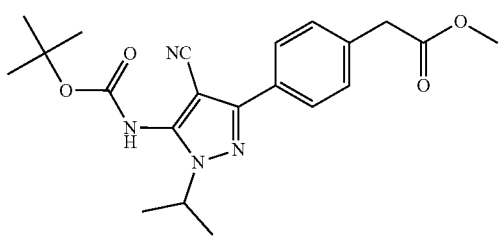 [SMILES: COC(=O)Cc1ccc(-c2nn(C(C)C)c(NC(=O)OC(C)(C)C)c2C#N)cc1]

To tert-butyl N-tert-butoxycarbonyl-N-(4-cyano-2-isopropyl-pyrazol-3-yl)carbamate (4.50 g, 12.8 mmol), bis(pinacolato)diboron (2.61 g, 10.3 mmol), [Ir(Ome)(1,5-cod)]2 (0.18 g, 0.267 mmol) and 4-tert-butyl-2-(4-tert-butyl-2-pyridyl)pyridine (0.15 g, 0.535 mmol) under N₂ is added THF (25 mL). The mixture is stirred at reflux for 4 hr. The mixture is cooled to RT and concentrated under reduced pressure. The residue is dissolved in a mixture of 4:1 DCM:EtOAc (20 mL) and the solution is passed through a pad of silica gel and washed with 3:1 DCM:EtOAc (2×10 mL). The filtrates are combined, concentrated under reduced pressure, and dried under vacuum to give a crude residue. To the residue under N₂ is added Cs₂CO₃ (10.5 g, 32.2 mmol) and methyl (4-bromophenyl)acetate (2.50 g, 10.9 mmol) in 1,4-dioxane (50 mL). Pd(dppf)Cl₂·CH₂Cl₂ (0.53 g, 0.642 mmol) and 4 Å molecular sieves are then added under Ar. The mixture is heated to 90° C. for 12 hr, cooled to RT, diluted with EtOAc, and filtered through diatomaceous earth. To the filtrate is added H₂O and the aqueous layer is extracted with EtOAc, washed with brine, dried over Na₂SO₄, filtered, and concentrated under reduced pressure. The crude brown oil is purified by silica gel chromatography, eluting with a gradient of 2% to 80% DCM in EtOAc to give the title compound as a white solid (3.80 g, 87%). ES/MS (m/z) 399 (M+H).

The following compounds in Table 10 are prepared essentially as described for methyl 2-[4-[5-(tert-butoxycarbonylamino)-4-cyano-1-isopropyl-pyrazol-3-yl]phenyl]acetate using the appropriate reagents, adjusting reaction time to determine completion of the reaction and purifying by chromatography as appropriate. K₂CO₃ can be substituted for Cs₂CO₃. Temperature can range from about 50-90° for the second coupling reaction. The mono and bis tert-butoxycarbonyl amino compounds can be isolated and both carried on to give a common product at a later step.

TABLE 10

| Prep No. | Chemical Name | Structure | ES/MS m/z (M + H) |
|---|---|---|---|
| 94 | Methyl 2-[4-[5-[bis(tert-butoxycarbonyl)amino]-4-cyano-1-isopropyl-pyrazol-3-yl]-3-fluorophenyl]acetate | 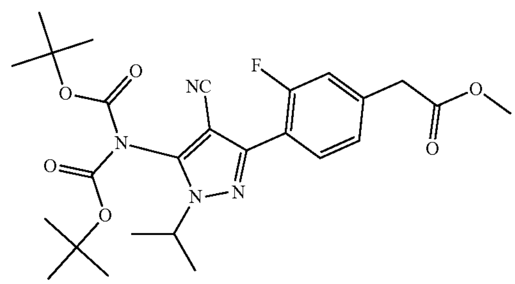 [SMILES: COC(=O)Cc1ccc(-c2nn(C(C)C)c(N(C(=O)OC(C)(C)C)C(=O)OC(C)(C)C)c2C#N)c(F)c1] | 517.4 |
| 95 | Ethyl 2-[4-[5-(tert-butoxycarbonylamino)-4-cyano-1-isopropyl-pyrazol-3-yl]-2-chloro-3-fluorophenyl]acetate | 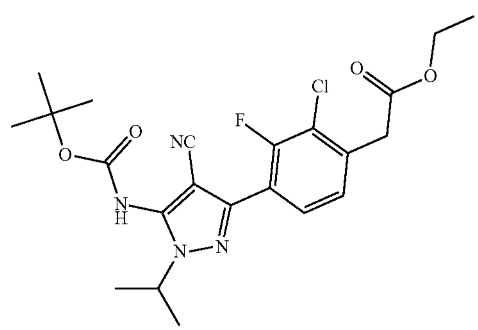 [SMILES: CCOC(=O)Cc1ccc(-c2nn(C(C)C)c(NC(=O)OC(C)(C)C)c2C#N)c(F)c1Cl] | 465 |
| 96 | Ethyl 2-[4-[5-[bis(tert-butoxycarbonyl)amino]-4-cyano-1-isopropyl-pyrazol-3-yl]-2-chloro-3-fluorophenyl]acetate | 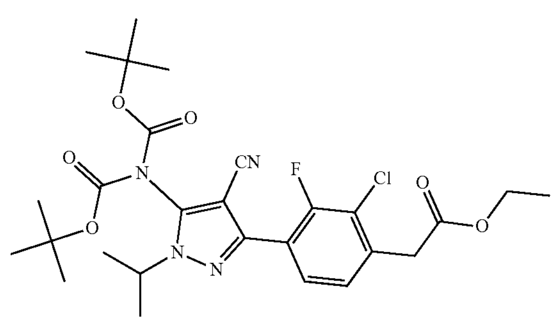 [SMILES: CCOC(=O)Cc1ccc(-c2nn(C(C)C)c(N(C(=O)OC(C)(C)C)C(=O)OC(C)(C)C)c2C#N)c(F)c1Cl] | 565 |

TABLE 10-continued

| Prep No. | Chemical Name | Structure | ES/MS m/z (M + H) |
|---|---|---|---|
| 97 | Methyl 2-[4-[5-[bis(tert-butoxycarbonyl)amino]-4-cyano-1-isopropyl-pyrazol-3-yl]-3-chloro-2-fluoro-phenyl]acetate | 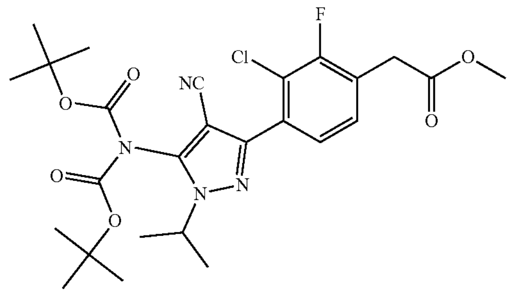 [SMILES: COC(=O)Cc1ccc(-c2nn(C(C)C)c(N(C(=O)OC(C)(C)C)C(=O)OC(C)(C)C)c2C#N)c(Cl)c1F] | 551 |
| 98 | Methyl 2-[4-[5-[bis(tert-butoxycarbonyl)amino]-4-cyano-1-isopropyl-pyrazol-3-yl]-3-methyl-phenyl]acetate | 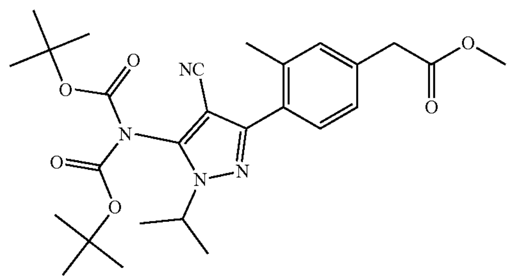 [SMILES: COC(=O)Cc1ccc(-c2nn(C(C)C)c(N(C(=O)OC(C)(C)C)C(=O)OC(C)(C)C)c2C#N)c(C)c1] | 512 |
| 99 | Methyl 2-[4-[5-[bis(tert-butoxycarbonyl)amino]-4-cyano-1-isopropyl-pyrazol-3-yl]-3-chloro-phenyl]acetate | 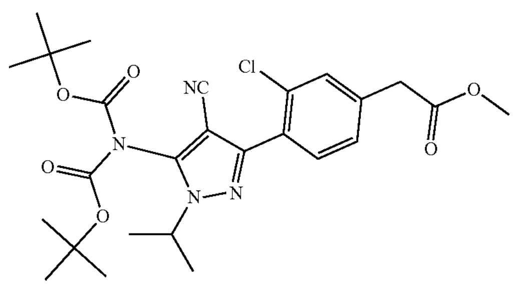 [SMILES: COC(=O)Cc1ccc(-c2nn(C(C)C)c(N(C(=O)OC(C)(C)C)C(=O)OC(C)(C)C)c2C#N)c(Cl)c1] | 533 |
| 100 | Methyl 2-[4-[5-(tert-butoxycarbonylamino)-4-cyano-1-isopropyl-pyrazol-3-yl]-3-chloro-phenyl]acetate | 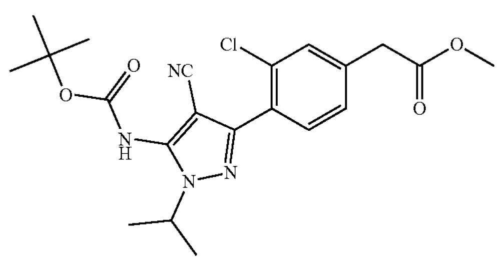 [SMILES: COC(=O)Cc1ccc(-c2nn(C(C)C)c(NC(=O)OC(C)(C)C)c2C#N)c(Cl)c1] | 433 |
| 101 | Ethyl 2-[4-[5-(tert-butoxycarbonylamino)-4-cyano-1-isopropyl-pyrazol-3-yl]-2,5-difluoro-phenyl]acetate | 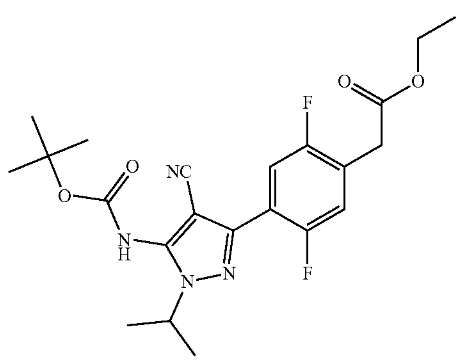 [SMILES: CCOC(=O)Cc1cc(F)c(-c2nn(C(C)C)c(NC(=O)OC(C)(C)C)c2C#N)cc1F] | 449 |

TABLE 10-continued

| Prep No. | Chemical Name | Structure | ES/MS m/z (M + H) |
|---|---|---|---|
| 102 | Methyl 2-[4-[5-[bis(tert-butoxycarbonyl)amino]-4-cyano-1-isopropyl-pyrazol-3-yl]-2,6-difluoro-phenyl]acetate | 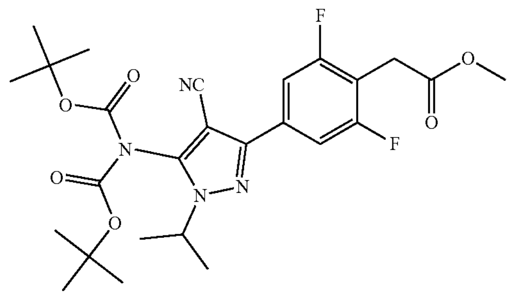 [SMILES: COC(=O)Cc1c(F)cc(-c2nn(C(C)C)c(N(C(=O)OC(C)(C)C)C(=O)OC(C)(C)C)c2C#N)cc1F] | 557 M + Na |

Preparation 103

2-[4-[5-(tert-Butoxycarbonylamino)-4-cyano-1-isopropyl-pyrazol-3-yl]phenyl]acetic acid

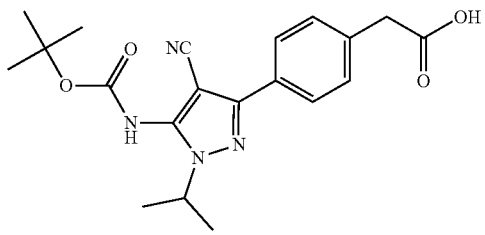 [SMILES: CC(C)n1nc(-c2ccc(CC(=O)O)cc2)c(C#N)c1NC(=O)OC(C)(C)C]

To a stirred solution of methyl 2-[4-[5-(tert-butoxycarbonylamino)-4-cyano-1-isopropyl-pyrazol-3-yl]phenyl]acetate (3.80 g, 9.54 mmol) in MeOH (40 mL) is added 2 M NaOH (14 mL, 28 mmol). The reaction mixture is stirred at 25° C. for 1 hr. The organic layer is concentrated. H$_2$O is added and KHSO$_4$ (3.92 g, 28.8 mmol) in H$_2$O is added dropwise. The precipitate formed is filtered, washed with H$_2$O, and dried under vacuum to give the title compound (2.88 g, 79%) which is used without further purification. ES/MS (m/z) 385 (M+H).

The following compounds in Table 11 are prepared essentially as described for 2-[4-[5-(tert-butoxycarbonylamino)-4-cyano-1-isopropyl-pyrazol-3-yl]phenyl]acetic acid and adjusting reaction time to determine completion of the reaction. 1,4-Dioxane can be substituted for MeOH, NH$_4$Cl can be substituted for KHSO$_4$ and the product can be extracted from H$_2$O if appropriate. The mono and bis tert-butoxycarbonyl amino compounds can be isolated and both carried on to give a common product at a later step.

TABLE 11

| Prep. No. | Chemical name | Structure | ES/MS m/z (M + H) |
|---|---|---|---|
| 104 | 2-[4-(5-Amino-4-carbamoyl-1-isopropyl-pyrazol-3-yl)-2-methoxy-phenyl]acetic acid | 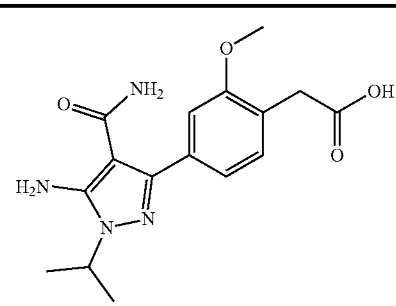 | 333.1 |
| 105 | 2-[4-(5-Amino-4-carbamoyl-1-isopropyl-pyrazol-3-yl)-2,6-difluoro-phenyl]acetic acid | 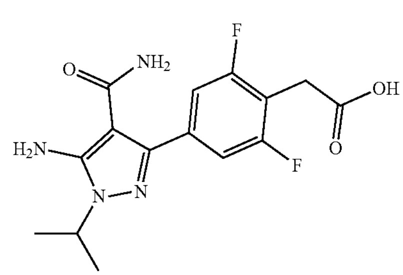 [SMILES: CC(C)n1nc(-c2cc(F)c(CC(=O)O)c(F)c2)c(C(N)=O)c1N] | 339 |

TABLE 11-continued

| Prep. No. | Chemical name | Structure | ES/MS m/z (M + H) |
|---|---|---|---|
| 106 | 2-[4-Bromo-3-(methoxymethyl)phenyl]acetic acid | 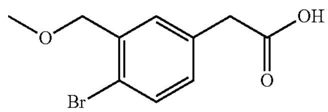 | 283 M + Na |
| 107 | 2-[4-[5-(tert-Butoxycarbonylamino)-4-cyano-1-isopropyl-pyrazol-3-yl]-3-fluoro-phenyl]acetic acid | 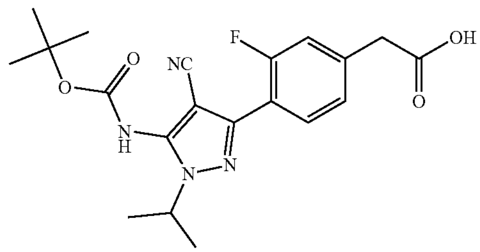 | 403.4 |
| 108 | 2-[4-[5-[bis(tert-Butoxycarbonyl)amino]-4-cyano-1-isopropyl-pyrazol-3-yl]-3-fluoro-phenyl]acetic acid | 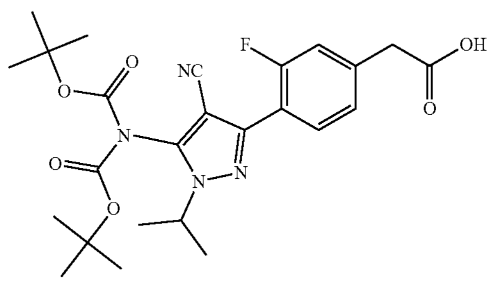 [SMILES: CC(C)n1nc(-c2ccc(CC(=O)O)cc2F)c(C#N)c1N(C(=O)OC(C)(C)C)C(=O)OC(C)(C)C] | 503 |
| 109 | 2-[4-[5-(tert-Butoxycarbonylamino)-4-cyano-1-isopropyl-pyrazol-3-yl]-3-methyl-phenyl]acetic acid | 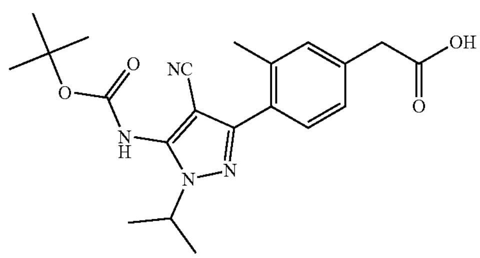 [SMILES: Cc1cc(CC(=O)O)ccc1-c1nn(C(C)C)c(NC(=O)OC(C)(C)C)c1C#N] | 399 |
| 110 | 2-[4-[5-(tert-Butoxycarbonylamino)-4-cyano-1-isopropyl-pyrazol-3-yl]-3-chloro-phenyl]acetic acid | 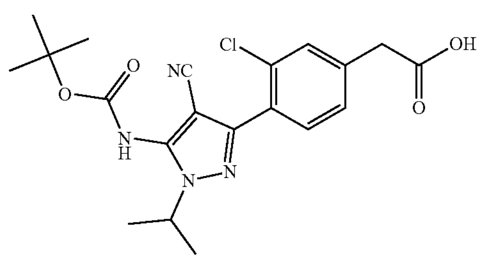 [SMILES: CC(C)n1nc(-c2ccc(CC(=O)O)cc2Cl)c(C#N)c1NC(=O)OC(C)(C)C] | 418 |
| 111 | 2-[4-[5-(tert-Butoxycarbonylamino)-4-cyano-1-isopropyl-pyrazol-3-yl]-2,6-difluoro-phenyl]acetic acid | 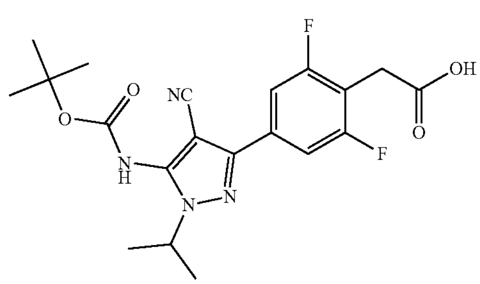 [SMILES: CC(C)n1nc(-c2cc(F)c(CC(=O)O)c(F)c2)c(C#N)c1NC(=O)OC(C)(C)C] | 421 |

Preparation 112

2-[4-[5-(tert-Butoxycarbonylamino)-4-cyano-1-isopropyl-pyrazol-3-yl]-2,3-difluoro-phenyl]acetic acid

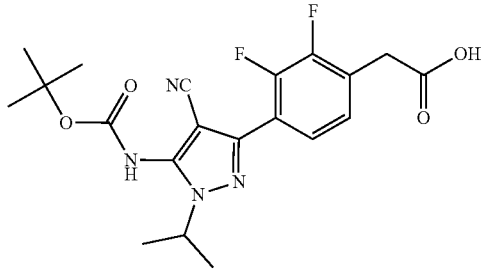 [SMILES: CC(C)n1nc(-c2ccc(CC(=O)O)c(F)c2F)c(C#N)c1NC(=O)OC(C)(C)C]

To methyl 2-[4-[5-(tert-butoxycarbonylamino)-4-cyano-1-isopropyl-pyrazol-3-yl]-2,3-difluoro-phenyl]acetate (0.64 g, 1.47 mmol) in 1,4-dioxane (6.5 mL) and H₂O (2 mL) is added 1 M LiOH hydrate (4.4 mL, 4.40 mmol). The mixture is stirred at RT overnight. The reaction mixture is concentrated and poured into H₂O and washed with EtOAc. The aqueous layer is acidified with 1 M aq. KHSO₄ to pH 2-3 then extracted with EtOAc (3×). The combined organic extracts are washed with brine, dried over Na₂SO₄, filtered, and concentrated under reduced pressure to give the title compound as a beige solid (0.54 g, 94% purity, 82%). ES/MS (m/z) 421 (M+1).

Preparation 113

Methyl 4-([[3-(2,2-dimethylpropyl)-1,2-oxazol-5-yl]carbamoyl]methyl)benzoate

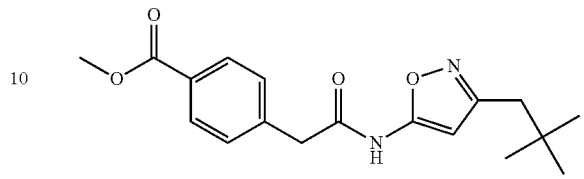

To a stirred solution of [4-(methoxycarbonyl)phenyl]acetic acid (20.0 g, 103 mmol) and 3-(2,2-dimethylpropyl)-1,2-oxazol-5-amine (17.5 g, 113 mmol) and DIPEA (89.5 mL, 514 mmol) in DMF (200 mL) is added T3P® (328 g, 515 mmol, 50% in DMF) in portions at 0° C. The mixture is stirred for 2 hr at 50° C. To the mixture is added EtOAc (1 L). The mixture is washed with H₂O (3×300 mL). The organic layer is separated, dried over anhydrous Na₂SO₄, filtered, and concentrated under reduced pressure. The residue is purified by silica gel chromatography, eluting with a gradient of 8:1 to 4:1 PE:EtOAc to give the title compound (31.0 g, 91%) as a light yellow solid. ES/MS (m/z) 331.2 (M+H).

The following compounds in Table 12 are prepared essentially as described for methyl 4-([[3-(2,2-dimethylpropyl)-1,2-oxazol-5-yl]carbamoyl]methyl)benzoate using the appropriate reagents, adjusting the reaction time to determine completion of the reaction and using appropriate chromatography conditions for purification or used without further purification. The reaction temperature can range from RT to 100° C. T3P® can be added in DCM instead of DMF.

TABLE 12

| Prep No. | Chemical Name | Structure | ES/MS m/z (M + H) |
|---|---|---|---|
| 114 | Methyl 4-([[3-(2-chloro-4-fluorophenyl)-1,2-oxazol-5-yl]carbamoyl]methyl)benzoate | 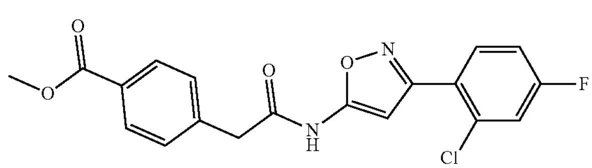 [SMILES: COC(=O)c1ccc(CC(=O)Nc2cc(-c3ccc(F)cc3Cl)no2)cc1] | 389.2 |
| 115 | Methyl 4-[([3-[4-(trifluoromethyl)bicyclo[2.2.1]heptan-1-yl]-1,2-oxazol-5-yl]carbamoyl)methyl]benzoate | 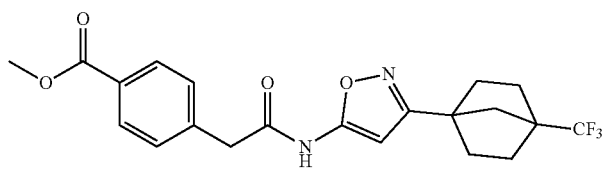 [SMILES: COC(=O)c1ccc(CC(=O)Nc2cc(C34CCC(C(F)(F)F)(CC3)C4)no2)cc1] | 423.1 |

TABLE 12-continued

| Prep No. | Chemical Name | Structure | ES/MS m/z (M + H) |
|---|---|---|---|
| 116 | Methyl 4-[[(3-[3-methylbicyclo[1.1.1]pentan-1-yl]-1,2-oxazol-5-yl)carbamoyl]methyl]benzoate | 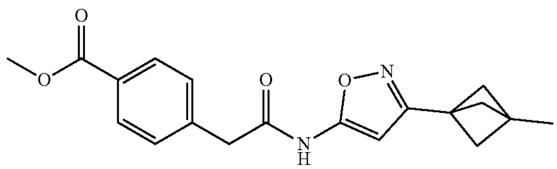 | 341.3 |

Preparation 117

4-([[3-(2,2-Dimethylpropyl)-1,2-oxazol-5-yl]carbamoyl]methyl)benzoic acid

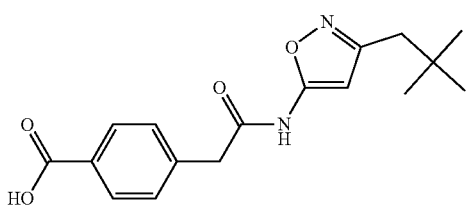 [SMILES: CC(C)(C)Cc1cc(NC(=O)Cc2ccc(C(=O)O)cc2)on1]

To a stirred solution of methyl 4-([[3-(2,2-dimethylpropyl)-1,2-oxazol-5-yl]carbamoyl]methyl)benzoate (31.0 g, 93.8 mmol) in THF (240 mL) and H₂O (80 mL) is added LiOH (11.2 g, 468 mmol) in portions at RT. The mixture is stirred overnight. The mixture is acidified to pH 5 with 2N HCl and extracted with EtOAc (3×200 mL). The combined organic extracts are washed with brine (3×50 mL), dried over anhydrous Na₂SO₄, filtered, and concentrated under reduced pressure to give the title compound (28.5 g, 96%) as a white solid. ES/MS (m/z) 317.2 (M+1).

The following compounds in Table 13 are prepared essentially as described for 4-([[3-(2,2-dimethylpropyl)-1,2-oxazol-5-yl]carbamoyl]methyl)benzoic acid using the appropriate ester, adjusting the reaction time to determine completion of the reaction, adjusting the pH to 1-5 after completion, and collecting by extraction or precipitation as appropriate. A solvent mixture of 1,4-dioxane/H₂O or MeOH/H₂O can be used if needed for solubility and the temperature can range from about RT to 50 CC. 1 M NaOH can be substituted for LiOH and citric acid or KHSO₄ can be substituted for HCL

TABLE 13

| Prep. No. | Chemical name | Structure | ES/MS m/z (M + H) |
|---|---|---|---|
| 118 | 4-([[3-(2-Chloro-4-fluorophenyl)-1,2-oxazol-5-yl]carbamoyl]methyl)benzoic acid | 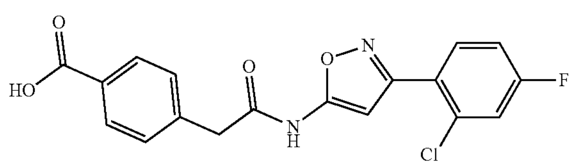 [SMILES: O=C(Cc1ccc(C(=O)O)cc1)Nc1cc(-c2ccc(F)cc2Cl)no1] | 375.1 |
| 119 | 4-[([3-[4-(Trifluoromethyl)bicyclo[2.2.1]heptan-1-yl]-1,2-oxazol-5-yl]carbamoyl)methyl]benzoic acid | 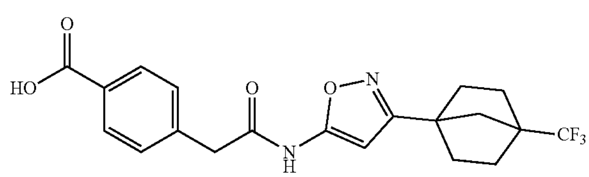 [SMILES: O=C(Cc1ccc(C(=O)O)cc1)Nc1cc(C23CCC(C(F)(F)F)(CC2)C3)no1] | 409.1 |
| 120 | 2-[4-Bromo-3-(tert-butoxymethyl)phenyl]acetic acid | 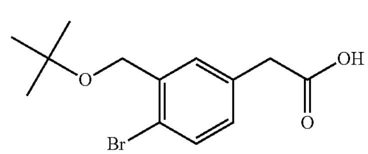 [SMILES: CC(C)(C)OCc1cc(CC(=O)O)ccc1Br] | 323.1 M + Na |

TABLE 13-continued

| Prep. No. | Chemical name | Structure | ES/MS m/z (M + H) |
|---|---|---|---|
| 121 | 2-[4-[5-(tert-Butoxycarbonylamino)-4-cyano-1-isopropyl-pyrazol-3-yl]-2-chloro-3-fluoro-phenyl]acetic acid | 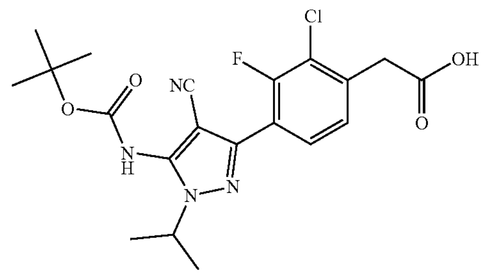 | 437 |
| 122 | 2-[4-[5-(tert-Butoxycarbonylamino)-4-cyano-1-isopropyl-pyrazol-3-yl]-3-chloro-2-fluoro-phenyl]acetic acid | 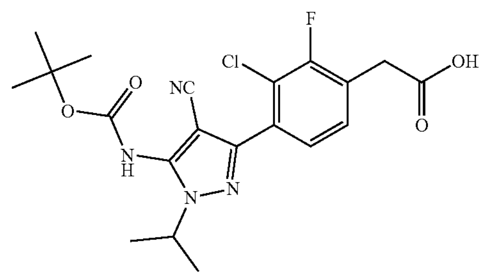 [SMILES: CC(C)n1nc(-c2ccc(CC(=O)O)c(F)c2Cl)c(C#N)c1NC(=O)OC(C)(C)C] | 437 |
| 123 | 2-[4-[5-(tert-Butoxycarbonylamino)-4-cyano-1-isopropyl-pyrazol-3-yl]-2,5-difluoro-phenyl]acetic acid | 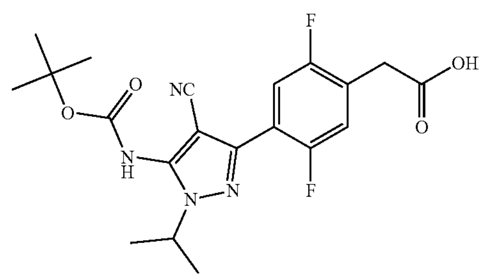 [SMILES: CC(C)n1nc(-c2cc(F)c(CC(=O)O)cc2F)c(C#N)c1NC(=O)OC(C)(C)C] | 421 |
| 124 | 4-[[(3-[3-Methylbicyclo[1.1.1]pentan-1-yl]-1,2-oxazol-5-yl)carbamoyl]methyl]benzoic acid | 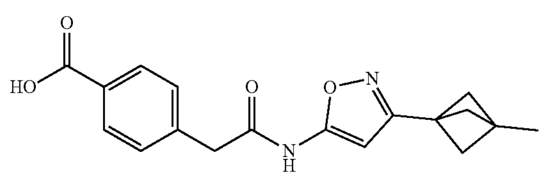 [SMILES: CC12CC(c3cc(NC(=O)Cc4ccc(C(=O)O)cc4)on3)(C1)C2] | 327.1 |

The following compounds in Table 14 are prepared essentially as described for methyl 4-([[3-(2,2-dimethylpropyl)-1,2-oxazol-5-yl]carbamoyl]methyl)benzoate using the appropriate reagents, adjusting the reaction time to determine completion of the reaction and using appropriate chromatography conditions for purification or used without further purification. The reaction temperature can range from RT to 100° C. T3P® can be added in DCM or EtOAc instead of DMF.

TABLE 14

| Prep No. | Chemical Name | Structure | ES/MS m/z (M + H) |
|---|---|---|---|
| 125 | 2-[4-Bromo-3-(methoxymethyl)phenyl]-N-[5-(1-methylcyclopentyl)isoxazol-3-yl]acetamide | 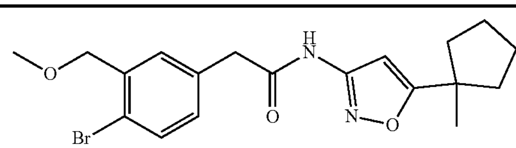 | 407 |

TABLE 14-continued

| Prep No. | Chemical Name | Structure | ES/MS m/z (M + H) |
|---|---|---|---|
| 126 | 2-[4-Bromo-2-(methoxymethyl)phenyl]-N-[5-(1-methylcyclopentyl)isoxazol-3-yl]acetamide | 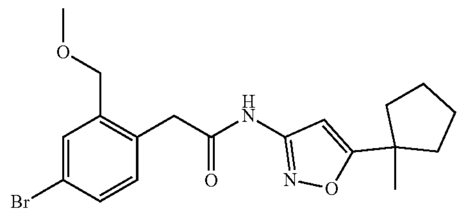 [SMILES: COCc1cc(Br)ccc1CC(=O)Nc1cc(C2(C)CCCC2)on1] | 408 |
| 127 | 2-[4-Bromo-2-(tert-butoxymethyl)phenyl]-N-[5-(1-methylcyclopentyl)isoxazol-3-yl]acetamide | 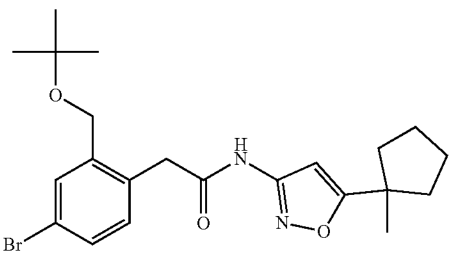 [SMILES: CC(C)(C)OCc1cc(Br)ccc1CC(=O)Nc1cc(C2(C)CCCC2)on1] | 449 |
| 128 | 2-[4-Bromo-3-(tert-butoxymethyl)phenyl]-N-[5-(1-methylcyclopentyl)isoxazol-3-yl]acetamide | 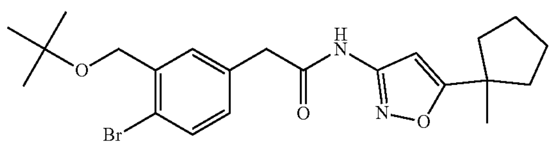 [SMILES: CC(C)(C)OCc1cc(CC(=O)Nc2cc(C3(C)CCCC3)on2)ccc1Br] | 449.2 |

Preparation 129

2-[4-Bromo-2-(hydroxymethyl)phenyl]-N-[5-(1-methylcyclopentyl)isoxazol-3-yl]acetamide

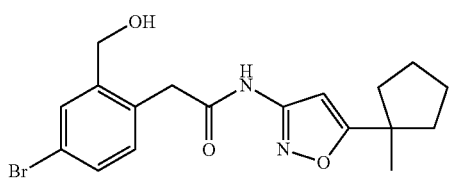 [SMILES: CC1(c2cc(NC(=O)Cc3ccc(Br)cc3CO)no2)CCCC1]

To TFA (16.6 mL), (2,2,2-trifluoroacetyl) 2,2,2-trifluoroacetate (5.42 g, 25.8 mmol) and triethylsilane (1.0 mL, 6.26 mmol) under $N_2$ is added 2-[4-bromo-2-(tert-butoxymethyl)phenyl]-N-[5-(1-methylcyclopentyl)isoxazol-3-yl]acetamide (0.29 g, 0.645 mmol) in DCM (8.29 mL). The reaction is stirred for 4 hr. The reaction mixture is concentrated under reduced pressure and dried under vacuum. The material is dissolved in THF (9 mL) and $H_2O$ (4.5 mL). Saturated aq. $NaHCO_3$ (4 mL) is added and the mixture is stirred at RT for 1 hr. THF is removed under vacuum. The mixture is diluted with DCM (10 mL) and the organic layer is separated, dried over $Na_2SO_4$, filtered, and concentrated under reduced pressure. The residue is purified by silica gel chromatography, eluting with a gradient of 1% to 10% MeOH in DCM to give the title compound (0.20 g, 79%). ES/MS (m/z) 394 (M+H).

Preparation 130

5-Amino-3-[2-(tert-butoxymethyl)-4-[2-[[5-(1-methylcyclopentyl)isoxazol-3-yl]amino]-2-oxo-ethyl]phenyl]-1-isopropyl-pyrazole-4-carboxamide

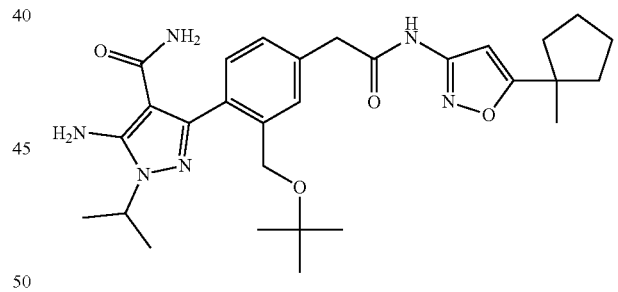

To bis(pinacolato)diboron (93 mg, 0.366 mmol), 2-[4-bromo-3-(tert-butoxymethyl)phenyl]-N-[5-(1-methylcyclopentyl)isoxazol-3-yl]acetamide (0.15 g, 0.334 mmol), KOAc (0.11 g, 1.12 mmol) and Pd(dppf)$Cl_2$·$CH_2Cl_2$ (28 mg, 0.033 mmol) under $N_2$ is added dry THF (4 mL). The reaction mixture is degassed with Ar for 15 min and then heated to 50° C. The reaction is stirred at 50° C. overnight, at 65° C. for a second night and then at 80° C. for 24 hr. The reaction mixture is cooled to RT. 5-Amino-3-bromo-1-isopropyl-pyrazole-4-carboxamide (0.11 g, 0.445 mmol) in THF (1.3 mL) and $K_3PO_4$ (0.22 g, 1.04 mmol) in $H_2O$ (1.3 mL) are added. The reaction mixture is degassed with Ar and XantPhos Pd G3 (17 mg, 0.0167 mmol) is added. The mixture is heated to 50° C. overnight. The mixture is filtered through a pad of talcum powder; $H_2O$ is added to the filtrate and the mixture is extracted with EtOAc (2×). The combined organic extracts are washed with brine, dried over Na₂SO₄, filtered, and concentrated under reduced pressure. The residue is purified by silica gel chromatography, eluting with a gradient of 1% to 10% MeOH in DCM to give the title compound as a brown powder (67 mg, 37%). ES/MS (m/z) 537 (M+H).

Preparation 131

2-[4-(2,2-Dicyano-1-hydroxyeth-1-en-1-yl)phenyl]-N-[3-(2,2-dimethylpropyl)-1,2-oxazol-5-yl]acetamide

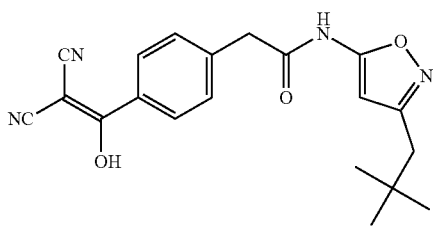 [SMILES: CC(C)(C)Cc1cc(NC(=O)Cc2ccc(C(O)=C(C#N)C#N)cc2)on1]

To a stirred solution of 4-([[3-(2,2-dimethylpropyl)-1,2-oxazol-5-yl]carbamoyl]methyl)benzoic acid (32.0 g, 101 mmol) and DMF (0.16 mL, 2.14 mmol) in DCM (350 mL) is added oxalyl chloride (10.6 mL, 124 mmol) dropwise at 0° C. The mixture is stirred for 2 hr at RT. The mixture is concentrated under reduced pressure to give crude 4-([[3-(2,2-dimethylpropyl)-1,2-oxazol-5-yl]carbamoyl]methyl) benzoyl chloride. To a solution of malononitrile (6.31 g, 95.5 mmol) in THF (100 mL) is added NaH (7.65 g, 191 mmol, 60% in mineral oil) at 0° C. The mixture is stirred for 15 min. 4-([[3-(2,2-Dimethylpropyl)-1,2-oxazol-5-yl]carbamoyl]methyl)benzoyl chloride (32.0 g, 95.6 mmol) in THF (150 mL) is added dropwise to the 0° C. solution and the mixture is stirred for 2 hr and allowed to warm to RT. The mixture is diluted with H₂O (300 mL), acidified to pH 5 with 2N HCl, and extracted with EtOAc (3×200 mL). The combined organic extracts are washed with brine (3×100 mL), dried over Na₂SO₄, filtered, and concentrated under reduced pressure to give the title compound (30.0 g, 82%). The crude product is used directly without further purification. ES/MS (m/z) 365.1 (M+H).

The following compounds in Table 15 are prepared essentially as described for 2-[4-(2,2-dicyano-1-hydroxyeth-1-en-1-yl)phenyl]-N-[3-(2,2-dimethylpropyl)-1,2-oxazol-5-yl] acetamide under N₂ if desired and adjusting the reaction time to determine completion of the reactions. The malononitrile in THF and NaH can be stirred from 15-30 min at 0° to RT. The reaction can be acidified or concentrated to dryness and purified by chromatography as appropriate.

TABLE 15

| Prep. No. | Chemical name | Structure | ES/MS m/z (M + H) |
|---|---|---|---|
| 132 | N-[3-(2-Chloro-4-fluorophenyl)-1,2-oxazol-5-yl]-2-[4-(2,2-dicyano-1-hydroxyeth-1-en-1-yl)phenyl]acetamide | 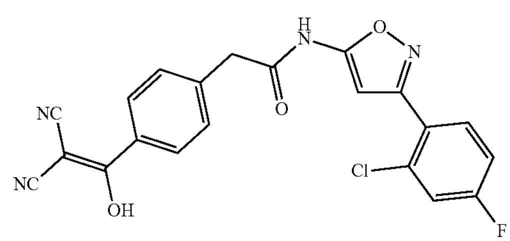 [SMILES: N#CC(C#N)=C(O)c1ccc(CC(=O)Nc2cc(-c3ccc(F)cc3Cl)no2)cc1] | 423.1 |
| 133 | 2-[4-(2,2-Dicyano-1-hydroxyeth-1-en-1-yl)phenyl]-N-[3-[4-(trifluoromethyl)bicyclo[2.2.1]heptan-1-yl]-1,2-oxazol-5-yl]acetamide | 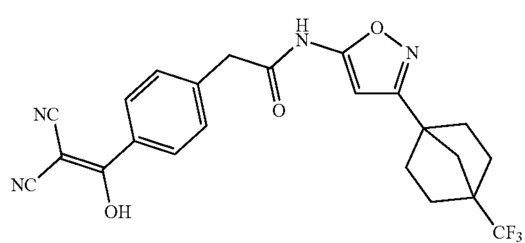 [SMILES: N#CC(C#N)=C(O)c1ccc(CC(=O)Nc2cc(C34CCC(C(F)(F)F)(CC3)C4)no2)cc1] | 457 |
| 134 | Methyl 2-(4-(2,2-dicyano-1-hydroxyvinyl)-3-fluorophenyl)acetate | 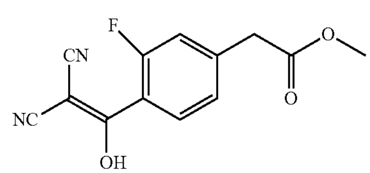 [SMILES: COC(=O)Cc1ccc(C(O)=C(C#N)C#N)c(F)c1] | |

TABLE 15-continued

| Prep. No. | Chemical name | Structure | ES/MS m/z (M + H) |
|---|---|---|---|
| 135 | 2-[4-(2,2-Dicyano-1-hydroxyeth-1-en-1-yl)phenyl]-N-(3-[3-methylbicyclo[1.1.1]pentan-1-yl]-1,2-oxazol-5-yl)acetamide | 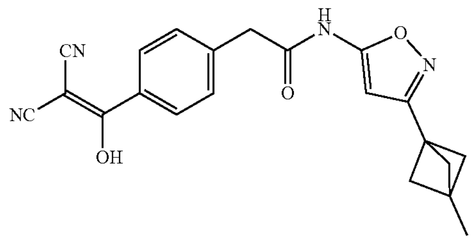 [SMILES: CC12CC(c3cc(NC(=O)Cc4ccc(C(O)=C(C#N)C#N)cc4)on3)(C1)C2] | 375.3 |

Preparation-136

2-[4-(2,2-Dicyano-1-methoxyeth-1-en-1-yl)phenyl]-N-[3-(2,2-dimethylpropyl)-1,2-oxazol-5-yl]acetamide

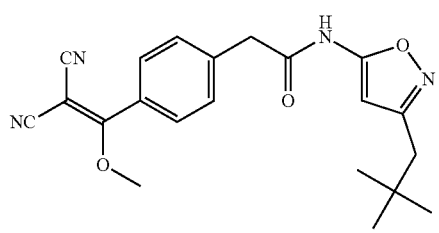 [SMILES: COC(=C(C#N)C#N)c1ccc(CC(=O)Nc2cc(CC(C)(C)C)no2)cc1]

To a stirred solution of 2-[4-(2,2-dicyano-1-hydroxyeth-1-en-1-yl)phenyl]-N-[3-(2,2-dimethylpropyl)-1,2-oxazol-5-yl]acetamide (25.0 g, 68.6 mmol) and TEA (28.7 mL, 206 mmol) in ACN (240 mL) is added dimethyl sulfate (39.0 mL, 411 mmol) dropwise at RT under $N_2$. The mixture is stirred for 14 hr at 50° C. under $N_2$. The mixture is diluted with EtOAc (500 mL), washed with brine (3×50 mL), dried over anhydrous $Na_2SO_4$, filtered, and concentrated under reduced pressure. The residue is purified by silica gel chromatography, eluting with a gradient of 8:1 to 2:1 PE:EtOAc to give the title compound (9.0 g, 35%) as a light yellow solid. ES/MS (m/z) 379.1 (M+H).

The following compounds in Table 16 are prepared essentially as described for 2-[4-(2,2-dicyano-1-methoxyeth-1-en-1-yl)phenyl]-N-[3-(2,2-dimethylpropyl)-1,2-oxazol-5-yl]acetamide adjusting the reaction time to determine completion of the reaction and purification as appropriate. The temperature can range from about 50° C. to 80° C.

TABLE 16

| Prep. No. | Chemical name | Structure | ES/MS m/z (M + H) |
|---|---|---|---|
| 137 | N-[3-(2-Chloro-4-fluorophenyl)-1,2-oxazol-5-yl]-2-[4-(2,2-dicyano-1-methoxyeth-1-en-1-yl)phenyl]acetamide | 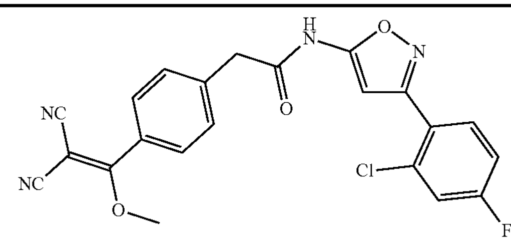 | 437.1 |
| 138 | 2-[4-(2,2-Dicyano-1-methoxyeth-1-en-1-yl)phenyl]-N-[3-[4-(trifluoromethyl)bicyclo[2.2.1]heptan-1-yl]-1,2-oxazol-5-yl]acetamide | 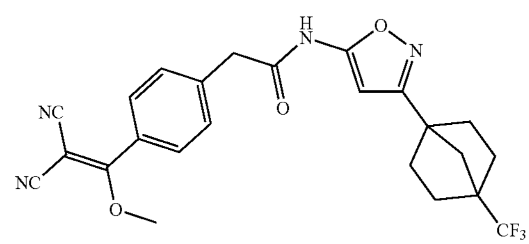 [SMILES: COC(=C(C#N)C#N)c1ccc(CC(=O)Nc2cc(C34CCC(C(F)(F)F)(CC3)C4)no2)cc1] | 471.2 |
| 139 | Methyl 2-(4-(2,2-dicyano-1-methoxyvinyl)-3-fluorophenyl)acetate | 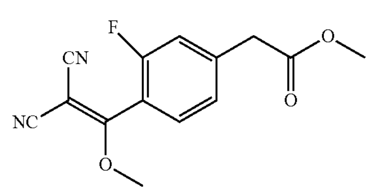 [SMILES: COC(=O)Cc1ccc(C(OC)=C(C#N)C#N)c(F)c1] | 292.2, M + NH$_3$ + H |

TABLE 16-continued

| Prep. No. | Chemical name | Structure | ES/MS m/z (M + H) |
|---|---|---|---|
| 140 | 2-[4-(2,2-Dicyano-1-methoxyeth-1-en-1-yl)phenyl]-N-(3-[3-methylbicyclo[1.1.1]pentan-1-yl]-1,2-oxazol-5-yl)acetamide | 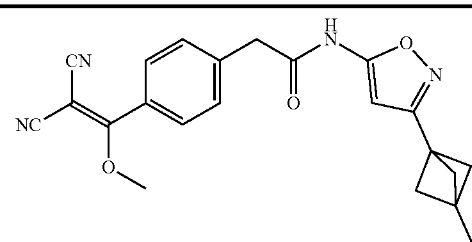 | 389.1 |

Preparation 141

Methyl 2-(4-(5-amino-4-cyano-1-(1-methylcyclopropyl)-1H-pyrazol-3-yl)phenyl)acetate

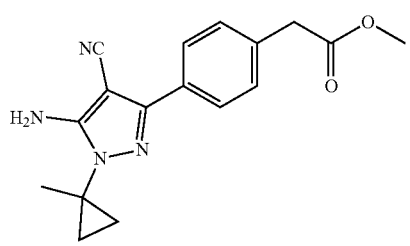 [SMILES: COC(=O)Cc1ccc(-c2nn(C3(C)CC3)c(N)c2C#N)cc1]

To a stirred mixture of (1-methylcyclopropyl)hydrazine HCl (crude, 2.00 g, 16.3 mmol) and TEA (1.6 mL, 11.5 mmol) in EtOH (20 mL) is added methyl 2-[4-(2,2-dicyano-1-methoxyeth-1-en-1-yl)phenyl]acetate (0.48 g, 1.87 mmol) in portions at RT under $N_2$. The mixture is stirred for 2 hr at 50° C. under $N_2$. The mixture is allowed to cool to RT and concentrated under reduced pressure. The residue is purified by reversed-phase chromatography (C18 column), eluting with a gradient of 30% to 50% ACN in $H_2O$ (0.1% $NH_4HCO_3$) to give the title compound (0.50 g, 86%) as a white solid. ES/MS (m/z) 311.3 (M+H).

The following compounds in Table 17 are prepared essentially as described for methyl 2-(4-(5-amino-4-cyano-1-(1-methylcyclopropyl)-1H-pyrazol-3-yl)phenyl)acetate using the appropriate reagents, adjusting reaction time to determine completion of the reaction and purifying by chromatography as appropriate. The reaction temperature can range from RT to 80° C., the solvent can be THF if appropriate, and the base can be DIPEA or TEA.

TABLE 17

| Prep No. | Chemical Name | Structure | ES/MS m/z (M + H) |
|---|---|---|---|
| 142 | Methyl 2-[4-[5-amino-4-cyano-1-(1,1,1-trifluoro-2-methylpropan-2-yl)pyrazol-3-yl]phenyl]acetate | 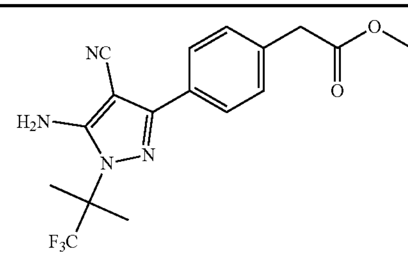 | 367.2 |
| 143 | Methyl 2-[4-[5-amino-4-cyano-1-(1-methoxy-2-methylpropan-2-yl)pyrazol-3-yl]phenyl]acetate | 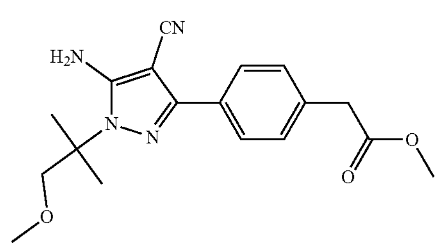 | 343.3 |
| 144 | Methyl 2-[4-[5-amino-4-cyano-1-(1,1,1-trifluoropropan-2-yl)pyrazol-3-yl]phenyl]acetate | 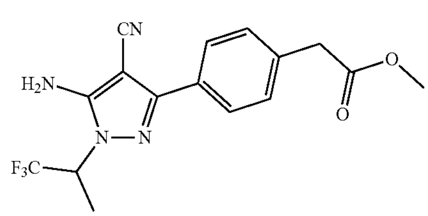 [SMILES: COC(=O)Cc1ccc(-c2nn(C(C)C(F)(F)F)c(N)c2C#N)cc1] | 353.2 |

TABLE 17-continued

| Prep No. | Chemical Name | Structure | ES/MS m/z (M + H) |
|---|---|---|---|
| 145 | Methyl 2-[4-[5-amino-4-cyano-1-(2,2,2-trifluoroethyl)pyrazol-3-yl]phenyl]acetate | 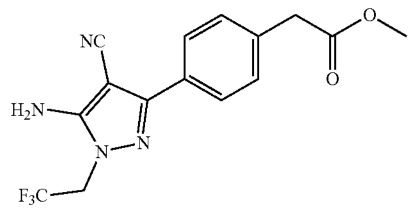 [SMILES: COC(=O)Cc1ccc(-c2nn(CC(F)(F)F)c(N)c2C#N)cc1] | 339.1 |
| 146 | Methyl 2-[4-(5-amino-4-cyano-1-cyclobutylpyrazol-3-yl)phenyl]acetate | 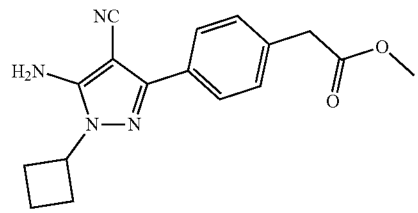 [SMILES: COC(=O)Cc1ccc(-c2nn(C3CCC3)c(N)c2C#N)cc1] | 311.2 |
| 147 | 2-[4-[5-Amino-4-cyano-1-(1-hydroxypropan-2-yl)pyrazol-3-yl]phenyl]-N-(3-[3-methylbicyclo[1.1.1]pentan-1-yl]-1,2-oxazol-5-yl)acetamide | 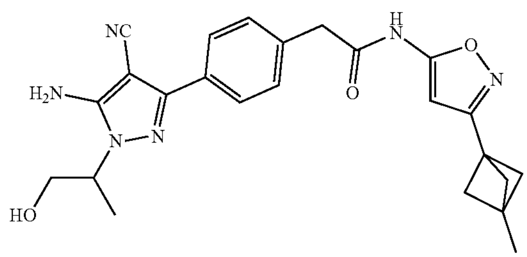 [SMILES: CC(CO)n1nc(-c2ccc(CC(=O)Nc3cc(C45CC(C)(C4)C5)no3)cc2)c(C#N)c1N] | 447.3 |
| 148 | 2-[4-[5-Amino-4-cyano-1-(1-hydroxy-2-methylpropan-2-yl)pyrazol-3-yl]phenyl]-N-(3-[3-methylbicyclo[1.1.1]pentan-1-yl]-1,2-oxazol-5-yl)acetamide | 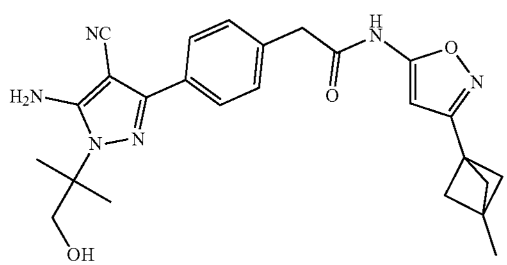 [SMILES: CC12CC(c3cc(NC(=O)Cc4ccc(-c5nn(C(C)(C)CO)c(N)c5C#N)cc4)on3)(C1)C2] | 461.2 |
| 149 | Methyl 2-[4-[5-amino-4-cyano-1-(1,1,1-trifluoro-2-methylpropan-2-yl)pyrazol-3-yl]phenyl]acetate | 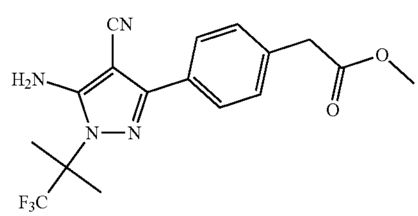 [SMILES: COC(=O)Cc1ccc(-c2nn(C(C)(C)C(F)(F)F)c(N)c2C#N)cc1] | 367.1 |
| 150 | Methyl 2-[4-(5-amino-1-tert-butyl-4-cyanopyrazol-3-yl)phenyl]acetate | 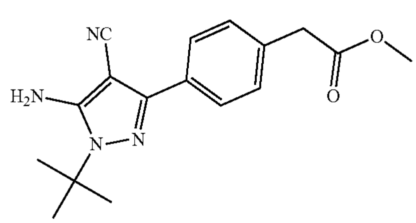 [SMILES: COC(=O)Cc1ccc(-c2nn(C(C)(C)C)c(N)c2C#N)cc1] | 313.2 |

TABLE 17-continued

| Prep No. | Chemical Name | Structure | ES/MS m/z (M + H) |
|---|---|---|---|
| 151 | 2-(4-(5-Amino-4-cyano-1-cyclopentyl-1H-pyrazol-3-yl)phenyl)acetate | 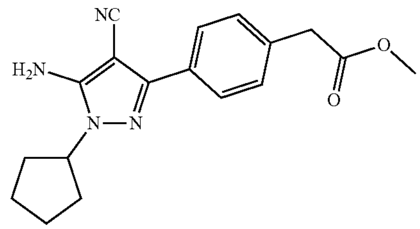 [SMILES: COC(=O)Cc1ccc(-c2nn(C3CCCC3)c(N)c2C#N)cc1] | 325 |
| 152 | Methyl 2-(4-(5-amino-4-cyano-1-(1,1,1-trifluoropropan-2-yl)-1H-pyrazol-3-yl)phenyl)acetate | 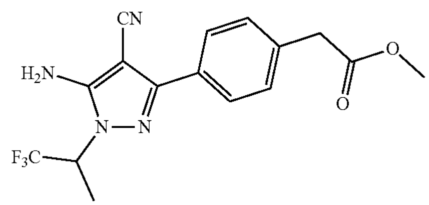 [SMILES: COC(=O)Cc1ccc(-c2nn(C(C)C(F)(F)F)c(N)c2C#N)cc1] | 375.1 M + Na |
| 153 | Methyl 2-[4-(5-amino-4-cyano-1-isopropyl-pyrazol-3-yl)phenyl]acetate | 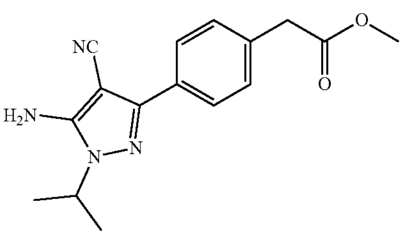 [SMILES: COC(=O)Cc1ccc(-c2nn(C(C)C)c(N)c2C#N)cc1] | 299 |
| 154 | Methyl 2-(4-(5-amino-4-cyano-1-(1-methylcyclopropyl)-1H-pyrazol-3-yl)-3-fluorophenyl)acetate | 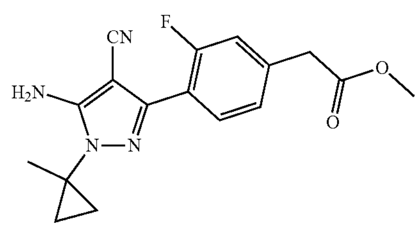 | 329.1 |

Preparation 155

2-(4-(5-Amino-4-cyano-1-(1-hydroxy-2-methylpropan-2-yl)-1H-pyrazol-3-yl)phenyl)-N-(3-neopentylisoxazol-5-yl)acetamide

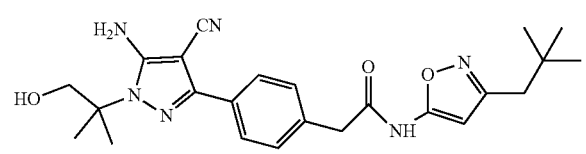 [SMILES: CC(C)(C)Cc1cc(NC(=O)Cc2ccc(-c3nn(C(C)(C)CO)c(N)c3C#N)cc2)on1]

2-Hydrazino-2-methylpropan-1-ol HCl (43 mg, 0.306 mmol), EtOH (1.5 mL), TEA (0.12 mL, 0.861 mmol), and 2-(4-(2,2-dicyano-1-methoxyvinyl)phenyl)-N-(3-neopentylisoxazol-5-yl)acetamide (0.11 g, 0.291 mmol) are added together and stirred for 18 hr at 45° C. The mixture is diluted with H₂O (1 mL) and extracted with EtOAc (3×3 mL). The organic extracts are concentrated under reduced pressure. The residue is purified by silica gel chromatography, eluting with a gradient of 0% to 100% EtOAc in hexanes to give the title compound (39 mg, 30%) as a white solid. ES/MS (m/z) 451.3 (M+H).

The following compounds in Table 18 are prepared essentially as described for 2-(4-(5-amino-4-cyano-1-(1-hydroxy-2-methylpropan-2-yl)-1H-pyrazol-3-yl)phenyl)-N-(3-neopentylisoxazol-5-yl)acetamide using the appropriate hydrazine from 1-3 equivalents, adjusting reaction time to determine completion of the reaction, and purification conditions as appropriate. The reaction temperature can range from RT to 45° C., and THF can be substituted for the solvent based on solubility.

TABLE 18

| Prep. No. | Chemical name | Structure | ES/MS m/z (M + H) |
|---|---|---|---|
| 156 | 2-(4-(5-Amino-4-cyano-1-(1-cyclopropylethyl)-1H-pyrazol-3-yl)phenyl)-N-(3-neopentylisoxazol-5-yl)acetamide | 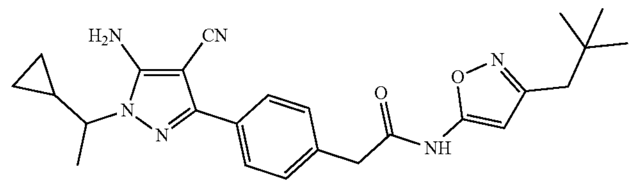 [SMILES: CC(C1CC1)n1nc(-c2ccc(CC(=O)Nc3cc(CC(C)(C)C)no3)cc2)c(C#N)c1N] | 447.2 |
| 157 | 2-(4-(5-Amino-4-cyano-1-(tetrahydrofuran-3-yl)-1H-pyrazol-3-yl)phenyl)-N-(3-neopentylisoxazol-5-yl)acetamide | 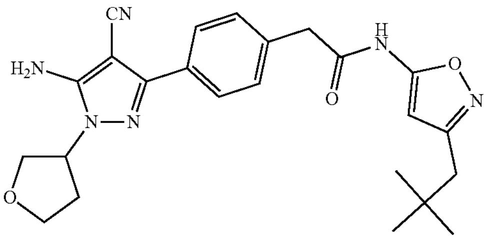 [SMILES: CC(C)(C)Cc1cc(NC(=O)Cc2ccc(-c3nn(C4CCOC4)c(N)c3C#N)cc2)on1] | 449.2 |
| 158 | 2-(4-(5-Amino-4-cyano-1-cyclopentyl-1H-pyrazol-3-yl)phenyl)-N-(3-neopentylisoxazol-5-yl)acetamide | 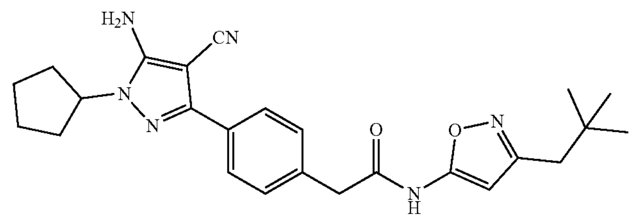 [SMILES: CC(C)(C)Cc1cc(NC(=O)Cc2ccc(-c3nn(C4CCCC4)c(N)c3C#N)cc2)on1] | 447.2 |
| 159 | 2-(4-(5-Amino-4-cyano-1-(tetrahydro-2H-pyran-3-yl)-1H-pyrazol-3-yl)phenyl)-N-(3-neopentylisoxazol-5-yl)acetamide | 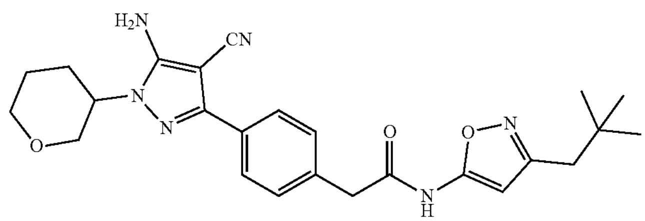 [SMILES: CC(C)(C)Cc1cc(NC(=O)Cc2ccc(-c3nn(C4CCCOC4)c(N)c3C#N)cc2)on1] | 463.2 |
| 160 | 2-(4-(5-Amino-4-cyano-1-(tetrahydro-2H-pyran-4-yl)-1H-pyrazol-3-yl)phenyl)-N-(3-neopentylisoxazol-5-yl)acetamide | 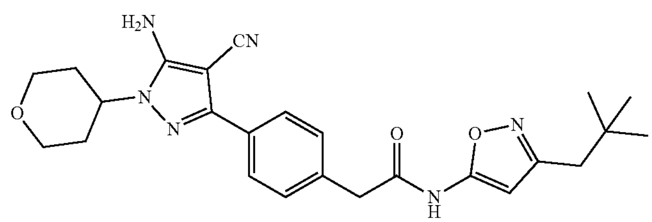 [SMILES: CC(C)(C)Cc1cc(NC(=O)Cc2ccc(-c3nn(C4CCOCC4)c(N)c3C#N)cc2)on1] | 463.2 |
| 161 | 2-(4-(5-Amino-4-cyano-1-((1R,3R)-3-ethoxycyclobutyl)-1H-pyrazol-3-yl)phenyl)-N-(3-neopentylisoxazol-5-yl)acetamide | 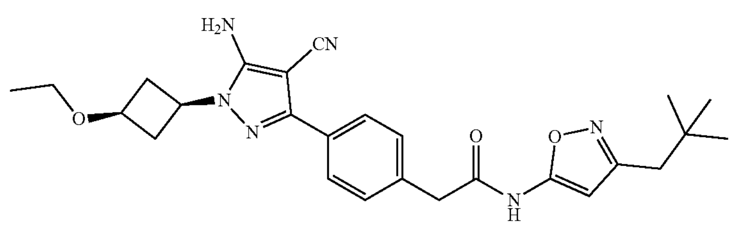 [SMILES: CCO[C@H]1C[C@@H](n2nc(-c3ccc(CC(=O)Nc4cc(CC(C)(C)C)no4)cc3)c(C#N)c2N)C1] | 477.2 |
| 162 | 2-(4-(5-Amino-4-cyano-1-(3-hydroxypropyl)-1H-pyrazol-3-yl)phenyl)-N-(3-neopentylisoxazol-5-yl)acetamide | 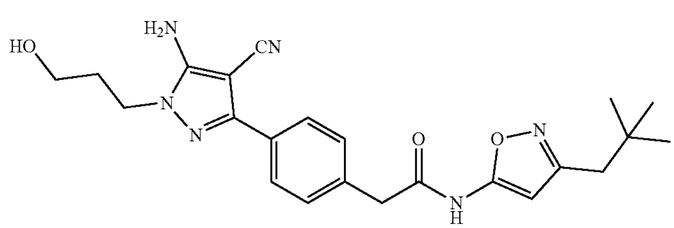 [SMILES: CC(C)(C)Cc1cc(NC(=O)Cc2ccc(-c3nn(CCCO)c(N)c3C#N)cc2)on1] | 437.2 |

TABLE 18-continued

| Prep. No. | Chemical name | Structure | ES/MS m/z (M + H) |
|---|---|---|---|
| 163 | 2-(4-(5-Amino-4-cyano-1-((tetrahydrofuran-3-yl)methyl)-1H-pyrazol-3-yl)phenyl)-N-(3-neopentylisoxazol-5-yl)acetamide | 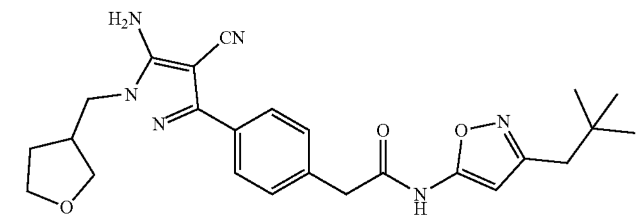 [SMILES: CC(C)(C)Cc1cc(NC(=O)Cc2ccc(C(=N)/C(C#N)=C(/N)NCC3CCOC3)cc2)on1] | 463.2 |
| 164 | 2-(4-(5-Amino-4-cyano-1-(1-hydroxypropan-2-yl)-1H-pyrazol-3-yl)phenyl)-N-(3-neopentylisoxazol-5-yl)acetamide | 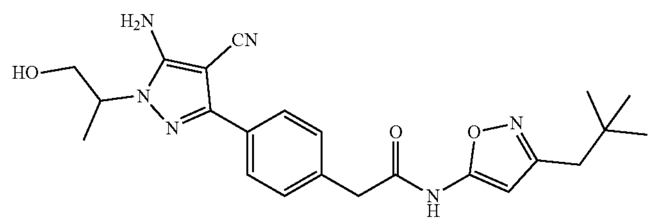 [SMILES: CC(CO)n1nc(-c2ccc(CC(=O)Nc3cc(CC(C)(C)C)no3)cc2)c(C#N)c1N] | 437.2 |
| 165 | 2-(4-(5-Amino-1-(tert-butyl)-4-cyano-1H-pyrazol-3-yl)phenyl)-N-(3-neopentylisoxazol-5-yl)acetamide | 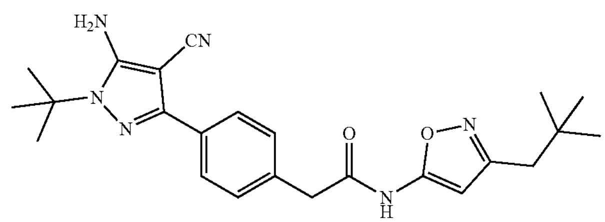 [SMILES: CC(C)(C)Cc1cc(NC(=O)Cc2ccc(-c3nn(C(C)(C)C)c(N)c3C#N)cc2)on1] | 435.2 |
| 166 | 2-[4-(5-Amino-4-cyano-1-cyclopropyl-pyrazol-3-yl)phenyl]-N-[3-(2,2-dimethylpropyl)isoxazol-5-yl]acetamide | 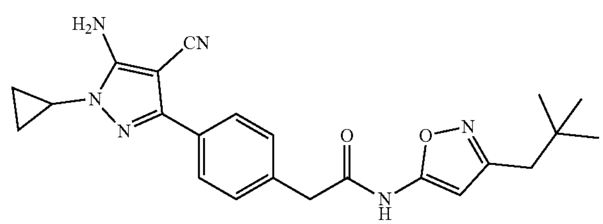 [SMILES: CC(C)(C)Cc1cc(NC(=O)Cc2ccc(-c3nn(C4CC4)c(N)c3C#N)cc2)on1] | 419.2 |
| 167 | 2-(4-(5-Amino-1-(bicyclo[1.1.1]pentan-1-yl)-4-cyano-1H-pyrazol-3-yl)phenyl)-N-(3-neopentylisoxazol-5-yl)acetamide | 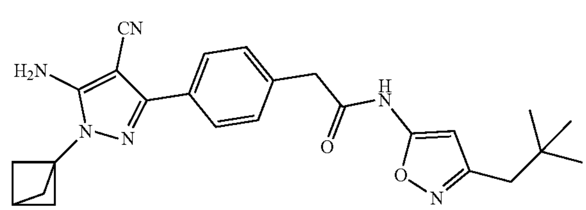 [SMILES: CC(C)(C)Cc1cc(NC(=O)Cc2ccc(-c3nn(C45CC(C4)C5)c(N)c3C#N)cc2)on1] | 445.2 |
| 168 | 2-(4-(5-Amino-4-cyano-1-(2,2,2-trifluoroethyl)-1H-pyrazol-3-yl)phenyl)-N-(3-neopentylisoxazol-5-yl)acetamide | 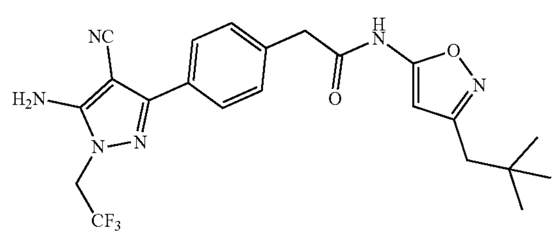 [SMILES: CC(C)(C)Cc1cc(NC(=O)Cc2ccc(-c3nn(CC(F)(F)F)c(N)c3C#N)cc2)on1] | 461.1 |

TABLE 18-continued

| Prep. No. | Chemical name | Structure | ES/MS m/z (M + H) |
|---|---|---|---|
| 169 | 2-[4-[5-Amino-4-cyano-1-(1-hydroxypropan-2-yl)pyrazol-3-yl]phenyl]-N-[3-(2-chloro-4-fluorophenyl)-1,2-oxazol-5-yl]acetamide | 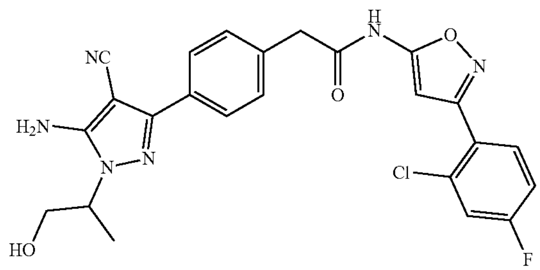 [SMILES: CC(CO)n1nc(-c2ccc(CC(=O)Nc3cc(-c4ccc(F)cc4Cl)no3)cc2)c(C#N)c1N] | 495.1 |
| 170 | 2-[4-[5-Amino-4-cyano-1-(1-hydroxy-2-methylpropan-2-yl)pyrazol-3-yl]phenyl]-N-[3-(2-chloro-4-fluorophenyl)-1,2-oxazol-5-yl]acetamide | 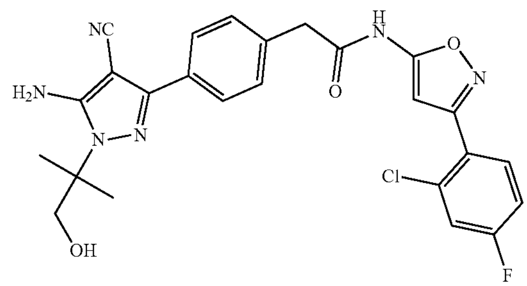 [SMILES: CC(C)(CO)n1nc(-c2ccc(CC(=O)Nc3cc(-c4ccc(F)cc4Cl)no3)cc2)c(C#N)c1N] | 509.3 |
| 171 | 2-[4-[5-Amino-4-cyano-1-(1-hydroxypropan-2-yl)pyrazol-3-yl]phenyl]-N-[3-[4-(trifluoromethyl)bicyclo[2.2.1]heptan-1-yl]-1,2-oxazol-5-yl]acetamide | 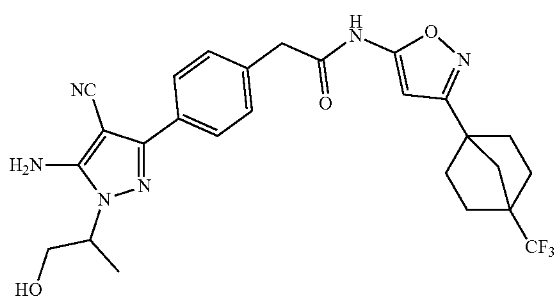 [SMILES: CC(CO)n1nc(-c2ccc(CC(=O)Nc3cc(C45CCC(C(F)(F)F)(CC4)C5)no3)cc2)c(C#N)c1N] | 529.1 |
| 172 | 2-[4-[5-Amino-4-cyano-1-(1-hydroxy-2-methylpropan-2-yl)pyrazol-3-yl]phenyl]-N-[3-[4-(trifluoromethyl)bicyclo[2.2.1]heptan-1-yl]-1,2-oxazol-5-yl]acetamide | 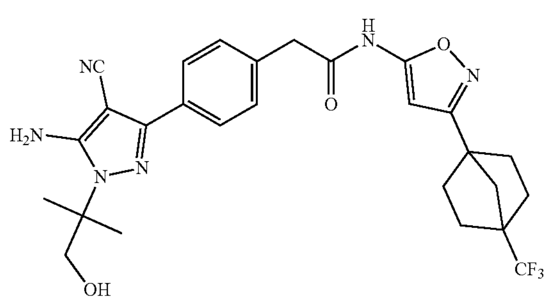 [SMILES: CC(C)(CO)n1nc(-c2ccc(CC(=O)Nc3cc(C45CCC(C(F)(F)F)(CC4)C5)no3)cc2)c(C#N)c1N] | 543.4 |

Preparation 173

2-(4-(5-Amino-4-carbamoyl-1-isopropyl-1H-pyrazol-3-yl)phenyl)acetic Acid

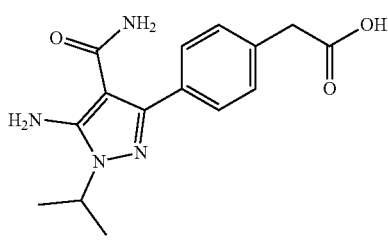 [SMILES: CC(C)n1nc(-c2ccc(CC(=O)O)cc2)c(C(N)=O)c1N]

To a mixture of methyl 2-[4-(5-amino-4-cyano-1-isopropylpyrazol-3-yl)phenyl]acetate (7.40 g, 24.8 mmol), NaOH (5.96 g, 149 mmol), H$_2$O (24 mL), DMSO (12 mL) and EtOH (60 mL) is added H$_2$O$_2$ (38.0 mL, 372 mmol, 30% in H$_2$O) at RT. The mixture is heated to 40° C. and stirred for 6 hr. The mixture is quenched with saturated aq. Na$_2$S2O3 and adjusted to pH 4 with dilute aq. HCl. The mixture is extracted with EtOAc (3×200 mL). The combined organic extracts are concentrated under reduced pressure and the resulting solid is triturated with EtOAc (20 mL). The precipitated solid is collected by filtration, washed with water (3×60 mL), and dried under reduced pressure to give the title compound (4.30 g, 57%) as a yellow solid. ES/MS (m/z) 303.1 (M+H).

Preparation 174

2-(4-(5-Amino-4-carbamoyl-1-(1-methylcyclopropyl)-1H-pyrazol-3-yl)phenyl)acetic Acid

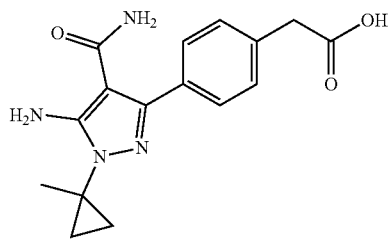 [SMILES: CC1(n2nc(-c3ccc(CC(=O)O)cc3)c(C(N)=O)c2N)CC1]

To a stirred mixture of methyl 2-(4-(5-amino-4-cyano-1-(1-methylcyclopropyl)-1H-pyrazol-3-yl)phenyl)acetate (0.50 g, 1.61 mmol) and NaOH (0.32 g, 8.00 mmol) in EtOH/H$_2$O/DMSO (5 mL/2 mL/1 mL) is added H$_2$O$_2$ (2.43 mL, 23.8 mmol, 30% in H$_2$O) dropwise at RT under N$_2$. The mixture is stirred overnight at 50° C. The reaction is quenched with saturated aq. Na$_2$SO$_3$ (10 mL) at RT. The residue is adjusted to pH 4 with 1N aq. HCl and extracted with EtOAc (5×50 mL). The combined organic extracts are washed with brine (2×100 mL), dried over anhydrous Na$_2$SO$_4$, filtered, and the filtrate is concentrated under reduced pressure. The resulting solid is triturated with EtOAc (10 mL) and the precipitated solids are collected by filtration and washed with EtOAc (3×5 mL) to give the title compound (0.20 g, 40%) as a white solid. ES/MS (m/z) 315.2 (M+H).

The following compounds in Table 19 are prepared essentially as described for 2-(4-(5-amino-4-carbamoyl-1-(1-methylcyclopropyl)-1H-pyrazol-3-yl)phenyl)acetic acid, adjusting the reaction time to determine completion of the reaction and purifying by titration or chromatography as appropriate. The reaction temperature can range from about RT to 50° C. and about 15-30 equiv of H$_2$O$_2$ can be used. The reagents can also be added together at about 0° C.

TABLE 19

| Prep No. | Chemical Name | Structure | ES/MS m/z (M + H) |
|---|---|---|---|
| 175 | [4-(5-Amino-4-carbamoyl-1-isopropylpyrazol-3-yl)-3-chlorophenyl]acetic acid | 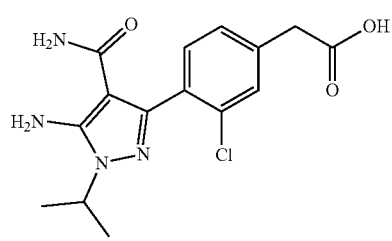 [SMILES: CC(C)n1nc(-c2ccc(CC(=O)O)cc2Cl)c(C(N)=O)c1N] | 337.1 |

TABLE 19-continued

| Prep No. | Chemical Name | Structure | ES/MS m/z (M + H) |
|---|---|---|---|
| 176 | [4-(5-Amino-1-tert-butyl-4-carbamoylpyrazol-3-yl)phenyl]acetic acid | 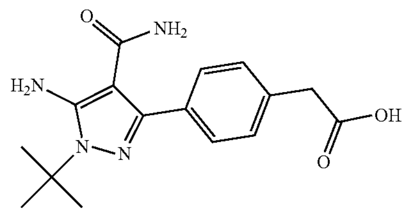 [SMILES: CC(C)(C)n1nc(-c2ccc(CC(=O)O)cc2)c(C(N)=O)c1N] | 317.1 |
| 177 | 2-(4-(5-Amino-4-carbamoyl-1-cyclopentyl-1H-pyrazol-3-yl)phenyl)acetic acid | 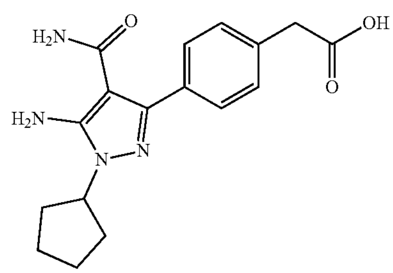 [SMILES: NC(=O)c1c(-c2ccc(CC(=O)O)cc2)nn(C2CCCC2)c1N] | 329 |
| 178 | 2-(4-(5-Amino-4-carbamoyl-1-(1,1,1-trifluoropropan-2-yl)-1H-pyrazol-3-yl)phenyl)acetic acid | 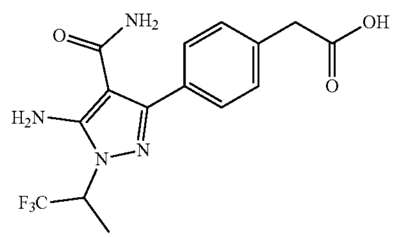 [SMILES: CC(n1nc(-c2ccc(CC(=O)O)cc2)c(C(N)=O)c1N)C(F)(F)F] | 357.1 |
| 179 | [4-(5-Amino-4-carbamoyl-1-isopropylpyrazol-3-yl)-2-fluorophenyl]acetic acid | 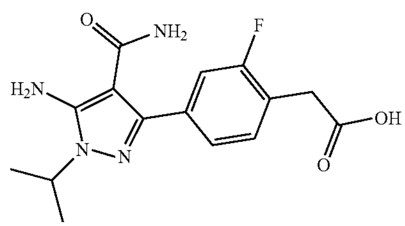 [SMILES: CC(C)n1nc(-c2ccc(CC(=O)O)c(F)c2)c(C(N)=O)c1N] | 321.1 |

Preparation 180

2-(4-(5-Amino-4-carbamoyl-1-(1,1,1-trifluoropropan-2-yl)-1H-pyrazol-3-yl)phenyl)acetic Acid, Isomer 1

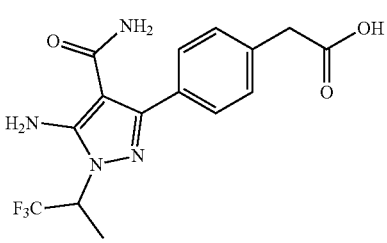 [SMILES: CC(n1nc(-c2ccc(CC(=O)O)cc2)c(C(N)=O)c1N)C(F)(F)F]

Preparation 181

2-(4-(5-Amino-4-carbamoyl-1-(1,1,1-trifluoropropan-2-yl)-1H-pyrazol-3-yl)phenyl)acetic Acid, Isomer 2

2-(4-(5-Amino-4-carbamoyl-1-(1,1,1-trifluoropropan-2-yl)-1H-pyrazol-3-yl)phenyl)acetic acid (0.500 g, 1.40 mmol) is separated by Chiral-HPLC with the following conditions: Column: CHIRALPAK IG, 2*25 cm, 5 μm; mobile phase A: hexanes (0.1% TFA), Mobile Phase B: IPA with a flow rate of 20 mL/min eluting with 25% B in 12.5 min; to give the title compound of Isomer 1 as a light yellow solid $t_{(R)}$ 6.7 min, (0.240 g, 48%), ES/MS (m/z) 357.1 (M+H), $[\alpha]_D^{25}$=−15.789 (C=0.304, MeOH) and Isomer 2 as a light yellow solid $t_{(R)}$ 9.5 min (0.210 g, 42%), ES/MS (m/z) 357.1 (M+H), $[\alpha]_D^{25}$=17.197 (C=0.314, MeOH).

Preparation 182

2-[4-(1-Isopropyl-6,6-dimethyl-4-oxo-5,7-dihydropyrazolo[3,4-d]pyrimidin-3-yl)phenyl]acetic Acid

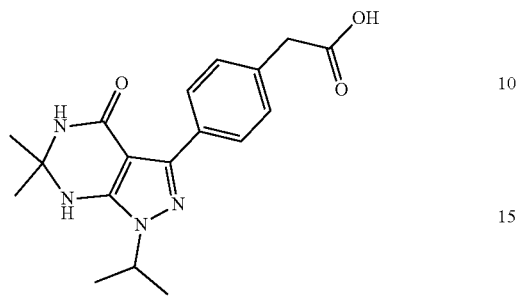

To 2-(4-(5-amino-4-carbamoyl-1-isopropyl-1H-pyrazol-3-yl)phenyl)acetic acid (0.100 g, 0.331 mmol) in acetone (5 mL) is added TFA (0.005 mL). The mixture is stirred for 2 hr at 50° C., concentrated under reduced pressure, and dried under vacuum to give the title compound as a yellow solid (0.113 g, 100%) which is used without further purification. ES/MS (m/z) 343.2 (M+H).

The following compounds in Table 20 are prepared essentially as described for 2-[4-(1-isopropyl-6,6-dimethyl-4-oxo-5,7-dihydropyrazolo[3,4-d]pyrimidin-3-yl)phenyl]acetic acid and adjusting reaction time to determine completion of the reaction.

TABLE 20

| Prep No. | Chemical Name | Structure | ES/MS m/z (M + H) |
|---|---|---|---|
| 183 | 2-[4-(1-Isopropyl-6,6-dimethyl-4-oxo-5,7-dihydropyrazolo[3,4-d]pyrimidin-3-yl)-2-methoxyphenyl]acetic acid; ½ TFA | 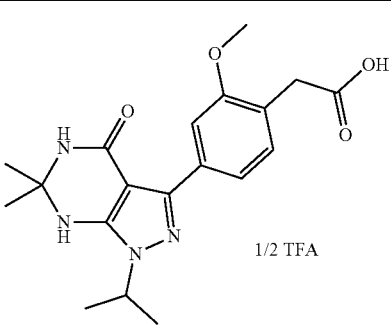 | 373.2 |
| [1]184 | 2-[2,6-Difluoro-4-(1-isopropyl-6,6-dimethyl-4-oxo-5,7-dihydropyrazolo[3,4-d]pyrimidin-3-yl)phenyl]acetic acid | 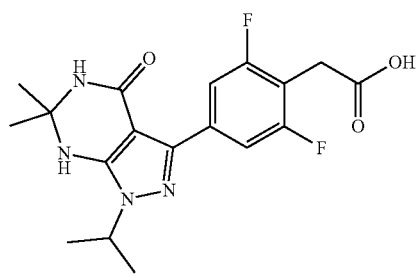 [SMILES: CC(C)n1nc(-c2cc(F)c(CC(=O)O)c(F)c2)c2c1NC(C)(C)NC2=O] | 379 |

[1] Ethoxyethane HCl is substituted for TFA and the mixture is stirred at RT for 30 min.

Preparation 185

2-(4-(5-Amino-4-cyano-1-(1-methylcyclopropyl)-1H-pyrazol-3-yl)phenyl)acetic Acid

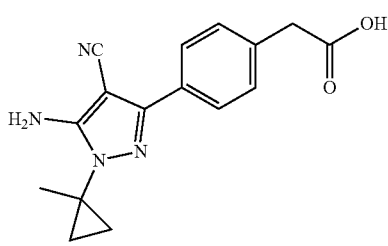 [SMILES: CC1(n2nc(-c3ccc(CC(=O)O)cc3)c(C#N)c2N)CC1]

A solution of methyl 2-(4-(5-amino-4-cyano-1-(1-methylcyclopropyl)-1H-pyrazol-3-yl)phenyl)acetate (4.30 g, 13.9 mmol) and LiOH (1.66 g, 69.3 mmol) in THF (40 mL) and $H_2O$ (10 mL) is stirred for 3 hr at RT under $N_2$. The mixture is concentrated under reduced pressure, diluted with $H_2O$ (10 mL) and acidified to pH 3 with 1N aq. HCl. The precipitated solids are collected by filtration and washed with $H_2O$ (3×30 mL) to give the title compound (4.00 g, 97%) as a white solid. ES/MS (m/z) 297.3 (M+H).

The following compounds in Table 21 are prepared essentially as described for 2-(4-(5-amino-4-cyano-1-(1-methylcyclopropyl)-1H-pyrazol-3-yl)phenyl)acetic acid using the appropriate ester, adjusting the reaction time to determine completion of the reaction, adjusting the pH to 1-5 after completion, and collecting by extraction or precipitation as appropriate. A solvent mixture of 1,4-dioxane/$H_2O$ or MeOH/$H_2O$ can be used if needed for solubility and the temperature can range from about RT to 50°. 1 M NaOH can be substituted for LiOH and citric acid or $KHSO_4$ can be substituted for HCL.

TABLE 21

| Prep. No. | Chemical name | Structure | ES/MS m/z (M + H) |
|---|---|---|---|
| 186 | [4-[5-Amino-4-cyano-1-(1,1,1-trifluoro-2-methylpropan-2-yl)pyrazol-3-yl]phenyl]acetic acid: | 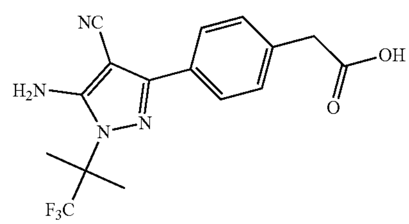 [SMILES: CC(C)(n1nc(-c2ccc(CC(=O)O)cc2)c(C#N)c1N)C(F)(F)F] | 353.1 |
| 187 | 2-[4-[5-Amino-4-cyano-1-(2-methoxy-1,1-dimethyl-ethyl)pyrazol-3-yl]phenyl]acetic acid | 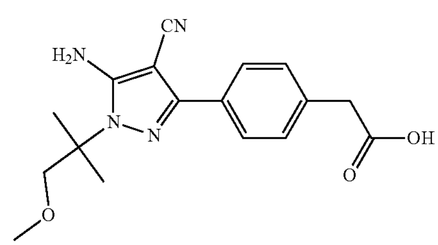 [SMILES: COCC(C)(C)n1nc(-c2ccc(CC(=O)O)cc2)c(C#N)c1N] | 329.2 |
| 188 | 2-[4-[5-Amino-4-cyano-1-(2,2,2-trifluoro-1-methyl-ethyl)pyrazol-3-yl]phenyl]acetic acid | 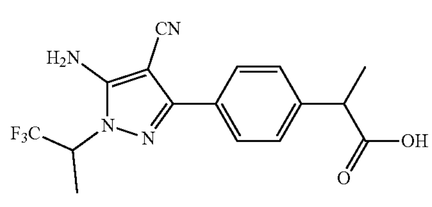 [SMILES: CC(C(=O)O)c1ccc(-c2nn(C(C)C(F)(F)F)c(N)c2C#N)cc1] | 339.2 M + Na |
| 189 | [4-[5-Amino-4-cyano-1-(2,2,2-trifluoroethyl)pyrazol-3-yl]phenyl]acetic acid | 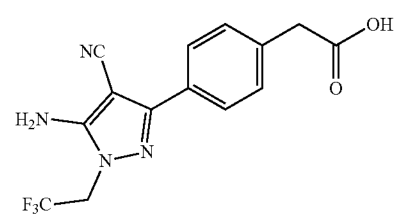 [SMILES: N#Cc1c(-c2ccc(CC(=O)O)cc2)nn(CC(F)(F)F)c1N] | 325.1 |

TABLE 21-continued

| Prep. No. | Chemical name | Structure | ES/MS m/z (M + H) |
|---|---|---|---|
| 190 | [4-(5-Amino-4-cyano-1-cyclobutylpyrazol-3-yl)phenyl]acetic acid | 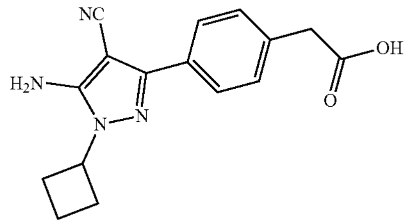 [SMILES: N#Cc1c(-c2ccc(CC(=O)O)cc2)nn(C2CCC2)c1N] | 297.2 |
| 191 | 4-[5-Amino-4-cyano-1-(1,1,1-trifluoro-2-methylpropan-2-yl)pyrazol-3-yl]phenyl]acetic acid | 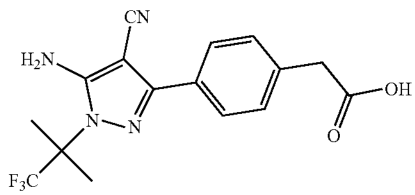 [SMILES: CC(C)(n1nc(-c2ccc(CC(=O)O)cc2)c(C#N)c1N)C(F)(F)F] | 353.2 |
| 192 | [4-(5-Amino-1-tert-butyl-4-cyanopyrazol-3-yl)phenyl]acetic acid | 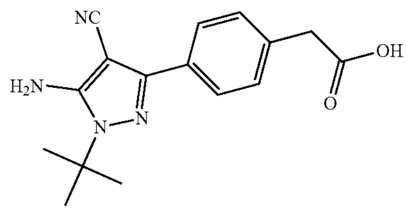 [SMILES: CC(C)(C)n1nc(-c2ccc(CC(=O)O)cc2)c(C#N)c1N] | 299.2 |
| 193 | [4-(5-Amino-1-tert-butyl-4-cyanopyrazol-3-yl)phenyl]acetic acid | 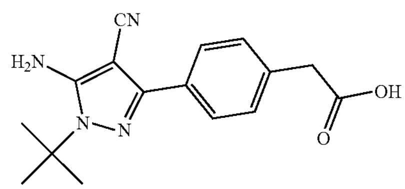 [SMILES: CC(C)(C)n1nc(-c2ccc(CC(=O)O)cc2)c(C#N)c1N] | 299.2 |
| 194 | 2-(4-(5-Amino-4-cyano-1-cyclopentyl-1H-pyrazol-3-yl)phenyl)acetic acid | 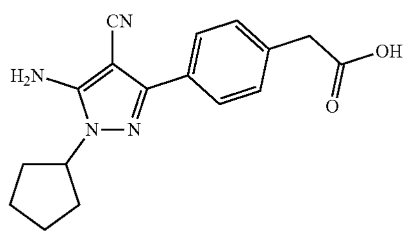 [SMILES: N#Cc1c(-c2ccc(CC(=O)O)cc2)nn(C2CCCC2)c1N] | 311 |
| 195 | 2-(4-(5-Amino-4-cyano-1-(1,1,1-trifluoropropan-2-yl)-1H-pyrazol-3-yl)phenyl)acetic acid | 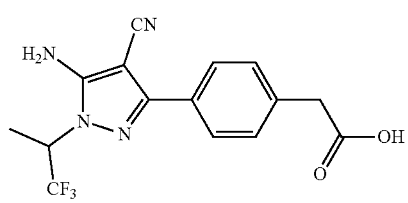 [SMILES: CC(n1nc(-c2ccc(CC(=O)O)cc2)c(C#N)c1N)C(F)(F)F] | 339.2 |
| 196 | [4-(5-Amino-4-cyano-1-isopropylpyrazol-3-yl)-2-fluorophenyl]acetic acid | 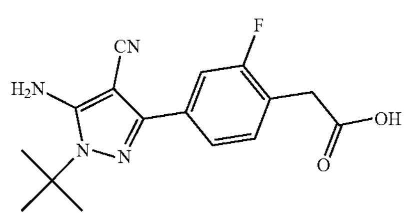 [SMILES: CC(C)(C)n1nc(-c2ccc(CC(=O)O)c(F)c2)c(C#N)c1N] | 303.2 |

TABLE 21-continued

| Prep. No. | Chemical name | Structure | ES/MS m/z (M + H) |
|---|---|---|---|
| 197 | 2-(4-(5-Amino-4-cyano-1-(1-methylcyclopropyl)-1H-pyrazol-3-yl)-3-fluorophenyl)acetic acid | 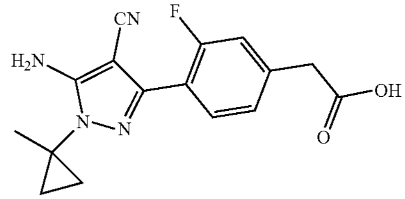 [SMILES: CC1(n2nc(-c3ccc(CC(=O)O)cc3F)c(C#N)c2N)CC1] | 315.2 |
| 198 | [4-(5-Amino-4-cyano-1-isopropylpyrazol-3-yl)-2,3-difluorophenyl]acetic acid | 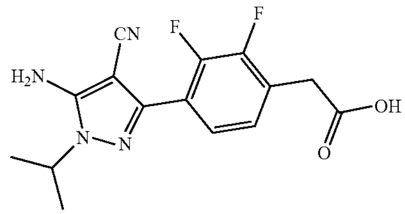 [SMILES: CC(C)n1nc(-c2ccc(CC(=O)O)c(F)c2F)c(C#N)c1N] | 321.1 |
| 199 | [4-(5-Amino-4-cyano-1-isopropylpyrazol-3-yl)phenyl]acetic acid | 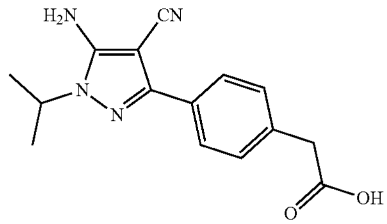 [SMILES: CC(C)n1nc(-c2ccc(CC(=O)O)cc2)c(C#N)c1N] | 285.1 |

Preparation 200

2-[(4-Bromo-2,3-difluorophenyl)(methoxy)methylidene]propanedinitrile

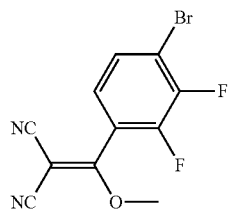 [SMILES: COC(=C(C#N)C#N)c1ccc(Br)c(F)c1F]

NaH (1.67 g, 41.8 mmol, 60% in mineral oil) and malononitrile (1.37 g, 20.7 mmol) are added to THF (50 mL) at 0° C. The mixture is stirred for 30 min at 0° C. under $N_2$. To this mixture is added 4-bromo-2,3-difluorobenzoyl chloride (5.30 g, 20.7 mmol) in THF (10 mL) dropwise at 0° C. The mixture is stirred for 1 hr at RT. The intermediate mixture of 2-[(4-bromo-2,3-difluoro-phenyl)-hydroxy-methylene]propanedinitrile is used directly without further purification. ES/MS (m/z) ($^{79}$Br/$^{81}$Br) 282.9/284.9 (M−H). Dimethyl sulfate (2.4 mL, 25.3 mmol) is added to the solution of 2-[(4-bromo-2,3-difluoro-phenyl)-hydroxy-methylene]propanedinitrile (theoretical 5.90 g, 20.7 mmol) in THF (60 mL). The mixture is stirred overnight at reflux under $N_2$. The solution is cooled to RT and concentrated under reduced pressure. The crude product is dissolved in EtOAc (200 mL) and diluted with $H_2O$ (200 mL) and extracted with EtOAc (3×300 mL). The organic extracts are washed with brine (2×100 mL), dried over anhydrous $Na_2SO_4$, filtered, and concentrated under reduced pressure. The crude product is purified by silica gel chromatography, eluting with a gradient of 3:1 to 2:1 PE:EtOAc to give the title compound (3.00 g, 48%) as a yellow solid.

Preparation 201

5-Amino-3-(4-bromo-2,3-difluorophenyl)-1-(1-methylcyclopropyl)pyrazole-4-carbonitrile

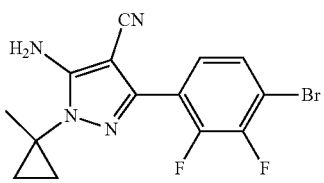 [SMILES: CC1(n2nc(-c3ccc(Br)c(F)c3F)c(C#N)c2N)CC1]

A solution of 2-[(4-bromo-2,3-difluorophenyl)(methoxy)methylidene]propanedinitrile (2.50 g, 8.36 mmol), (1-methylcyclopropyl)hydrazine HCl (3.07 g, 25.0 mmol), and TEA (5.8 mL, 41.6 mmol) in THF (30 mL) is stirred for 1 hr at RT under $N_2$. The reaction is concentrated under reduced pressure and the residue is purified by silica gel chromatography, eluting with a gradient of 3:1 to 2:1 PE:EtOAc to give the title compound (2.50 g, 85%) as a light yellow solid. ES/MS (m/z) ($^{79}$Br/$^{81}$Br) 353.1/355.1 (M+H).

Preparation 202 tert-Butyl 2-[4-[5-amino-4-cyano-1-(1-methylcyclopropyl)pyrazol-3-yl]-2,3-difluorophenyl]acetate

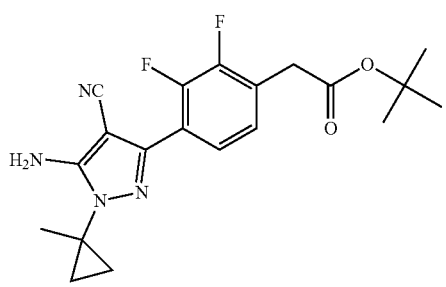 [SMILES: CC(C)(C)OC(=O)Cc1ccc(-c2nn(C3(C)CC3)c(N)c2C#N)c(F)c1F]

A solution of 5-amino-3-(4-bromo-2,3-difluorophenyl)-1-(1-methylcyclopropyl)pyrazole-4-carbonitrile (1.80 g, 5.10 mmol), tert-butyl 2-(bromozincio)acetate (3.98 g, 15.3 mmol) and Pd(t-Bu$_3$P)$_2$ (0.26 g, 0.509 mmol) in THF (20 mL) is stirred for 1 hr at 80° C. under N$_2$ and allowed to cool to RT. The solution is concentrated under reduced pressure and the residue is purified by silica gel chromatography, eluting with a gradient of 2:1 to 1:1 PE:EtOAc to give the title compound (0.50 g, 25%) as a yellow solid. ES/MS (m/z) 389.2 (M+H).

Preparation 203

2-[4-[5-Amino-4-cyano-1-(1-methylcyclopropyl)pyrazol-3-yl]-2,3-difluoro-phenyl]acetic Acid

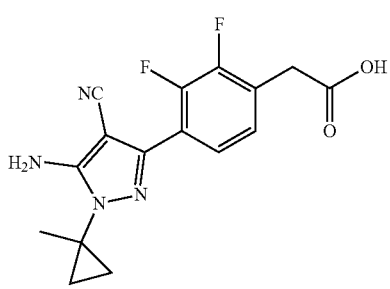 [SMILES: CC1(n2nc(-c3ccc(CC(=O)O)c(F)c3F)c(C#N)c2N)CC1]

A solution of tert-butyl 2-[4-[5-amino-4-cyano-1-(1-methylcyclopropyl)pyrazol-3-yl]-2,3-difluorophenyl]acetate (0.49 g, 1.26 mmol) and TFA (5 mL) in DCM (10 mL) is stirred for 2 hr at RT under N$_2$ and concentrated under reduced pressure. The mixture is diluted with Et$_2$O (20 mL) and concentrated under reduced pressure to give the title compound (0.40 g, 96%) as a yellow solid. ES/MS (m/z) 333.1 (M+H).

Preparation 204

2-[4-[5-Amino-4-cyano-1-(1-methylcyclopropyl)pyrazol-3-yl]-2,3-difluorophenyl]-N-(3-[3-fluorobicyclo[1.1.1]pentan-1-yl]-1,2-oxazol-5-yl)acetamide

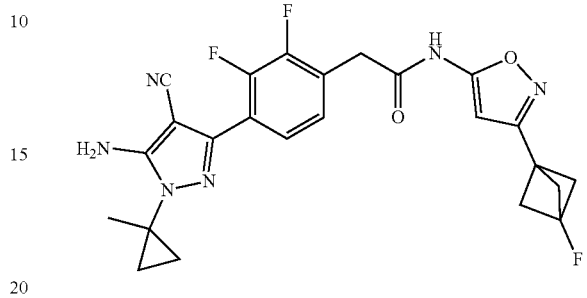

A solution of 2-[4-[5-amino-4-cyano-1-(1-methylcyclopropyl)pyrazol-3-yl]-2,3-difluoro-phenyl]acetic acid (80 mg, 0.241 mmol), 3-(3-fluorobicyclo[1.1.1]pentan-1-yl)isoxazol-5-amine (49 mg, 0.291 mmol), DIPEA (0.25 mL, 1.44 mmol), and T3P® (0.46 g, 0.723 mmol, 50% in EtOAc) in DCM (3.00 mL) is stirred for 1 hr at 50° C. under N$_2$. The mixture is cooled to RT and concentrated under reduced pressure. The residue is purified by reversed-phase chromatography (C18 column), eluting with a gradient of 40% to 60% ACN in H$_2$O (0.1% FA) to give the title compound (60 mg, 52%) as a yellow solid. ES/MS (m/z) 483.1 (M+H).

Preparation 205

2-[4-[5-Amino-4-cyano-1-(1-methylcyclopropyl)pyrazol-3-yl]-2,3-difluorophenyl]-N-(3-[3-methylbicyclo[1.1.1]pentan-1-yl]-1,2-oxazol-5-yl)acetamide

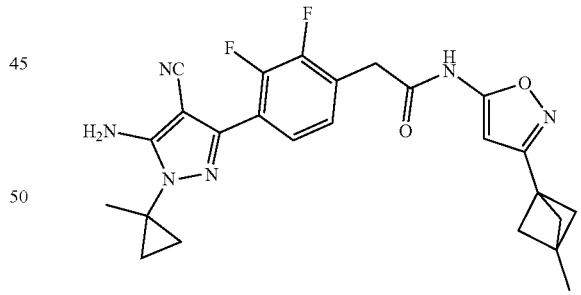

To a solution of 2-[4-[5-amino-4-cyano-1-(1-methylcyclopropyl)pyrazol-3-yl]-2,3-difluoro-phenyl]acetic acid (80 mg, 0.241 mmol), 3-[3-methylbicyclo[1.1.1]pentan-1-yl]-1,2-oxazol-5-amine (47 mg, 0.286 mmol) and DIPEA (0.13 mL, 0.746 mmol) in DCM (3 mL) is added T3P® (0.46 g, 0.723 mmol, 50% in EtOAc). The reaction is stirred for 2 hr at 50° C. in a sealed tube. The mixture is cooled to RT and concentrated under reduced pressure. The residue is purified by reversed-phase chromatography (C18 column), eluting with a gradient of 40% to 60% ACN in H$_2$O (0.1% NH$_4$HCO$_3$) to give the title compound (70 mg, 61%) as a white solid. ES/MS (m/z) 479.1 (M+H).

Preparation 206

2-(4-(5-Amino-4-cyano-1-(1-methylcyclopropyl)-1H-pyrazol-3-yl)phenyl)-N-(3-(2-chloro-4-fluorophenyl)isoxazol-5-yl)acetamide

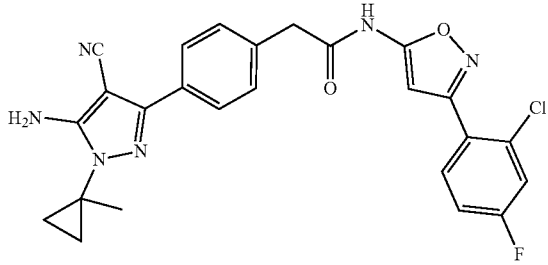 [SMILES: CC1(n2nc(-c3ccc(CC(=O)Nc4cc(-c5ccc(F)cc5Cl)no4)cc3)c(C#N)c2N)CC1]

2-(4-(5-Amino-4-cyano-1-(1-methylcyclopropyl)-1H-pyrazol-3-yl)phenyl)acetic acid (60 mg, 0.202 mmol) is dissolved in DCM (0.41 mL) and treated with 3-(2-chloro-4-fluoro-phenyl)isoxazol-5-amine (47 mg, 0.221 mmol), T3P® (0.77 g, 1.21 mmol, 50% in EtOAc), and DIPEA (0.21 mL, 1.18 mmol) at 0° C. The mixture is stirred for about 20 min, evaporated to dryness, and used without further purification. ES/MS (m/z) 491.1 (M+H).

Preparation 207

2-[4-(5-Amino-4-cyano-1-isopropylpyrazol-3-yl)phenyl]-N-[3-(pyridin-2-yl)-1,2-oxazol-5-yl]acetamide

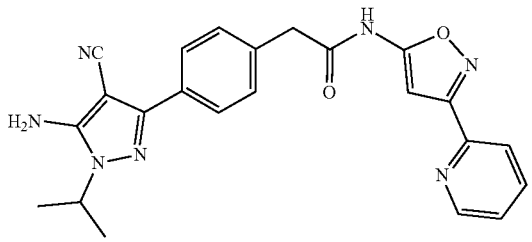 [SMILES: CC(C)n1nc(-c2ccc(CC(=O)Nc3cc(-c4ccccn4)no3)cc2)c(C#N)c1N]

To a stirred mixture of [4-(5-amino-4-cyano-1-isopropylpyrazol-3-yl)phenyl]acetic acid (0.100 g, 0.352 mmol) and 3-(pyridin-2-yl)-1,2-oxazol-5-amine (62 mg, 0.385 mmol) in DCM (3 mL) is added T3P® (0.337 g, 0.530 mmol, 50% in EtOAc) and DIPEA (0.31 mL, 1.78 mmol). The mixture is stirred for 2 hr at RT and concentrated under reduced pressure. The residue is purified by reversed-phase chromatography (C18 column), eluting with a gradient of 10% to 50% ACN in $H_2O$ (0.1% FA) to give the title compound (70 mg, 47%) as a light yellow solid. ES/MS (m/z) 428.2 (M+H).

The following compounds in Table 22 are prepared essentially as described for 2-[4-(5-amino-4-cyano-1-isopropylpyrazol-3-yl)phenyl]-N-[3-(pyridin-2-yl)-1,2-oxazol-5-yl] acetamide using the appropriate amine and carboxylic acid with a coupling reagent, about 1-6 equivalents, base, about 1-4 equiv, and solvent, about 0.3-6 mL, adjusting the reaction time to determine completion of the reaction, and purification conditions as appropriate. The reaction temperature can range from −20° C. to 50° C., T3P® can be added in 50% EtOAc, 50% DMF, or 50% MeTHF. TCFH can be added in portions and the reaction can be done under $N_2$ and in a sealed tube.

*Coupling reagents: 1 T3P®, 2 TCFH, 3 BTFFH, 4 COMU®, 5 TBTU, 6 TFFH, 7 HATU 8 EDCI/HOBT Bases: a NMI, b pyridine, c DIPEA Solvents: I EtOAc, II ACN, III DMF, IV DCM, V MeTHF

TABLE 22

| Prep. No. | Chemical name | Structure | ES/MS m/z (M + H) | * |
|---|---|---|---|---|
| 208 | 2-(4-(5-Amino-4-cyano-1-isopropyl-1H-pyrazol-3-yl)phenyl)-N-(3-(3,3,3-trifluoro-2,2-dimethylpropyl)isoxazol-5-yl)acetamide | 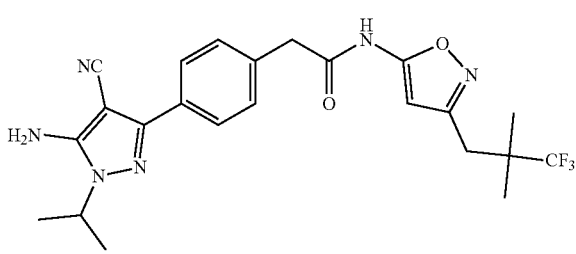 [SMILES: CC(C)n1nc(-c2ccc(CC(=O)Nc3cc(CC(C)(C)C(F)(F)F)no3)cc2)c(C#N)c1N] | 474.9 | 1, b, I |

TABLE 22-continued

| Prep. No. | Chemical name | Structure | ES/MS m/z (M + H) | * |
|---|---|---|---|---|
| 209 | 2-(4-(5-Amino-4-cyano-1-isopropyl-1H-pyrazol-3-yl)phenyl)-N-(3-(4-fluorobicyclo[2.2.2]octan-1-yl)isoxazol-5-yl)acetamide | 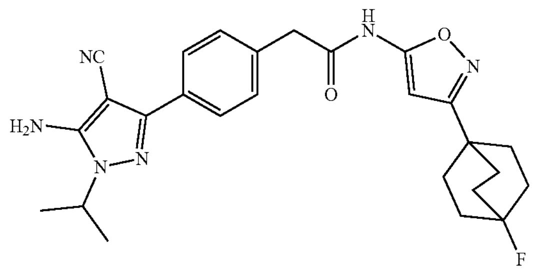 [SMILES: CC(C)n1nc(-c2ccc(CC(=O)Nc3cc(C45CCC(F)(CC4)CC5)no3)cc2)c(C#N)c1N] | 477.2 | 1, b, I |
| 210 | 2-(4-(5-Amino-4-cyano-1-cyclobutyl-1H-pyrazol-3-yl)phenyl)-N-(3-neopentylisoxazol-5-yl)acetamide | 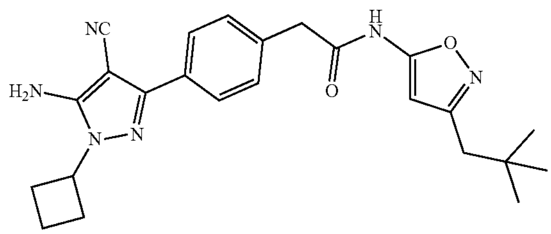 [SMILES: CC(C)(C)Cc1cc(NC(=O)Cc2ccc(-c3nn(C4CCC4)c(N)c3C#N)cc2)on1] | 433.2 | 1, c, III |
| 211 | 2-(4-(5-Amino-4-cyano-1-(2,2,2-trifluoroethyl)-1H-pyrazol-3-yl)phenyl)-N-(3-neopentylisoxazol-5-yl)acetamide | 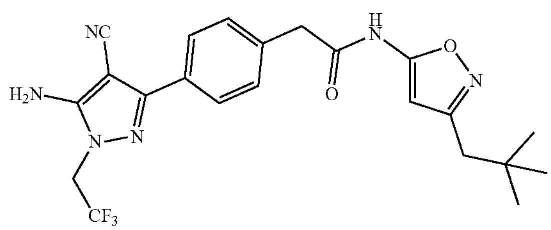 [SMILES: CC(C)(C)Cc1cc(NC(=O)Cc2ccc(-c3nn(CC(F)(F)F)c(N)c3C#N)cc2)on1] | 461.1 | 1, c, III |
| 212 | 2-(4-(5-Amino-4-cyano-1-isopropyl-1H-pyrazol-3-yl)phenyl)-N-(3-benzylisoxazol-5-yl)acetamide | 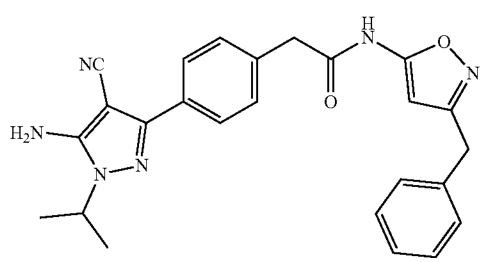 [SMILES: CC(C)n1nc(-c2ccc(CC(=O)Nc3cc(Cc4ccccc4)no3)cc2)c(C#N)c1N] | 441.1 | 1, c, III |
| 213 | 2-(4-(5-Amino-4-cyano-1-isopropyl-1H-pyrazol-3-yl)phenyl)-N-(3-(bicyclo[1.1.1]pentan-1-ylmethyl)isoxazol-5-yl)acetamide | 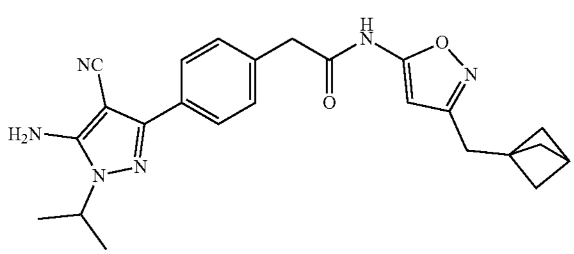 [SMILES: CC(C)n1nc(-c2ccc(CC(=O)Nc3cc(CC45CC(C4)C5)no3)cc2)c(C#N)c1N] | 431.2 | 1, b, I & III |
| 214 | 2-(4-(5-Amino-4-cyano-1-(1-methylcyclopropyl)-1H-pyrazol-3-yl)phenyl)-N-(3-neopentylisoxazol-5-yl)acetamide | 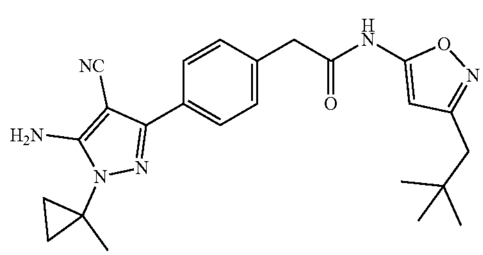 [SMILES: CC(C)(C)Cc1cc(NC(=O)Cc2ccc(-c3nn(C4(C)CC4)c(N)c3C#N)cc2)on1] | 433.2 | 1, c, III |

TABLE 22-continued

| Prep. No. | Chemical name | Structure | ES/MS m/z (M + H) | * |
|---|---|---|---|---|
| 215 | 2-[4-(5-Amino-4-cyano-1-isopropylpyrazol-3-yl)phenyl]-N-[5-(2-methylbutan-2-yl)-1,2-oxazol-3-yl]acetamide | 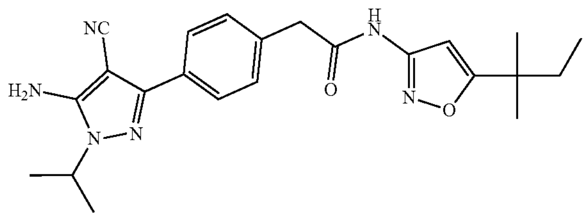 [SMILES: CCC(C)(C)c1cc(NC(=O)Cc2ccc(-c3nn(C(C)C)c(N)c3C#N)cc2)no1] | 421.2 | 1, c, IV |
| 216 | 2-[4-(5-Amino-4-cyano-1-isopropylpyrazol-3-yl)phenyl]-N-[3-(3,5-dichloropyridin-2-yl)-1,2-oxazol-5-yl]acetamide | 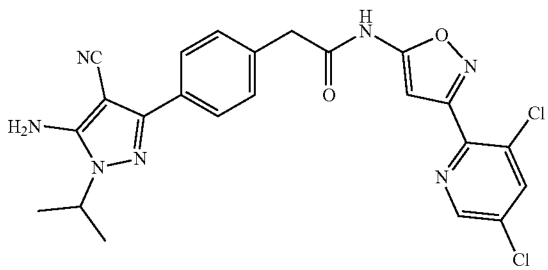 [SMILES: CC(C)n1nc(-c2ccc(CC(=O)Nc3cc(-c4ncc(Cl)cc4Cl)no3)cc2)c(C#N)c1N] | 496.1 | 1, c, IV |
| 217 | 2-[4-(5-Amino-4-cyano-1-isopropylpyrazol-3-yl)phenyl]-N-[5-(2,2-dimethylpropyl)-1,2-thiazol-3-yl]acetamide | 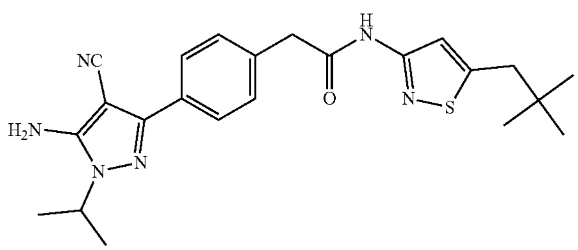 [SMILES: CC(C)n1nc(-c2ccc(CC(=O)Nc3cc(CC(C)(C)C)sn3)cc2)c(C#N)c1N] | 437.1 | 2, a, II |
| 219 | 2-[4-(5-Amino-4-cyano-1-isopropylpyrazol-3-yl)phenyl]-N-[5-(2,2-dimethylpropyl)-1,3-thiazol-2-yl]acetamide | | 437.1 | 1, c, IV |
| 219 | 2-[4-(5-Amino-4-cyano-1-isopropylpyrazol-3-yl)phenyl]-N-[5-(2,2-dimethylpropyl)-4-methyl-1,3-thiazol-2-yl]acetamide | | 451.1 | 2, a, II |
| 220 | 2-[4-[5-Amino-4-cyano-1-(1,1,1-trifluoro-2-methylpropan-2-yl)pyrazol-3-yl]phenyl]-N-[3-(2,2-dimethylpropyl)-1,2-oxazol-5-yl]acetamide | 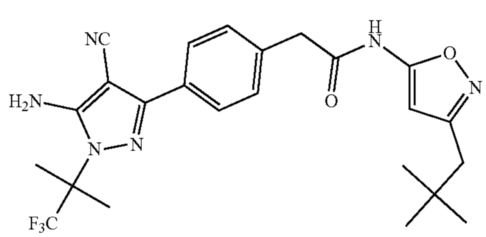 [SMILES: CC(C)(C)Cc1cc(NC(=O)Cc2ccc(-c3nn(C(C)(C)C(F)(F)F)c(N)c3C#N)cc2)on1] | 489.3 | 1, c, IV |

TABLE 22-continued

| Prep. No. | Chemical name | Structure | ES/MS m/z (M + H) | * |
|---|---|---|---|---|
| 221 | 2-[4-[5-amino-4-cyano-1-(1-methylcyclopropyl)pyrazol-3-yl]phenyl]-N-[3-(3,3-dimethylcyclobutyl)-1,2-oxazol-5-yl]acetamide | 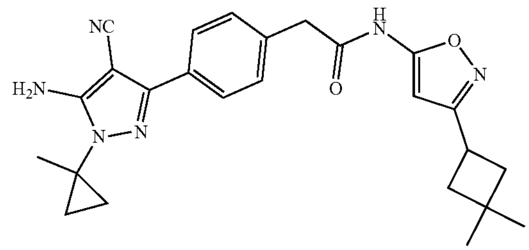 | 445.4 | 1, c, IV |
| 222 | 2-(4-(5-amino-4-cyano-1-(1-methylcyclopropyl)-1H-pyrazol-3-yl)phenyl)-N-(5-neopentylisoxazol-3-yl)acetamide | 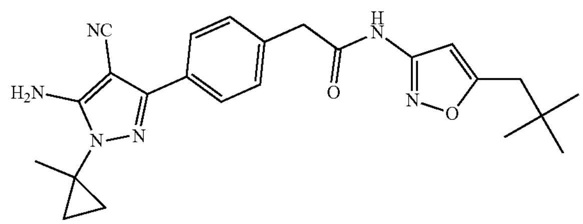 [SMILES: CC(C)(C)Cc1cc(NC(=O)Cc2ccc(-c3nn(C4(C)CC4)c(N)c3C#N)cc2)no1] | 433.2 | 1, c, IV |
| 223 | 2-[4-[5-Amino-4-cyano-1-(1-methoxy-2-methylpropan-2-yl)pyrazol-3-yl]phenyl]-N-[3-(2,2-dimethylpropyl)-1,2-oxazol-5-yl]acetamide | 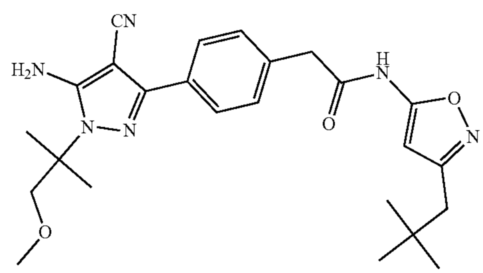 [SMILES: COCC(C)(C)n1nc(-c2ccc(CC(=O)Nc3cc(CC(C)(C)C)no3)cc2)c(C#N)c1N] | 487.2 M + Na | 1, c, IV |
| 224 | 2-[4-[5-Amino-4-cyano-1-(1-methylcyclopropyl)pyrazol-3-yl]phenyl]-N-[3-[3-(trifluoromethyl)bicyclo[1.1.1]pentan-1-yl]-1,2-oxazol-5-yl]acetamide | 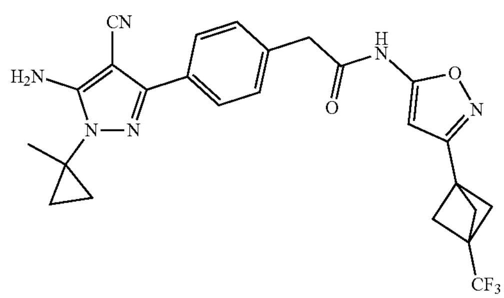 [SMILES: CC1(n2nc(-c3ccc(CC(=O)Nc4cc(C56CC(C(F)(F)F)(C5)C6)no4)cc3)c(C#N)c2N)CC1] | 497.3 | 1, c, IV |
| 225 | 2-[4-[5-Amino-4-cyano-1-(1,1,1-trifluoropropan-2-yl)pyrazol-3-yl]phenyl]-N-[3-[3-(trifluoromethyl)bicyclo[1.1.1]pentan-1-yl]-1,2-oxazol-5-yl]acetamide | 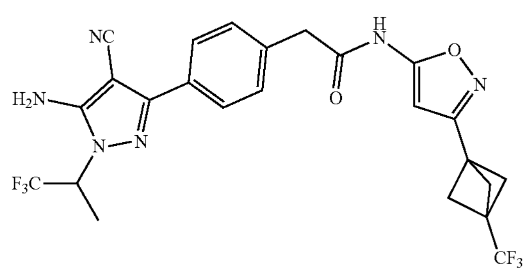 [SMILES: CC(n1nc(-c2ccc(CC(=O)Nc3cc(C45CC(C(F)(F)F)(C4)C5)no3)cc2)c(C#N)c1N)C(F)(F)F] | 539.2 | 1, c, IV |

TABLE 22-continued

| Prep. No. | Chemical name | Structure | ES/MS m/z (M + H) | * |
|---|---|---|---|---|
| 226 | 2-(4-(5-Amino-4-cyano-1-(2,2,2-trifluoroethyl)-1H-pyrazol-3-yl)phenyl)-N-(3-(3-(trifluoromethyl)bicyclo[1.1.1]pentan-1-yl)isoxazol-5-yl)acetamide | 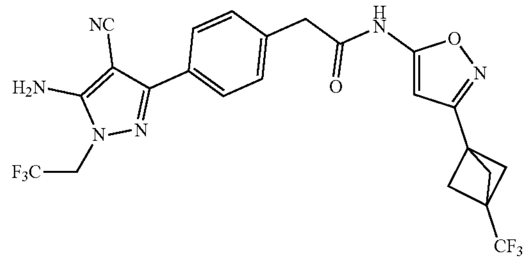 | 525.2 | 1, c, IV |
| 227 | 2-[4-(5-amino-4-cyano-1-cyclobutylpyrazol-3-yl)phenyl]-N-[3-[3-(trifluoromethyl)bicyclo[1.1.1]pentan-1-yl]-1,2-oxazol-5-yl]acetamide | 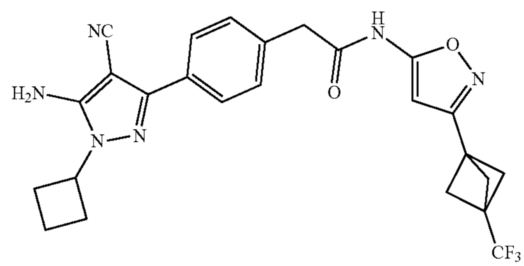 [SMILES: N#Cc1c(-c2ccc(CC(=O)Nc3cc(C45CC(C(F)(F)F)(C4)C5)no3)cc2)nn(C2CCC2)c1N] | 497.2 | 1, c, IV |
| 228 | 2-[4-[5-Amino-4-cyano-1-(1,1,1-trifluoro-2-methylpropan-2-yl)pyrazol-3-yl]phenyl]-N-(3-[3-methylbicyclo[1.1.1]pentan-1-yl]-1,2-oxazol-5-yl)acetamide | 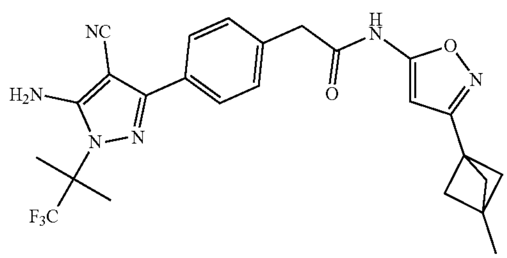 [SMILES: CC12CC(c3cc(NC(=O)Cc4ccc(-c5nn(C(C)(C)C(F)(F)F)c(N)c5C#N)cc4)on3)(C1)C2] | 499.2 | 1, c, IV |
| 229 | 2-[4-(5-Amino-1-tert-butyl-4-cyanopyrazol-3-yl)phenyl]-N-(3-[3-methylbicyclo[1.1.1]pentan-1-yl]-1,2-oxazol-5-yl)acetamide | 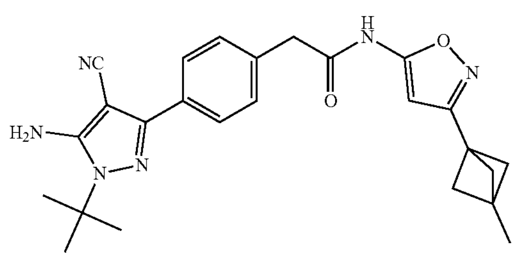 [SMILES: CC12CC(c3cc(NC(=O)Cc4ccc(-c5nn(C(C)(C)C)c(N)c5C#N)cc4)on3)(C1)C2] | 445.3 | 1, c, IV |
| 230 | 2-[4-[5-Amino-4-cyano-1-(1-methylcyclopropyl)pyrazol-3-yl]phenyl]-N-[3-[4-(trifluoromethyl)bicyclo[2.2.1]heptan-1-yl]-1,2-oxazol-5-yl]acetamide | 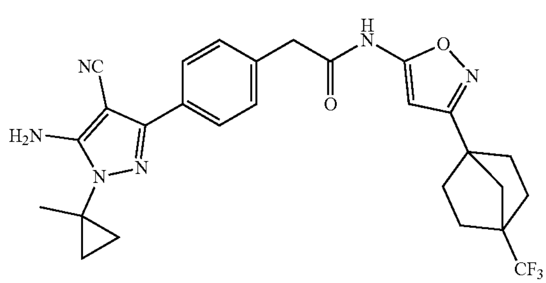 [SMILES: CC1(n2nc(-c3ccc(CC(=O)Nc4cc(C56CCC(C(F)(F)F)(CC5)C6)no4)cc3)c(C#N)c2N)CC1] | 525.2 | 1, c, IV |

TABLE 22-continued

| Prep. No. | Chemical name | ES/MS m/z (M + H) | * |
|---|---|---|---|
| 231 | 2-[4-[5-Amino-4-cyano-1-(1,1,1-trifluoro-2-methylpropan-2-yl)pyrazol-3-yl]phenyl]-N-[3-[4-(trifluoromethyl)bicyclo[2.2.1]heptan-1-yl]-1,2-oxazol-5-yl]acetamide | 581.1 | 1, c, IV |
| 232 | 2-[4-(5-Amino-1-tert-butyl-4-cyanopyrazol-3-yl)phenyl]-N-[3-[4-(trifluoromethyl)bicyclo[2.2.1]heptan-1-yl]-1,2-oxazol-5-yl]acetamide | 527.3 | 1, c, IV |
| 233 | 2-(4-(5-Amino-4-cyano-1-(1-methylcyclopropyl)-1H-pyrazol-3-yl)-3-fluorophenyl)-N-(3-(3-methylbicyclo[1.1.1]pentan-1-yl)isoxazol-5-yl)acetamide | 461.1 | 1, c, IV |
| 234 | 2-(4-(5-Amino-4-cyano-1-(1-methylcyclopropyl)-1H-pyrazol-3-yl)-3-fluorophenyl)-N-(3-(3-(trifluoromethyl)bicyclo[1.1.1]pentan-1-yl)isoxazol-5-yl)acetamide | 515.1 | 1, c, IV |
| 235 | 2-[4-[5-Amino-4-cyano-1-(1-methylcyclopropyl)pyrazol-3-yl]-2,3-difluorophenyl]-N-[3-[3-(trifluoromethyl)bicyclo[1.1.1]pentan-1-yl]-1,2-oxazol-5-yl]acetamide | 533.2 | 1, c, IV |

TABLE 22-continued

| Prep. No. | Chemical name | Structure | ES/MS m/z (M + H) | * |
|---|---|---|---|---|
| 236 | 2-[4-[5-Amino-4-cyano-1-(1-methylcyclopropyl)pyrazol-3-yl]-2,3-difluorophenyl]-N-[3-[4-(trifluoromethyl)bicyclo[2.2.1]heptan-1-yl]-1,2-oxazol-5-yl]acetamide | 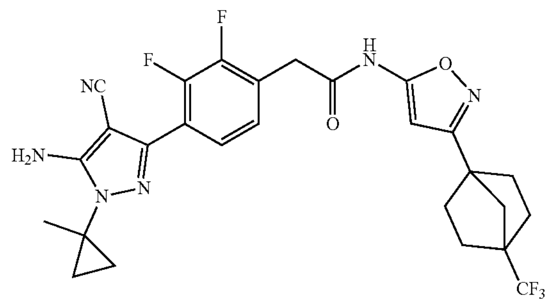 [SMILES: CC1(n2nc(-c3ccc(CC(=O)Nc4cc(C56CCC(C(F)(F)F)(CC5)C6)no4)c(F)c3F)c(C#N)c2N)CC1] | 561.1 | 1, c, IV |
| 237 | 2-(4-(5-Amino-4-cyano-1-(1-methylcyclopropyl)-1H-pyrazol-3-yl)-3-fluorophenyl)-N-(3-(4-(trifluoromethyl)bicyclo[2.2.1]heptan-1-yl)isoxazol-5-yl)acetamide | 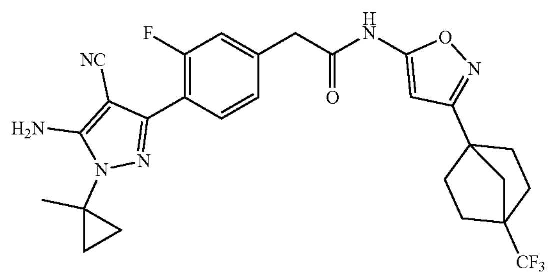 [SMILES: CC1(n2nc(-c3ccc(CC(=O)Nc4cc(C56CCC(C(F)(F)F)(CC5)C6)no4)cc3F)c(C#N)c2N)CC1] | 543.1 | 1, c, IV |
| 238 | 2-[4-(5-Amino-4-cyano-1-isopropylpyrazol-3-yl)-2,3-difluorophenyl]-N-[3-[4-(trifluoromethyl)bicyclo[2.2.1]heptan-1-yl]-1,2-oxazol-5-yl]acetamide | 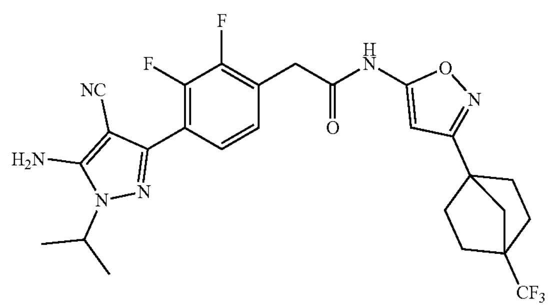 [SMILES: CC(C)n1nc(-c2ccc(CC(=O)Nc3cc(C45CCC(C(F)(F)F)(CC4)C5)no3)c(F)c2F)c(C#N)c1N] | 549.3 | 1, c, IV |
| 239 | 2-[4-(5-Amino-4-cyano-1-isopropylpyrazol-3-yl)-2,3-difluorophenyl]-N-(3-[3-methylbicyclo[1.1.1]pentan-1-yl]-1,2-oxazol-5-yl)acetamide | 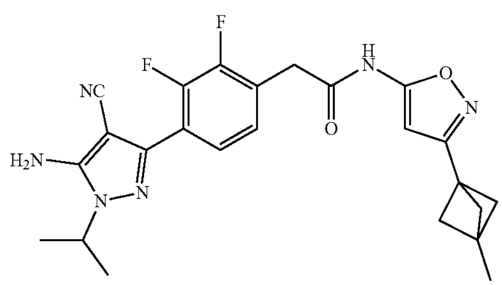 [SMILES: CC(C)n1nc(-c2ccc(CC(=O)Nc3cc(C45CC(C)(C4)C5)no3)c(F)c2F)c(C#N)c1N] | 467.2 | 1, c, IV |
| 240 | 2-[4-[5-Amino-4-cyano-1-(1-methylcyclopropyl)pyrazol-3-yl]phenyl]-N-(3-[3-methylbicyclo[1.1.1]pentan-1-yl]-1,2-oxazol-5-yl)acetamide | 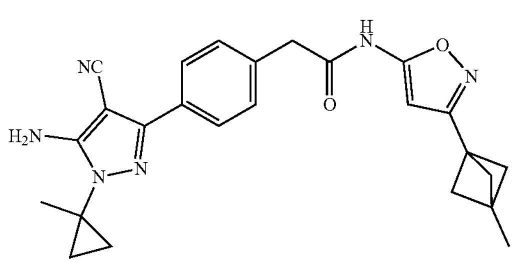 [SMILES: CC12CC(c3cc(NC(=O)Cc4ccc(-c5nn(C6(C)CC6)c(N)c5C#N)cc4)on3)(C1)C2] | 443.2 | 1, c, IV |

TABLE 22-continued

| Prep. No. | Chemical name | Structure | ES/MS m/z (M + H) | * |
|---|---|---|---|---|
| 241 | 2-(4-(5-Amino-4-cyano-1-isopropyl-1H-pyrazol-3-yl)phenyl)-N-(3-(1,1-difluoroethyl)isoxazol-5-yl)acetamide | 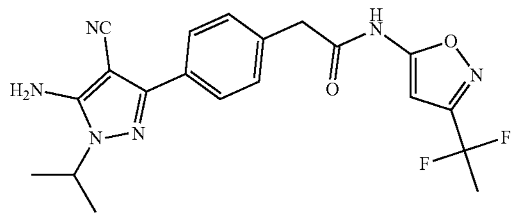 [SMILES: CC(C)n1nc(-c2ccc(CC(=O)Nc3cc(C(C)(F)F)no3)cc2)c(C#N)c1N] | 415.2 | 1, c, IV |
| 242 | 2-[4-(5-Amino-4-cyano-1-isopropylpyrazol-3-yl)phenyl]-N-[3-(2,2-dimethylpropyl)-1,2-oxazol-5-yl]acetamide | 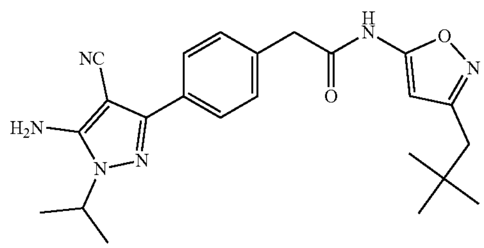 [SMILES: CC(C)n1nc(-c2ccc(CC(=O)Nc3cc(CC(C)(C)C)no3)cc2)c(C#N)c1N] | 421.1 | 1, c, IV |
| 243 | tert-Butyl N-[4-cyano-5-[4-[2-[[3-(2,2-dimethylcyclopropyl)isoxazol-5-yl]amino]-2-oxo-ethyl]phenyl]-2-isopropyl-pyrazol-3-yl]carbamate | 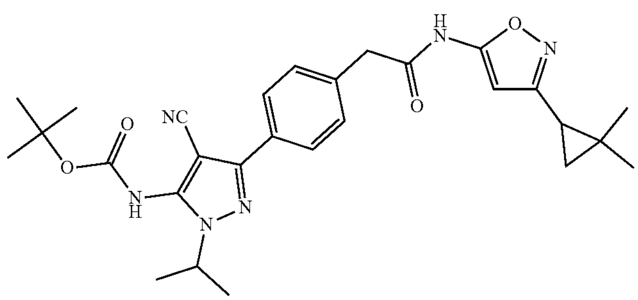 [SMILES: CC(C)n1nc(-c2ccc(CC(=O)Nc3cc(C4CC4(C)C)no3)cc2)c(C#N)c1NC(=O)OC(C)(C)C] | 518 | 1, b, V |
| 244 | tert-Butyl N-[4-cyano-2-isopropyl-5-[4-[2-oxo-2-[(3-spiro[2.2]pentan-2-ylisoxazol-5-yl)amino]ethyl]phenyl]pyrazol-3-yl]carbamate | 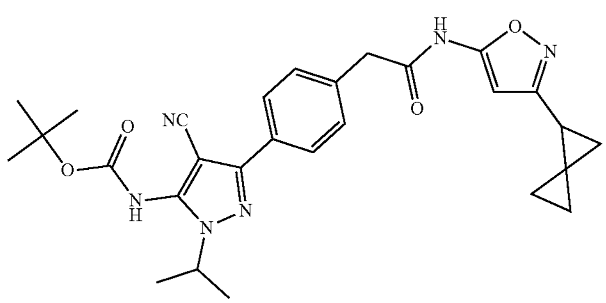 [SMILES: CC(C)n1nc(-c2ccc(CC(=O)Nc3cc(C4CC45CC5)no3)cc2)c(C#N)c1NC(=O)OC(C)(C)C] | 517 | 1, b, V |
| 245 | tert-Butyl N-[4-cyano-5-[4-[2-[[3-[(2,2-difluorocyclopropyl)methyl]isoxazol-5-yl]amino]-2-oxo-ethyl]phenyl]-2-isopropyl-pyrazol-3-yl]carbamate | 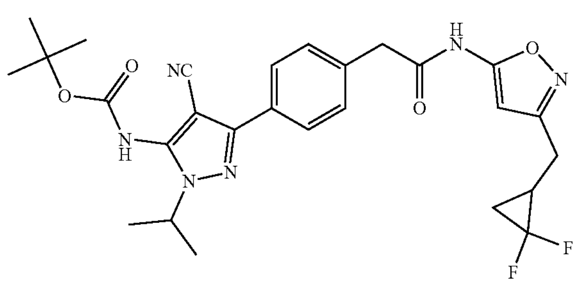 [SMILES: CC(C)n1nc(-c2ccc(CC(=O)Nc3cc(CC4CC4(F)F)no3)cc2)c(C#N)c1NC(=O)OC(C)(C)C] | 541 | 1, b, V |

TABLE 22-continued

| Prep. No. | Chemical name | Structure | ES/MS m/z (M + H) | * |
|---|---|---|---|---|
| 246 | tert-Butyl N-[4-cyano-5-[4-[2-[[3-(3,3-difluorocyclopentyl)isoxazol-5-yl]amino]-2-oxo-ethyl]phenyl]-2-isopropyl-pyrazol-3-yl]carbamate | 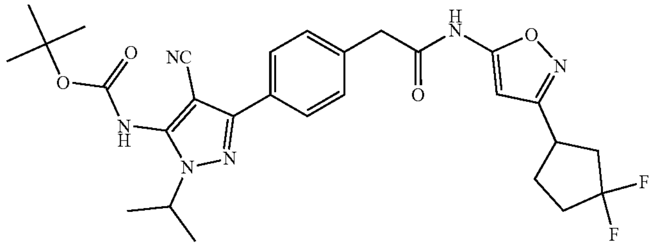 [SMILES: CC(C)n1nc(-c2ccc(CC(=O)Nc3cc(C4CCC(F)(F)C4)no3)cc2)c(C#N)c1NC(=O)OC(C)(C)C] | 555 | 1, b, V |
| 247 | tert-Butyl N-[4-cyano-2-isopropyl-5-[4-[2-oxo-2-[(3-spiro[2.3]hexan-2-ylisoxazol-5-yl)amino]ethyl]phenyl]pyrazol-3-yl]carbamate | 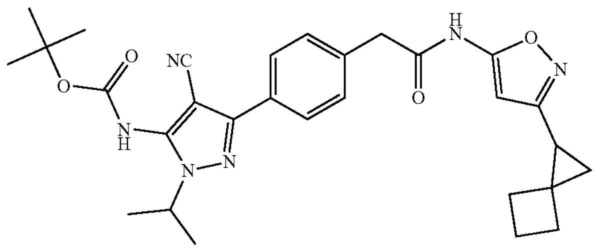 [SMILES: CC(C)n1nc(-c2ccc(CC(=O)Nc3cc(C4CC45CCC5)no3)cc2)c(C#N)c1NC(=O)OC(C)(C)C] | 531.5 | 1, b, V |
| 248 | tert-Butyl N-[4-cyano-2-isopropyl-5-[4-[2-oxo-2-[(5-spiro[2.3]hexan-2-ylisoxazol-3-yl)amino]ethyl]phenyl]pyrazol-3-yl]carbamate | 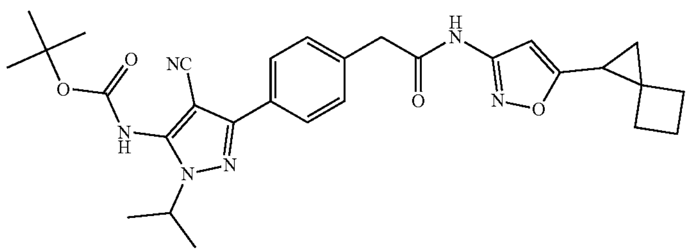 [SMILES: CC(C)n1nc(-c2ccc(CC(=O)Nc3cc(C4CC45CCC5)on3)cc2)c(C#N)c1NC(=O)OC(C)(C)C] | 531 | 1, b, V |
| 249 | tert-Butyl N-[4-cyano-5-[4-[2-[[5-(2,2-dimethylcyclobutyl)isoxazol-3-yl]amino]-2-oxo-ethyl]phenyl]-2-isopropyl-pyrazol-3-yl]carbamate | 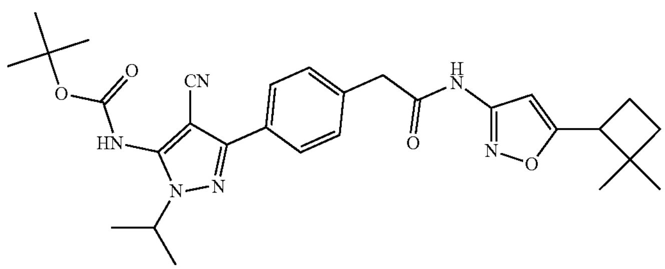 [SMILES: CC(C)n1nc(-c2ccc(CC(=O)Nc3cc(C4CCC4(C)C)on3)cc2)c(C#N)c1NC(=O)OC(C)(C)C] | 533 | 1, b, V |
| 250 | tert-Butyl N-[4-cyano-5-[4-[2-[[3-(2,2-dimethylcyclobutyl)isoxazol-5-yl]amino]-2-oxo-ethyl]phenyl]-2-isopropyl-pyrazol-3-yl]carbamate | 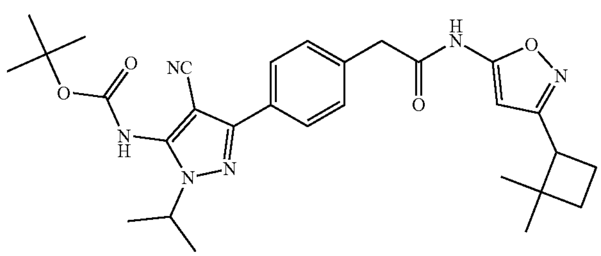 [SMILES: CC(C)n1nc(-c2ccc(CC(=O)Nc3cc(C4CCC4(C)C)no3)cc2)c(C#N)c1NC(=O)OC(C)(C)C] | 533.5 | 1, b, V |
| 251 | 2-[4-(1-Isopropyl-6,6-dimethyl-4-oxo-5,7-dihydropyrazolo[3,4-d]pyrimidin-3-yl)phenyl]-N-[5-[1-(trifluoromethyl)cyclopropyl]isoxazol-3-yl]acetamide | 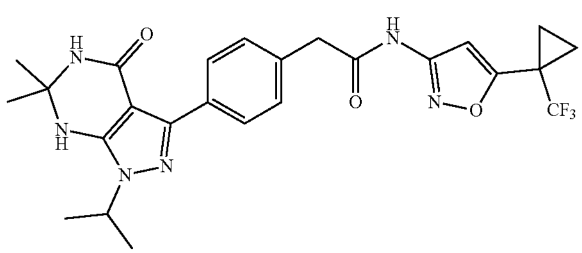 [SMILES: CC(C)n1nc(-c2ccc(CC(=O)Nc3cc(C4(C(F)(F)F)CC4)on3)cc2)c2c1NC(C)(C)NC2=O] | 517.4 | 1, c, III |

TABLE 22-continued

| Prep. No. | Chemical name | Structure | ES/MS m/z (M + H) | * |
|---|---|---|---|---|
| 252 | 2-[4-(1-Isopropyl-6,6-dimethyl-4-oxo-5,7-dihydropyrazolo[3,4-d]pyrimidin-3-yl)-2-methoxy-phenyl]-N-[5-(1-methylcyclopentyl)isoxazol-3-yl]acetamide | 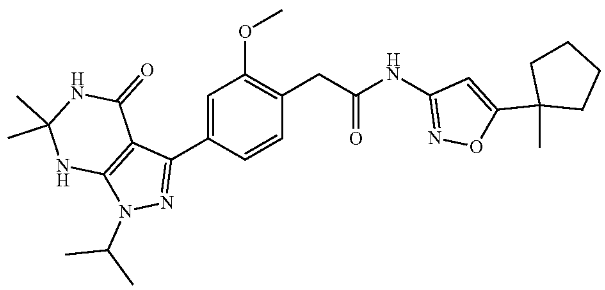 [SMILES: COc1cc(-c2nn(C(C)C)c3c2C(=O)NC(C)(C)N3)ccc1CC(=O)Nc1cc(C2(C)CCCC2)on1] | 520 | 1, c, III |
| 253 | 2-[2,6-Difluoro-4-(1-isopropyl-6,6-dimethyl-4-oxo-5,7-dihydropyrazolo[3,4-d]pyrimidin-3-yl)phenyl]-N-[5-(2,2,2-trifluoro-1,1-dimethyl-ethyl)isoxazol-3-yl]acetamide | 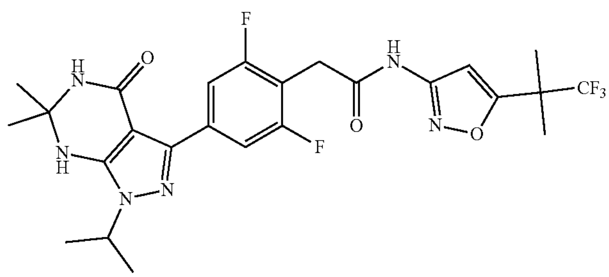 [SMILES: CC(C)n1nc(-c2cc(F)c(CC(=O)Nc3cc(C(C)(C)C(F)(F)F)on3)c(F)c2)c2c1NC(C)(C)NC2=O] | 555 | 1, c, III |
| 254 | N-[3-(2,4-Dichlorophenyl)isoxazol-5-yl]-2-[4-(1-isopropyl-6,6-dimethyl-4-oxo-5,7-dihydropyrazolo[3,4-d]pyrimidin-3-yl)-2-methoxy-phenyl]acetamide | 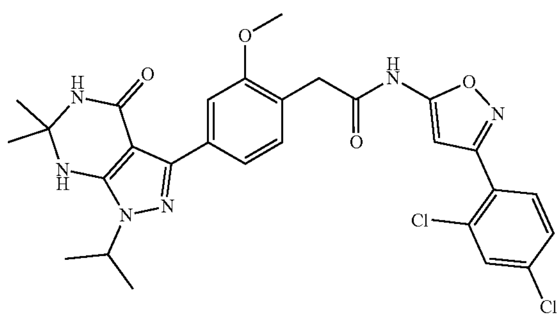 [SMILES: COc1cc(-c2nn(C(C)C)c3c2C(=O)NC(C)(C)N3)ccc1CC(=O)Nc1cc(-c2ccc(Cl)cc2Cl)no1] | 583 | 1, c, III |
| 255 | tert-Butyl N-[4-cyano-5-[4-[2-[[3-(2,2-dimethylpropyl)isoxazol-5-yl]amino]-2-oxo-ethyl]-2-fluoro-phenyl]-2-isopropyl-pyrazol-3-yl]carbamate | 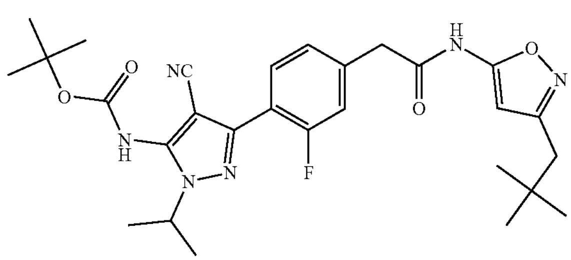 [SMILES: CC(C)n1nc(-c2ccc(CC(=O)Nc3cc(CC(C)(C)C)no3)cc2F)c(C#N)c1NC(=O)OC(C)(C)C] | 539 | 1, b, V |
| 256 | tert-Butyl N-[5-[3-chloro-4-[2-[[3-(2,2-dimethylpropyl)isoxazol-5-yl]amino]-2-oxo-ethyl]-2-fluoro-phenyl]-4-cyano-2-isopropyl-pyrazol-3-yl]carbamate | 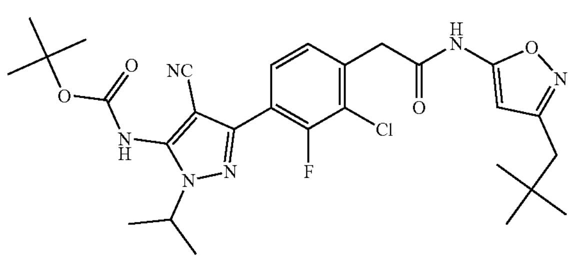 [SMILES: CC(C)n1nc(-c2ccc(CC(=O)Nc3cc(CC(C)(C)C)no3)c(Cl)c2F)c(C#N)c1NC(=O)OC(C)(C)C] | 573.4 | 1, b, V |

TABLE 22-continued

| Prep. No. | Chemical name | Structure | ES/MS m/z (M + H) | * |
|---|---|---|---|---|
| 257 | tert-Butyl N-[5-[2-chloro-4-[2-[[3-(2,2-dimethylpropyl)isoxazol-5-yl]amino]-2-oxo-ethyl]-3-fluoro-phenyl]-4-cyano-2-isopropyl-pyrazol-3-yl]carbamate | 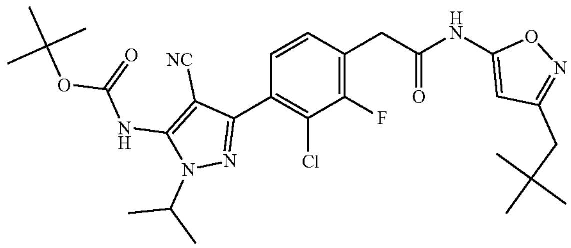 | 573.4 | 1, b, V |
| 258 | tert-Butyl N-[4-cyano-5-[4-[2-[[3-(2,2-dimethylpropyl)isoxazol-5-yl]amino]-2-oxo-ethyl]-2-methyl-phenyl]-2-isopropyl-pyrazol-3-yl]carbamate | 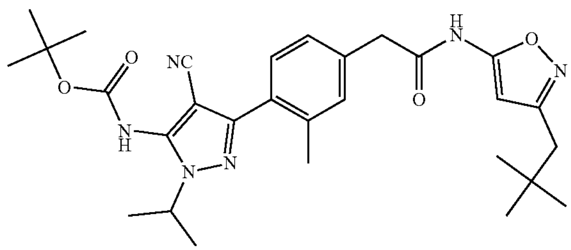 [SMILES: Cc1cc(CC(=O)Nc2cc(CC(C)(C)C)no2)ccc1-c1nn(C(C)C)c(NC(=O)OC(C)(C)C)c1C#N] | 535.5 | 1, c, III |
| 259 | tert-Butyl N-[4-cyano-5-[4-[2-[[3-(cyclobutylmethyl)isoxazol-5-yl]amino]-2-oxo-ethyl]phenyl]-2-isopropyl-pyrazol-3-yl]carbamate | 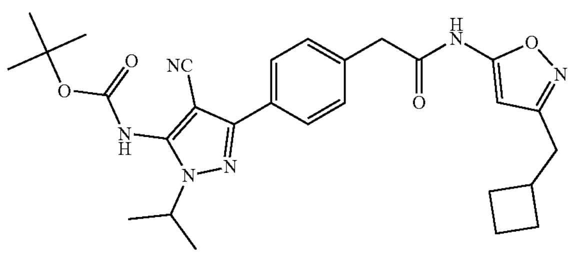 [SMILES: CC(C)n1nc(-c2ccc(CC(=O)Nc3cc(CC4CCC4)no3)cc2)c(C#N)c1NC(=O)OC(C)(C)C] | 519.4 | 1, c, III |
| 260 | tert-Butyl N-[5-[2-chloro-4-[2-[[3-(2,2-dimethylpropyl)isoxazol-5-yl]amino]-2-oxo-ethyl]phenyl]-4-cyano-2-isopropyl-pyrazol-3-yl]carbamate | 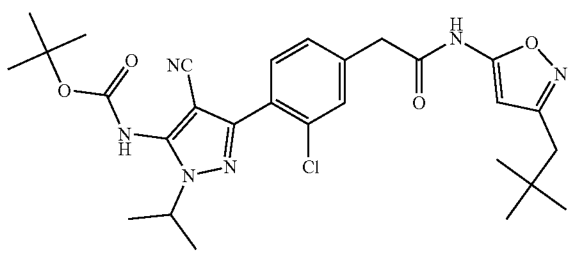 [SMILES: CC(C)n1nc(-c2ccc(CC(=O)Nc3cc(CC(C)(C)C)no3)cc2Cl)c(C#N)c1NC(=O)OC(C)(C)C] | 555.4 | 1, c, III |
| 261 | tert-Butyl N-[4-cyano-2-isopropyl-5-[4-[2-[[3-[(1-methylcyclobutyl)methyl]isoxazol-5-yl]amino]-2-oxo-ethyl]phenyl]pyrazol-3-yl]carbamate | 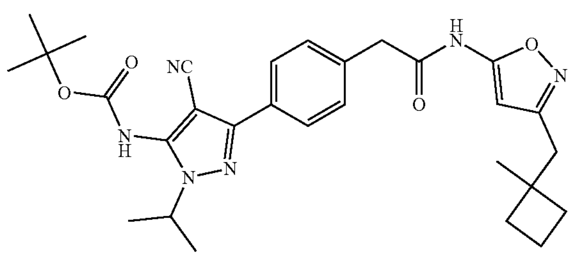 [SMILES: CC(C)n1nc(-c2ccc(CC(=O)Nc3cc(CC4(C)CCC4)no3)cc2)c(C#N)c1NC(=O)OC(C)(C)C] | 533.5 | 1, b, V |
| 262 | tert-Butyl N-[4-cyano-5-[4-[2-[[3-(3,3-difluoro-1-methyl-cyclobutyl)isoxazol-5-yl]amino]-2-oxo-ethyl]phenyl]-2-isopropyl-pyrazol-3-yl]carbamate | 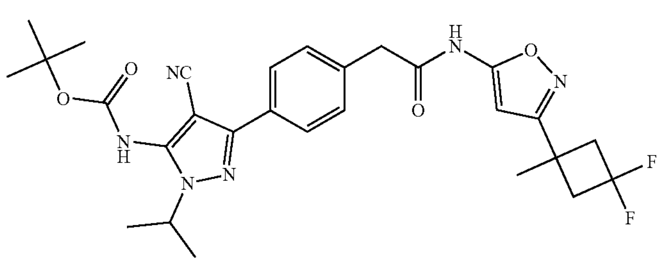 [SMILES: CC(C)n1nc(-c2ccc(CC(=O)Nc3cc(C4(C)CC(F)(F)C4)no3)cc2)c(C#N)c1NC(=O)OC(C)(C)C] | 555 | 1, b, V |

TABLE 22-continued

| Prep. No. | Chemical name | Structure | ES/MS m/z (M + H) | * |
|---|---|---|---|---|
| 263 | tert-Butyl N-[4-cyano-5-[4-[2-[[3-(3,3-dimethylcyclobutyl)isoxazol-5-yl]amino]-2-oxo-ethyl]-2-fluoro-phenyl]-2-isopropyl-pyrazol-3-yl]carbamate | 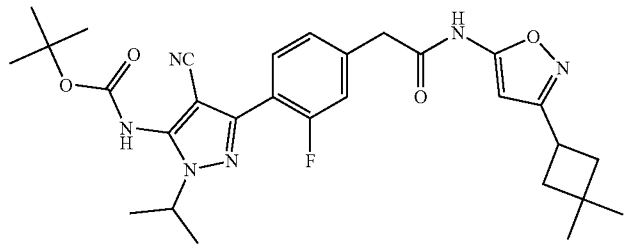 [SMILES: CC(C)n1nc(-c2ccc(CC(=O)Nc3cc(C4CC(C)(C)C4)no3)cc2F)c(C#N)c1NC(=O)OC(C)(C)C] | 551.5 | 1, b, V |
| 264 | tert-Butyl N-[5-[2-chloro-4-[2-[[3-(3,3-dimethylcyclobutyl)isoxazol-5-yl]amino]-2-oxo-ethyl]phenyl]-4-cyano-2-isopropyl-pyrazol-3-yl]carbamate | 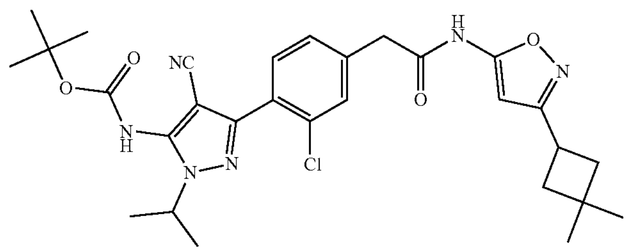 [SMILES: CC(C)n1nc(-c2ccc(CC(=O)Nc3cc(C4CC(C)(C)C4)no3)cc2Cl)c(C#N)c1NC(=O)OC(C)(C)C] | 567.4 | 1, b, V |
| 265 | tert-Butyl N-[5-[2-chloro-4-[2-[[3-(3,3-dimethylcyclobutyl)isoxazol-5-yl]amino]-2-oxo-ethyl]-3-fluoro-phenyl]-4-cyano-2-isopropyl-pyrazol-3-yl]carbamate | 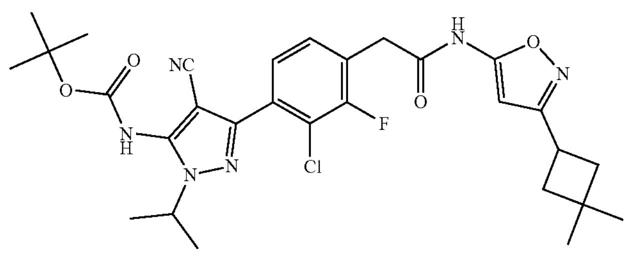 | 585.4 | 1, b, V |
| 266 | tert-Butyl N-[4-cyano-5-[4-[2-[[3-(1,1-difluoro-2,2-dimethyl-propyl)isoxazol-5-yl]amino]-2-oxo-ethyl]phenyl]-2-isopropyl-pyrazol-3-yl]carbamate | 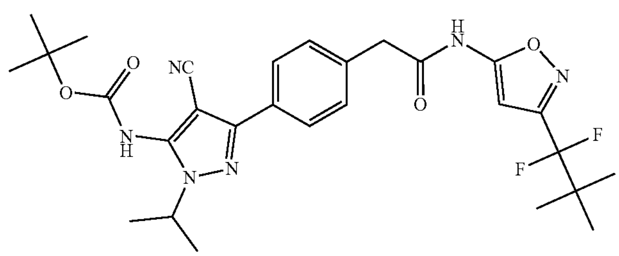 [SMILES: CC(C)n1nc(-c2ccc(CC(=O)Nc3cc(C(F)(F)C(C)(C)C)no3)cc2)c(C#N)c1NC(=O)OC(C)(C)C] | 557.4 | 1, b, V |
| 267 | tert-Butyl N-[4-cyano-5-[2-fluoro-4-[2-[[3-(3-methyl-1-bicyclo[1.1.1]pentanyl)isoxazol-5-yl]amino]-2-oxo-ethyl]phenyl]-2-isopropyl-pyrazol-3-yl]carbamate | 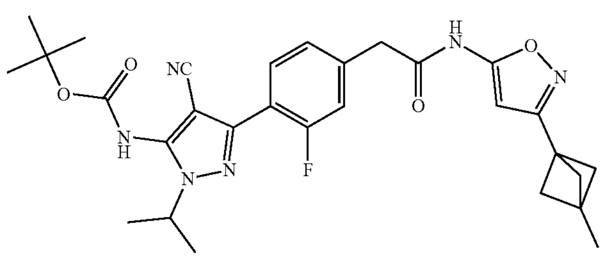 [SMILES: CC(C)n1nc(-c2ccc(CC(=O)Nc3cc(C45CC(C)(C4)C5)no3)cc2F)c(C#N)c1NC(=O)OC(C)(C)C] | 549.5 | 1, b, V |
| 268 | tert-Butyl N-[4-cyano-5-[4-[2-[[3-(3,3-dimethylcyclobutyl)isoxazol-5-yl]amino]-2-oxo-ethyl]-2,3-difluoro-phenyl]-2-isopropyl-pyrazol-3-yl]carbamate | 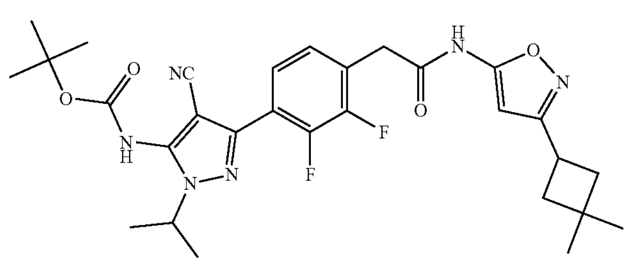 [SMILES: CC(C)n1nc(-c2ccc(CC(=O)Nc3cc(C4CC(C)(C)C4)no3)c(F)c2F)c(C#N)c1NC(=O)OC(C)(C)C] | 569.4 | 1, b, V |

TABLE 22-continued

| Prep. No. | Chemical name | Structure | ES/MS m/z (M + H) | * |
|---|---|---|---|---|
| 269 | tert-Butyl N-[4-cyano-5-[4-[2-[[3-(2,2-dimethylpropyl)isoxazol-5-yl]amino]-2-oxo-ethyl]-2,5-difluoro-phenyl]-2-isopropyl-pyrazol-3-yl]carbamate | 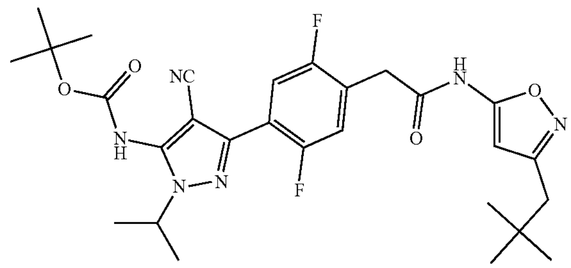 [SMILES: CC(C)n1nc(-c2cc(F)c(CC(=O)Nc3cc(CC(C)(C)C)no3)cc2F)c(C#N)c1NC(=O)OC(C)(C)C] | 557 | 1, b, V |
| 270 | tert-Butyl N-[4-cyano-5-[4-[2-[[5-(3,3-dimethylcyclobutyl)isoxazol-3-yl]amino]-2-oxo-ethyl]phenyl]-2-isopropyl-pyrazol-3-yl]carbamate | 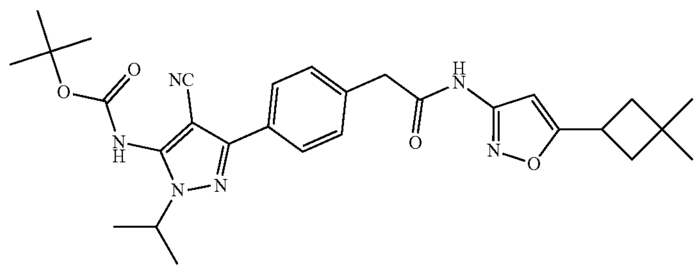 [SMILES: CC(C)n1nc(-c2ccc(CC(=O)Nc3cc(C4CC(C)(C)C4)on3)cc2)c(C#N)c1NC(=O)OC(C)(C)C] | 533 | 1, b, V |
| 271 | tert-Butyl N-[4-cyano-5-[4-[2-[[3-(2,2-dimethylpropyl)isoxazol-5-yl]amino]-2-oxo-ethyl]-3,5-difluoro-phenyl]-2-isopropyl-pyrazol-3-yl]carbamate | 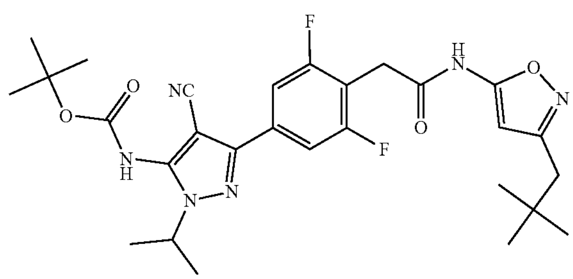 [SMILES: CC(C)n1nc(-c2cc(F)c(CC(=O)Nc3cc(CC(C)(C)C)no3)c(F)c2)c(C#N)c1NC(=O)OC(C)(C)C] | 557 | 1, b, V |
| 272 | tert-Butyl N-[5-[2-chloro-4-[2-[[3-(3-methyl-1-bicyclo[1.1.1]pentanyl)isoxazol-5-yl]amino]-2-oxo-ethyl]phenyl]-4-cyano-2-isopropyl-pyrazol-3-yl]carbamate | 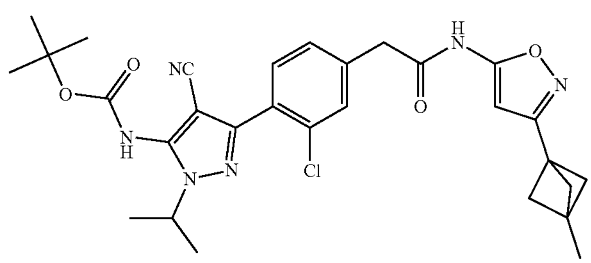 [SMILES: CC(C)n1nc(-c2ccc(CC(=O)Nc3cc(C45CC(C)(C4)C5)no3)cc2Cl)c(C#N)c1NC(=O)OC(C)(C)C] | 565 | 1, b, V |
| 273 | tert-Butyl N-[5-[2-chloro-3-fluoro-4-[2-[[3-(3-methyl-1-bicyclo[1.1.1]pentanyl)isoxazol-5-yl]amino]-2-oxo-ethyl]phenyl]-4-cyano-2-isopropyl-pyrazol-3-yl]carbamate | 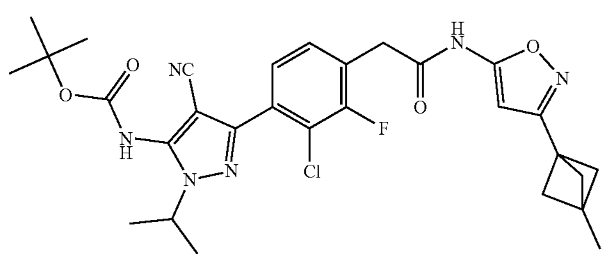 [SMILES: CC(C)n1nc(-c2ccc(CC(=O)Nc3cc(C45CC(C)(C4)C5)no3)c(F)c2Cl)c(C#N)c1NC(=O)OC(C)(C)C] | 583 | 1, b, V |

TABLE 22-continued

| Prep. No. | Chemical name | Structure | ES/MS m/z (M + H) | * |
|---|---|---|---|---|
| 274 | tert-Butyl N-[4-cyano-5-[4-[2-[[3-(3,3-dimethylcyclobutyl)-4-fluoro-isoxazol-5-yl]amino]-2-oxo-ethyl]phenyl]-2-isopropyl-pyrazol-3-yl]carbamate | 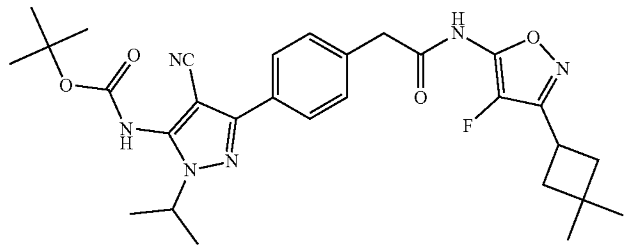 [SMILES: CC(C)n1nc(-c2ccc(CC(=O)Nc3onc(C4CC(C)(C)C4)c3F)cc2)c(C#N)c1NC(=O)OC(C)(C)C] | 551.4 | 1, b, V |
| 275 | tert-Butyl N-[4-cyano-5-[3,5-difluoro-4-[2-[[3-(3-methyl-1-bicyclo[1.1.1]pentanyl)isoxazol-5-yl]amino]-2-oxo-ethyl]phenyl]-2-isopropyl-pyrazol-3-yl]carbamate | 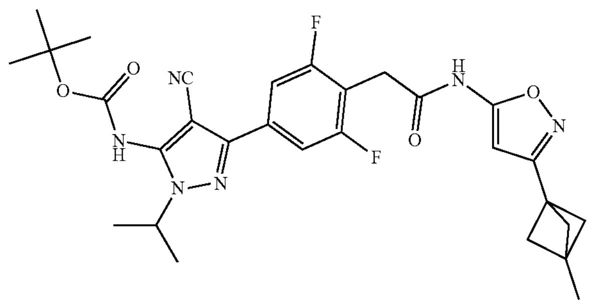 [SMILES: CC(C)n1nc(-c2cc(F)c(CC(=O)Nc3cc(C45CC(C)(C4)C5)no3)c(F)c2)c(C#N)c1NC(=O)OC(C)(C)C] | 567 | 1, b, V |
| 276 | tert-Butyl N-[4-cyano-5-[4-[2-[[3-(2,2-dimethylpropyl)-4-fluoro-isoxazol-5-yl]amino]-2-oxo-ethyl]phenyl]-2-isopropyl-pyrazol-3-yl]carbamate | 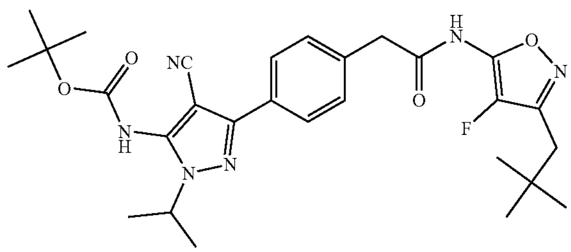 [SMILES: CC(C)n1nc(-c2ccc(CC(=O)Nc3onc(CC(C)(C)C)c3F)cc2)c(C#N)c1NC(=O)OC(C)(C)C] | 539 | 1, b, V |
| 277 | tert-Butyl N-[4-cyano-5-[4-[2-[[4-fluoro-3-(3-methyl-1-bicyclo[1.1.1]pentanyl)isoxazol-5-yl]amino]-2-oxo-ethyl]phenyl]-2-isopropyl-pyrazol-3-yl]carbamate | 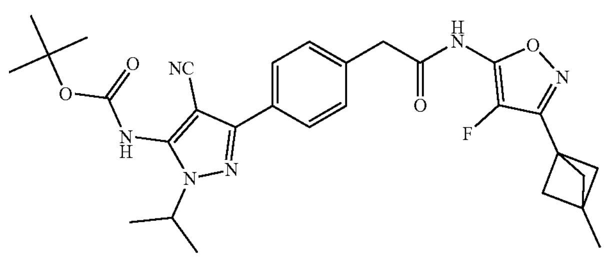 [SMILES: CC(C)n1nc(-c2ccc(CC(=O)Nc3onc(C45CC(C)(C4)C5)c3F)cc2)c(C#N)c1NC(=O)OC(C)(C)C] | 549 | 1, b, V |

Preparation 278 tert-Butyl N-[4-cyano-5-[4-[2-[[3-(2,2-dimethylpropyl)isoxazol-5-yl]amino]-2-oxo-ethyl]-2,3-difluoro-phenyl]-2-isopropyl-pyrazol-3-yl]carbamate

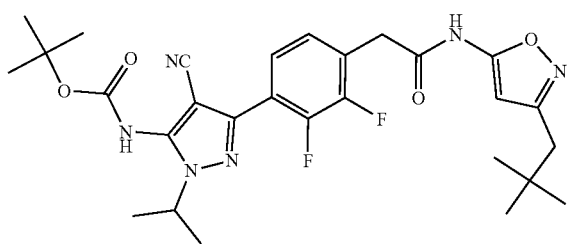 [SMILES: CC(C)n1nc(-c2ccc(CC(=O)Nc3cc(CC(C)(C)C)no3)c(F)c2F)c(C#N)c1NC(=O)OC(C)(C)C]

3-(2,2-Dimethylpropyl)-1,2-oxazol-5-amine (58 mg, 0.376 mmol), 2-[4-[5-(tert-butoxycarbonylamino)-4-cyano-1-isopropyl-pyrazol-3-yl]-2,3-difluoro-phenyl]acetic acid (0.100 g, 0.238 mmol) and DIPEA (98 μL, 0.563 mmol) are added together in DMF (0.69 mL) under $N_2$. T3P® (0.454 g, 0.713 mmol, 50% in MeTHF) is added and the reaction is stirred at RT overnight. The mixture is quenched with saturated aq. $NH_4Cl$ and the aqueous layer is extracted with EtOAc (3×). The combined organic extracts are washed with brine, dried over $Na_2SO_4$, filtered, and concentrated under reduced pressure. The residue is purified by silica gel chromatography, eluting with a gradient of 10% to 50% EtOAc in cyclohexane to give the title compound (45 mg, 95% purity, 32%) as a white solid. ES/MS (m/z) 557 (M+H).

Preparation 279 tert-Butyl N-[4-carbamoyl-5-[4-[2-[[3-(2,2-dimethylpropyl)isoxazol-5-yl]amino]-2-oxo-ethyl]-2,3-difluoro-phenyl]-2-isopropyl-pyrazol-3-yl]carbamate

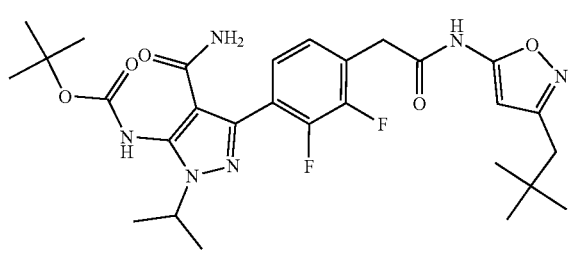 [SMILES: CC(C)n1nc(-c2ccc(CC(=O)Nc3cc(CC(C)(C)C)no3)c(F)c2F)c(C(N)=O)c1NC(=O)OC(C)(C)C]

To tert-butyl N-[4-cyano-5-[4-[2-[[3-(2,2-dimethylpropyl)isoxazol-5-yl]amino]-2-oxo-ethyl]-2,3-difluoro-phenyl]-2-isopropyl-pyrazol-3-yl]carbamate (75 mg, 0.135 mmol) and Parkins catalyst (5.8 mg, 0.0135 mmol) under $N_2$ is added a mixture of tert-BuOH (1.8 mL) and $H_2O$ (0.9 mL). The mixture is heated to 65° C. for 16 hr. The reaction mixture is cooled to RT and diluted with EtOAc. The organic layer is washed with brine, dried over $Na_2SO_4$, filtered, and concentrated under reduced pressure. The crude material is purified by silica gel chromatography, eluting with a gradient of 1% to 10% DCM in MeOH to give the title compound (48 mg, 62%) as a white solid. ES/MS (m/z) 597 (M+Na).

Preparation 280 tert-Butyl N-[4-carbamoyl-5-[4-[2-[[3-(2,2-dimethylcyclopropyl)isoxazol-5-yl]amino]-2-oxo-ethyl]phenyl]-2-isopropyl-pyrazol-3-yl]carbamate

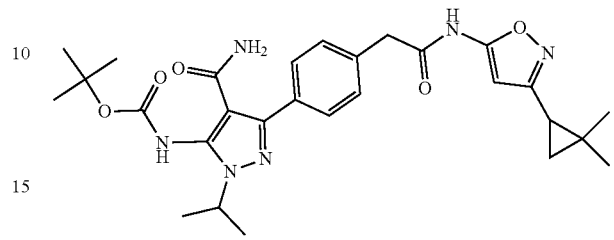

To a stirred solution of tert-butyl N-[4-cyano-5-[4-[2-[[3-(2,2-dimethylcyclopropyl)isoxazol-5-yl]amino]-2-oxo-ethyl]phenyl]-2-isopropyl-pyrazol-3-yl]carbamate (0.365 g, 0.704 mmol) in tert-BuOH (10 mL) and $H_2O$ (5 mL) under $N_2$ is added Parkins catalyst (15 mg, 0.0352 mmol). The reaction mixture is stirred at 60° C. for 4 hr. The reaction mixture is quenched with saturated aq. $NH_4Cl$. The aqueous layer is extracted with EtOAc (3×). The combined organic extracts are washed with brine, dried over $Na_2SO_4$, filtered, and concentrated under reduced pressure. The material is purified by silica gel chromatography, eluting with a gradient of 3000 to 800% EtOAc in cyclohexane to give the title compound (0.363 g, 960) as a white solid. ES/MS (m/z) 559.4 (M+Na).

The following compounds in Table 23 are prepared essentially as described for tert-butyl N-[4-carbamoyl-5-[4-[2-[[3-(2,2-dimethylcyclopropyl)isoxazol-5-yl]amino]-2-oxo-ethyl]phenyl]-2-isopropyl-pyrazol-3-yl]carbamate adjusting reaction time to determine completion of the reaction, using t-BuOH or 4:1 EtOH:$H_2O$ as solvent, and using appropriate chromatography conditions for purification. Temperature can range from about 60-70'° C.

TABLE 23

| Prep. No. | Chemical name | Structure | ES/MS m/z (M + H) |
|---|---|---|---|
| 281 | tert-Butyl N-[4-carbamoyl-2-isopropyl-5-[4-[2-oxo-2-[(3-spiro[2.2]pentan-2-ylisoxazol-5-yl)amino]ethyl]phenyl]pyrazol-3-yl]carbamate | 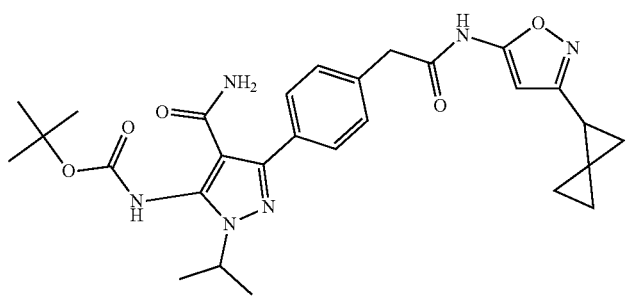 [SMILES: CC(C)n1nc(-c2ccc(CC(=O)Nc3cc(C4CC45CC5)no3)cc2)c(C(N)=O)c1NC(=O)OC(C)(C)C] | 535 |

TABLE 23-continued

| Prep. No. | Chemical name | Structure | ES/MS m/z (M + H) |
|---|---|---|---|
| 282 | tert-Butyl N-[4-carbamoyl-5-[4-[2-[[3-[(2,2-difluorocyclopropyl)methyl]isoxazol-5-yl]amino]-2-oxo-ethyl]phenyl]-2-isopropyl-pyrazol-3-yl]carbamate | 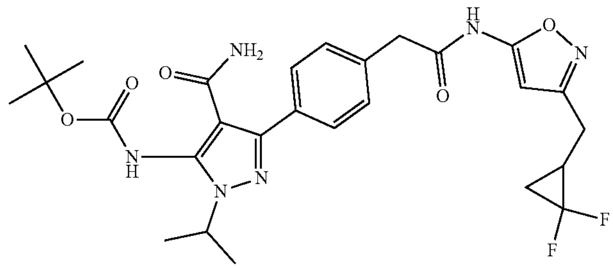 [SMILES: CC(C)n1nc(-c2ccc(CC(=O)Nc3cc(CC4CC4(F)F)no3)cc2)c(C(N)=O)c1NC(=O)OC(C)(C)C] | 581 M + Na |
| 283 | tert-Butyl N-[4-carbamoyl-5-[4-[2-[[3-(3,3-difluorocyclopentyl)isoxazol-5-yl]amino]-2-oxo-ethyl]phenyl]-2-isopropyl-pyrazol-3-yl]carbamate | 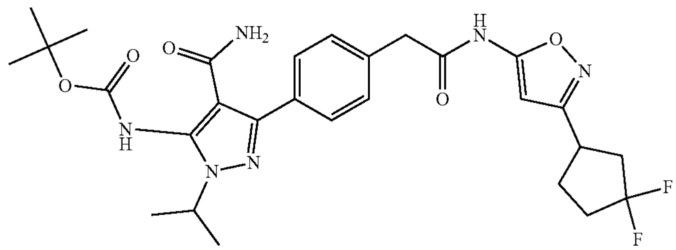 [SMILES: CC(C)n1nc(-c2ccc(CC(=O)Nc3cc(C4CCC(F)(F)C4)no3)cc2)c(C(N)=O)c1NC(=O)OC(C)(C)C] | 595.4 M + Na |
| 284 | tert-Butyl N-[4-carbamoyl-2-isopropyl-5-[4-[2-oxo-2-[(3-spiro[2.3]hexan-2-ylisoxazol-5-yl)amino]ethyl]phenyl]pyrazol-3-yl]carbamate | 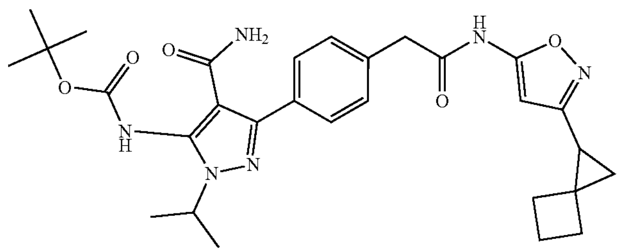 [SMILES: CC(C)n1nc(-c2ccc(CC(=O)Nc3cc(C4CC45CCC5)no3)cc2)c(C(N)=O)c1NC(=O)OC(C)(C)C] | 549.4 |
| 285 | tert-Butyl N-[4-carbamoyl-2-isopropyl-5-[4-[2-oxo-2-[(5-spiro[2.3]hexan-2-ylisoxazol-3-yl)amino]ethyl]phenyl]pyrazol-3-yl]carbamate | 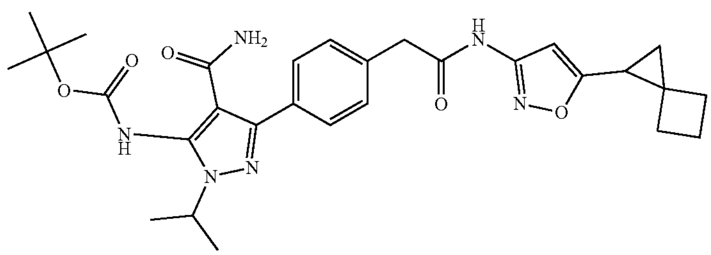 [SMILES: CC(C)n1nc(-c2ccc(CC(=O)Nc3cc(C4CC45CCC5)on3)cc2)c(C(N)=O)c1NC(=O)OC(C)(C)C] | 549 |
| 286 | tert-Butyl N-[4-carbamoyl-5-[4-[2-[[5-(2,2-dimethylcyclobutyl)isoxazol-3-yl]amino]-2-oxo-ethyl]phenyl]-2-isopropyl-pyrazol-3-yl]carbamate | 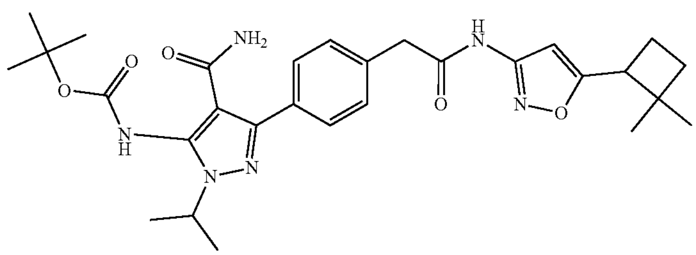 [SMILES: CC(C)n1nc(-c2ccc(CC(=O)Nc3cc(C4CCC4(C)C)on3)cc2)c(C(N)=O)c1NC(=O)OC(C)(C)C] | 551 |
| 287 | tert-Butyl N-[4-carbamoyl-5-[4-[2-[[3-(2,2-dimethylcyclobutyl)isoxazol-5-yl]amino]-2-oxo-ethyl]phenyl]-2-isopropyl-pyrazol-3-yl]carbamate | 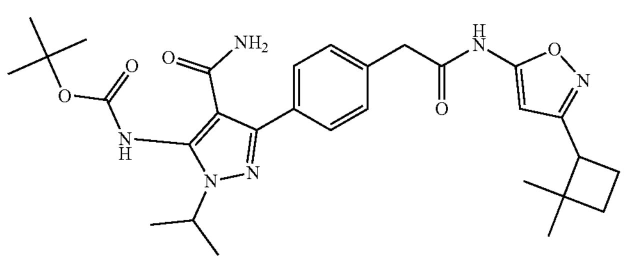 [SMILES: CC(C)n1nc(-c2ccc(CC(=O)Nc3cc(C4CCC4(C)C)no3)cc2)c(C(N)=O)c1NC(=O)OC(C)(C)C] | 551.4 |

TABLE 23-continued

| Prep. No. | Chemical name | Structure | ES/MS m/z (M + H) |
|---|---|---|---|
| 288 | tert-Butyl N-[4-carbamoyl-5-[4-[2-[[3-(2,2-dimethylpropyl)isoxazol-5-yl]amino]-2-oxo-ethyl]-2-fluoro-phenyl]-2-isopropyl-pyrazol-3-yl]carbamate | 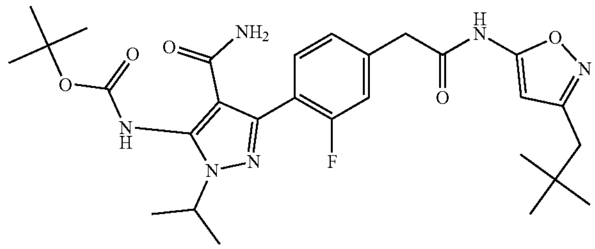 [SMILES: CC(C)n1nc(-c2ccc(CC(=O)Nc3cc(CC(C)(C)C)no3)cc2F)c(C(N)=O)c1NC(=O)OC(C)(C)C] | 557.5 |
| 289 | tert-Butyl N-[4-carbamoyl-5-[3-chloro-4-[2-[[3-(2,2-dimethylpropyl)isoxazol-5-yl]amino]-2-oxo-ethyl]-2-fluoro-phenyl]-2-isopropyl-pyrazol-3-yl]carbamate | 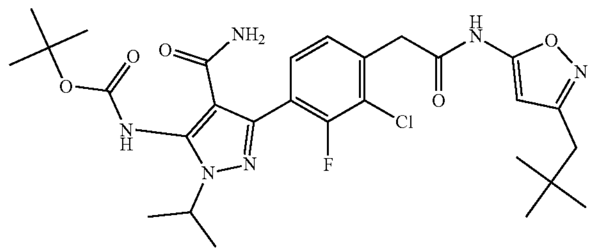 [SMILES: CC(C)n1nc(-c2ccc(CC(=O)Nc3cc(CC(C)(C)C)no3)c(Cl)c2F)c(C(N)=O)c1NC(=O)OC(C)(C)C] | 613.4 M + Na |
| 290 | tert-Butyl N-[4-carbamoyl-5-[2-chloro-4-[2-[[3-(2,2-dimethylpropyl)isoxazol-5-yl]amino]-2-oxo-ethyl]-3-fluoro-phenyl]-2-isopropyl-pyrazol-3-yl]carbamate | 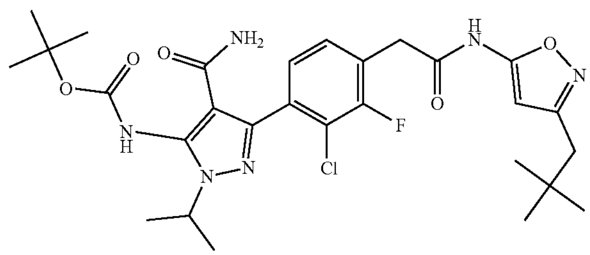 [SMILES: CC(C)n1nc(-c2ccc(CC(=O)Nc3cc(CC(C)(C)C)no3)c(F)c2Cl)c(C(N)=O)c1NC(=O)OC(C)(C)C] | 613.4 M + Na |
| 291 | tert-Butyl N-[4-carbamoyl-5-[4-[2-[[3-(2,2-dimethylpropyl)isoxazol-5-yl]amino]-2-oxo-ethyl]-2-methyl-phenyl]-2-isopropyl-pyrazol-3-yl]carbamate | 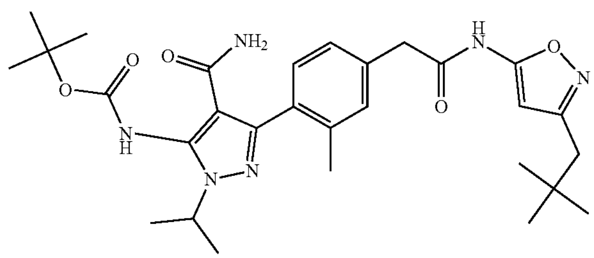 [SMILES: Cc1cc(CC(=O)Nc2cc(CC(C)(C)C)no2)ccc1-c1nn(C(C)C)c(NC(=O)OC(C)(C)C)c1C(N)=O] | 575.4 M + Na |
| 292 | tert-Butyl N-[4-carbamoyl-5-[4-[2-[[3-(cyclobutylmethyl)isoxazol-5-yl]amino]-2-oxo-ethyl]phenyl]-2-isopropyl-pyrazol-3-yl]carbamate | 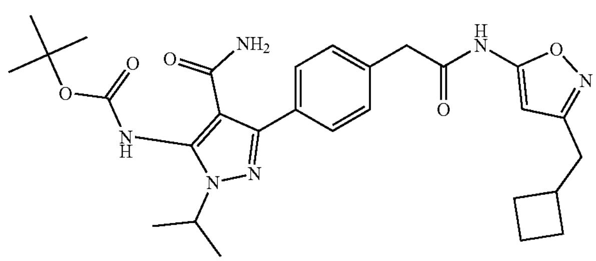 [SMILES: CC(C)n1nc(-c2ccc(CC(=O)Nc3cc(CC4CCC4)no3)cc2)c(C(N)=O)c1NC(=O)OC(C)(C)C] | 559.4 M + Na |
| 293 | tert-Butyl N-[4-carbamoyl-2-isopropyl-5-[4-[2-[[3-[(1-methylcyclobutyl)methyl]isoxazol-5-yl]amino]-2-oxo-ethyl]phenyl]pyrazol-3-yl]carbamate | 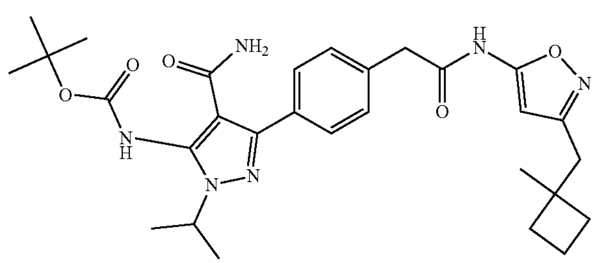 [SMILES: CC(C)n1nc(-c2ccc(CC(=O)Nc3cc(CC4(C)CCC4)no3)cc2)c(C(N)=O)c1NC(=O)OC(C)(C)C] | 573, M + Na |

TABLE 23-continued

| Prep. No. | Chemical name | Structure | ES/MS m/z (M + H) |
|---|---|---|---|
| 294 | tert-Butyl N-[4-carbamoyl-5-[4-[2-[[3-(3,3-dimethylcyclobutyl)isoxazol-5-yl]amino]-2-oxo-ethyl]-2-fluoro-phenyl]-2-isopropyl-pyrazol-3-yl]carbamate | 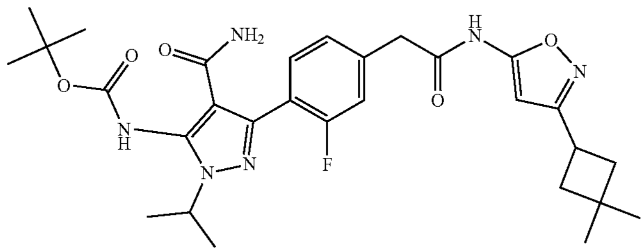 [SMILES: CC(C)n1nc(-c2ccc(CC(=O)Nc3cc(C4CC(C)(C)C4)no3)cc2F)c(C(N)=O)c1NC(=O)OC(C)(C)C] | 591.4 M + Na |
| 295 | tert-Butyl N-[4-carbamoyl-5-[2-chloro-4-[2-[[3-(3,3-dimethylcyclobutyl)isoxazol-5-yl]amino]-2-oxo-ethyl]phenyl]-2-isopropyl-pyrazol-3-yl]carbamate | 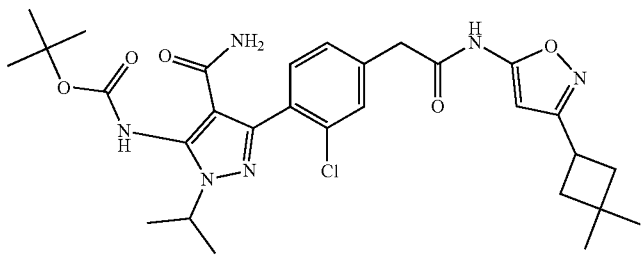 [SMILES: CC(C)n1nc(-c2ccc(CC(=O)Nc3cc(C4CC(C)(C)C4)no3)cc2Cl)c(C(N)=O)c1NC(=O)OC(C)(C)C] | 607.4 M + Na |
| 296 | tert-Butyl N-[4-carbamoyl-5-[2-chloro-4-[2-[[3-(3,3-dimethylcyclobutyl)isoxazol-5-yl]amino]-2-oxo-ethyl]-3-fluoro-phenyl]-2-isopropyl-pyrazol-3-yl]carbamate | 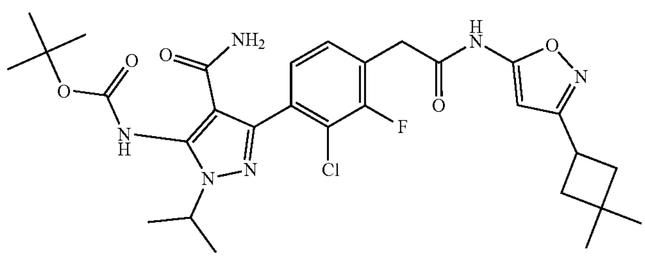 [SMILES: CC(C)n1nc(-c2ccc(CC(=O)Nc3cc(C4CC(C)(C)C4)no3)c(F)c2Cl)c(C(N)=O)c1NC(=O)OC(C)(C)C] | 625.4 M + Na |
| 297 | tert-Butyl N-[4-carbamoyl-5-[4-[2-[[3-(1,1-difluoro-2,2-dimethyl-propyl)isoxazol-5-yl]amino]-2-oxo-ethyl]phenyl]-2-isopropyl-pyrazol-3-yl]carbamate | 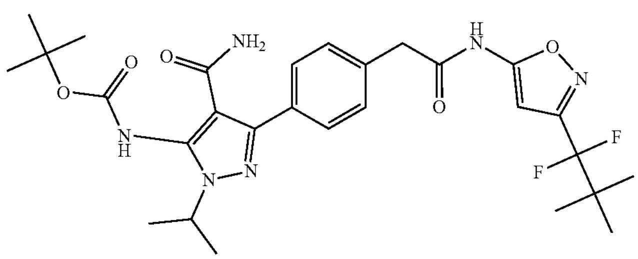 [SMILES: CC(C)n1nc(-c2ccc(CC(=O)Nc3cc(C(F)(F)C(C)(C)C)no3)cc2)c(C(N)=O)c1NC(=O)OC(C)(C)C] | 575.4 |
| 298 | tert-Butyl N-[4-carbamoyl-5-[2-fluoro-4-[2-[[3-(3-methyl-1-bicyclo[1.1.1]pentanyl)isoxazol-5-yl]amino]-2-oxo-ethyl]phenyl]-2-isopropyl-pyrazol-3-yl]carbamate | 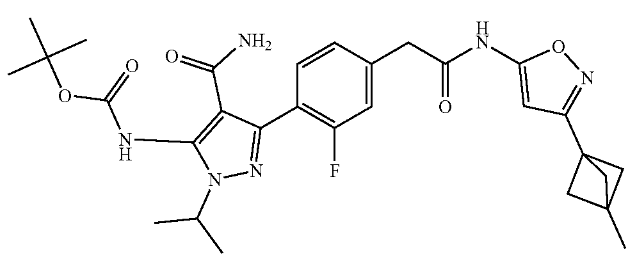 [SMILES: CC(C)n1nc(-c2ccc(CC(=O)Nc3cc(C45CC(C)(C4)C5)no3)cc2F)c(C(N)=O)c1NC(=O)OC(C)(C)C] | 589.4 M + Na |
| 299 | tert-Butyl N-[4-carbamoyl-5-[4-[2-[[3-(3,3-dimethylcyclobutyl)isoxazol-5-yl]amino]-2-oxo-ethyl]-2,3-difluoro-phenyl]-2-isopropyl-pyrazol-3-yl]carbamate | 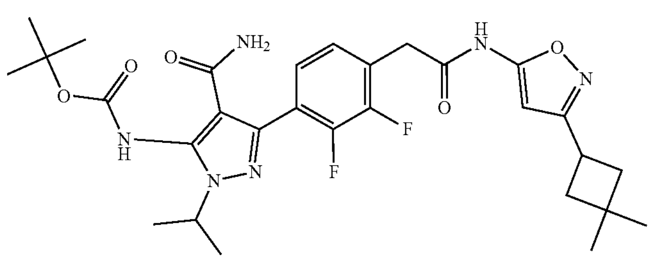 [SMILES: CC(C)n1nc(-c2ccc(CC(=O)Nc3cc(C4CC(C)(C)C4)no3)c(F)c2F)c(C(N)=O)c1NC(=O)OC(C)(C)C] | 609.4, M + Na |

TABLE 23-continued

| Prep. No. | Chemical name | Structure | ES/MS m/z (M + H) |
|---|---|---|---|
| 300 | tert-Butyl N-[4-carbamoyl-5-[4-[2-[[3-(2,2-dimethylpropyl)isoxazol-5-yl]amino]-2-oxo-ethyl]-2,5-difluoro-phenyl]-2-isopropyl-pyrazol-3-yl]carbamate | 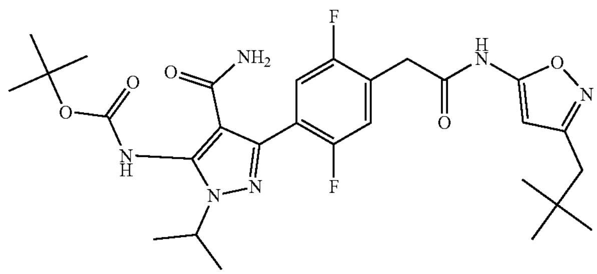 [SMILES: CC(C)n1nc(-c2cc(F)c(CC(=O)Nc3cc(CC(C)(C)C)no3)cc2F)c(C(N)=O)c1NC(=O)OC(C)(C)C] | 575 |
| 301 | tert-Butyl N-[4-carbamoyl-5-[4-[2-[[5-(3,3-dimethylcyclobutyl)isoxazol-3-yl]amino]-2-oxo-ethyl]phenyl]-2-isopropyl-pyrazol-3-yl]carbamate | 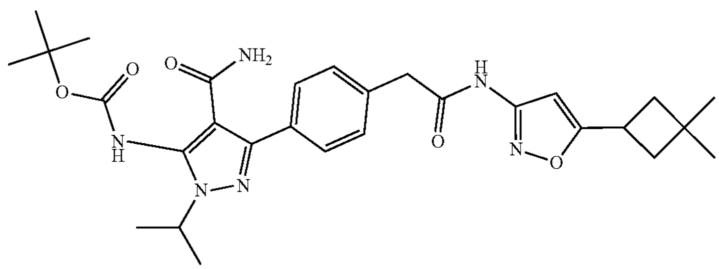 [SMILES: CC(C)n1nc(-c2ccc(CC(=O)Nc3cc(C4CC(C)(C)C4)on3)cc2)c(C(N)=O)c1NC(=O)OC(C)(C)C] | 551 |
| 302 | tert-Butyl N-[4-carbamoyl-5-[4-[2-[[3-(2,2-dimethylpropyl)isoxazol-5-yl]amino]-2-oxo-ethyl]-3,5-difluoro-phenyl]-2-isopropyl-pyrazol-3-yl]carbamate | 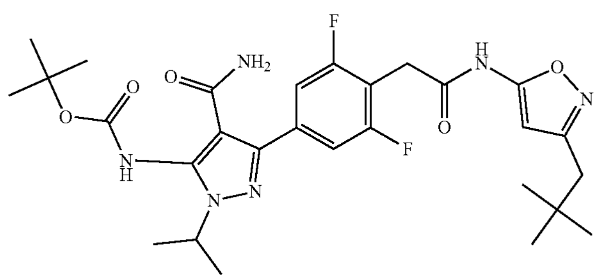 [SMILES: CC(C)n1nc(-c2cc(F)c(CC(=O)Nc3cc(CC(C)(C)C)no3)c(F)c2)c(C(N)=O)c1NC(=O)OC(C)(C)C] | 597 M + Na |
| 303 | tert-Butyl N-[4-carbamoyl-5-[2-chloro-4-[2-[[3-(3-methyl-1-bicyclo[1.1.1]pentanyl)isoxazol-5-yl]amino]-2-oxo-ethyl]phenyl]-2-isopropyl-pyrazol-3-yl]carbamate | 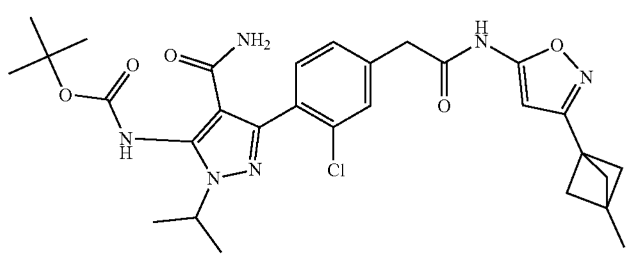 [SMILES: CC(C)n1nc(-c2ccc(CC(=O)Nc3cc(C45CC(C)(C4)C5)no3)cc2Cl)c(C(N)=O)c1NC(=O)OC(C)(C)C] | 605 M + Na |
| 304 | tert-Butyl N-[4-carbamoyl-5-[2-chloro-3-fluoro-4-[2-[[3-(3-methyl-1-bicyclo[1.1.1]pentanyl)isoxazol-5-yl]amino]-2-oxo-ethyl]phenyl]-2-isopropyl-pyrazol-3-yl]carbamate | 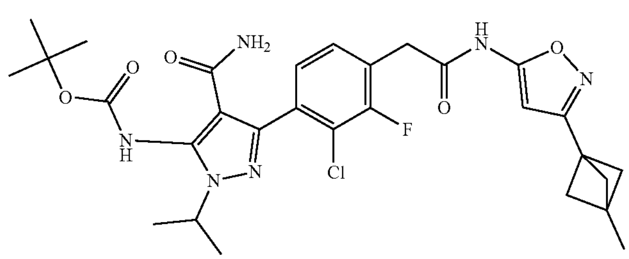 [SMILES: CC(C)n1nc(-c2ccc(CC(=O)Nc3cc(C45CC(C)(C4)C5)no3)c(F)c2Cl)c(C(N)=O)c1NC(=O)OC(C)(C)C] | 623 M + Na |

TABLE 23-continued

| Prep. No. | Chemical name | Structure | ES/MS m/z (M + H) |
|---|---|---|---|
| 305 | tert-Butyl N-[4-carbamoyl-5-[4-[2-[[3-(3,3-dimethylcyclobutyl)-4-fluoro-isoxazol-5-yl]amino]-2-oxo-ethyl]phenyl]-2-isopropyl-pyrazol-3-yl]carbamate | 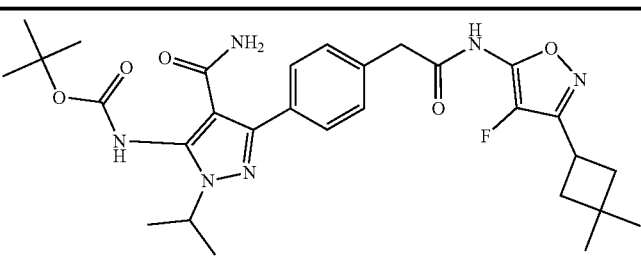 | 569.5 |
| 306 | tert-Butyl N-[4-carbamoyl-5-[3,5-difluoro-4-[2-[[3-(3-methyl-1-bicyclo[1.1.1]pentanyl)isoxazol-5-yl]amino]-2-oxo-ethyl]phenyl]-2-isopropyl-pyrazol-3-yl]carbamate | 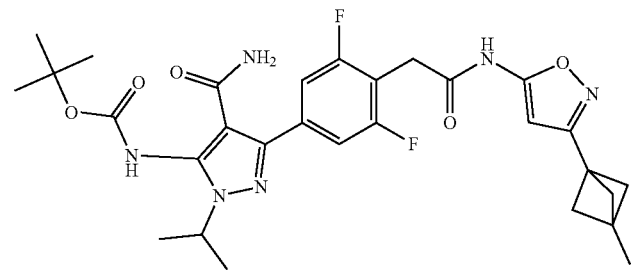 [SMILES: CC(C)n1nc(-c2cc(F)c(CC(=O)Nc3cc(C45CC(C)(C4)C5)no3)c(F)c2)c(C(N)=O)c1NC(=O)OC(C)(C)C] | 607 M + Na |
| 307 | tert-Butyl N-[4-carbamoyl-5-[4-[2-[[3-(2,2-dimethylpropyl)-4-fluoro-isoxazol-5-yl]amino]-2-oxo-ethyl]phenyl]-2-isopropyl-pyrazol-3-yl]carbamate | 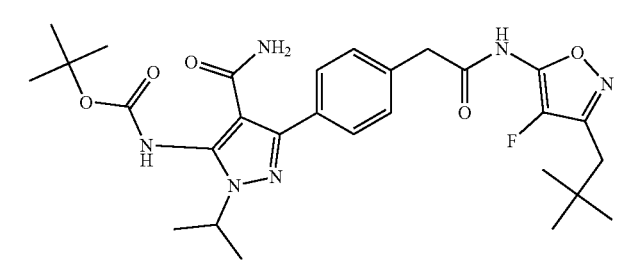 [SMILES: CC(C)n1nc(-c2ccc(CC(=O)Nc3onc(CC(C)(C)C)c3F)cc2)c(C(N)=O)c1NC(=O)OC(C)(C)C] | 557 |
| 308 | tert-Butyl N-[4-carbamoyl-5-[4-[2-[[4-fluoro-3-(3-methyl-1-bicyclo[1.1.1]pentanyl)isoxazol-5-yl]amino]-2-oxo-ethyl]phenyl]-2-isopropyl-pyrazol-3-yl]carbamate | 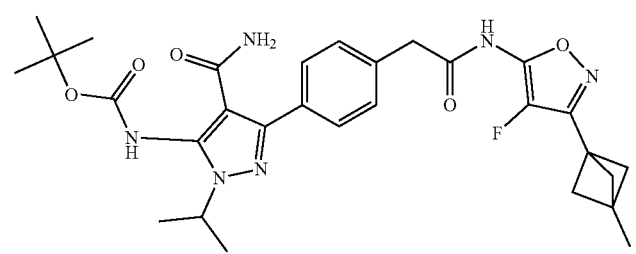 [SMILES: CC(C)n1nc(-c2ccc(CC(=O)Nc3onc(C45CC(C)(C4)C5)c3F)cc2)c(C(N)=O)c1NC(=O)OC(C)(C)C] | 589 M + Na |
| 309 | tert-Butyl (4-carbamoyl-3-(2,3-difluoro-4-(2-((3-(3-fluorobicyclo[1.1.1]pentan-1-yl)isoxazol-5-yl)amino)-2-oxoethyl)phenyl)-1-isopropyl-1H-pyrazol-5-yl)carbamate | 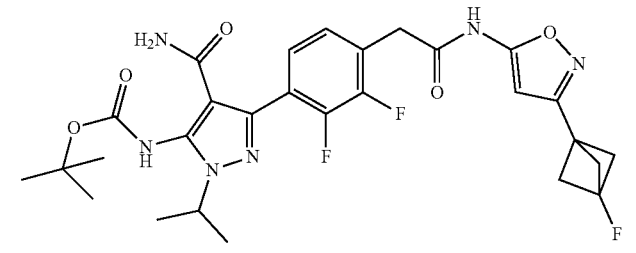 [SMILES: CC(C)n1nc(-c2ccc(CC(=O)Nc3cc(C45CC(F)(C4)C5)no3)c(F)c2F)c(C(N)=O)c1NC(=O)OC(C)(C)C] | 589.4 |
| 310 | tert-Butyl (4-carbamoyl-3-(2,3-difluoro-4-(2-oxo-2-((3-(3-(trifluoromethyl)bicyclo[1.1.1]pentan-1-yl)isoxazol-5-yl)amino)ethyl)phenyl)-1-isopropyl-1H-pyrazol-5-yl)carbamate | 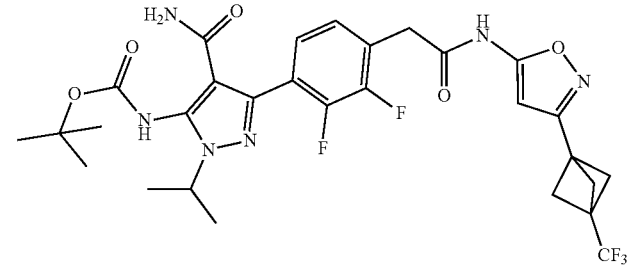 [SMILES: CC(C)n1nc(-c2ccc(CC(=O)Nc3cc(C45CC(C(F)(F)F)(C4)C5)no3)c(F)c2F)c(C(N)=O)c1NC(=O)OC(C)(C)C] | 639.4 |

TABLE 23-continued

| Prep. No. | Chemical name | Structure | ES/MS m/z (M + H) |
|---|---|---|---|
| 311 | tert-Butyl N-[4-carbamoyl-5-[3-chloro-4-[2-[[3-(2,4-dichlorophenyl)isoxazol-5-yl]amino]-2-oxo-ethyl]phenyl]-2-isopropyl-pyrazol-3-yl]carbamate | 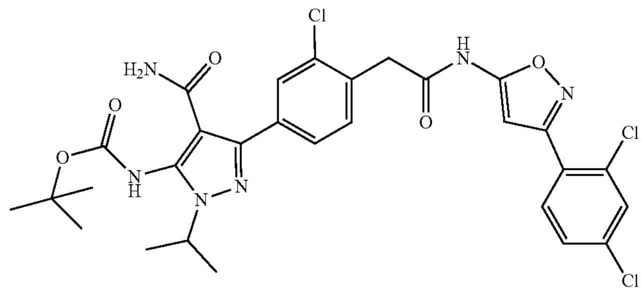 [SMILES: CC(C)n1nc(-c2ccc(CC(=O)Nc3cc(-c4ccc(Cl)cc4Cl)no3)c(Cl)c2)c(C(N)=O)c1NC(=O)OC(C)(C)C] | 649.1 |
| 312 | tert-Butyl 3-(5-amino-4-carbamoyl-3-(4-(2-((3-neopentylisoxazol-5-yl)amino)-2-oxoethyl)phenyl)-1H-pyrazol-1-yl)azetidine-1-carboxylate | 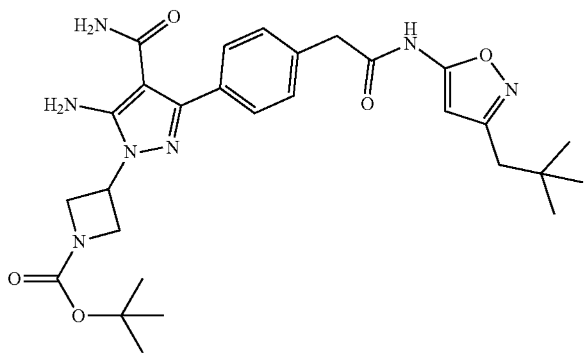 [SMILES: CC(C)(C)Cc1cc(NC(=O)Cc2ccc(-c3nn(C4CN(C(=O)OC(C)(C)C)C4)c(N)c3C(N)=O)cc2)on1] | 552.3 |
| 313 | tert-Butyl N-tert-butoxycarbonyl-N-[4-carbamoyl-5-[4-[2-[[3-[2,4-dichloro-5-[(dimethylamino)methyl]phenyl]isoxazol-5-yl]amino]-2-oxo-ethyl]phenyl]-2-isopropyl-pyrazol-3-yl]carbamate | 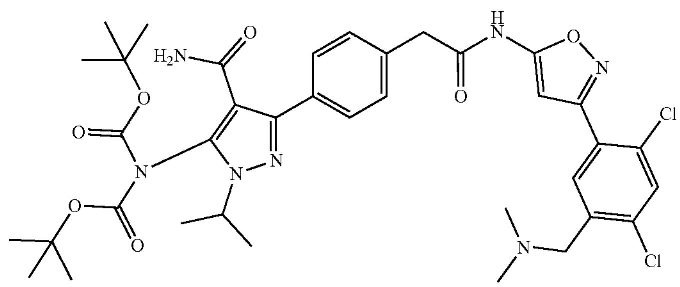 [SMILES: CC(C)n1nc(-c2ccc(CC(=O)Nc3cc(-c4cc(CN(C)C)c(Cl)cc4Cl)no3)cc2)c(C(N)=O)c1N(C(=O)OC(C)(C)C)C(=O)OC(C)(C)C] | 771.7 |

Preparation 314

3-(2,4-Dichloro-3-fluoro-phenyl)-3-oxo-propanenitrile

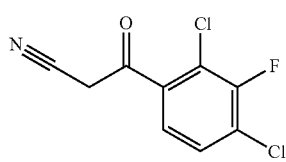 [SMILES: N#CCC(=O)c1ccc(Cl)c(F)c1Cl]

To a stirred solution of LDA (1.35 mL, 2.69 mmol) in THF (4 mL) is added ACN (0.13 mL, 2.47 mmol) dropwise at −78° C. under $N_2$. The reaction is stirred 1 hr at −78° C. then a solution of methyl 2,4-dichloro-3-fluorobenzoate in THF is added dropwise. Once the addition is complete the reaction is stirred at RT for 2 hr. The reaction is quenched with saturated aq. $NH_4Cl$. The pH is adjusted to pH 5 with HCl (1N) then extracted with EtOAc. The organic layer is washed with brine, dried over $Na_2SO_4$, filtered, and concentrated to afford the title compound (0.83 g). This crude material is used without further purification in the preparation of 3-(2,4-dichloro-3-fluoro-phenyl)isoxazol-5-amine.

Preparation 315

3-(2,4-Dichloro-3-fluoro-phenyl)isoxazol-5-amine

A solution of 3-(2,4-dichloro-3-fluoro-phenyl)-3-oxo-propanenitrile (0.27 g, 1.15 mmol) in EtOH (3.7 mL) and H$_2$O (3.7 mL) is treated with hydroxyamine HCl (0.40 g, 5.74 mmol) and KOAc (0.68 g, 6.89 mmol). The mixture is stirred at 60° C. for 1 hr. The reaction is extracted with EtOAc and the organic layer is concentrated in vacuo. The residue is purified by normal phase silica gel chromatography, eluting with 0% to 100% EtOAc in hexanes followed by 0% to 20% MeOH in EtOAc to afford the title compound (0.18 g, 65%). ES/MS (m/z) 247.0 (M+H).

Preparation 316

2-[5-(5-amino-4-cyano-1-ethyl-pyrazol-3-yl)-2-pyridyl]acetate

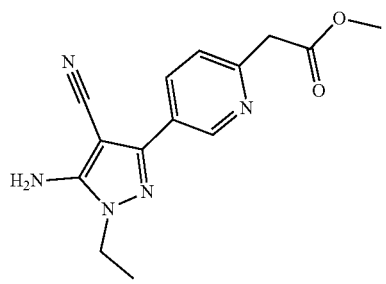 [SMILES: CCn1nc(-c2ccc(CC(=O)OC)nc2)c(C#N)c1N]

A mixture of 5-amino-3-bromo-1-ethyl-pyrazole-4-carbonitrile (233.58 mg, 1.09 mmol), K$_2$CO$_3$ (299.78 mg, 2.17 mmol), Pd(dppf)Cl$_2$ (79.48 mg, 0.11 mmol), and methyl 2-[5-(4,4,5,5-tetramethyl-1,3,2-dioxaborolan-2-yl)-2-pyridyl]acetate (301 mg, 1.09 mmol) in a reaction vial with 1,4-dioxane (9.05 mL) and H$_2$O (1.81 mL) is sparged with nitrogen and heated to 80° C. for 90 min. The reaction is partitioned between DCM and H$_2$O and extracted through a phase separator with DCM (3×). Organic are combined and concentrated in vacuo. The residue is purified by silica chromatography eluting with 0% to 100% EtOAc in hexanes to give the title compound (172 mg, 55.5%). ES/MS (m/z) 286.1 (M+H).

Preparation 317

Methyl 2-[6-(5-amino-4-cyano-1-isopropyl-pyrazol-3-yl)-3-pyridyl]acetate

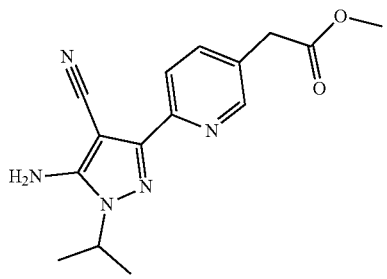 [SMILES: COC(=O)Cc1ccc(-c2nn(C(C)C)c(N)c2C#N)nc1]

Methyl 2-(6-chloropyridin-3-yl)acetate (2.00 g, 10.78 mmol), hexabutyldistannane (9.38 g, 16.16 mmol), and Pd(PPh$_3$)$_4$ (7.47 g, 6.46 mmol) are combined in 1,4-dioxane (40 mL) under N$_2$ and the reaction is stirred for three days at 65° C.

5-amino-3-bromo-1-isopropylpyrazole-4-carbonitrile (0.75 g, 3.30 mmol) is added to a portion (25%) of the above reaction mixture under N$_2$ and the reaction is stirred for 12 hr at 75° C. The solvent is removed under reduced pressure. The residue is purified by silica gel chromatography, eluting with a gradient of 2:1 to 1:1 PE:EtOAc to afford crude product. The product is further purified by reversed-phase chromatography (C18 gel column), eluting with a gradient of 20% to 50% ACN in H$_2$O (0.1% FA) to give the title compound (0.12 g, 15%) as a yellow solid. ES/MS (m/z) 300.2 (M+H).

Preparation 318

Methyl 2-[5-(5-amino-4-cyano-1-isopropyl-pyrazol-3-yl)-2-pyridyl]acetate

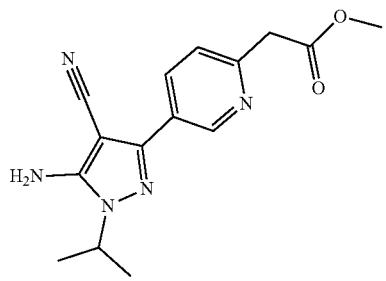 [SMILES: COC(=O)Cc1ccc(-c2nn(C(C)C)c(N)c2C#N)cn1]

Methyl 2-(5-bromopyridin-2-yl)acetate (1.00 g, 4.35 mmol), bis(pinacolato)diboron (1.33 g, 5.22 mmol), KOAc (0.85 g, 8.70 mmol), Pd(dppf)Cl$_2$ (0.32 g, 0.43 mmol) and 1,4-dioxane (30 mL) are added together. The reaction mixture is stirred under N$_2$ at 100° C. for 2 hr. The reaction is filtered, and the filtrate is concentrated under vacuum to give an intermediate residue.

The residue, 5-amino-3-bromo-1-isopropylpyrazole-4-carbonitrile (0.99 g, 4.33 mmol), potassium carbonate (1.19 g, 8.60 mmol), Pd(dppf)Cl$_2$ (0.32 g, 0.43 mmol), 1,4-dioxane (30 mL), and H$_2$O (7 mL) are added together. The reaction mixture is stirred under N$_2$ at 100° C. for 2 hr. The reaction is diluted with H$_2$O (50 mL) is extracted with EtOAc (3×100 mL). The combined organic extracts are washed with brine (2×100 mL), dried over Na$_2$SO$_4$, filtered, and concentrated under vacuum. The residue is purified by silica gel chromatography, eluting with a gradient of 6:1 to 2:1 PE:EtOAc to give the title compound (0.65 g, 50%) as a yellow solid. ES/MS (m/z) 300.1 (M+H).

The following compounds in Table 24 are prepared essentially as described for methyl 2-[5-(5-amino-4-cyano-1-isopropyl-pyrazol-3-yl)-2-pyridyl]acetate and adjusting reaction time to determine completion of the reaction.

TABLE 24

| Prep No. | Chemical Name | Structure | ES/MS m/z (M + H) |
|---|---|---|---|
| 319 | Ethyl 2-[5-(5-amino-4-cyano-1-isopropyl-pyrazol-3-yl)pyrimidin-2-yl]acetate | 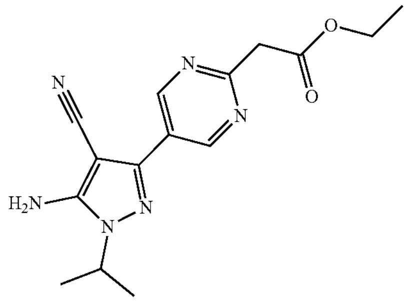 [SMILES: CCOC(=O)Cc1ncc(-c2nn(C(C)C)c(N)c2C#N)cn1] | 315.2 |
| 320 | Methyl 2-[5-(5-amino-4-cyano-1-ethyl-pyrazol-3-yl)-2-pyridyl]acetate | 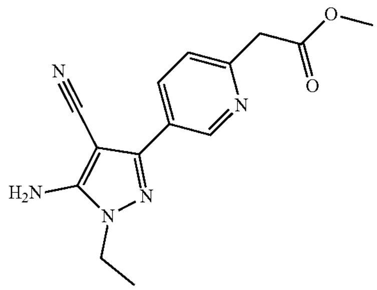 [SMILES: CCn1nc(-c2ccc(CC(=O)OC)nc2)c(C#N)c1N] | 286.1 |

Preparation 321

2-[6-(5-Amino-4-cyano-1-isopropyl-pyrazol-3-yl)-3-pyridyl]acetic Acid

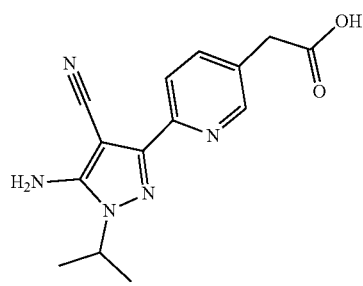 [SMILES: CC(C)n1nc(-c2ccc(CC(=O)O)cn2)c(C#N)c1N]

To methyl 2-[6-(5-amino-4-cyano-1-isopropyl-pyrazol-3-yl)-3-pyridyl]acetate (0.10 g, 0.33 mmol) in methanol (2 mL) and H₂O (2 mL) is added LiOH (0.024 g, 1.00 mmol). The mixture is stirred at 60° C. for 2 hr. The reaction mixture is acidified with 1 M aq. HCl to pH 5 then extracted with EtOAc (2×30 mL). The combined organic extracts are washed with brine (2×20 mL), dried over Na₂SO₄, filtered, and concentrated under reduced pressure. The residue is purified by reversed-phase chromatography (C18 gel column), eluting with a gradient of 5% to 60% ACN in H₂O (0.1% FA) to give the title compound (0.080 g, 80%) as a yellow solid. ES/MS (m/z) 286.4 (M+H).

The following compounds in Table 25 are prepared essentially as described for 2-[6-(5-amino-4-cyano-1-isopropyl-pyrazol-3-yl)-3-pyridyl]acetic acid and adjusting reaction time to determine completion of the reaction.

TABLE 25

| Prep No. | Chemical Name | Structure | ES/MS m/z (M + H) |
|---|---|---|---|
| 322 | 2-[5-(5-Amino-4-cyano-1-isopropyl-pyrazol-3-yl)-2-pyridyl]acetic acid | 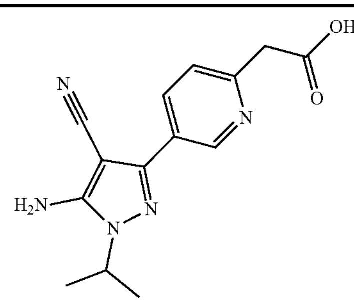 | 286.1 |

TABLE 25-continued

| Prep No. | Chemical Name | Structure | ES/MS m/z (M + H) |
|---|---|---|---|
| 323 | 2-[5-(5-Amino-4-cyano-1-isopropyl-pyrazol-3-yl)pyrimidin-2-yl]acetic acid | 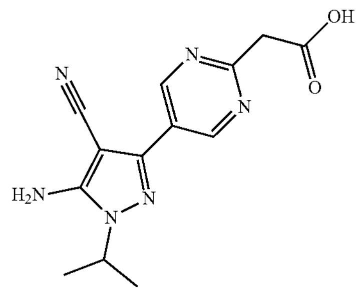 [SMILES: CC(C)n1nc(-c2cnc(CC(=O)O)nc2)c(C#N)c1N] | 287.1 |

Preparation 324

Lithium 2-[5-(5-amino-4-cyano-1-isopropyl-pyrazol-3-yl)-2-pyridyl]acetate

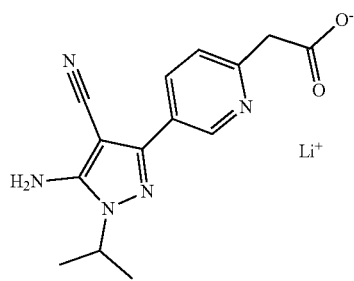 [SMILES: CC(C)n1nc(-c2ccc(CC(=O)[O-])nc2)c(C#N)c1N ; [Li+]]

To methyl 2-[5-(5-amino-4-cyano-1-isopropyl-pyrazol-3-yl)-2-pyridyl]acetate (2.40 g, 8.00 mmol) in THF (20 mL) and H$_2$O (4 mL) is added LiOH (0.17 g, 7.20 mmol). The mixture is stirred at RT for 2 hr. The reaction mixture is diluted with H$_2$O (20 mL) then washed with EtOAc (3×50 mL). The aqueous layer is concentrated under reduced pressure to give the title compound (1.50 g, 65%) as a yellow solid. ES/MS (m/z) 286.1 (M+H).

The following compounds in Table 26 are prepared essentially as described for lithium 2-[5-(5-amino-4-cyano-1-isopropyl-pyrazol-3-yl)-2-pyridyl]acetate and adjusting reaction time to determine completion of the reaction.

TABLE 26

| Prep No. | Chemical Name | Structure | ES/MS m/z (M + H) |
|---|---|---|---|
| 325 | Lithium 2-[5-(5-amino-4-cyano-1-isopropyl-pyrazol-3-yl)pyrimidin-2-yl]acetate | 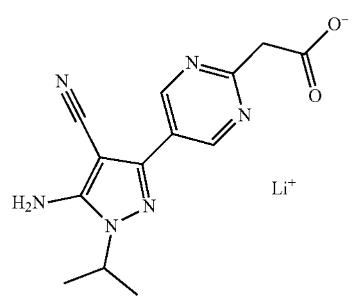 [SMILES: CC(C)n1nc(-c2cnc(CC(=O)[O-])nc2)c(C#N)c1N ; [Li+]] | 287.1 |
| 326 | Lithium 2-[5-(5-amino-4-cyano-1-ethyl-pyrazol-3-yl)-2-pyridyl]acetate | 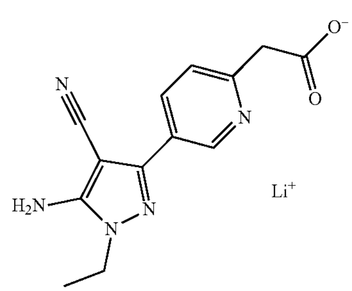 [SMILES: CCn1nc(-c2ccc(CC(=O)[O-])nc2)c(C#N)c1N ; [Li+]] | 272.0 |

Preparation 327

5-Amino-3-(5-chloropyrazin-2-yl)-1-isopropyl-pyrazole-4-carbonitrile

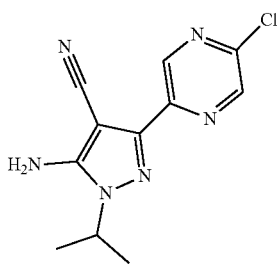 [SMILES: CC(C)n1nc(-c2cnc(Cl)cn2)c(C#N)c1N]

To a stirred solution of 5-chloropyrazine-2-carbaldehyde (0.30 g, 2.11 mmol) and isopropylhydrazinehydrochloride (0.26 g, 2.32 mmol) in DMF (4 mL) is added DIPEA (0.30 g, 2.32 mmol) in portions at RT under $N_2$. The mixture is stirred for 1 hr at 80° C. then is cooled to RT. To the mixture is added a solution of N-bromosuccinimide (0.41 g, 2.32 mmol) in DMF (4 mL) in portions over 5 min. The mixture is stirred for 2 hr at RT.

At the same time, to a stirred solution of malonitrile (0.15 g, 2.32 mmol) in EtOH (2 mL) is added sodium ethoxide (0.39 g, 5.80 mmol) at 0° C. under $N_2$. The mixture is stirred for 30 min at RT.

To the second mixture at 0° C. under $N_2$ is added the first mixture dropwise over 30 min. The reaction is stirred for 2 hr at 80° C. The mixture is diluted with EtOAc and washed with $H_2O$. The organic layer is concentrated under vacuum. The residue is purified by silica gel chromatography, eluting with a gradient of 3:1 to 2:1 PE:EtOAc to give the title compound (0.26 g, 47%) as a white solid. $^1$H NMR ($d_6$-DMSO, 300 MHz) δ (ppm) 8.88 (d, 1H), 8.82 (d, 1H), 6.80 (s, 2H), 4.56 (m, 1H), 1.37 (d, 6H).

The following compounds in Table 27 are prepared essentially as described for 5-amino-3-(5-chloropyrazin-2-yl)-1-isopropyl-pyrazole-4-carbonitrile and adjusting reaction time to determine completion of the reaction.

TABLE 27

| Prep No. | Chemical Name | Structure | ES/MS m/z (M + H) |
|---|---|---|---|
| 328 | 5-Amino-3-(5-bromopyrimidin-2-yl)-1-isopropyl-pyrazole-4-carbonitrile | 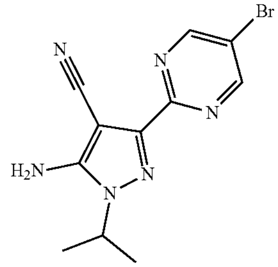 [SMILES: CC(C)n1nc(-c2ncc(Br)cn2)c(C#N)c1N] | 307.1 309.1 |

Preparation 329 tert-Butyl N-[5-(5-bromopyrimidin-2-yl)-4-cyano-2-isopropyl-pyrazol-3-yl]-N-tert-butoxycarbonyl-carbamate

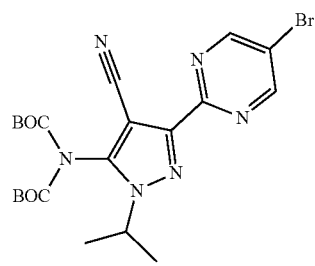 [SMILES: CC(C)n1nc(-c2ncc(Br)cn2)c(C#N)c1N(C(=O)OC(C)(C)C)C(=O)OC(C)(C)C]

A mixture of 5-amino-3-(5-bromopyrimidin-2-yl)-1-isopropyl-pyrazole-4-carbonitrile (0.35 g, 1.14 mmol), di-tert-butyl dicarbonate (0.50 g, 2.28 mmol), and DMAP (0.029 g, 0.23 mmol) in THF (10 mL) is stirred for 4 hr at RT. The mixture is concentrated under reduced pressure. The residue is purified by silica gel chromatography, eluting with a gradient of 10:1 to 1:1 PE:EtOAc to give the title compound (0.40 g, 69%) as a yellow solid. ES/MS (m/z) 507.0, 509.1 (M+H).

Preparation 330 tert-Butyl 2-[2-[5-(tert-butoxycarbonylamino)-4-cyano-1-isopropyl-pyrazol-3-yl]pyrimidin-5-yl]acetate

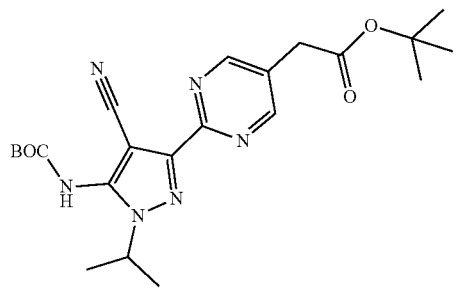 [SMILES: CC(C)n1nc(-c2ncc(CC(=O)OC(C)(C)C)cn2)c(C#N)c1NC(=O)OC(C)(C)C]

A solution of tert-butyl N-[5-(5-bromopyrimidin-2-yl)-4-cyano-2-isopropyl-pyrazol-3-yl]-N-tert-butoxycarbonyl-carbamate (0.39 g, 0.77 mmol), tert-butyl 2-(bromozincio)acetate (0.40 g, 1.54 mmol) and Pd(t-Bu$_3$P)$_2$ (0.079 g, 0.15 mmol) in THF (20 mL) is stirred for 4 hr at 80° C. under $N_2$ and allowed to cool to RT. The solution is concentrated under reduced pressure and the residue is purified by silica gel chromatography, eluting with EtOAc to afford crude product. The product is further purified by reversed-phase chromatography (C18 column), eluting with a gradient of 30% to 50% ACN in $H_2O$ (0.1% FA) to give the title compound (0.24 g, 71%) as a yellow solid. ES/MS (m/z) 443.2 (M+H).

The following compounds in Table 28 are prepared essentially as described for tert-butyl 2-[2-[5-(tert-butoxycarbonylamino)-4-cyano-1-isopropyl-pyrazol-3-yl]pyrimidin-5-yl]acetate and adjusting reaction time to determine completion of the reaction.

TABLE 28

| Prep No. | Chemical Name | Structure | ES/MS m/z (M + H) |
|---|---|---|---|
| 331 | tert-Butyl 2-[5-(5-amino-4-cyano-1-isopropyl-pyrazol-3-yl)pyrazin-2-yl]acetate | 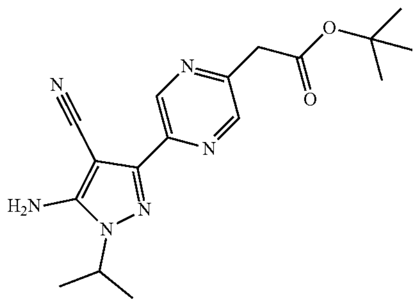 [SMILES: CC(C)n1nc(-c2cnc(CC(=O)OC(C)(C)C)cn2)c(C#N)c1N] | 343.3 |

Preparation 332

2-[5-(5-Amino-4-cyano-1-isopropyl-pyrazol-3-yl)pyrazin-2-yl]acetic Acid

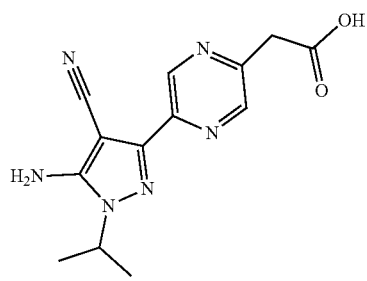 [SMILES: CC(C)n1nc(-c2cnc(CC(=O)O)cn2)c(C#N)c1N]

To tert-butyl 2-[5-(5-amino-4-cyano-1-isopropyl-pyrazol-3-yl)pyrazin-2-yl]acetate (0.26 g, 0.76 mmol) is added TFA (10 mL). The mixture is stirred for 30 min at RT and concentrated under reduced pressure to give the title compound as a yellow solid (0.20 g, 91%) which is used without further purification.

Preparation 333

2-[2-(5-Amino-4-cyano-1-isopropyl-pyrazol-3-yl)pyrimidin-5-yl]acetic Acid

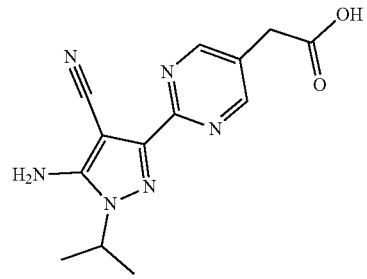

To tert-butyl 2-[2-[5-(tert-butoxycarbonylamino)-4-cyano-1-isopropyl-pyrazol-3-yl]pyrimidin-5-yl]acetate (0.22 g, 0.50 mmol) is added 4 M HCl in 1,4-dioxane (10 mL). The mixture is stirred for 1 hr at RT and concentrated under reduced pressure. The reaction is adjusted to pH 6 with saturated aqueous NaHCO₃, then extracted with EtOAc (3×50 mL). The combined organic extracts are concentrated under reduced pressure. The residue is purified by reversed-phase chromatography (C18 column), eluting with a gradient of 30% to 40% ACN in H₂O (0.1% FA) to give the title compound (0.075 g, 53%) as a yellow solid. ES/MS (m/z) 287.1 (M+H).

Example 1

5-Amino-1-isopropyl-3-(4-(2-((3-((1-methylcyclopropyl)methyl)isoxazol-5-yl)amino)-2-oxoethyl)phenyl)-1H-pyrazole-4-carboxamide

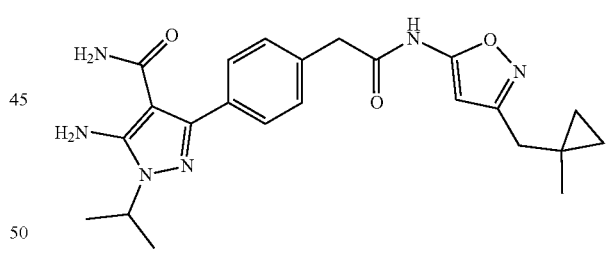

3-[(1-Methylcyclopropyl)methyl]isoxazol-5-amine (62 mg, 0.407 mmol) and 2-(4-(5-amino-4-carbamoyl-1-isopropyl-1H-pyrazol-3-yl)phenyl)acetic acid (0.10 g, 0.331 mmol) are combined in EtOAc (0.38 mL), pyridine (0.64 mL) and ACN (0.64 mL). The mixture is stirred for 5 min and a cloudy suspension is observed. The mixture is cooled to −20° C. and T3P® (0.58 mL, 0.99 mmol, 50% in DMF) is added dropwise. The solution is stirred at −20° C. for 45 min. The mixture is diluted with H₂O (50 mL) and extracted with EtOAc (2×50 mL). The combined organic extracts are dried over Na₂SO₄, filtered, and concentrated under reduced pressure. The residue is purified by silica gel chromatography, eluting with a gradient of 10% to 100% EtOAc in hexanes to give the title compound (28 mg, 19%). ES/MS (m/z) 437.2 (M+H).

Example 2

5-Amino-1-isopropyl-3-(4-(2-oxo-2-((5-(1,1,1-trifluoro-2-methylpropan-2-yl)isoxazol-3-yl)amino)ethyl)phenyl)-1H-pyrazole-4-carboxamide

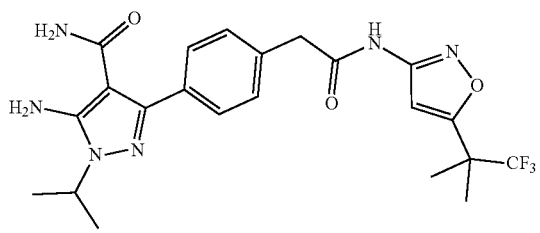 [SMILES: CC(C)n1nc(-c2ccc(CC(=O)Nc3cc(C(C)(C)C(F)(F)F)on3)cc2)c(C(N)=O)c1N]

5-(2,2,2-Trifluoro-1,1-dimethyl-ethyl)isoxazol-3-amine (0.394 g, 2.03 mmol)) and 2-(4-(5-amino-4-carbamoyl-1-isopropyl-1H-pyrazol-3-yl)phenyl)acetic acid (0.500 g, 1.65 mmol) are combined in ACN (20 mL), EtOAc (16 mL) and pyridine (2 mL). The mixture is stirred for 2 min until a clear and colorless solution results. The solution is cooled to −20° C. and T3P® (1.89 mL, 3.23 mmol, 50% in DMF) is added dropwise. The solution is stirred at −20° C. for 30 min. The reaction is diluted with $H_2O$ (8 mL) and extracted with EtOAc (2×10 mL). The combined organic extracts are dried over $Na_2SO_4$, filtered, and concentrated under reduced pressure. The residue is purified by silica gel chromatography, eluting with a gradient of 0% to 100% EtOAc in hexanes followed by 0% to 10% MeOH (with 0.1% $NH_4OH$) in EtOAc to give the title compound (0.363 g, 46%). ES/MS (m/z) 478.8 (M+H).

Example 3

5-Amino-1-isopropyl-3-(4-(2-((3-(1-methylcyclopentyl)isoxazol-5-yl)amino)-2-oxoethyl)phenyl)-1H-pyrazole-4-carboxamide

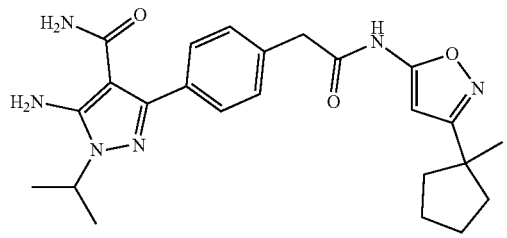 [SMILES: CC(C)n1nc(-c2ccc(CC(=O)Nc3cc(C4(C)CCCC4)no3)cc2)c(C(N)=O)c1N]

To a mixture of 2-(4-(5-amino-4-carbamoyl-1-isopropyl-1H-pyrazol-3-yl)phenyl)acetic acid (20 mg, 0.066 mmol), 3-(1-methylcyclopentyl)isoxazol-5-amine (11 mg, 0.066 mmol) and [[(E)-(1-cyano-2-ethoxy-2-oxo-ethylidene)amino]oxy-morpholino-methylene]-dimethyl-ammonium hexafluorophosphate (34 mg, 0.079 mmol) in DMF (3 mL) is added DIPEA (0.034 mL, 0.195 mmol) and the mixture is stirred at RT for 6 hr. The mixture is diluted with $H_2O$ (20 mL) and extracted with EtOAc (2×20 mL). The combined organic extracts are washed with brine (20 mL), dried over $Na_2SO_4$, filtered, and concentrated under reduced pressure. The residue is purified by silica gel chromatography, eluting with a gradient of 0% to 100% EtOAc in hexanes to give the title compound (3.4 mg, 11%). ES/MS (m/z) 451.2 (M+H).

Example 4

5-Amino-3-(4-(2-((3-(3-fluorobicyclo[1.1.1]pentan-1-yl)isoxazol-5-yl)amino)-2-oxoethyl)phenyl)-1-isopropyl-1H-pyrazole-4-carboxamide

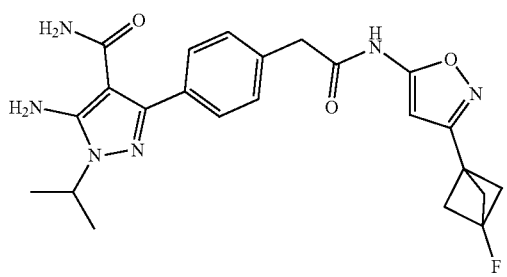 [SMILES: CC(C)n1nc(-c2ccc(CC(=O)Nc3cc(C45CC(F)(C4)C5)no3)cc2)c(C(N)=O)c1N]

2-(4-(5-Amino-4-carbamoyl-1-isopropyl-1H-pyrazol-3-yl)phenyl)acetic acid (0.100 g, 0.331 mmol), 3-(3-fluorobicyclo[1.1.1]pentan-1-yl)isoxazol-5-amine (61 mg, 0.363 mmol), T3P® (0.28 mL, 0.470 mmol, 50% in EtOAc) and DIPEA (0.17 mL, 0.976 mmol) are added together in DCM (5 mL) in a sealed tube and stirred for 10 hr at RT under $N_2$. The mixture is concentrated under reduced pressure and the residue is purified by reversed-phase chromatography (C18 column), eluting with a gradient of 20% to 50% ACN in $H_2O$ (0.1% $NH_4HCO_3$), to give the title compound (67 mg, 45%) as a white solid. ES/MS (m/z) 453.1 (M+H).

Example 5

5-Amino-3-(4-[[(3-[bicyclo[1.1.1]pentan-1-yl]-1,2-oxazol-5-yl)carbamoyl]methyl]phenyl)-1-isopropylpyrazole-4-carboxamide

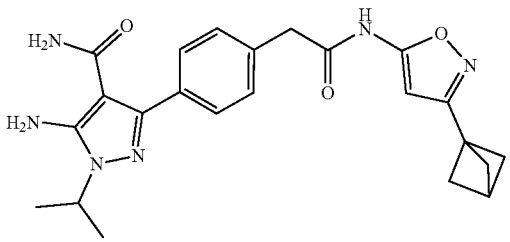 [SMILES: CC(C)n1nc(-c2ccc(CC(=O)Nc3cc(C45CC(C4)C5)no3)cc2)c(C(N)=O)c1N]

2-(4-(5-Amino-4-carbamoyl-1-isopropyl1H-pyrazol-3-yl)phenyl)acetic acid (0.100 g, 0.331 mmol), 3-[bicyclo[1.1.1]pentan-1-yl]-1,2-oxazol-5-amine (60 mg, 0.400 mmol) and DIPEA (0.17 mL, 0.976 mmol) are added together in DCM (10 mL). T3P® (0.30 mL, 0.504 mmol, 50% in EtOAc) is added and the mixture is stirred for 2 hr at RT under $N_2$. The solution is concentrated under reduced pressure and re-dissolved in ACN (5 mL). The residue is purified by reversed-phase chromatography (C18 column), eluting with a gradient of 20% to 60% ACN in $H_2O$ (0.1% $NH_4HCO_3$) to give the title compound (24 mg, 17%) as white solid. ES/MS (m/z) 435.3 (M+H).

Example 6

5-Amino-1-(1-methylcyclopropyl)-3-[4-([[5-(1,1,1-trifluoro-2-methylpropan-2-yl)-1,2-oxazol-3-yl]carbamoyl]methyl)phenyl]pyrazole-4-carboxamide

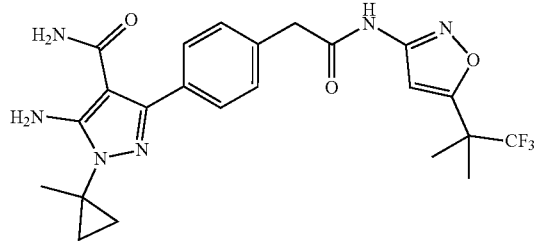 [SMILES: CC1(n2nc(-c3ccc(CC(=O)Nc4cc(C(C)(C)C(F)(F)F)on4)cc3)c(C(N)=O)c2N)CC1]

To a stirred mixture of 2-(4-(5-Amino-4-carbamoyl-1-(1-methylcyclopropyl)-1H-pyrazol-3-yl)phenyl)acetic acid (70 mg, 0.223 mmol) and NMI (55 mg, 0.670 mmol) in ACN (5 mL) is added 5-(1,1,1-trifluoro-2-methylpropan-2-yl)-1,2-oxazol-3-amine (65 mg, 0.335 mmol) and TCFH (94 mg, 0.335 mmol) in portions at RT under $N_2$. The mixture is stirred for 2 hr at 50° C. under $N_2$. The mixture is cooled to RT and concentrated under reduced pressure to a residue. The residue is purified by preparative TLC, eluting with 100% EtOAc and further purified by reversed-phase chromatography (C18 column), eluting with a gradient of 40% to 50% ACN in $H_2O$ to give the title compound (20 mg, 18%) as a white solid. ES/MS (m/z) 491.2 (M+H).

Example 7

5-Amino-1-isopropyl-3-[4-([[3-(1-methylcyclopropyl)-1,2-oxazol-5-yl]carbamoyl]methyl)phenyl]pyrazole-4-carboxamide

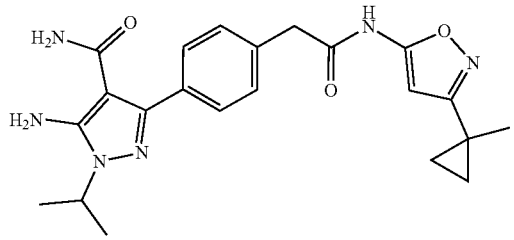 [SMILES: CC(C)n1nc(-c2ccc(CC(=O)Nc3cc(C4(C)CC4)no3)cc2)c(C(N)=O)c1N]

To a stirred mixture of 2-(4-(5-amino-4-carbamoyl-1-isopropyl-1H-pyrazol-3-yl)phenyl)acetic acid (0.300 g, 0.992 mmol) and 3-(1-methylcyclopropyl)-1,2-oxazol-5-amine (0.151 g, 1.09 mmol) in DCM (10 mL) is added DIPEA (0.26 mL, 1.49 mmol) and T3P® (0.71 mL, 1.19 mmol, 50% in EtOAc) in portions at RT under $N_2$. The mixture is stirred for 3 hr at RT under $N_2$ and concentrated to dryness. The residue is purified by reversed-phase chromatography (C18 column), eluting with a gradient of 30% to 40% ACN in $H_2O$ (0.1% $NH_4HCO_3$) to give the title compound (69 mg, 16%) as a white solid. ES/MS (m/z) 423.3 (M+H).

Example 8

5-Amino-3-[4-([[1-methyl-5-(1,1,1-trifluoro-2-methylpropan-2-yl)-1H-pyrazol-3yl]carbamoyl]methyl)phenyl]-1-(propan-2-yl)-1H-pyrazole-4-carboxamide

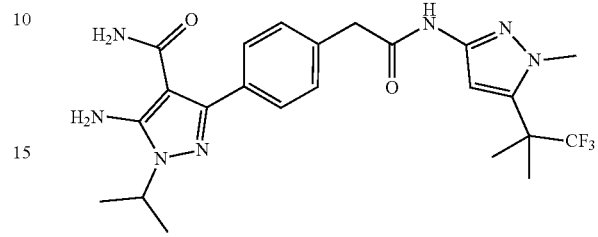

A solution of 1-methyl-5-(1,1,1-trifluoro-2-methylpropan-2-yl)-1H-pyrazol-3-amine (35 mg, 0.169 mmol), 2-(4-(5-amino-4-carbamoyl-1-isopropyl-1H-pyrazol-3-yl)phenyl)acetic acid (56 mg, 0.185 mmol), HATU (96 mg, 0.252 mmol) and DIPEA (0.088 mL, 0.505 mmol) in DMF (2 mL) is stirred for 2 hr at RT under $N_2$. The mixture is purified by reversed-phase chromatography (C18 gel column), eluting with a gradient of 50% to 70% ACN in $H_2O$ (0.1% FA) to give the title compound (28 mg, 34%) as a white solid. ES/MS (m/z) 492.3 (M+H).

Example 9

5-Amino-1-isopropyl-3-[4-([[3-(1,1,1-trifluoro-2-methylpropan-2-yl)-1,2-oxazol-5-yl]carbamoyl]methyl)phenyl]pyrazole-4-carboxamide

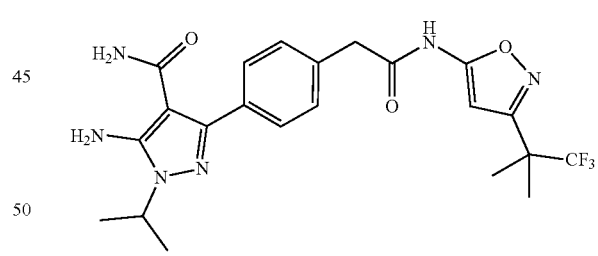

A solution of 2-(4-(5-amino-4-carbamoyl-1-isopropyl-1H-pyrazol-3-yl)phenyl)acetic acid (0.150 g, 0.496 mmol), 3-(1,1,1-trifluoro-2-methylpropan-2-yl)-1,2-oxazol-5-amine (0.106 g, 0.546 mmol), DIPEA (0.35 mL, 2.01 mmol) and T3P® (0.59 mL, 0.991 mmol, 50% in EtOAc) in DCM (5 mL) is stirred for 2 hr at RT under $N_2$. The mixture is concentrated and the residue is purified by reversed-phase chromatography (C18 gel column), eluting with a gradient of 30% to 50% ACN in $H_2O$ (0.1% FA). The product is further purified by reversed-phase preparative HPLC (Phenomenex Gemini C6-Phenyl column), eluting with a gradient of 37% to 45% ACN in $H_2O$ (0.05% FA) to give the title compound (81 mg, 34%) as a white solid. ES/MS (m/z) 479.3 (M+H).

Example 10

5-Amino-3-(4-(2-((5-(tert-butyl)isothiazol-3-yl)amino)-2-oxoethyl)phenyl)-1-isopropyl-1H-pyrazole-4-carboxamide

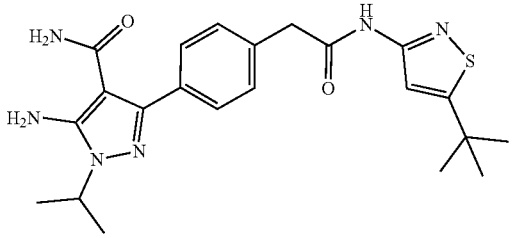 [SMILES: CC(C)n1nc(-c2ccc(CC(=O)Nc3cc(C(C)(C)C)sn3)cc2)c(C(N)=O)c1N]

5-tert-Butylisothiazol-3-amine (47 mg, 0.301 mmol)) and 2-[4-(5-amino-4-carbamoyl-1-isopropyl-pyrazol-3-yl)phenyl]acetic acid (60 mg, 0.198 mmol) are combined in ACN (1.05 mL), EtOAc (0.65 mL) and pyridine (0.31 mL). The mixture is stirred for 2 min until a clear and colorless solution results. The solution is cooled to −20° C. and T3P® (0.26 mL, 0.437 mmol, 50% in EtOAc) is added dropwise. The solution is stirred at −20° C. for 30 mins. The reaction is diluted with $H_2O$ (8 mL) and extracted with DCM (2×10 mL). The combined organic extracts are dried over $Na_2SO_4$, filtered, and concentrated under reduced pressure. The residue is purified by silica gel chromatography, eluting with a gradient of 0% to 100% EtOAc in hexanes followed by 0% to 20% MeOH (with 1% $NH_4OH$) in EtOAc to give the title compound (21 mg, 24%) as a pale yellow solid. ES/MS (m/z) 441.2 (M+H).

Example 11

5-Amino-1-isopropyl-3-(4-[[(3-[3-methylbicyclo[1.1.1]pentan-1-yl]-1,2-oxazol-5-yl)carbamoyl]methyl]phenyl)pyrazole-4-carboxamide

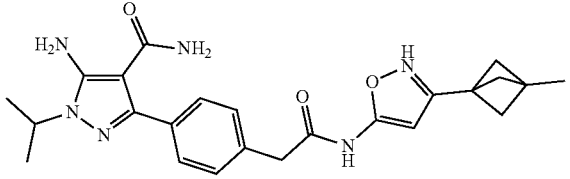

To a stirred mixture of 2-(4-(5-amino-4-carbamoyl-1-isopropyl-1H-pyrazol-3-yl)phenyl)acetic acid (0.300 g, 0.992 mmol) and 3-[3-methylbicyclo[1.1.1]pentan-1-yl]-1,2-oxazol-5-amine (0.163 g, 0.993 mmol) in DCM (20 mL) is added DIPEA (0.52 mL, 2.99 mmol) and T3P® (0.89 mL, 1.50 mmol, 50% in EtOAc) at RT. The mixture is stirred for 1 hr at 50° C. under $N_2$ in a sealed tube. The mixture is concentrated under reduced pressure and purified by reversed-phase chromatography (C18 column), eluting with a gradient of 30% to 40% ACN in $H_2O$ (0.1% $NH_4HCO_3$) to give the title compound (90 mg, 20%) as a white solid. ES/MS (m/z) 449.2 (M+H).

Example 12

5-Amino-1-isopropyl-3-(4-(2-oxo-2-((3-(2-(trifluoromethyl)phenyl)isoxazol-5-yl)amino)ethyl)phenyl)-1H-pyrazole-4-carboxamide

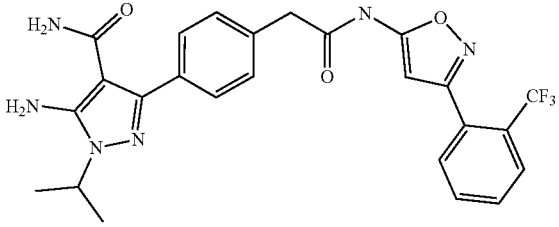 [SMILES: CC(C)n1nc(-c2ccc(CC(=O)Nc3cc(-c4ccccc4C(F)(F)F)no3)cc2)c(C(N)=O)c1N]

2-(4-(5-Amino-4-carbamoyl-1-isopropyl-1H-pyrazol-3-yl)phenyl)acetic acid (75 mg, 0.248 mmol) and 3-[2-(trifluoromethyl)phenyl]isoxazol-5-amine (53 mg, 0.232 mmol) in EtOAc (0.14 mL) and ACN (0.14 mL) is treated with pyridine (0.14 mL) and T3P® (0.28 mL, 0.470 mmol, 50% in EtOAc). The mixture is stirred at 0° C. for 20 min under $N_2$, then partitioned between $H_2O$ and EtOAc. The organic layer is concentrated and purified by reversed-phase preparative HPLC, eluting with a gradient of 5% to 95% ACN in $H_2O$ (0.2% TFA) to give the title compound (4.1 mg, 3.4%). ES/MS (m/z) 513.1 (M+H).

The following compounds in Table 29 are prepared essentially as described for 5-amino-1-isopropyl-3-(4-(2-oxo-2-((3-(2-(trifluoromethyl)phenyl)isoxazol-5-yl)amino)ethyl)phenyl)-1H-pyrazole-4-carboxamide using the appropriate amine and carboxylic acid with a coupling reagent, about 1-6 equivalents, base, about 1-4 equiv and solvent, about 0.3-20 mL, adjusting the reaction time to determine completion of the reaction, and purification conditions as appropriate. The reaction temperature can range from −20° C. to 50° C., T3P® can be added in 50% EtOAc, 50% DMF and TCFH can be added in portions.

*Coupling reagents: 1 T3P®, 2 TCFH, 3 BTFFH, 4 COMU®, 5 TBTU, 6 TFFH, 7 HATU, 8 EDCI/HOBT
Bases: a NMI, b pyridine, c DIPEA
Solvents: I EtOAc, II ACN, III DMF, IV DCM, V THF

TABLE 29

| Ex. No. | Chemical name | Structure | ES/MS m/z (M + H) | * |
|---|---|---|---|---|
| 13 | 5-Amino-1-isopropyl-3-(4-(2-((5-(1-methylcyclohexyl)isoxazol-3-yl)amino)-2-oxoethyl)phenyl)-1H-pyrazole-4-carboxamide | 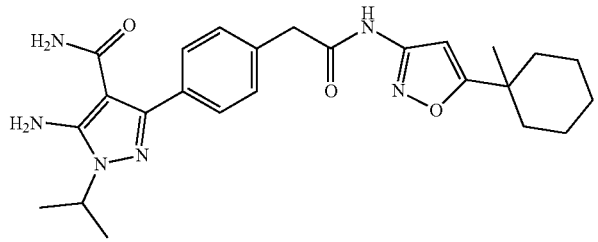 [SMILES: CC(C)n1nc(-c2ccc(CC(=O)Nc3cc(C4(C)CCCCC4)on3)cc2)c(C(N)=O)c1N] | 465 | 3, a, II |

TABLE 29-continued

| Ex. No. | Chemical name | Structure | ES/MS m/z (M + H) | * |
|---|---|---|---|---|
| 14 | 5-Amino-3-(4-(2-((3-(2-chlorophenyl)isoxazol-5-yl)amino)-2-oxoethyl)phenyl)-1-isopropyl-1H-pyrazole-4-carboxamide | 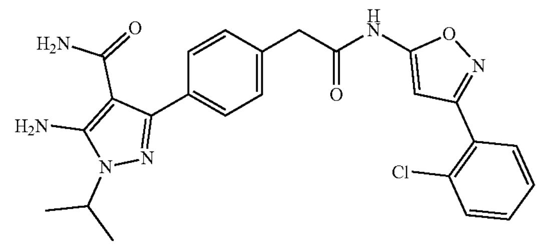 [SMILES: CC(C)n1nc(-c2ccc(CC(=O)Nc3cc(-c4ccccc4Cl)no3)cc2)c(C(N)=O)c1N] | 479.2 | 1, b, II |
| 15 | 5-Amino-3-(4-(2-((3-(2-fluoropropan-2-yl)isoxazol-5-yl)amino)-2-oxoethyl)phenyl)-1-isopropyl-1H-pyrazole-4-carboxamide | 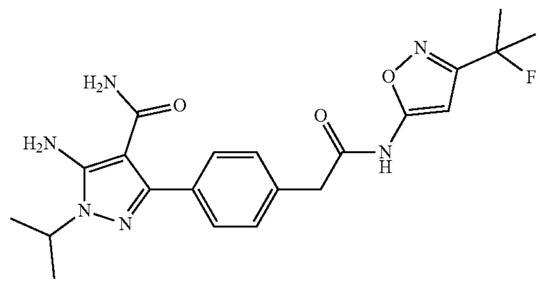 [SMILES: CC(C)n1nc(-c2ccc(CC(=O)Nc3cc(C(C)(C)F)no3)cc2)c(C(N)=O)c1N] | 429.1 | 2, a, III |
| 16 | 5-Amino-1-isopropyl-3-(4-(2-((4-((4-methylpiperazin-1-yl)methyl)-3-(trifluoromethyl)phenyl)amino)-2-oxoethyl)phenyl)-1H-pyrazole-4-carboxamide | 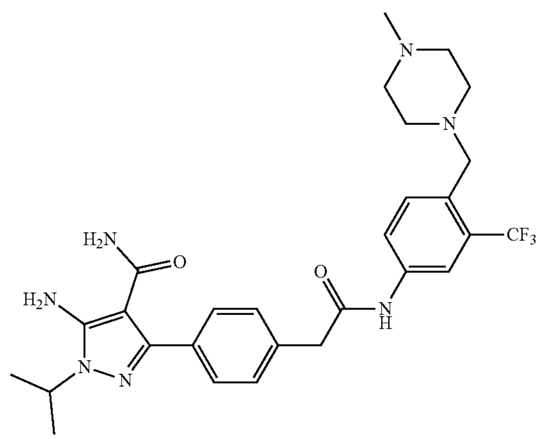 [SMILES: CC(C)n1nc(-c2ccc(CC(=O)Nc3ccc(CN4CCN(C)CC4)c(C(F)(F)F)c3)cc2)c(C(N)=O)c1N] | 558.3 | 2, a, III |
| 17 | 5-Amino-3-(4-(2-((3-cyclohexylisoxazol-5-yl)amino)-2-oxoethyl)-3-fluorophenyl)-1-isopropyl-1H-pyrazole-4-carboxamide | 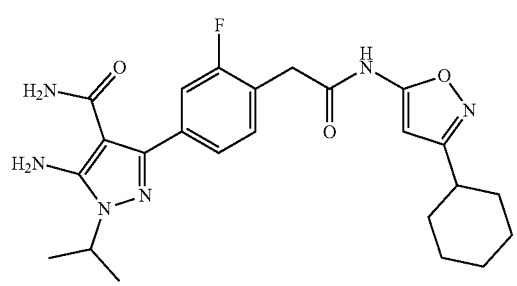 [SMILES: CC(C)n1nc(-c2ccc(CC(=O)Nc3cc(C4CCCCC4)no3)c(F)c2)c(C(N)=O)c1N] | 469.2 | 4, c, III |
| 18 | 5-Amino-3-(4-(2-((3-cyclohexylisoxazol-5-yl)amino)-2-oxoethyl)phenyl)-1-isopropyl-1H-pyrazole-4-carboxamide | 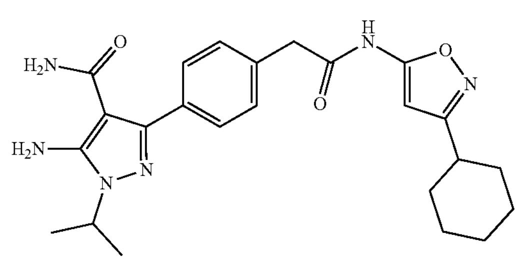 [SMILES: CC(C)n1nc(-c2ccc(CC(=O)Nc3cc(C4CCCCC4)no3)cc2)c(C(N)=O)c1N] | 450.8 | 2, a, III |

TABLE 29-continued

| Ex. No. | Chemical name | Structure | ES/MS m/z (M + H) | * |
|---|---|---|---|---|
| 19 | 5-Amino-1-isopropyl-3-(4-(2-oxo-2-((2-(trifluoromethyl)pyridin-4-yl)amino)ethyl)phenyl)-1H-pyrazole-4-carboxamide | 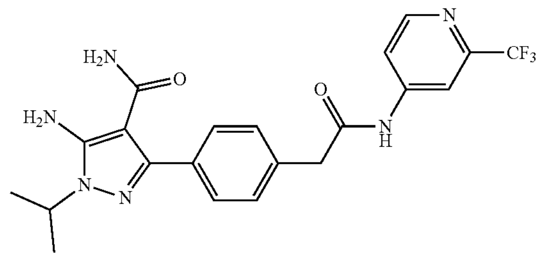 [SMILES: CC(C)n1nc(-c2ccc(CC(=O)Nc3ccnc(C(F)(F)F)c3)cc2)c(C(N)=O)c1N] | 447.2 | 3, a, I & II |
| 20 | 5-Amino-1-isopropyl-3-(4-(2-oxo-2-((4-(trifluoromethyl)pyridin-2-yl)amino)ethyl)phenyl)-1H-pyrazole-4-carboxamide | 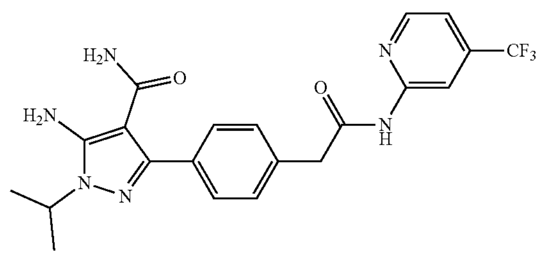 [SMILES: CC(C)n1nc(-c2ccc(CC(=O)Nc3cc(C(F)(F)F)ccn3)cc2)c(C(N)=O)c1N] | 447.2 | 3, a, I & II |
| 21 | 5-Amino-3-(4-(2-((3,5-bis(trifluoromethyl)phenyl)amino)-2-oxoethyl)phenyl)-1-isopropyl-1H-pyrazole-4-carboxamide | 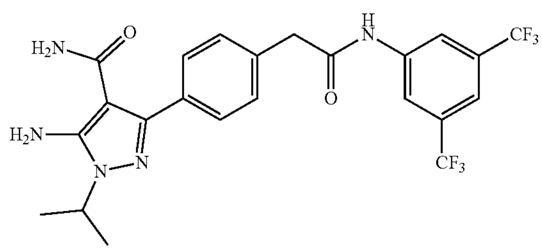 [SMILES: CC(C)n1nc(-c2ccc(CC(=O)Nc3cc(C(F)(F)F)cc(C(F)(F)F)c3)cc2)c(C(N)=O)c1N] | 513.7 | 2, a, III |
| 22 | 5-Amino-1-isopropyl-3-(4-(2-((4-isopropyl-3-(trifluoromethyl)phenyl)amino)-2-oxoethyl)phenyl)-1H-pyrazole-4-carboxamide | 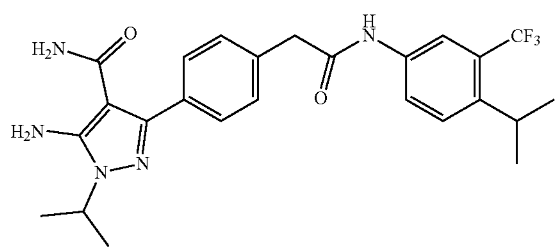 [SMILES: CC(C)c1ccc(NC(=O)Cc2ccc(-c3nn(C(C)C)c(N)c3C(N)=O)cc2)cc1C(F)(F)F] | 488.2 | 6, a, I & II |
| 23 | 5-Amino-3-(4-(2-((4-(dimethylphosphoryl)phenyl)amino)-2-oxoethyl)phenyl)-1-isopropyl-1H-pyrazole-4-carboxamide | 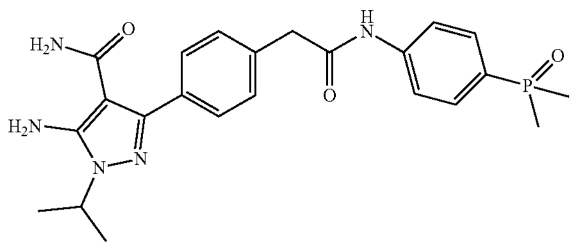 [SMILES: CC(C)n1nc(-c2ccc(CC(=O)Nc3ccc(P(C)(C)=O)cc3)cc2)c(C(N)=O)c1N] | 454.2 | 5, c, IV |
| 24 | 5-Amino-1-isopropyl-3-(4-(2-oxo-2-((3-(spiro[3.3]heptan-2-yl)isoxazol-5-yl)amino)ethyl)phenyl)-1H-pyrazole-4-carboxamide | 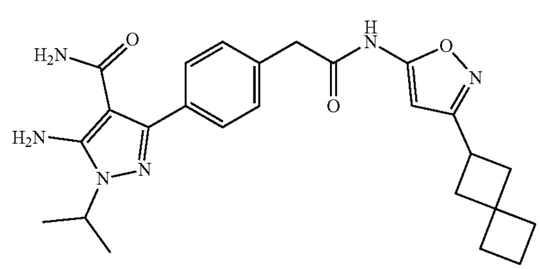 [SMILES: CC(C)n1nc(-c2ccc(CC(=O)Nc3cc(C4CC5(CCC5)C4)no3)cc2)c(C(N)=O)c1N] | 463.2 | 2, a, I & II |

TABLE 29-continued

| Ex. No. | Chemical name | Structure | ES/MS m/z (M + H) | * |
|---|---|---|---|---|
| 25 | 5-Amino-3-(4-(2-((5-(4-chloro-2-fluorophenyl)-1,3,4-thiadiazol-2-yl)amino)-2-oxoethyl)phenyl)-1-isopropyl-1H-pyrazole-4-carboxamide | 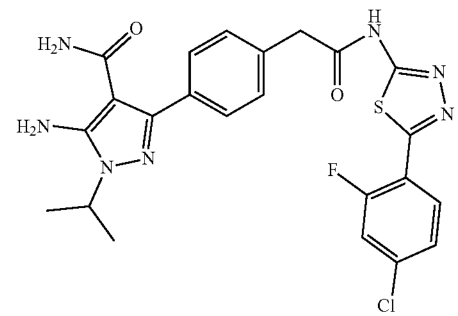 [SMILES: CC(C)n1nc(-c2ccc(CC(=O)Nc3nnc(-c4ccc(Cl)cc4F)s3)cc2)c(C(N)=O)c1N] | 514.2 | 2, a, I & II |
| 26 | 5-Amino-1-isopropyl-3-(4-(2-oxo-2-((4-(pentafluoro-λ6-sulfanyl)phenyl)amino)ethyl)phenyl)-1H-pyrazole-4-carboxamide | 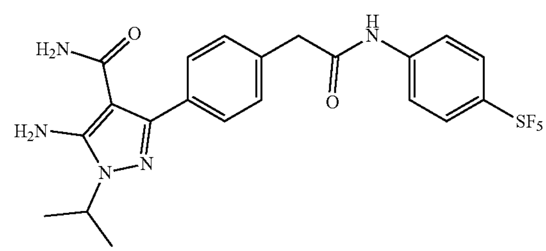 | 504.2 | 5, c, IV |
| 27 | 5-Amino-1-isopropyl-3-(4-(2-oxo-2-((3-(spiro[2.3]hexan-5-yl)isoxazol-5-yl)amino)ethyl)phenyl)-1H-pyrazole-4-carboxamide | 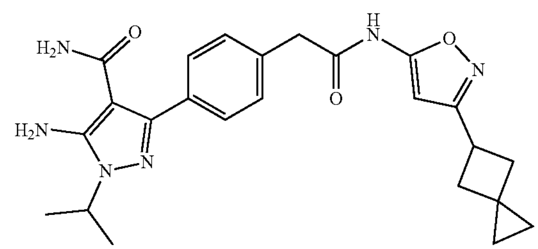 [SMILES: CC(C)n1nc(-c2ccc(CC(=O)Nc3cc(C4CC5(CC5)C4)no3)cc2)c(C(N)=O)c1N] | 449.2 | 2, a, I & II |
| 28 | 5-Amino-1-isopropyl-3-(4-(2-((3-(2-methylcyclopropyl)isoxazol-5-yl)amino)-2-oxoethyl)phenyl)-1H-pyrazole-4-carboxamide | 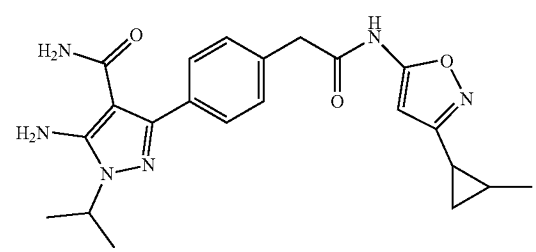 [SMILES: CC1CC1c1cc(NC(=O)Cc2ccc(-c3nn(C(C)C)c(N)c3C(N)=O)cc2)on1] | 423.8 | 2, a, III |
| 29 | 5-Amino-1-isopropyl-3-(4-(2-((3-(2-methoxyphenyl)isoxazol-5-yl)amino)-2-oxoethyl)phenyl)-1H-pyrazole-4-carboxamide | 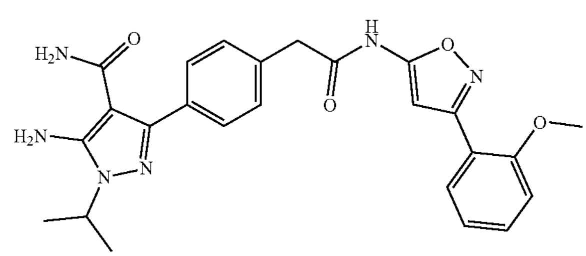 [SMILES: COc1ccccc1-c1cc(NC(=O)Cc2ccc(-c3nn(C(C)C)c(N)c3C(N)=O)cc2)on1] | 475.2 | 1, b, I & II |

TABLE 29-continued

| Ex. No. | Chemical name | Structure | ES/MS m/z (M + H) | * |
|---|---|---|---|---|
| 30 | 5-Amino-3-(4-(2-((3-(2-chloro-4-fluorophenyl)isoxazol-5-yl)amino)-2-oxoethyl)phenyl)-1-isopropyl-1H-pyrazole-4-carboxamide | 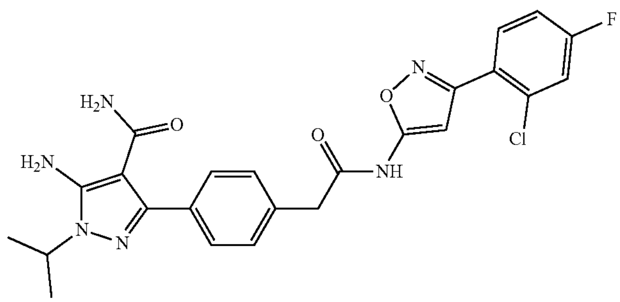 [SMILES: CC(C)n1nc(-c2ccc(CC(=O)Nc3cc(-c4ccc(F)cc4Cl)no3)cc2)c(C(N)=O)c1N] | 497.1 | 2, a, III |
| 31 | 5-Amino-3-(4-(2-((5-(bicyclo[2.2.1]heptan-2-yl)isoxazol-3-yl)amino)-2-oxoethyl)phenyl)-1-isopropyl-1H-pyrazole-4-carboxamide | 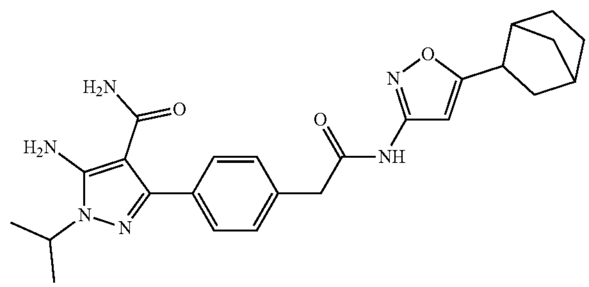 [SMILES: CC(C)n1nc(-c2ccc(CC(=O)Nc3cc(C4CC5CCC4C5)on3)cc2)c(C(N)=O)c1N] | 463.2 | 2, a, III |
| 32 | 5-Amino-1-isopropyl-3-(4-(2-oxo-2-((4-(pyrrolidin-1-ylmethyl)-3-(trifluoromethyl)phenyl)amino)ethyl)phenyl)-1H-pyrazole-4-carboxamide | 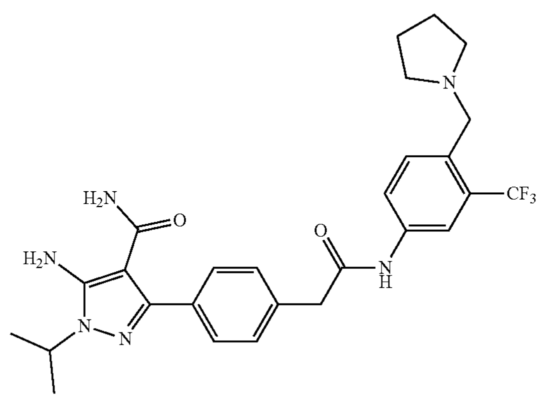 [SMILES: CC(C)n1nc(-c2ccc(CC(=O)Nc3ccc(CN4CCCC4)c(C(F)(F)F)c3)cc2)c(C(N)=O)c1N] | 529.2 | 2, a, I & II |
| 33 | 5-Amino-1-isopropyl-3-(4-(2-((5-neopentylisoxazol-3-yl)amino)-2-oxoethyl)phenyl)-1H-pyrazole-4-carboxamide | 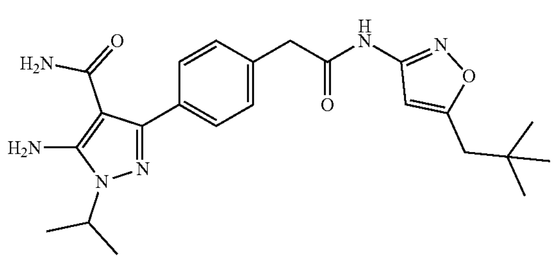 [SMILES: CC(C)n1nc(-c2ccc(CC(=O)Nc3cc(CC(C)(C)C)on3)cc2)c(C(N)=O)c1N] | 439.3 | 3, a, I & II |
| 34 | 5-Amino-1-isopropyl-3-(4-(2-((4-(4-methoxypiperidin-1-yl)-3-(trifluoromethyl)phenyl)amino)-2-oxoethyl)phenyl)-1H-pyrazole-4-carboxamide | 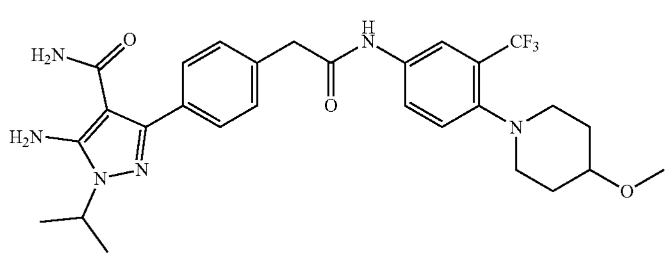 [SMILES: COC1CCN(c2ccc(NC(=O)Cc3ccc(-c4nn(C(C)C)c(N)c4C(N)=O)cc3)cc2C(F)(F)F)CC1] | 559.2 | 6, a, I & II |

TABLE 29-continued

| Ex. No. | Chemical name | Structure | ES/MS m/z (M + H) | * |
|---|---|---|---|---|
| 35 | 5-Amino-3-(4-(2-((5-(cyclopentylmethyl)isoxazol-3-yl)amino)-2-oxoethyl)phenyl)-1-isopropyl-1H-pyrazole-4-carboxamide | 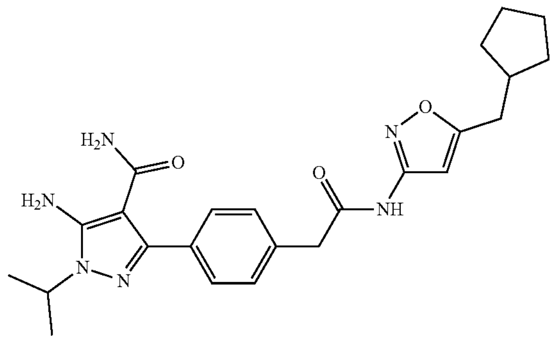 [SMILES: CC(C)n1nc(-c2ccc(CC(=O)Nc3cc(CC4CCCC4)on3)cc2)c(C(N)=O)c1N] | 451.2 | 6, a, III |
| 36 | 5-Amino-3-(4-(2-((3-(2,3-dihydro-1H-inden-5-yl)isoxazol-5-yl)amino)-2-oxoethyl)phenyl)-1-isopropyl-1H-pyrazole-4-carboxamide | 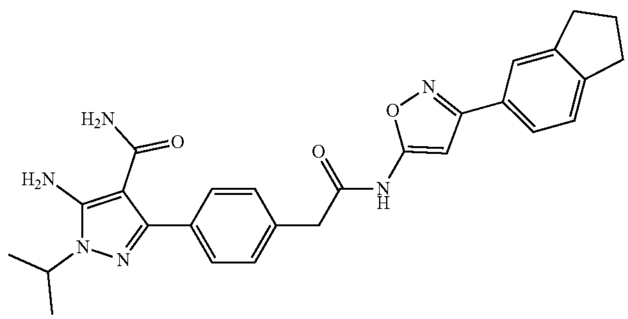 [SMILES: CC(C)n1nc(-c2ccc(CC(=O)Nc3cc(-c4ccc5c(c4)CCC5)no3)cc2)c(C(N)=O)c1N] | 485.2 | 2, a, III |
| 37 | 5-Amino-1-isopropyl-3-(4-(2-((3-(1-methylcyclohexyl)isoxazol-5-yl)amino)-2-oxoethyl)phenyl)-1H-pyrazole-4-carboxamide | 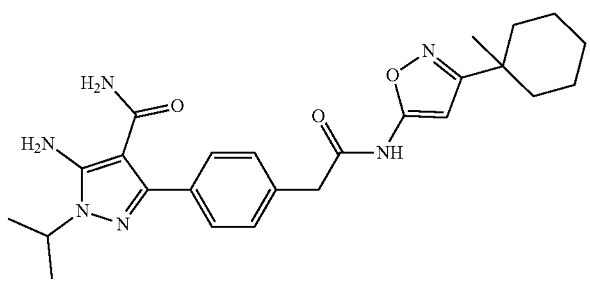 [SMILES: CC(C)n1nc(-c2ccc(CC(=O)Nc3cc(C4(C)CCCCC4)no3)cc2)c(C(N)=O)c1N] | 465.2 | 2, a, III |
| 38 | 5-Amino-3-(4-(2-((3-(bicyclo[2.2.1]heptan-2-yl)isoxazol-5-yl)amino)-2-oxoethyl)phenyl)-1-isopropyl-1H-pyrazole-4-carboxamide | 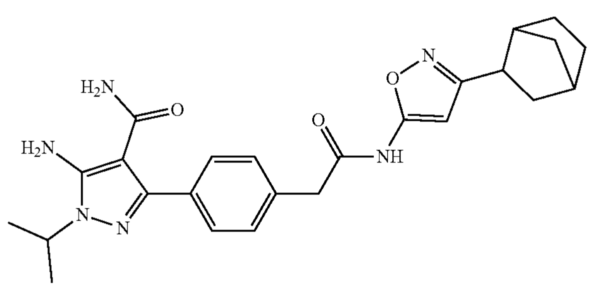 [SMILES: CC(C)n1nc(-c2ccc(CC(=O)Nc3cc(C4CC5CCC4C5)no3)cc2)c(C(N)=O)c1N] | 462.8 | 2, a, III |
| 39 | 5-Amino-3-(4-(2-((5-(bicyclo[2.2.1]heptan-2-yl)-1H-pyrazol-3-yl)amino)-2-oxoethyl)phenyl)-1-isopropyl-1H-pyrazole-4-carboxamide | 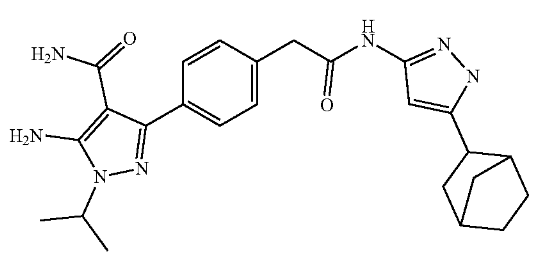 [SMILES: CC(C)n1nc(-c2ccc(CC(=O)Nc3cc(C4CC5CCC4C5)[nH]n3)cc2)c(C(N)=O)c1N] | 462.2 | 1, b, I & II |

TABLE 29-continued

| Ex. No. | Chemical name | Structure | ES/MS m/z (M + H) | * |
|---|---|---|---|---|
| 40 | 5-Amino-1-isopropyl-3-(4-(2-((5-methyl-4-phenylthiazol-2-yl)amino)-2-oxoethyl)phenyl)-1H-pyrazole-4-carboxamide | 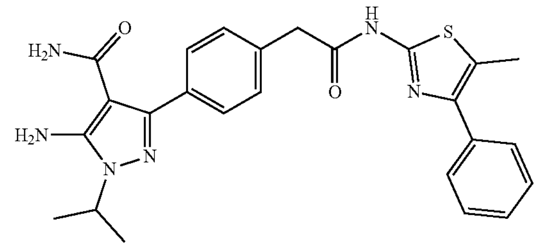 [SMILES: Cc1sc(NC(=O)Cc2ccc(-c3nn(C(C)C)c(N)c3C(N)=O)cc2)nc1-c1ccccc1] | 474.8 | 2, a, III |
| 41 | 5-Amino-1-isopropyl-3-(4-(2-oxo-2-((5-(tetrahydro-2H-pyran-4-yl)isoxazol-3-yl)amino)ethyl)phenyl)-1H-pyrazole-4-carboxamide | 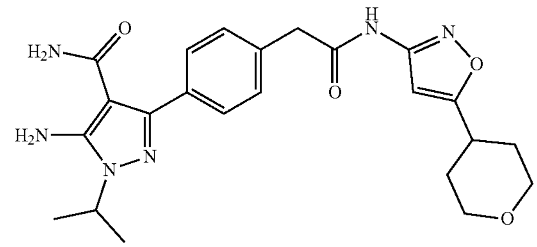 [SMILES: CC(C)n1nc(-c2ccc(CC(=O)Nc3cc(C4CCOCC4)on3)cc2)c(C(N)=O)c1N] | 452.8 | 2, a, III |
| 42 | 5-Amino-1-isopropyl-3-(4-(2-((5-neopentyl-1,3,4-thiadiazol-2-yl)amino)-2-oxoethyl)phenyl)-1H-pyrazole-4-carboxamide | 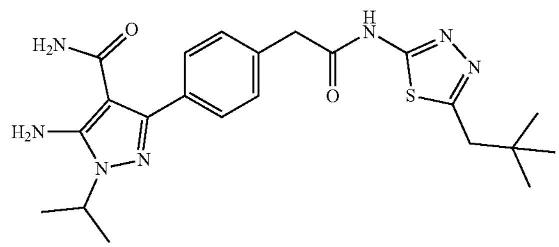 [SMILES: CC(C)n1nc(-c2ccc(CC(=O)Nc3nnc(CC(C)(C)C)s3)cc2)c(C(N)=O)c1N] | 455.8 | 2, a, III |
| 43 | 5-Amino-1-isopropyl-3-(4-(2-oxo-2-((5,5,8,8-tetramethyl-5,6,7,8-tetrahydronaphthalen-2-yl)amino)ethyl)phenyl)-1H-pyrazole-4-carboxamide | 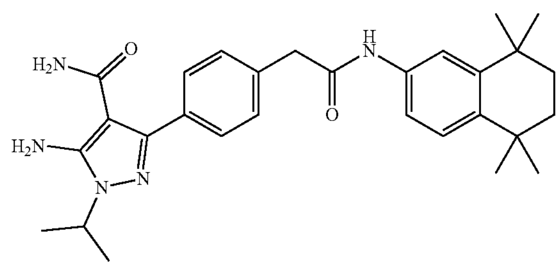 [SMILES: CC(C)n1nc(-c2ccc(CC(=O)Nc3ccc4c(c3)C(C)(C)CCC4(C)C)cc2)c(C(N)=O)c1N] | 488.2 | 5, c, IV |
| 44 | 5-Amino-1-isopropyl-3-(4-(2-oxo-2-((1,1,3,3-tetramethyl-2,3-dihydro-1H-inden-5-yl)amino)ethyl)phenyl)-1H-pyrazole-4-carboxamide | 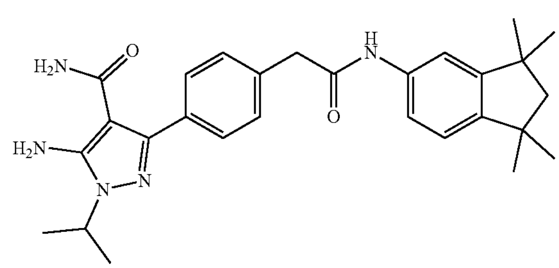 [SMILES: CC(C)n1nc(-c2ccc(CC(=O)Nc3ccc4c(c3)C(C)(C)CC4(C)C)cc2)c(C(N)=O)c1N] | 474.2 | 5, c, IV |
| 45 | 5-Amino-1-isopropyl-3-(4-(2-oxo-2-((3-(p-tolyl)isoxazol-5-yl)amino)ethyl)phenyl)-1H-pyrazole-4-carboxamide | 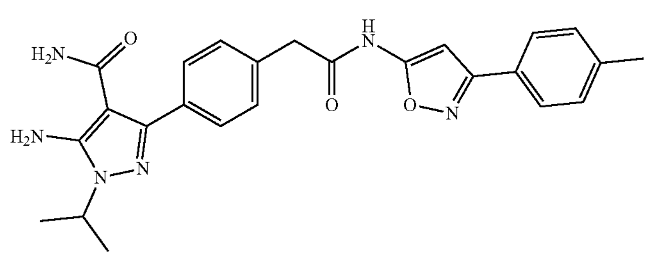 [SMILES: Cc1ccc(-c2cc(NC(=O)Cc3ccc(-c4nn(C(C)C)c(N)c4C(N)=O)cc3)on2)cc1] | 459.2 | 1, b, I & II |

TABLE 29-continued

| Ex. No. | Chemical name | Structure | ES/MS m/z (M + H) | * |
|---|---|---|---|---|
| 46 | 5-Amino-3-(4-(2-((2,3-dihydro-1H-inden-5-yl)amino)-2-oxoethyl)phenyl)-1-isopropyl-1H-pyrazole-4-carboxamide | 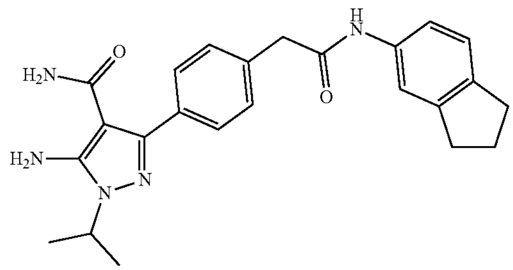 [SMILES: CC(C)n1nc(-c2ccc(CC(=O)Nc3ccc4c(c3)CCC4)cc2)c(C(N)=O)c1N] | 418.2 | 5, c, IV |
| 47 | 5-Amino-1-isopropyl-3-(4-(2-((3-(4-methoxyphenyl)isoxazol-5-yl)amino)-2-oxoethyl)phenyl)-1H-pyrazole-4-carboxamide | 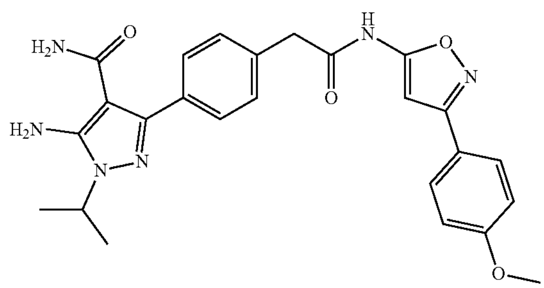 [SMILES: COc1ccc(-c2cc(NC(=O)Cc3ccc(-c4nn(C(C)C)c(N)c4C(N)=O)cc3)on2)cc1] | 474.2 | 1, b, I & II |
| 48 | 5-Amino-3-(4-(2-((4-cyclopropyl-3-methylphenyl)amino)-2-oxoethyl)phenyl)-1-isopropyl-1H-pyrazole-4-carboxamide | 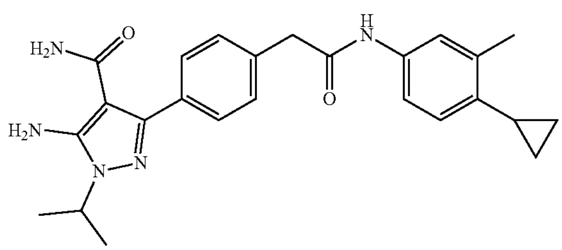 [SMILES: Cc1cc(NC(=O)Cc2ccc(-c3nn(C(C)C)c(N)c3C(N)=O)cc2)ccc1C1CC1] | 432.2 | 5, c, IV |
| 49 | 5-Amino-1-isopropyl-3-(4-(2-oxo-2-((3-(2-(trifluoromethyl)spiro[3.3]heptan-2-yl)isoxazol-5-yl)amino)ethyl)phenyl)-1H-pyrazole-4-carboxamide | 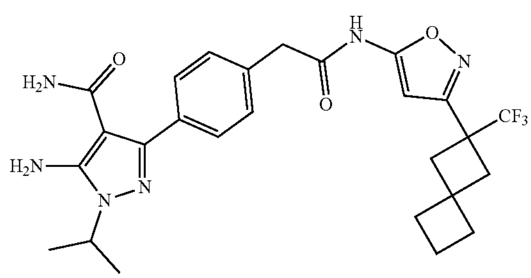 [SMILES: CC(C)n1nc(-c2ccc(CC(=O)Nc3cc(C4(C(F)(F)F)CC5(CCC5)C4)no3)cc2)c(C(N)=O)c1N] | 531.2 | 2, a, I & II |
| 50 | 5-amino-1-isopropyl-3-[4-[2-oxo-2-[3-(pentafluoro-λ$^6$-sulfanyl)anilino]ethyl]phenyl]pyrazole-4-carboxamide | 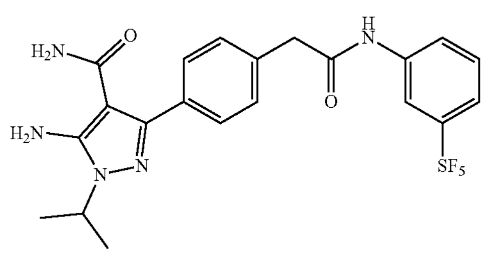 | 503.2 | 5, c, IV |

TABLE 29-continued

| Ex. No. | Chemical name | Structure | ES/MS m/z (M + H) | * |
|---|---|---|---|---|
| 51 | 5-Amino-3-(4-(2-((3-(2-fluorophenyl)isoxazol-5-yl)amino)-2-oxoethyl)phenyl)-1-isopropyl-1H-pyrazole-4-carboxamide | 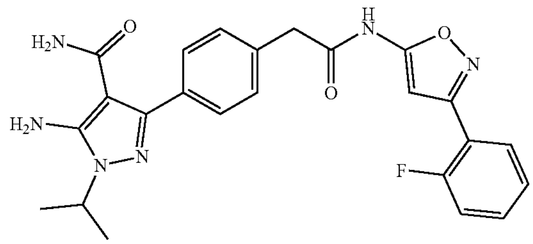 | 463.2 | 1, b, I & II |
| 52 | 5-Amino-1-isopropyl-3-(4-(2-oxo-2-((5-(3-(trifluoromethyl)phenyl)-1,3,4-thiadiazol-2-yl)amino)ethyl)phenyl)-1H-pyrazole-4-carboxamide | 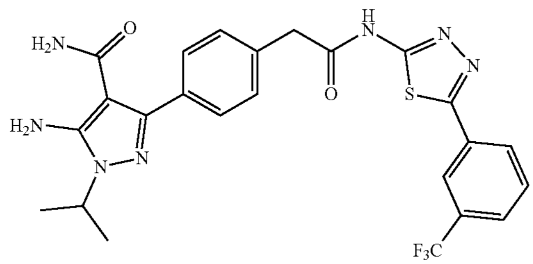 [SMILES: CC(C)n1nc(-c2ccc(CC(=O)Nc3nnc(-c4cccc(C(F)(F)F)c4)s3)cc2)c(C(N)=O)c1N] | 530.2 | 2, a, I & II |
| 53 | 5-Amino-1-isopropyl-3-(4-(2-((3-isopropyl-4-(trifluoromethyl)phenyl)amino)-2-oxoethyl)phenyl)-1H-pyrazole-4-carboxamide | 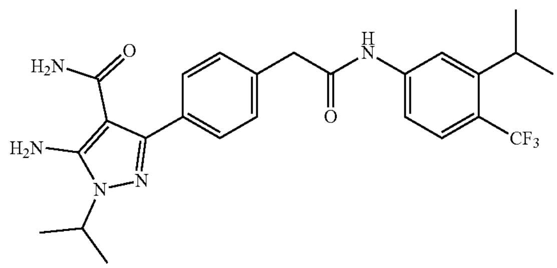 [SMILES: CC(C)c1cc(NC(=O)Cc2ccc(-c3nn(C(C)C)c(N)c3C(N)=O)cc2)ccc1C(F)(F)F] | 488.2 | 5, c, IV |
| 54 | 5-Amino-3-(4-(2-((3-(2,2-difluorocyclopropyl)phenyl)amino)-2-oxoethyl)phenyl)-1-isopropyl-1H-pyrazole-4-carboxamide | 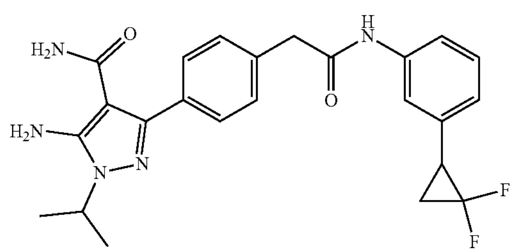 [SMILES: CC(C)n1nc(-c2ccc(CC(=O)Nc3cccc(C4CC4(F)F)c3)cc2)c(C(N)=O)c1N] | 453.2 | 5, c, IV |
| 55 | 5-Amino-3-(4-(2-((5-cyclopropylisoxazol-3-yl)amino)-2-oxoethyl)phenyl)-1-isopropyl-1H-pyrazole-4-carboxamide | 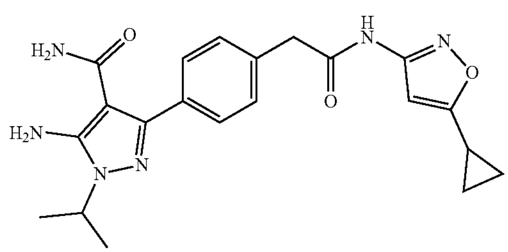 [SMILES: CC(C)n1nc(-c2ccc(CC(=O)Nc3cc(C4CC4)on3)cc2)c(C(N)=O)c1N] | 409.2 | 1, b, I & II |
| 56 | 5-Amino-3-(4-(2-((3-(2,4-dimethylphenyl)isoxazol-5-yl)amino)-2-oxoethyl)phenyl)-1-isopropyl-1H-pyrazole-4-carboxamide | 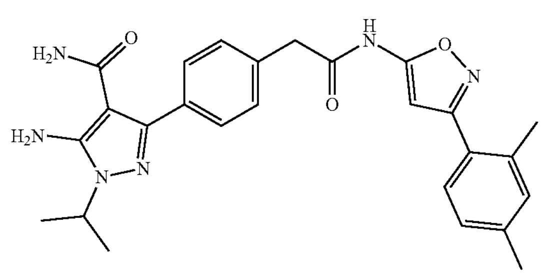 [SMILES: Cc1ccc(-c2cc(NC(=O)Cc3ccc(-c4nn(C(C)C)c(N)c4C(N)=O)cc3)on2)c(C)c1] | 473.2 | 1, b, I & II |

TABLE 29-continued

| Ex. No. | Chemical name | Structure | ES/MS m/z (M + H) | * |
|---|---|---|---|---|
| 57 | 5-Amino-3-(4-(2-((3-(4-chlorophenyl)isoxazol-5-yl)amino)-2-oxoethyl)phenyl)-1-isopropyl-1H-pyrazole-4-carboxamide | 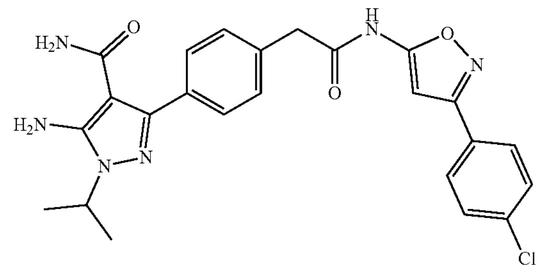 | 479.1 | 1, b, I & II |
| 58 | 5-Amino-1-isopropyl-3-(4-(2-oxo-2-((3-(o-tolyl)isoxazol-5-yl)amino)ethyl)phenyl)-1H-pyrazole-4-carboxamide | 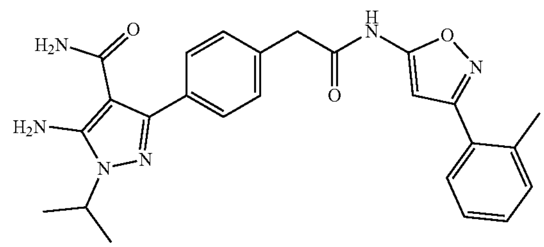 [SMILES: Cc1ccccc1-c1cc(NC(=O)Cc2ccc(-c3nn(C(C)C)c(N)c3C(N)=O)cc2)on1] | 459.2 | 1, b, I & II |
| 59 | 5-Amino-3-(4-(2-((3-(3-fluorophenyl)isoxazol-5-yl)amino)-2-oxoethyl)phenyl)-1-isopropyl-1H-pyrazole-4-carboxamide | 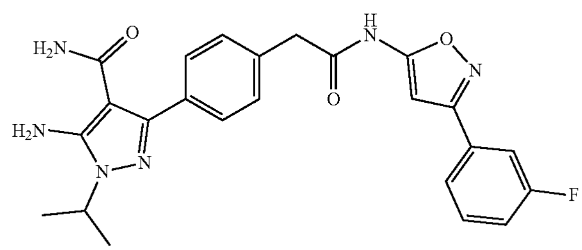 [SMILES: CC(C)n1nc(-c2ccc(CC(=O)Nc3cc(-c4cccc(F)c4)no3)cc2)c(C(N)=O)c1N] | 463.2 | 1, b, I & II |
| 60 | 5-Amino-3-(4-(2-((3-(bicyclo[2.2.1]heptan-2-ylmethyl)isoxazol-5-yl)amino)-2-oxoethyl)phenyl)-1-isopropyl-1H-pyrazole-4-carboxamide | 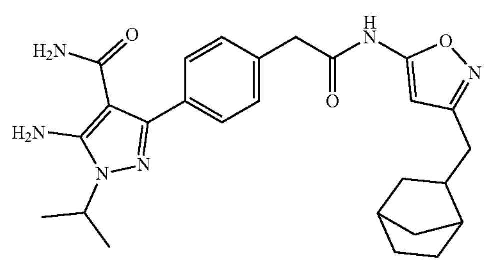 [SMILES: CC(C)n1nc(-c2ccc(CC(=O)Nc3cc(CC4CC5CCC4C5)no3)cc2)c(C(N)=O)c1N] | 477.2 | 1, b, I & II |
| 61 | 5-Amino-1-isopropyl-3-(4-(2-oxo-2-((5-phenylisoxazol-3-yl)amino)ethyl)phenyl)-1H-pyrazole-4-carboxamide | 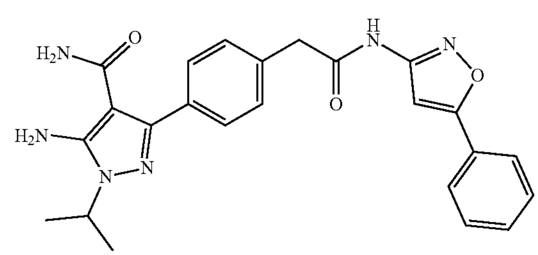 [SMILES: CC(C)n1nc(-c2ccc(CC(=O)Nc3cc(-c4ccccc4)on3)cc2)c(C(N)=O)c1N] | 445.1 | 1, b, I & II |

TABLE 29-continued

| Ex. No. | Chemical name | Structure | ES/MS m/z (M + H) | * |
|---|---|---|---|---|
| 62 | 5-Amino-3-(4-(2-((3-(4-(difluoromethoxy)phenyl)isoxazol-5-yl)amino)-2-oxoethyl)phenyl)-1-isopropyl-1H-pyrazole-4-carboxamide | 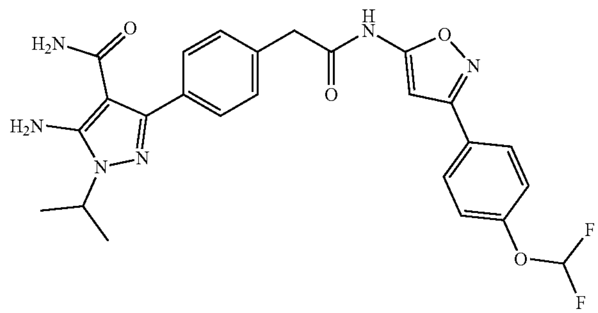 [SMILES: CC(C)n1nc(-c2ccc(CC(=O)Nc3cc(-c4ccc(OC(F)F)cc4)no3)cc2)c(C(N)=O)c1N] | 511.1 | 1, b, I & II |
| 63 | 5-Amino-1-isopropyl-3-(4-(2-((3-(2-(methylsulfonyl)propan-2-yl)isoxazol-5-yl)amino)-2-oxoethyl)phenyl)-1H-pyrazole-4-carboxamide | 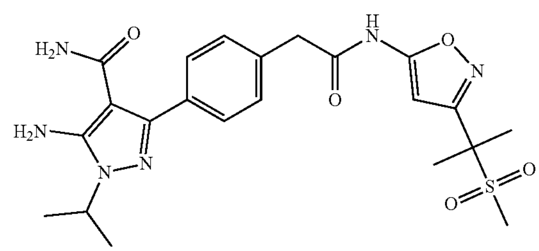 [SMILES: CC(C)n1nc(-c2ccc(CC(=O)Nc3cc(C(C)(C)S(C)(=O)=O)no3)cc2)c(C(N)=O)c1N] | 489.2 | 1, b, I & II |
| 64 | 5-Amino-3-(4-(2-((3-(4-fluorophenyl)isoxazol-5-yl)amino)-2-oxoethyl)phenyl)-1-isopropyl-1H-pyrazole-4-carboxamide | 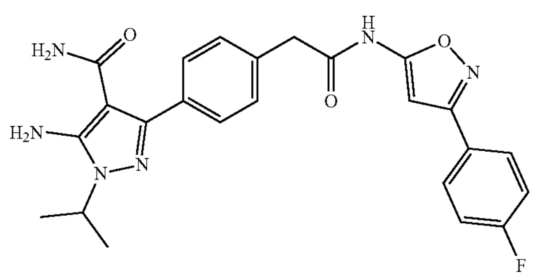 | 463.1 | 1, b, I & II |
| 65 | 5-Amino-3-(4-(2-((5-cycloheptyl-1H-pyrazol-3-yl)amino)-2-oxoethyl)phenyl)-1-isopropyl-1H-pyrazole-4-carboxamide | 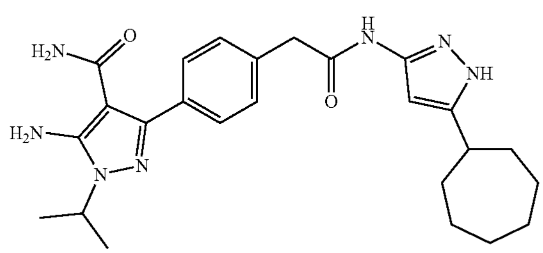 [SMILES: CC(C)n1nc(-c2ccc(CC(=O)Nc3cc(C4CCCCCC4)[nH]n3)cc2)c(C(N)=O)c1N] | 464.1 | 1, b, I & II |
| 66 | 5-Amino-3-(4-(2-((5-(2,4-difluorophenyl)isoxazol-3-yl)amino)-2-oxoethyl)phenyl)-1-isopropyl-1H-pyrazole-4-carboxamide | 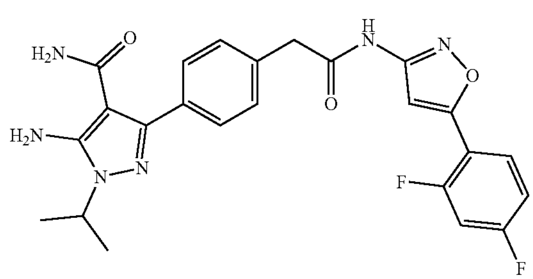 [SMILES: CC(C)n1nc(-c2ccc(CC(=O)Nc3cc(-c4ccc(F)cc4F)on3)cc2)c(C(N)=O)c1N] | 481.1 | 1, b, I & II |

TABLE 29-continued

| Ex. No. | Chemical name | Structure | ES/MS m/z (M + H) | * |
|---|---|---|---|---|
| 67 | 5-Amino-3-(4-(2-((5-(3-chlorophenyl)isoxazol-3-yl)amino)-2-oxoethyl)phenyl)-1-isopropyl-1H-pyrazole-4-carboxamide | 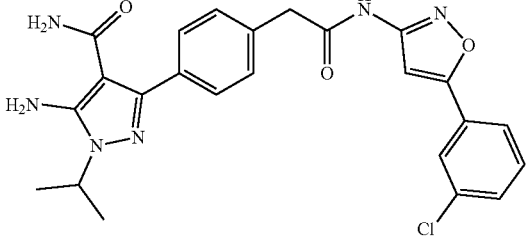 | 479.1 | 4, c, III |
| 68 | 5-Amino-3-(4-(2-((5-cyclobutylisoxazol-3-yl)amino)-2-oxoethyl)phenyl)-1-isopropyl-1H-pyrazole-4-carboxamide | 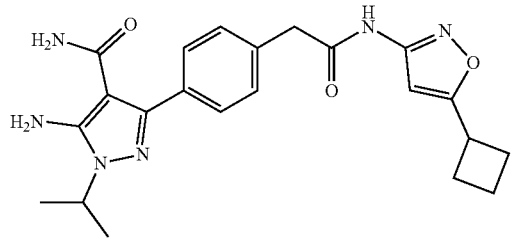 [SMILES: CC(C)n1nc(-c2ccc(CC(=O)Nc3cc(C4CCC4)on3)cc2)c(C(N)=O)c1N] | 423.2 | 1, b, I & II |
| 69 | 5-Amino-3-(4-(2-((5-(3-fluorophenyl)isoxazol-3-yl)amino)-2-oxoethyl)phenyl)-1-isopropyl-1H-pyrazole-4-carboxamide | 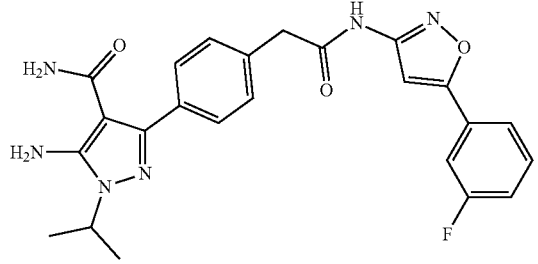 [SMILES: CC(C)n1nc(-c2ccc(CC(=O)Nc3cc(-c4cccc(F)c4)on3)cc2)c(C(N)=O)c1N] | 463.1 | 1, b, I & II |
| 70 | 5-Amino-1-isopropyl-3-(3-methyl-4-(2-oxo-2-((5-(1,1,1-trifluoro-2-methylpropan-2-yl)isoxazol-3-yl)amino)ethyl)phenyl)-1H-pyrazole-4-carboxamide | 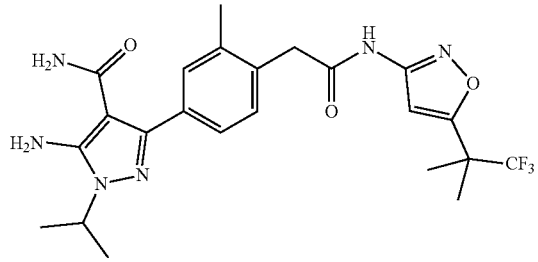 [SMILES: Cc1cc(-c2nn(C(C)C)c(N)c2C(N)=O)ccc1CC(=O)Nc1cc(C(C)(C)C(F)(F)F)on1] | 493.2 | 1, b, I & II |
| 71 | 5-Amino-3-(4-(2-((1-(tert-butyl)-5-methyl-1H-pyrazol-3-yl)amino)-2-oxoethyl)phenyl)-1-isopropyl-1H-pyrazole-4-carboxamide | 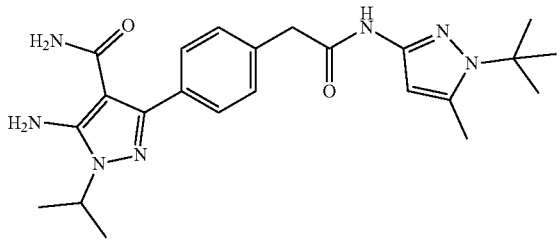 [SMILES: Cc1cc(NC(=O)Cc2ccc(-c3nn(C(C)C)c(N)c3C(N)=O)cc2)nn1C(C)(C)C] | 438.2 | 1, b, I & II |

TABLE 29-continued

| Ex. No. | Chemical name | Structure | ES/MS m/z (M + H) | * |
|---|---|---|---|---|
| 72 | 5-Amino-3-(4-(2-((5-(2-fluorophenyl)isoxazol-3-yl)amino)-2-oxoethyl)phenyl)-1-isopropyl-1H-pyrazole-4-carboxamide | 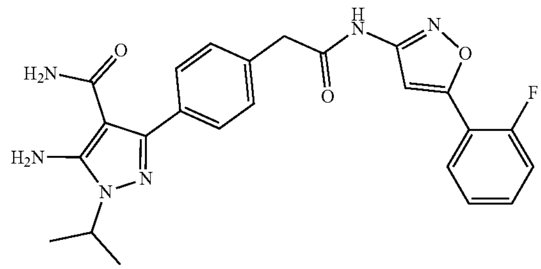 [SMILES: CC(C)n1nc(-c2ccc(CC(=O)Nc3cc(-c4ccccc4F)on3)cc2)c(C(N)=O)c1N] | 463.1 | 1, b, I & II |
| 73 | 5-Amino-1-isopropyl-3-(4-(2-((3-(3-methoxyphenyl)isoxazol-5-yl)amino)-2-oxoethyl)phenyl)-1H-pyrazole-4-carboxamide | 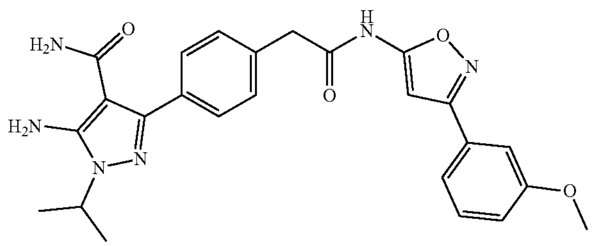 [SMILES: COc1cccc(-c2cc(NC(=O)Cc3ccc(-c4nn(C(C)C)c(N)c4C(N)=O)cc3)on2)c1] | 475.1 | 1, b, I & II |
| 74 | 5-Amino-3-(4-(2-((3-(3-bromophenyl)isoxazol-5-yl)amino)-2-oxoethyl)phenyl)-1-isopropyl-1H-pyrazole-4-carboxamide | 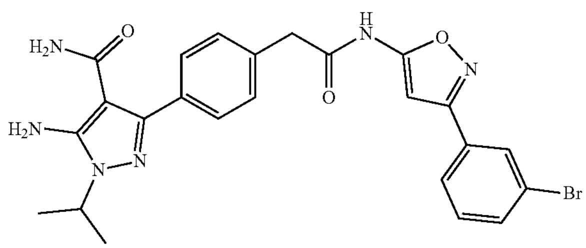 [SMILES: CC(C)n1nc(-c2ccc(CC(=O)Nc3cc(-c4cccc(Br)c4)no3)cc2)c(C(N)=O)c1N] | 525.1 | 1, b, I & II |
| 75 | 5-Amino-1-isopropyl-3-(4-(2-((3-(2-methyltetrahydrofuran-2-yl)isoxazol-5-yl)amino)-2-oxoethyl)phenyl)-1H-pyrazole-4-carboxamide | 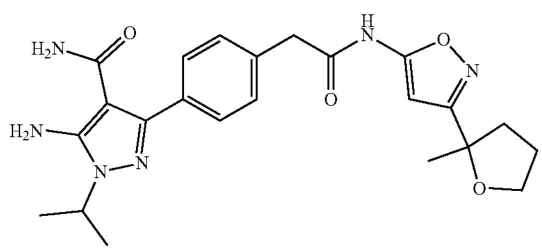 [SMILES: CC(C)n1nc(-c2ccc(CC(=O)Nc3cc(C4(C)CCCO4)no3)cc2)c(C(N)=O)c1N] | 453.2 | 1, b, I & II |
| 76 | 5-Amino-1-isopropyl-3-(4-(2-oxo-2-((3-(2,4,6-trifluorophenyl)isoxazol-5-yl)amino)ethyl)phenyl)-1H-pyrazole-4-carboxamide | 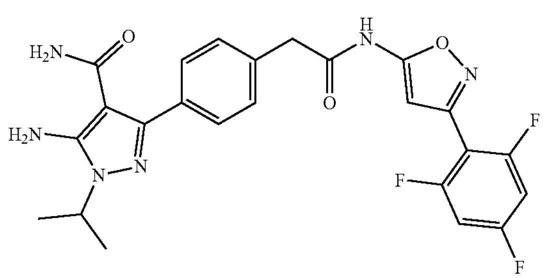 [SMILES: CC(C)n1nc(-c2ccc(CC(=O)Nc3cc(-c4c(F)cc(F)cc4F)no3)cc2)c(C(N)=O)c1N] | 499.1 | 1, b, I & II |
| 77 | 5-Amino-3-(4-(2-((3-(bicyclo[3.1.0]hexan-3-yl)isoxazol-5-yl)amino)-2-oxoethyl)phenyl)-1-isopropyl-1H-pyrazole-4-carboxamide | 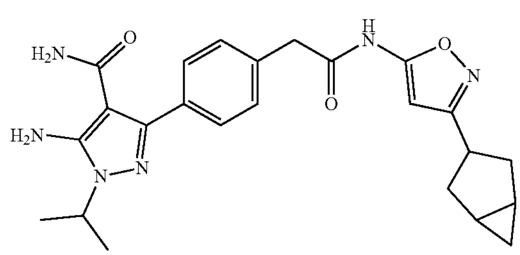 [SMILES: CC(C)n1nc(-c2ccc(CC(=O)Nc3cc(C4CC5CC5C4)no3)cc2)c(C(N)=O)c1N] | 449.2 | 1, b, I & II |

| Ex. No. | Chemical name | Structure | ES/MS m/z (M + H) | * |
|---|---|---|---|---|
| 78 | 5-Amino-1-isopropyl-3-(4-(2-oxo-2-((3-(tetrahydrofuran-3-yl)isoxazol-5-yl)amino)ethyl)phenyl)-1H-pyrazole-4-carboxamide | 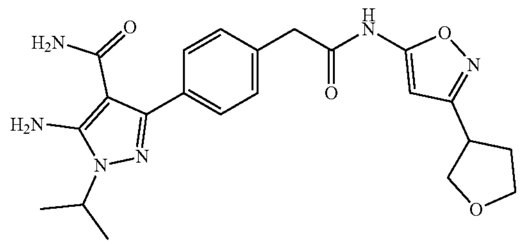 [SMILES: CC(C)n1nc(-c2ccc(CC(=O)Nc3cc(C4CCOC4)no3)cc2)c(C(N)=O)c1N] | 438.8 | 1, b, I & II |
| 79 | 5-Amino-3-(4-(2-((3-cyclobutylisoxazol-5-yl)amino)-2-oxoethyl)phenyl)-1-isopropyl-1H-pyrazole-4-carboxamide | 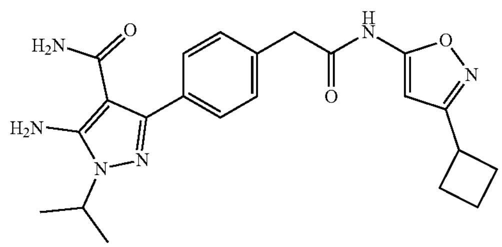 [SMILES: CC(C)n1nc(-c2ccc(CC(=O)Nc3cc(C4CCC4)no3)cc2)c(C(N)=O)c1N] | 423.1 | 1, b, I & II |
| 80 | 5-Amino-3-(4-(2-((3-cyclopropylisoxazol-5-yl)amino)-2-oxoethyl)phenyl)-1-isopropyl-1H-pyrazole-4-carboxamide | 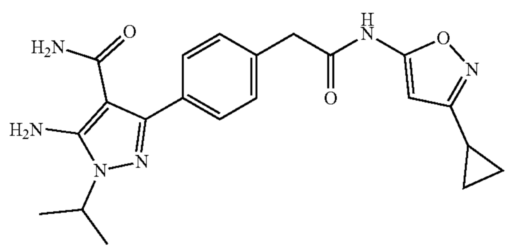 [SMILES: CC(C)n1nc(-c2ccc(CC(=O)Nc3cc(C4CC4)no3)cc2)c(C(N)=O)c1N] | 408.5 | 1, b, I & II |
| 81 | 5-Amino-3-(4-(2-((3-cyclopropylisoxazol-5-yl)amino)-2-oxoethyl)phenyl)-1-isopropyl-1H-pyrazole-4-carboxamide | 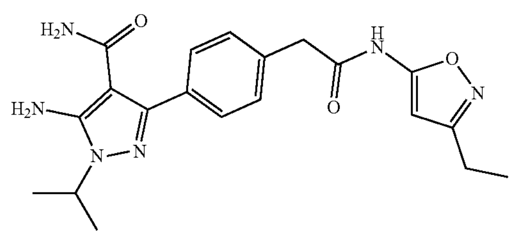 [SMILES: CCc1cc(NC(=O)Cc2ccc(-c3nn(C(C)C)c(N)c3C(N)=O)cc2)on1] | 396.8 | 1, b, I & II |
| 82 | 5-Amino-1-isopropyl-3-(4-(2-oxo-2-((3-(((1-(trifluoromethyl)cyclopropyl)methyl)isoxazol-5-yl)amino)ethyl)phenyl)-1H-pyrazole-4-carboxamide | 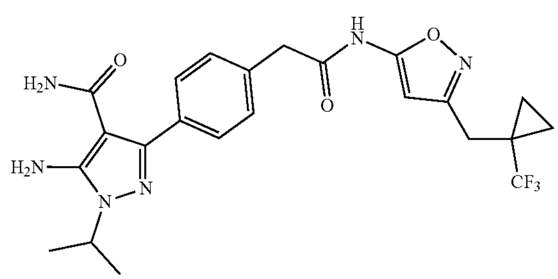 [SMILES: CC(C)n1nc(-c2ccc(CC(=O)Nc3cc(CC4(C(F)(F)F)CC4)no3)cc2)c(C(N)=O)c1N] | 491.2 | 1, b, I & II |
| 83 | 5-Amino-1-isopropyl-3-(4-(2-oxo-2-((3-(tert-pentyl)isoxazol-5-yl)amino)ethyl)phenyl)-1H-pyrazole-4-carboxamide | 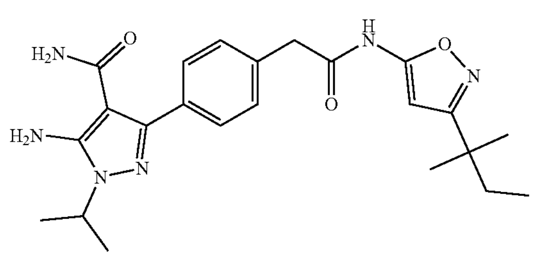 [SMILES: CCC(C)(C)c1cc(NC(=O)Cc2ccc(-c3nn(C(C)C)c(N)c3C(N)=O)cc2)on1] | 438.8 | 1, b, I & II |

TABLE 29-continued

| Ex. No. | Chemical name | Structure | ES/MS m/z (M + H) | * |
|---|---|---|---|---|
| 84 | 5-Amino-1-isopropyl-3-(4-(2-oxo-2-((3-(4-(trifluoromethyl)bicyclo[2.2.1]heptan-1-yl)isoxazol-5-yl)amino)ethyl)phenyl)-1H-pyrazole-4-carboxamide | 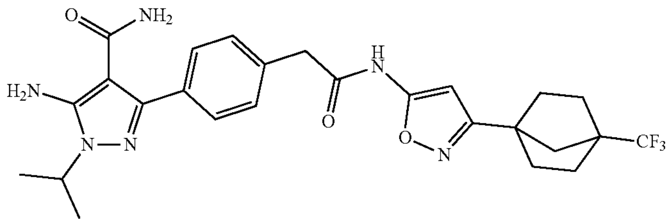 [SMILES: CC(C)n1nc(-c2ccc(CC(=O)Nc3cc(C45CCC(C(F)(F)F)(CC4)C5)no3)cc2)c(C(N)=O)c1N] | 531.2 | 1, c, III |
| 85 | 5-Amino-3-(3-chloro-4-(2-oxo-2-((5-(1,1,1-trifluoro-2-methylpropan-2-yl)isoxazol-3-yl)amino)ethyl)phenyl)-1-isopropyl-1H-pyrazole-4-carboxamide | 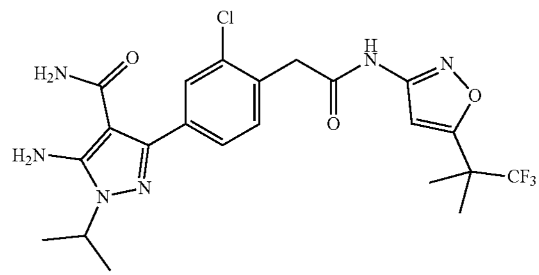 | 513.1 | 1, b, I & II |
| 86 | 5-Amino-3-(4-(2-((3-(cyclopropylmethyl)isoxazol-5-yl)amino)-2-oxoethyl)phenyl)-1-isopropyl-1H-pyrazole-4-carboxamide | 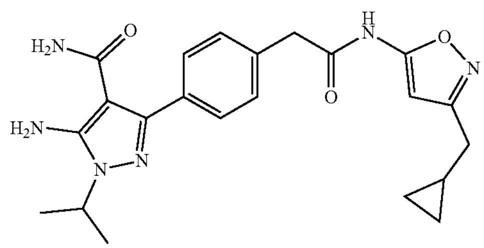 [SMILES: CC(C)n1nc(-c2ccc(CC(=O)Nc3cc(CC4CC4)no3)cc2)c(C(N)=O)c1N] | 423.1 | 1, b, I & II |
| 87 | 5-Amino-1-isopropyl-3-(4-(2-oxo-2-((3-phenylisoxazol-5-yl)amino)ethyl)phenyl)-1H-pyrazole-4-carboxamide | 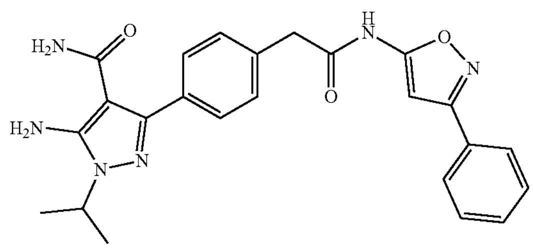 [SMILES: CC(C)n1nc(-c2ccc(CC(=O)Nc3cc(-c4ccccc4)no3)cc2)c(C(N)=O)c1N] | 445.2 | 1, b, I & II |
| 88 | 5-Amino-3-(4-(2-((3-(3,3-dimethylcyclobutyl)isoxazol-5-yl)amino)-2-oxoethyl)phenyl)-1-isopropyl-1H-pyrazole-4-carboxamide | 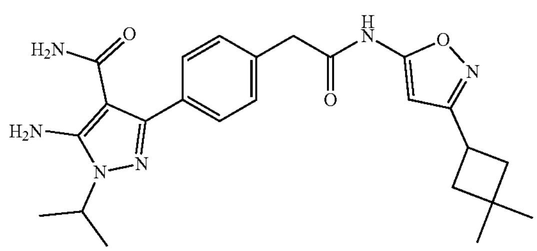 [SMILES: CC(C)n1nc(-c2ccc(CC(=O)Nc3cc(C4CC(C)(C)C4)no3)cc2)c(C(N)=O)c1N] | 451.2 | 2, a, III |
| 89 | 5-Amino-1-isopropyl-3-(4-(2-oxo-2-((3-(3-(trifluoromethyl)phenyl)isoxazol-5-yl)amino)ethyl)phenyl)-1H-pyrazole-4-carboxamide | 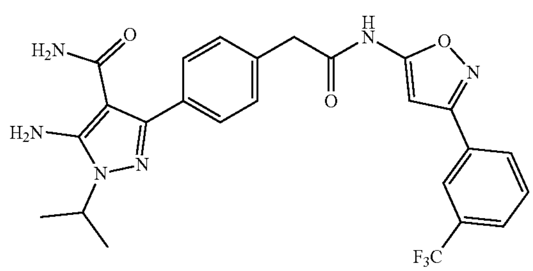 [SMILES: CC(C)n1nc(-c2ccc(CC(=O)Nc3cc(-c4cccc(C(F)(F)F)c4)no3)cc2)c(C(N)=O)c1N] | 513.2 | 1, b, I & II |

TABLE 29-continued

| Ex. No. | Chemical name | Structure | ES/MS m/z (M + H) | * |
|---|---|---|---|---|
| 90 | 5-Amino-3-(4-(2-((5-(tert-butyl)isoxazol-3-yl)amino)-2-oxoethyl)phenyl)-1-isopropyl-1H-pyrazole-4-carboxamide | 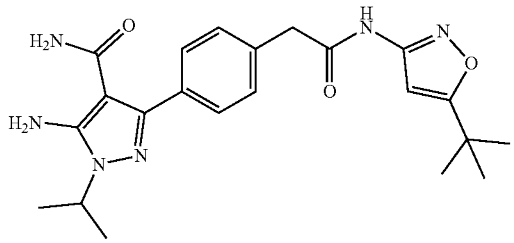 [SMILES: CC(C)n1nc(-c2ccc(CC(=O)Nc3cc(C(C)(C)C)on3)cc2)c(C(N)=O)c1N] | 425.2 | 1, b, I & II |
| 91 | 5-Amino-3-(4-(2-((3-((difluoromethyl)thio)phenyl)amino)-2-oxoethyl)phenyl)-1-isopropyl-1H-pyrazole-4-carboxamide | 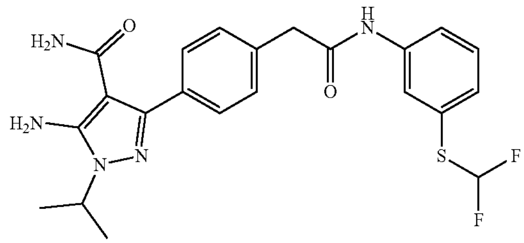 [SMILES: CC(C)n1nc(-c2ccc(CC(=O)Nc3cccc(SC(F)F)c3)cc2)c(C(N)=O)c1N] | 459.2 | 5, c, IV |
| 92 | 5-Amino-3-(4-(2-((5-(2,4-dichlorophenyl)isoxazol-3-yl)amino)-2-oxoethyl)phenyl)-1-isopropyl-1H-pyrazole-4-carboxamide | 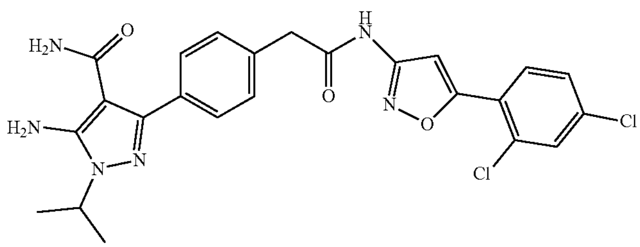 [SMILES: CC(C)n1nc(-c2ccc(CC(=O)Nc3cc(-c4ccc(Cl)cc4Cl)on3)cc2)c(C(N)=O)c1N] | 514.2 | 2, a, I & II |
| 93 | 5-Amino-3-(4-(2-((3-(2,4-dichlorophenyl)isoxazol-5-yl)amino)-2-oxoethyl)phenyl)-1-isopropyl-1H-pyrazole-4-carboxamide | 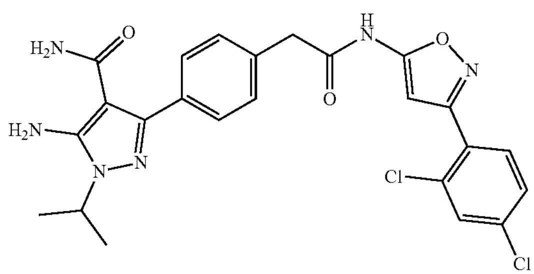 [SMILES: CC(C)n1nc(-c2ccc(CC(=O)Nc3cc(-c4ccc(Cl)cc4Cl)no3)cc2)c(C(N)=O)c1N] | 512.2 | 2, a, I & II |
| 94 | 5-Amino-3-(4-(2-((5-(2,3-dichlorobenzyl)thiazol-2-yl)amino)-2-oxoethyl)phenyl)-1-isopropyl-1H-pyrazole-4-carboxamide | 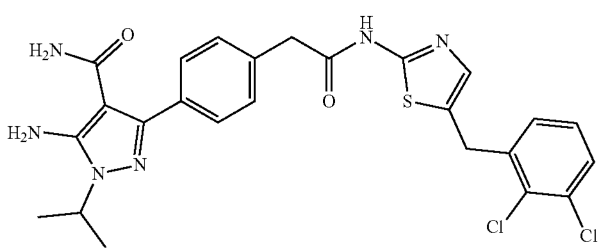 [SMILES: CC(C)n1nc(-c2ccc(CC(=O)Nc3ncc(Cc4cccc(Cl)c4Cl)s3)cc2)c(C(N)=O)c1N] | 543.2 | 2, a, I & II |
| 95 | 5-Amino-3-(4-(2-((3-(tert-butyl)isothiazol-5-yl)amino)-2-oxoethyl)phenyl)-1-isopropyl-1H-pyrazole-4-carboxamide | 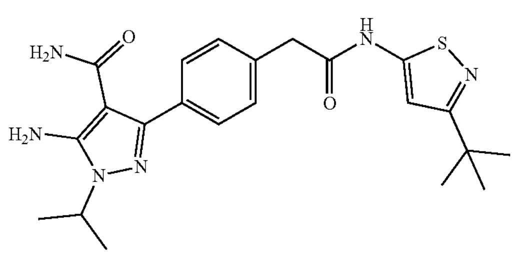 [SMILES: CC(C)n1nc(-c2ccc(CC(=O)Nc3cc(C(C)(C)C)ns3)cc2)c(C(N)=O)c1N] | 441.2 | 1, b, I & II |

TABLE 29-continued

| Ex. No. | Chemical name | Structure | ES/MS m/z (M + H) | * |
|---|---|---|---|---|
| 96 | 5-Amino-3-(4-(2-((3,4-diethylphenyl)amino)-2-oxoethyl)phenyl)-1-isopropyl-1H-pyrazole-4-carboxamide | 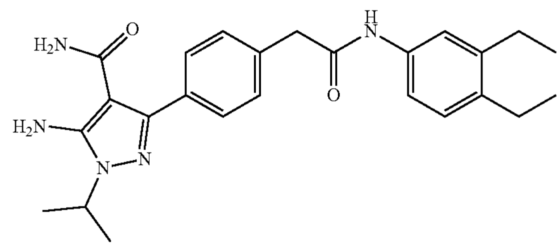 [SMILES: CCc1ccc(NC(=O)Cc2ccc(-c3nn(C(C)C)c(N)c3C(N)=O)cc2)cc1CC] | 434.2 | 5, c, IV |
| 97 | 5-Amino-1-isopropyl-3-(4-(2-((4-(morpholinomethyl)-3-(trifluoromethyl)phenyl)amino)-2-oxoethyl)phenyl)-1H-pyrazole-4-carboxamide | 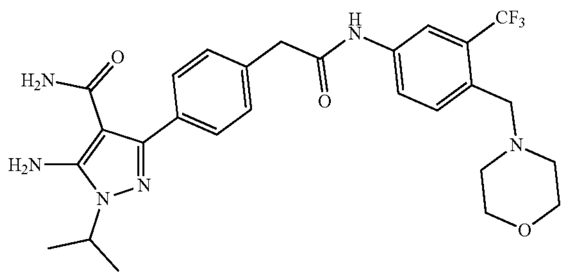 [SMILES: CC(C)n1nc(-c2ccc(CC(=O)Nc3ccc(CN4CCOCC4)c(C(F)(F)F)c3)cc2)c(C(N)=O)c1N] | 545.2 | 5, c, IV |
| 98 | 5-Amino-3-(4-(2-((3-(tert-butyl)phenyl)amino)-2-oxoethyl)phenyl)-1-isopropyl-1H-pyrazole-4-carboxamide | 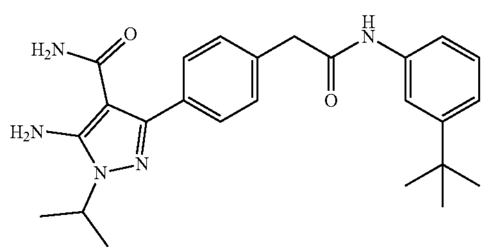 [SMILES: CC(C)n1nc(-c2ccc(CC(=O)Nc3cccc(C(C)(C)C)c3)cc2)c(C(N)=O)c1N] | 434.2 | 5, c, IV |
| 99 | 5-Amino-3-(4-(2-((3-ethyl-4-methylphenyl)amino)-2-oxoethyl)phenyl)-1-isopropyl-1H-pyrazole-4-carboxamide | 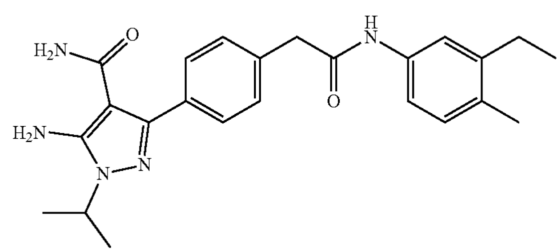 [SMILES: CCc1cc(NC(=O)Cc2ccc(-c3nn(C(C)C)c(N)c3C(N)=O)cc2)ccc1C] | 420.2 | 5, c, IV |
| 100 | 5-Amino-3-(4-(2-((3-(6,6-difluorospiro[3.3]heptan-2-yl)isoxazol-5-yl)amino)-2-oxoethyl)phenyl)-1-isopropyl-1H-pyrazole-4-carboxamide | 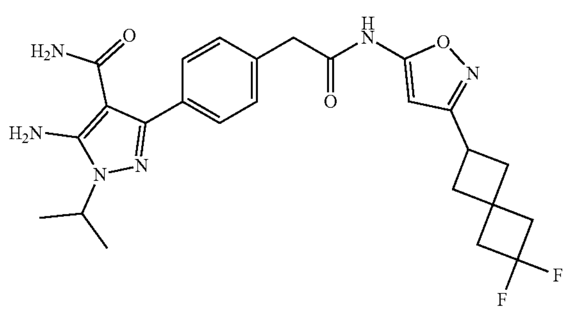 [SMILES: CC(C)n1nc(-c2ccc(CC(=O)Nc3cc(C4CC5(C4)CC(F)(F)C5)no3)cc2)c(C(N)=O)c1N] | 499.2 | 2, a, I & II |

TABLE 29-continued

| Ex. No. | Chemical name | ES/MS m/z (M + H) | * |
|---|---|---|---|
| 101 | 5-Amino-3-(4-(2-((4-ethyl-3-methylphenyl)amino)-2-oxoethyl)phenyl)-1-isopropyl-1H-pyrazole-4-carboxamide | 420.2 | 5, c, IV |
| 102 | 5-Amino-3-(4-(2-((3-(3,3-difluorocyclobutyl)isoxazol-5-yl)amino)-2-oxoethyl)phenyl)-1-isopropyl-1H-pyrazole-4-carboxamide | 459.2 | 2, a, I & II |
| 103 | 5-Amino-3-(4-(2-((5-(2,4-dichlorophenyl)isoxazol-3-yl)amino)-2-oxoethyl)phenyl)-1-isopropyl-1H-pyrazole-4-carboxamide | 514.2 | 2, a, II & III |
| 104 | 5-Amino-1-isopropyl-3-(4-(2-((3-(1-methylcyclopropyl)phenyl)amino)-2-oxoethyl)phenyl)-1H-pyrazole-4-carboxamide | 432.2 | 3, a, III |
| 105 | 5-Amino-1-isopropyl-3-(4-(2-oxo-2-((5-(2,2,2-trifluoroethyl)-1,3,4-thiadiazol-2-yl)amino)ethyl)phenyl)-1H-pyrazole-4-carboxamide | 468.1 | 2, a, II |
| 106 | 5-Amino-1-isopropyl-3-(4-(2-((3-methyl-5-(trifluoromethyl)phenyl)amino)-2-oxoethyl)phenyl)-1H-pyrazole-4-carboxamide | 460.2 | 2, a, III |

TABLE 29-continued

| Ex. No. | Chemical name | Structure | ES/MS m/z (M + H) | * |
|---|---|---|---|---|
| 107 | 5-Amino-3-(4-(2-((3-(cyclohexylmethyl)isoxazol-5-yl)amino)-2-oxoethyl)phenyl)-1-isopropyl-1H-pyrazole-4-carboxamide | 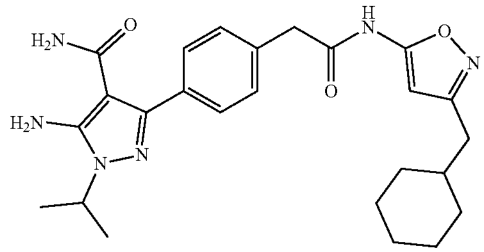 [SMILES: CC(C)n1nc(-c2ccc(CC(=O)Nc3cc(CC4CCCCC4)no3)cc2)c(C(N)=O)c1N] | 465.2 | 2, a, II |
| 108 | 5-Amino-3-(4-(2-((3-(3-chlorophenyl)isoxazol-5-yl)amino)-2-oxoethyl)phenyl)-1-isopropyl-1H-pyrazole-4-carboxamide | 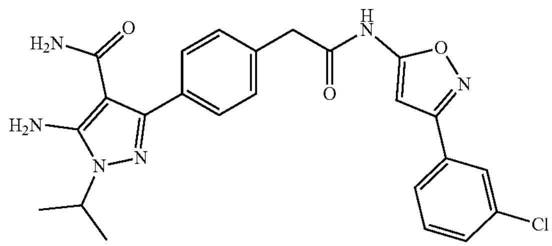 [SMILES: CC(C)n1nc(-c2ccc(CC(=O)Nc3cc(-c4cccc(Cl)c4)no3)cc2)c(C(N)=O)c1N] | 479.1 | 1, b, I |
| 109 | 5-Amino-1-isopropyl-3-(4-(2-((4-methyl-3-(trifluoromethyl)phenyl)amino)-2-oxoethyl)phenyl)-1H-pyrazole-4-carboxamide | 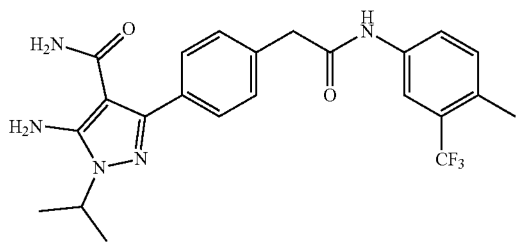 [SMILES: Cc1ccc(NC(=O)Cc2ccc(-c3nn(C(C)C)c(N)c3C(N)=O)cc2)cc1C(F)(F)F] | 460.7 | 2, a, III |
| 110 | 5-Amino-3-(4-(2-((5-(1,1-difluoroethyl)isoxazol-3-yl)amino)-2-oxoethyl)phenyl)-1-isopropyl-1H-pyrazole-4-carboxamide | 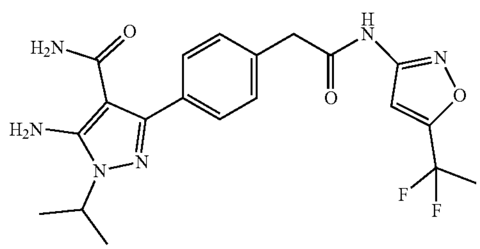 [SMILES: CC(C)n1nc(-c2ccc(CC(=O)Nc3cc(C(C)(F)F)on3)cc2)c(C(N)=O)c1N] | 433.1 | 3, a, III |
| 111 | 5-Amino-1-isopropyl-3-(4-(2-((5-(1-methylcyclopentyl)isoxazol-3-yl)amino)-2-oxoethyl)phenyl)-1H-pyrazole-4-carboxamide | 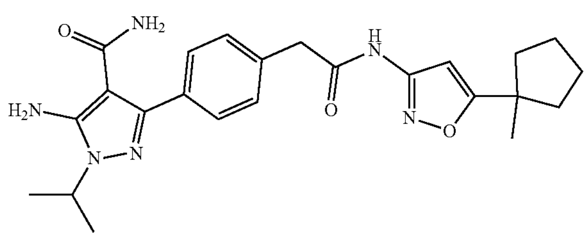 [SMILES: CC(C)n1nc(-c2ccc(CC(=O)Nc3cc(C4(C)CCCC4)on3)cc2)c(C(N)=O)c1N] | 451.2 | 4, c, III |
| 112 | 5-Amino-1-isopropyl-3-(4-(2-oxo-2-((5-(trifluoromethyl)pyridin-3-yl)amino)ethyl)phenyl)-1H-pyrazole-4-carboxamide | 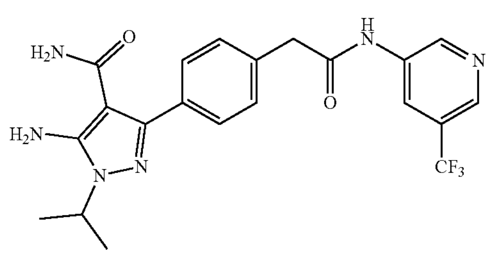 [SMILES: CC(C)n1nc(-c2ccc(CC(=O)Nc3cncc(C(F)(F)F)c3)cc2)c(C(N)=O)c1N] | 447.3 | 3, a, III |

TABLE 29-continued

| Ex. No. | Chemical name | Structure | ES/MS m/z (M + H) | * |
|---|---|---|---|---|
| 113 | 5-Amino-3-(4-(2-((3-fluoro-5-(trifluoromethyl)phenyl)amino)-2-oxoethyl)phenyl)-1-isopropyl-1H-pyrazole-4-carboxamide | 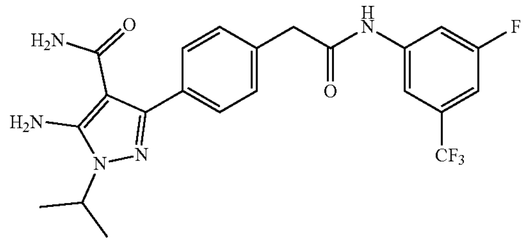 [SMILES: CC(C)n1nc(-c2ccc(CC(=O)Nc3cc(F)cc(C(F)(F)F)c3)cc2)c(C(N)=O)c1N] | 464.7 | 2, a, III |
| 114 | 5-Amino-1-isopropyl-3-(4-(2-((5-isopropylisoxazol-3-yl)amino)-2-oxoethyl)phenyl)-1H-pyrazole-4-carboxamide | 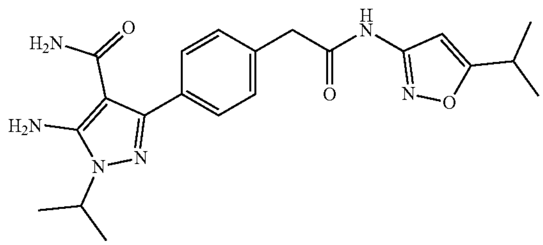 [SMILES: CC(C)c1cc(NC(=O)Cc2ccc(-c3nn(C(C)C)c(N)c3C(N)=O)cc2)no1] | 410.8 | 2, a, I & II |
| 115 | 5-Amino-3-(4-(2-((3-(1-cyclopropylethyl)isoxazol-5-yl)amino)-2-oxoethyl)phenyl)-1-isopropyl-1H-pyrazole-4-carboxamide | 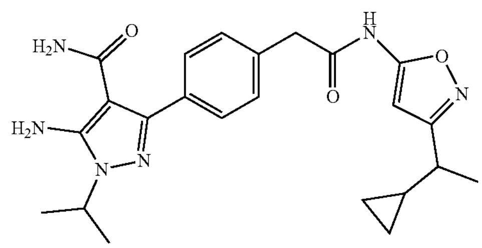 [SMILES: CC(c1cc(NC(=O)Cc2ccc(-c3nn(C(C)C)c(N)c3C(N)=O)cc2)on1)C1CC1] | 437.2 | 2, a, II |
| 116 | 5-Amino-3-(4-(2-((3-cyclopentylisoxazol-5-yl)amino)-2-oxoethyl)phenyl)-1-isopropyl-1H-pyrazole-4-carboxamide | 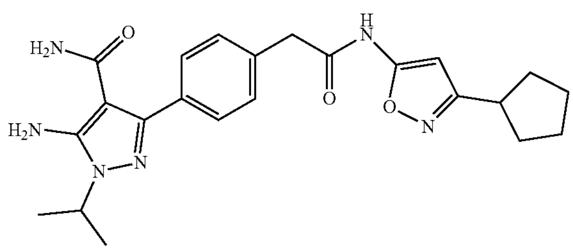 [SMILES: CC(C)n1nc(-c2ccc(CC(=O)Nc3cc(C4CCCC4)no3)cc2)c(C(N)=O)c1N] | 437.1 | 6, a, II |
| 117 | 5-Amino-3-(4-(2-((4-fluoro-3-(trifluoromethyl)phenyl)amino)-2-oxoethyl)phenyl)-1-isopropyl-1H-pyrazole-4-carboxamide | 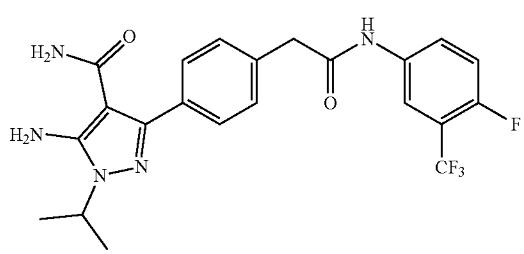 [SMILES: CC(C)n1nc(-c2ccc(CC(=O)Nc3ccc(F)c(C(F)(F)F)c3)cc2)c(C(N)=O)c1N] | 463.7 | 2, a, III |
| 118 | 5-Amino-3-(4-(2-((3-(2,6-difluorophenyl)isoxazol-5-yl)amino)-2-oxoethyl)phenyl)-1-isopropyl-1H-pyrazole-4-carboxamide | 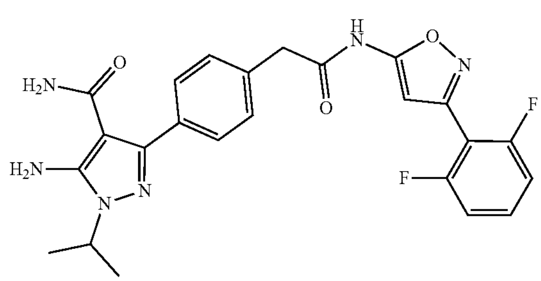 [SMILES: CC(C)n1nc(-c2ccc(CC(=O)Nc3cc(-c4c(F)cccc4F)no3)cc2)c(C(N)=O)c1N] | 481.1 | 2, a, I & II |

TABLE 29-continued

| Ex. No. | Chemical name | Structure | ES/MS m/z (M + H) | * |
|---|---|---|---|---|
| 119 | 5-Amino-3-(4-(2-((3-(4-bromophenyl)isoxazol-5-yl)amino)-2-oxoethyl)phenyl)-1-isopropyl-1H-pyrazole-4-carboxamide | 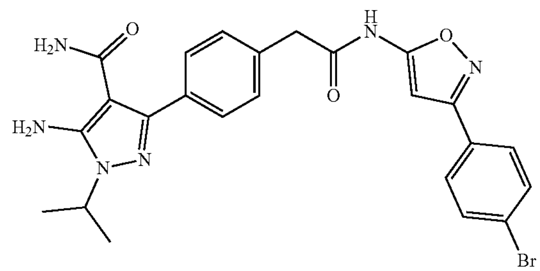 [SMILES: CC(C)n1nc(-c2ccc(CC(=O)Nc3cc(-c4ccc(Br)cc4)no3)cc2)c(C(N)=O)c1N] | 524.6 | 2, a, I & II |
| 120 | 5-Amino-3-(4-(2-((3-(2,4-difluorophenyl)isoxazol-5-yl)amino)-2-oxoethyl)phenyl)-1-isopropyl-1H-pyrazole-4-carboxamide | 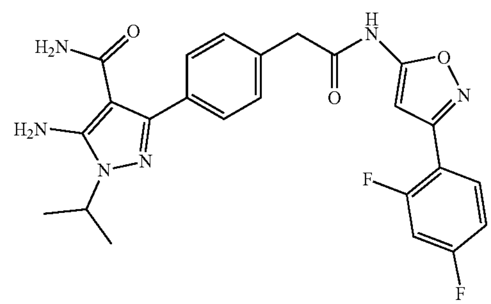 [SMILES: CC(C)n1nc(-c2ccc(CC(=O)Nc3cc(-c4ccc(F)cc4F)no3)cc2)c(C(N)=O)c1N] | 481.2 | 2, a, II |
| 121 | 5-Amino-1-(propan-2-yl)-3-[4-([[3-(trifluoromethyl)phenyl]carbamoyl]methyl)phenyl]-1H-pyrazole-4-carboxamide | 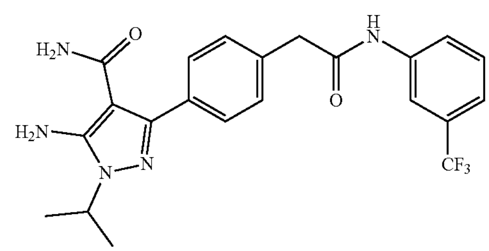 [SMILES: CC(C)n1nc(-c2ccc(CC(=O)Nc3cccc(C(F)(F)F)c3)cc2)c(C(N)=O)c1N] | 446.3 | 7, c, III |
| 122 | 5-Amino-1-(propan-2-yl)-3-[4-([[3-(1,1,1-trifluoro-2-methylpropan-2-yl)-1H-pyrazol-5-yl]carbamoyl]methyl)phenyl]-1H-pyrazole-4-carboxamide | 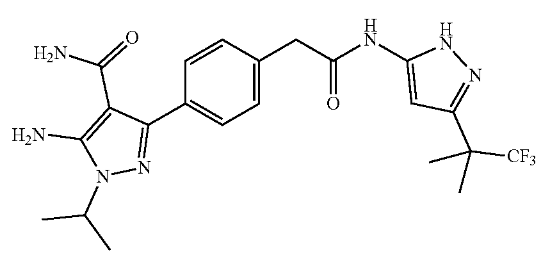 [SMILES: CC(C)n1nc(-c2ccc(CC(=O)Nc3cc(C(C)(C)C(F)(F)F)n[nH]3)cc2)c(C(N)=O)c1N] | 478.2 | 7, c, III |
| 123 | 5-Amino-1-(propan-2-yl)-3-[4-([[7-(trifluoromethyl)-1,3-benzothiazol-2-yl]carbamoyl]methyl)phenyl]-1H-pyrazole-4-carboxamide | 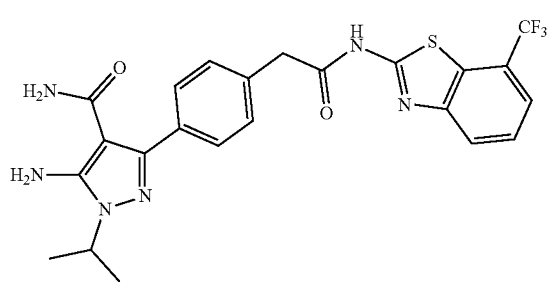 [SMILES: CC(C)n1nc(-c2ccc(CC(=O)Nc3nc4cccc(C(F)(F)F)c4s3)cc2)c(C(N)=O)c1N] | 503.1 | 8, V |

TABLE 29-continued

| Ex. No. | Chemical name | Structure | ES/MS m/z (M + H) | * |
|---|---|---|---|---|
| 124 | 5-Amino-1-tert-butyl-3-[4-([[5-(1,1,1-trifluoro-2-methylpropan-2-yl)-1,2-oxazol-3-yl]carbamoyl]methyl)phenyl]pyrazole-4-carboxamide | 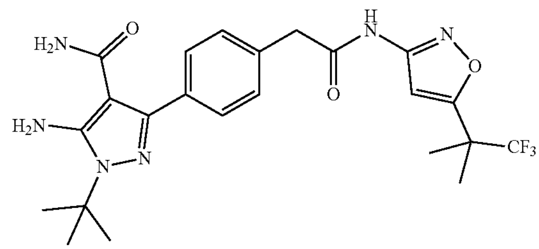 [SMILES: CC(C)(C)n1nc(-c2ccc(CC(=O)Nc3cc(C(C)(C)C(F)(F)F)on3)cc2)c(C(N)=O)c1N] | 493.3 | 7, c, III |
| 125 | 5-Amino-1-cyclopentyl-3-(4-(2-oxo-2-((5-(1,1,1-trifluoro-2-methylpropan-2-yl)isoxazol-3-yl)amino)ethyl)phenyl)-1H-pyrazole-4-carboxamide | 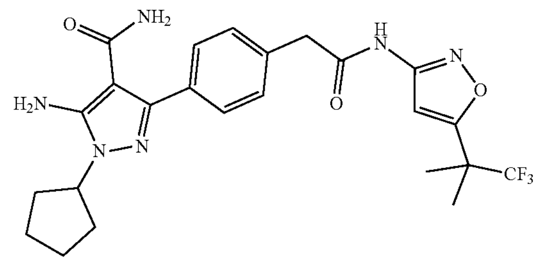 [SMILES: CC(C)(c1cc(NC(=O)Cc2ccc(-c3nn(C4CCCC4)c(N)c3C(N)=O)cc2)no1)C(F)(F)F] | 505.2 | 1, c, III |
| 126 | 5-Amino-3-(4-(2-oxo-2-((5-(1,1,1-trifluoro-2-methylpropan-2-yl)isoxazol-3-yl)amino)ethyl)phenyl)-1-(1,1,1-trifluoropropan-2-yl)-1H-pyrazole-4-carboxamide, Isomer 1 | 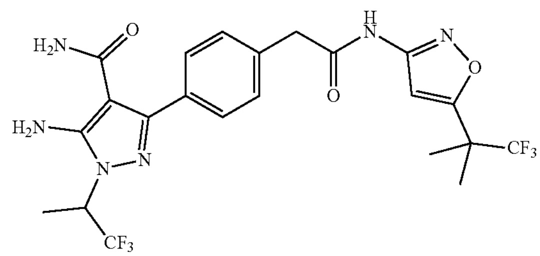 [SMILES: CC(n1nc(-c2ccc(CC(=O)Nc3cc(C(C)(C)C(F)(F)F)on3)cc2)c(C(N)=O)c1N)C(F)(F)F] | 533.1 | 1, c, III |
| 127 | 5-Amino-3-(4-(2-oxo-2-((5-(1,1,1-trifluoro-2-methylpropan-2-yl)isoxazol-3-yl)amino)ethyl)phenyl)-1-(1,1,1-trifluoropropan-2-yl)-1H-pyrazole-4-carboxamide, Isomer 2 | 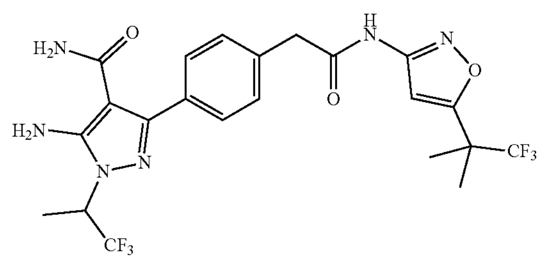 [SMILES: CC(n1nc(-c2ccc(CC(=O)Nc3cc(C(C)(C)C(F)(F)F)on3)cc2)c(C(N)=O)c1N)C(F)(F)F] | 533.1 | 1, c, III |
| 128 | 5-Amino-3-[3-fluoro-4-([[3-(trifluoromethyl)phenyl]carbamoyl]methyl)phenyl]-1-isopropylpyrazole-4-carboxamide | 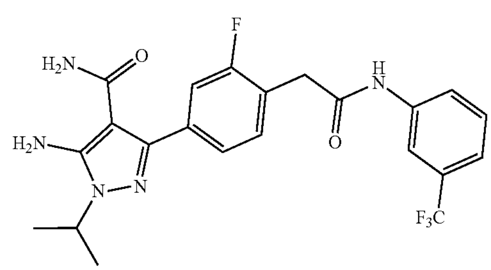 [SMILES: CC(C)n1nc(-c2ccc(CC(=O)Nc3cccc(C(F)(F)F)c3)c(F)c2)c(C(N)=O)c1N] | 464.1 | 7, c, III |
| 129 | 5-Amino-3-[3-fluoro-4-([[5-(1,1,1-trifluoro-2-methylpropan-2-yl)-1,2-oxazol-3-yl]carbamoyl]methyl)phenyl]-1-isopropylpyrazole-4-carboxamide | 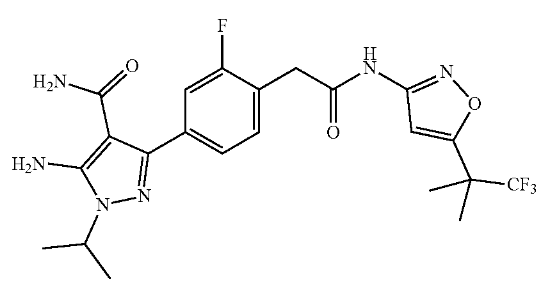 [SMILES: CC(C)n1nc(-c2ccc(CC(=O)Nc3cc(C(C)(C)C(F)(F)F)on3)c(F)c2)c(C(N)=O)c1N] | 497.3 | 1, c, III |

TABLE 29-continued

| Ex. No. | Chemical name | Structure | ES/MS m/z (M + H) | * |
|---|---|---|---|---|
| 130 | 5-Amino-3-(3-fluoro-4-(2-oxo-2-((5-(1,1,1-trifluoro-2-methylpropan-2-yl)-1H-pyrazol-3-yl)amino)ethyl)phenyl)-1-isopropyl-1H-pyrazole-4-carboxamide | 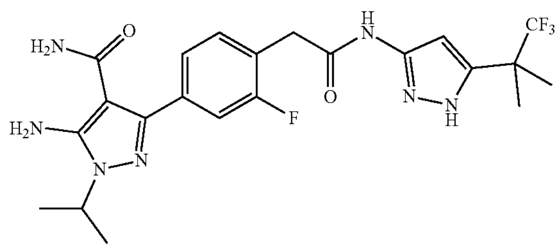 [SMILES: CC(C)n1nc(-c2ccc(CC(=O)Nc3cc(C(C)(C)C(F)(F)F)[nH]n3)c(F)c2)c(C(N)=O)c1N] | 496.2 | 1, c, 125 |
| 131 | 5-Amino-3-[3-fluoro-4-([[1-methyl-5-(1,1,1-trifluoro-2-methylpropan-2-yl)pyrazol-3-yl]carbamoyl]methyl)phenyl]-1-isopropylpyrazole-4-carboxamide | 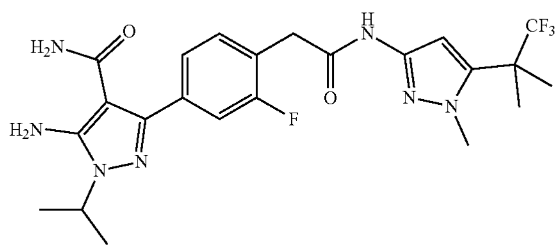 [SMILES: CC(C)n1nc(-c2ccc(CC(=O)Nc3cc(C(C)(C)C(F)(F)F)n(C)n3)c(F)c2)c(C(N)=O)c1N] | 510.3 | 7, c, III |
| 132 | 5-Amino-3-[3-fluoro-4-([[3-(1,1,1-trifluoro-2-methylpropan-2-yl)-1,2-oxazol-5-yl]carbamoyl]methyl)phenyl]-1-isopropylpyrazole-4-carboxamide | 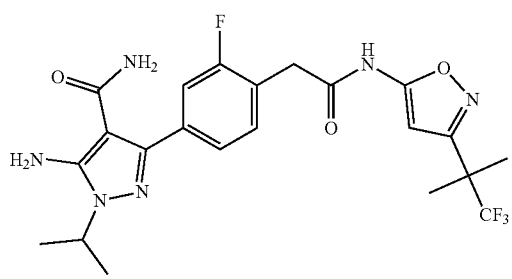 [SMILES: CC(C)n1nc(-c2ccc(CC(=O)Nc3cc(C(C)(C)C(F)(F)F)no3)c(F)c2)c(C(N)=O)c1N] | 497.3 | 1, c, IV |
| 133 | 5-Amino-3-(3-fluoro-4-(2-oxo-2-((7-(trifluoromethyl)benzo[d]thiazol-2-yl)amino)ethyl)phenyl)-1-isopropyl-1H-pyrazole-4-carboxamide | 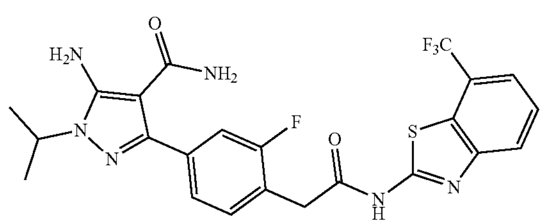 [SMILES: CC(C)n1nc(-c2ccc(CC(=O)Nc3nc4cccc(C(F)(F)F)c4s3)c(F)c2)c(C(N)=O)c1N] | 521.2 | 8, V |
| 134 | 5-Amino-1-cyclopentyl-3-(4-(2-oxo-2-((5-(1,1,1-trifluoro-2-methylpropan-2-yl)-1H-pyrazol-3-yl)amino)ethyl)phenyl)-1H-pyrazole-4-carboxamide | 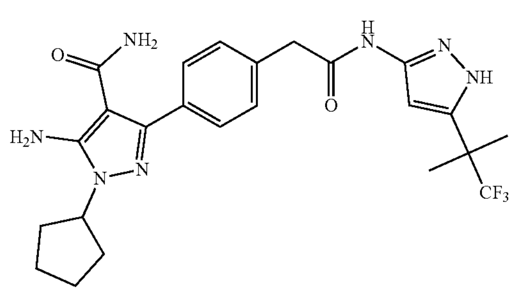 [SMILES: CC(C)(c1cc(NC(=O)Cc2ccc(-c3nn(C4CCCC4)c(N)c3C(N)=O)cc2)n[nH]1)C(F)(F)F] | 504.2 | 1, c, III |

TABLE 29-continued

| Ex. No. | Chemical name | Structure | ES/MS m/z (M + H) | * |
|---|---|---|---|---|
| 135 | 5-Amino-1-cyclopentyl-3-(4-(2-(1-methyl-5-(1,1,1-trifluoro-2-methylpropan-2-yl)-1H-pyrazol-3-ylamino)-2-oxoethyl)phenyl)-1H-pyrazole-4-carboxamide | 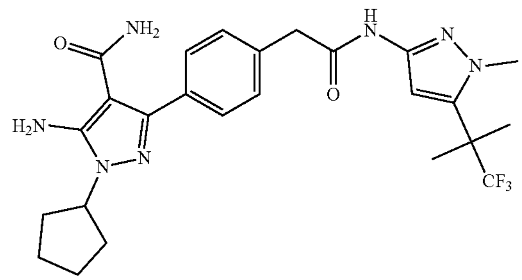 [SMILES: Cn1nc(NC(=O)Cc2ccc(-c3nn(C4CCCC4)c(N)c3C(N)=O)cc2)cc1C(C)(C)C(F)(F)F] | 518.3 | 7, c, III |
| 136 | 5-Amino-1-cyclopentyl-3-[4-([[3-(1,1,1-trifluoro-2-methylpropan-2-yl)-1,2-oxazol-5-yl]carbamoyl]methyl)phenyl]pyrazole-4-carboxamide | 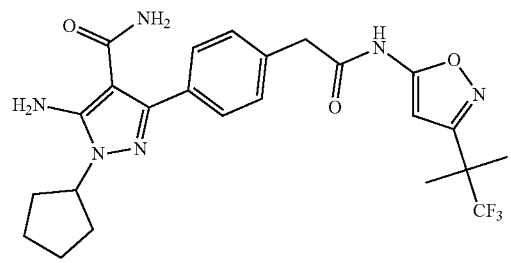 [SMILES: CC(C)(c1cc(NC(=O)Cc2ccc(-c3nn(C4CCCC4)c(N)c3C(N)=O)cc2)on1)C(F)(F)F] | 505.2 | 1, c, III |
| 137 | 5-Amino-1-cyclopentyl-3-(4-(2-oxo-2-((7-(trifluoromethyl)benzo[d]thiazol-2-yl)amino)ethyl)phenyl)-1H-pyrazole-4-carboxamide | 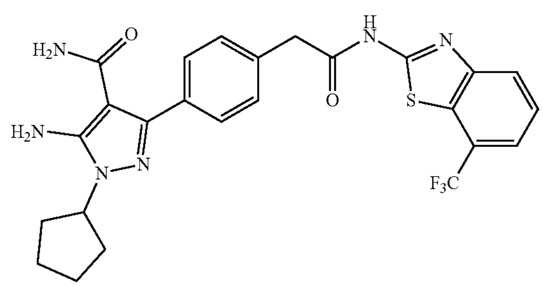 [SMILES: NC(=O)c1c(-c2ccc(CC(=O)Nc3nc4cccc(C(F)(F)F)c4s3)cc2)nn(C2CCCC2)c1N] | 529.3 | 8, V |
| 138 | 5-Amino-1-isopropyl-3-(4-(2-((5-(1-methylcyclopropyl)isoxazol-3-yl)amino)-2-oxoethyl)phenyl)-1H-pyrazole-4-carboxamide | 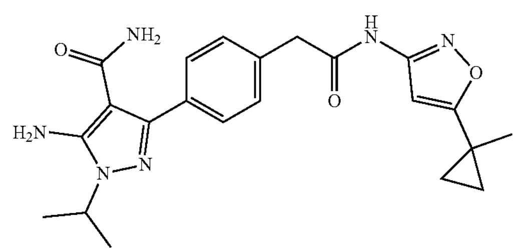 [SMILES: CC(C)n1nc(-c2ccc(CC(=O)Nc3cc(C4(C)CC4)on3)cc2)c(C(N)=O)c1N] | 423.3 | 1, c, III |
| 139 | 5-Amino-3-(3-fluoro-4-[[[(5-phenyl-1H-pyrazol-3-yl)carbamoyl]methyl]phenyl)-1-isopropylpyrazole-4-carboxamide | 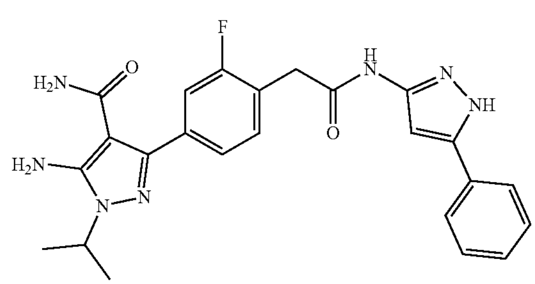 [SMILES: CC(C)n1nc(-c2ccc(CC(=O)Nc3cc(-c4ccccc4)[nH]n3)c(F)c2)c(C(N)=O)c1N] | 462.2 | 1, c, III |

TABLE 29-continued

| Ex. No. | Chemical name | Structure | ES/MS m/z (M + H) | * |
|---|---|---|---|---|
| 140 | 5-Amino-3-(3-fluoro-4-[[(1-methyl-5-phenylpyrazol-3-yl)carbamoyl]methyl]phenyl)-1-isopropylpyrazole-4-carboxamide | 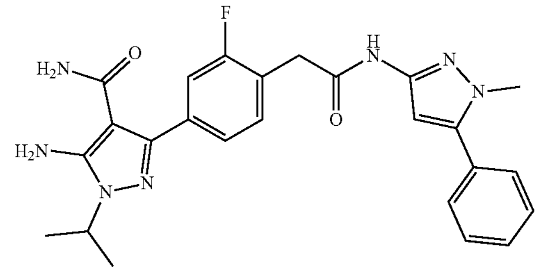 [SMILES: CC(C)n1nc(-c2ccc(CC(=O)Nc3cc(-c4ccccc4)n(C)n3)c(F)c2)c(C(N)=O)c1N] | 476.2 | 7, c, III |
| 141 | 5-Amino-3-[2-chloro-4-([[5-(1,1,1-trifluoro-2-methylpropan-2-yl)-1,2-oxazol-3-yl]carbamoyl]methyl)phenyl]-1-isopropylpyrazole-4-carboxamide | 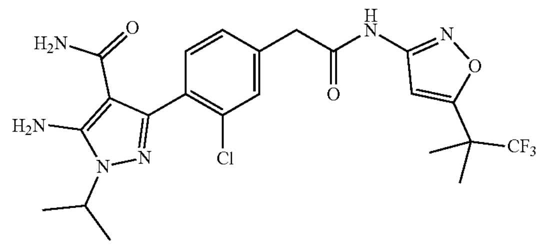 [SMILES: CC(C)n1nc(-c2ccc(CC(=O)Nc3cc(C(C)(C)C(F)(F)F)on3)cc2Cl)c(C(N)=O)c1N] | 513.3 | 1, c, III |
| 142 | 5-Amino-3-(4-(2-((3-(3-chloropyridin-2-yl)isoxazol-5-yl)amino)-2-oxoethyl)phenyl)-1-isopropyl-1H-pyrazole-4-carboxamide | 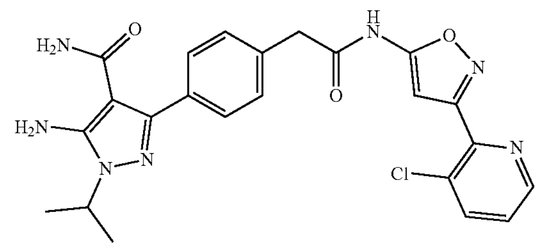 | 480.2 | 1, c, IV |
| 143 | 5-Amino-1-isopropyl-3-[4-([[3-(2-methylpyridin-3-yl)-1,2-oxazol-5-yl]carbamoyl]methyl)phenyl]pyrazole-4-carboxamide | 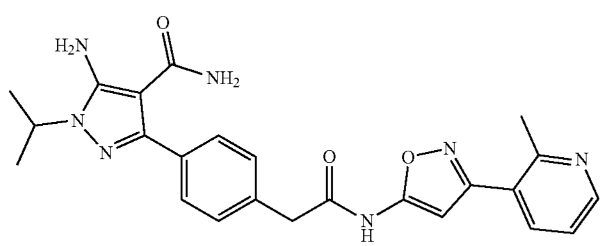 [SMILES: Cc1ncccc1-c1cc(NC(=O)Cc2ccc(-c3nn(C(C)C)c(N)c3C(N)=O)cc2)on1] | 230.6 (M + 2H)/2 | 1, c, IV |
| 144 | 5-Amino-1-isopropyl-3-[4-([[3-(4-methylpyridin-3-yl)-1,2-oxazol-5-yl]carbamoyl]methyl)phenyl]pyrazole-4-carboxamide | 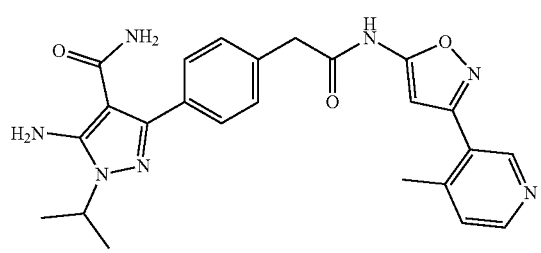 [SMILES: Cc1ccncc1-c1cc(NC(=O)Cc2ccc(-c3nn(C(C)C)c(N)c3C(N)=O)cc2)on1] | 460.1 | 1, c, IV |
| 145 | 5-Amino-3-[4-([[3-(2,4-dichlorophenyl)-1,2-oxazol-5-yl]carbamoyl]methyl)-3-fluorophenyl]-1-isopropylpyrazole-4-carboxamide | 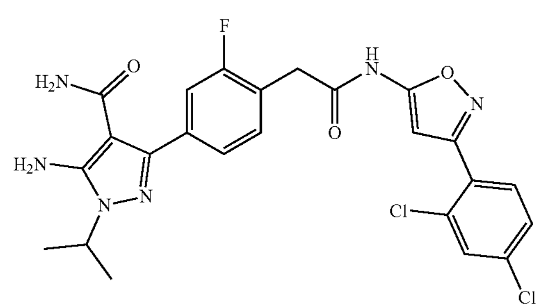 [SMILES: CC(C)n1nc(-c2ccc(CC(=O)Nc3cc(-c4ccc(Cl)cc4Cl)no3)c(F)c2)c(C(N)=O)c1N] | 531.1 | 1, c, IV |

TABLE 29-continued

| Ex. No. | Chemical name | Structure | ES/MS m/z (M + H) | * |
|---|---|---|---|---|
| 146 | 5-Amino-3-(4-[[(3-[3-cyanobicyclo[1.1.1]pentan-1-yl]-1,2-oxazol-5-yl)carbamoyl]methyl]phenyl)-1-isopropylpyrazole-4-carboxamide | 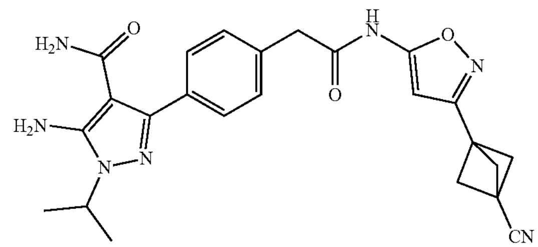 [SMILES: CC(C)n1nc(-c2ccc(CC(=O)Nc3cc(C45CC(C#N)(C4)C5)no3)cc2)c(C(N)=O)c1N] | 460.2 | 1, c, IV |
| 147 | 5-Amino-3-[3-fluoro-4-[([3-[3-(trifluoromethyl)bicyclo[1.1.1]pentan-1-yl]-1,2-oxazol-5-yl]carbamoyl)methyl]phenyl]-1-isopropylpyrazole-4-carboxamide | 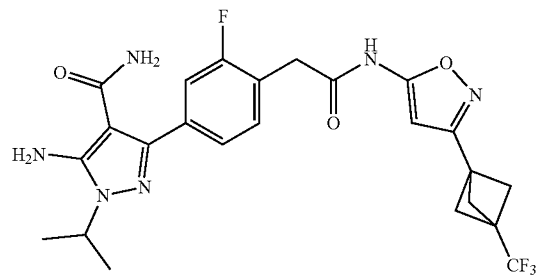 [SMILES: CC(C)n1nc(-c2ccc(CC(=O)Nc3cc(C45CC(C(F)(F)F)(C4)C5)no3)c(F)c2)c(C(N)=O)c1N] | 521.2 | 1, c, IV |
| 148 | 5-Amino-3-(3-fluoro-4-[[[(3-[3-methylbicyclo[1.1.1]pentan-1-yl]-1,2-oxazol-5-yl)carbamoyl]methyl]phenyl)-1-isopropylpyrazole-4-carboxamide | 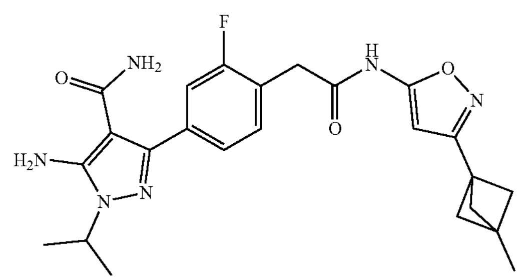 [SMILES: CC(C)n1nc(-c2ccc(CC(=O)Nc3cc(C45CC(C)(C4)C5)no3)c(F)c2)c(C(N)=O)c1N] | 467.3 | 1, c, IV |
| 149 | 5-Amino-1-isopropyl-3-[4-(([5-(pyridin-3-yl)-1,2-oxazol-3-yl]carbamoyl]methyl)phenyl]pyrazole-4-carboxamide | 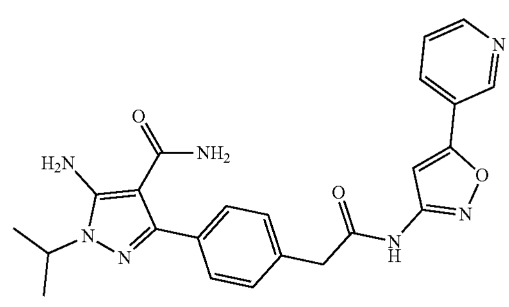 [SMILES: CC(C)n1nc(-c2ccc(CC(=O)Nc3cc(-c4cccnc4)on3)cc2)c(C(N)=O)c1N] | 446.2 | 1, c, IV |
| 150 | 5-Amino-1-isopropyl-3-[4-(([5-(pyridin-4-yl)-1,2-oxazol-3-yl]carbamoyl]methyl)phenyl]pyrazole-4-carboxamide | 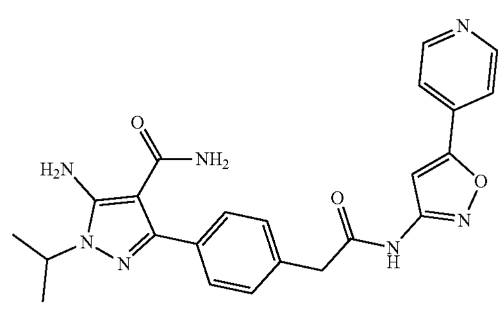 [SMILES: CC(C)n1nc(-c2ccc(CC(=O)Nc3cc(-c4ccncc4)on3)cc2)c(C(N)=O)c1N] | 446.3 | 1, c, IV |

TABLE 29-continued

| Ex. No. | Chemical name | Structure | ES/MS m/z (M + H) | * |
|---|---|---|---|---|
| 151 | 5-Amino-3-[4-([[3-(1-cyano-1-methylethyl)-1,2-oxazol-5-yl]carbamoyl]methyl)phenyl]-1-isopropylpyrazole-4-carboxamide | 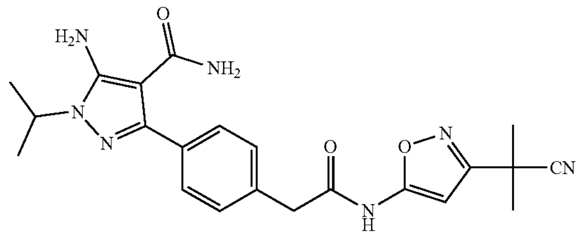 [SMILES: CC(C)n1nc(-c2ccc(CC(=O)Nc3cc(C(C)(C)C#N)no3)cc2)c(C(N)=O)c1N] | 436.2 | 1, c, IV |
| 152 | 5-Amino-1-isopropyl-3-(4-[[(3-[3-methylbicyclo[1.1.1]pentan-1-yl]-1,2-oxazol-5-yl)carbamoyl]methyl]phenyl)pyrazole-4-carboxamide | 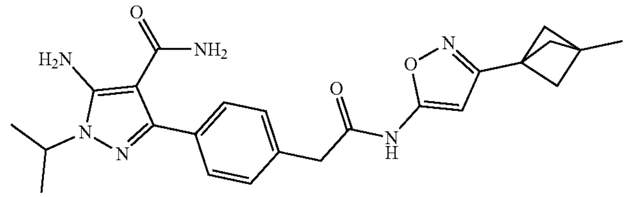 [SMILES: CC(C)n1nc(-c2ccc(CC(=O)Nc3cc(C45CC(C)(C4)C5)no3)cc2)c(C(N)=O)c1N] | 449.2 | 1, c, IV |

Example 153

5-Amino-1-isopropyl-3-(4-(2-oxo-2-((3-(3-(trifluoromethyl)bicyclo[1.1.1]pentan-1-yl)isoxazol-5-yl)amino)ethyl)phenyl)-1H-pyrazole-4-carboxamide

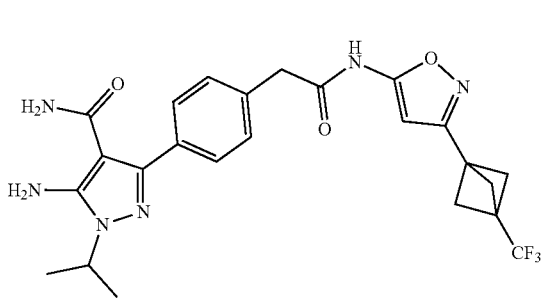 [SMILES: CC(C)n1nc(-c2ccc(CC(=O)Nc3cc(C45CC(C(F)(F)F)(C4)C5)no3)cc2)c(C(N)=O)c1N]

2-(4-(5-Amino-4-carbamoyl-1-isopropyl-1H-pyrazol-3-yl)phenyl)acetic acid (196 mg, 0.65 mmol) and 3-(3-(trifluoromethyl)bicyclo[1.1.1]pentan-1-yl)isoxazol-5-amine (140.00 mg, 0.65 mmol) are combined in DCM. DIPEA (251.36 mg, 1.95 mmol) and T3P® (536.32 mg. 0.84 mmol, 50 wt % in EtOAc) are added dropwise at RT and under N₂ and the reaction is stirred for 1 hr at 50° C. in a sealed tube. The reaction is concentrated under reduced pressure and the residue is purified by reversed phase flash chromatography (C18 column), eluting with a gradient of 40% to 50% ACN in H₂O (0.1% NH₄HCO₃) to give the title compound (120 mg). The material is triturated with hexanes (3 mL). The precipitated solids are collected by filtration and washed with hexanes (3×3 mL) to give the title product (85.1 mg, 34%) as a white solid ES/MS (m/z) 503.2 (M+H).

Example 154

5-Amino-3-[4-[2-[[3-(2,2-dimethylpropyl)isoxazol-5-yl]amino]-2-oxo-ethyl]-2,3-difluoro-phenyl]-1-isopropyl-pyrazole-4-carboxamide

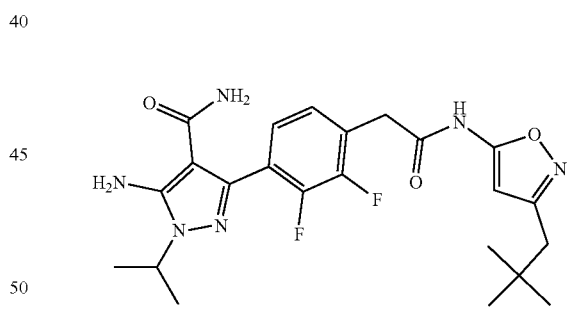

To tert-butyl N-[4-carbamoyl-5-[4-[2-[[3-(2,2-dimethylpropyl)isoxazol-5-yl]amino]-2-oxo-ethyl]-2,3-difluoro-phenyl]-2-isopropyl-pyrazol-3-yl]carbamate (45 mg, 0.078 mmol) in DCM (0.55 mL) is added TFA (0.23 mL, 3.12 mmol) at RT. The mixture is stirred for 3 hr. The reaction mixture is concentrated under reduced pressure, the pH of the residue is made basic with saturated aq. NaHCO₃ and extracted with EtOAc. The organic extract is washed with brine and concentrated under reduced pressure. The residue is purified by silica gel chromatography, eluting with a gradient of 1% to 10% MeOH in DCM to give a white solid. This solid is triturated in iPr₂O at RT, filtered, washed with iPr₂O, and dried under vacuum at 80° C. overnight to give the title compound (26 mg, 70%) as a white solid. ES/MS (m/z) 475 (M+H).

Example 155

5-Amino-3-(2,3-difluoro-4-(2-((3-(3-fluorobicyclo[1.1.1]pentan-1-yl)isoxazol-5-yl)amino)-2-oxoethyl)phenyl)-1-isopropyl-1H-pyrazole-4-carboxamide

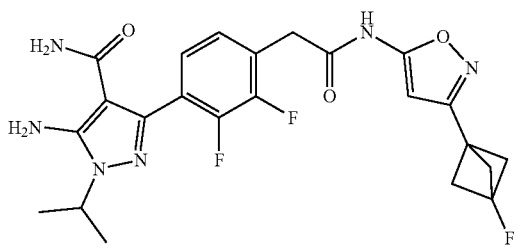 [SMILES: CC(C)n1nc(-c2ccc(CC(=O)Nc3cc(C45CC(F)(C4)C5)no3)c(F)c2F)c(C(N)=O)c1N]

To tert-butyl (4-carbamoyl-3-(2,3-difluoro-4-(2-((3-(3-fluorobicyclo[1.1.1]pentan-1-yl)isoxazol-5-yl)amino)-2-oxoethyl)phenyl)-1-isopropyl-1H-pyrazol-5-yl)carbamate (30 mg, 0.051 mmol) in DCM (2 mL) is added TFA (0.39 mL, 5.10 mmol). The reaction mixture is stirred at RT for 2 hr. The reaction mixture is quenched with cold saturated aq. NaHCO₃ and the aqueous layer is extracted with EtOAc. The organic extract is washed with brine, dried over Na₂SO₄, filtered, and concentrated under reduced pressure. The crude material is purified by silica gel chromatography, eluting with a gradient of 10% to 100% EtOAc in heptane to give the title compound (10 mg, 40%). ES/MS (m/z) 489.4 (M+H).

The following compounds in Table 30 are prepared essentially as described for 5-amino-3-(2,3-difluoro-4-(2-((3-(3-fluorobicyclo[1.1.1]pentan-1-yl)isoxazol-5-yl)amino)-2-oxoethyl)phenyl)-1-isopropyl-1H-pyrazole-4-carboxamide adjusting reaction time to determine completion of the reaction, using appropriate chromatography conditions for purification, and/or titration in an appropriate solvent if needed. TFA can also be added dropwise to the reaction. THF can be substituted for DCM if appropriate for solubility.

TABLE 30

| Prep. No. | Chemical name | Structure | ES/MS m/z (M + H) |
|---|---|---|---|
| 156 | 5-Amino-3-(2,3-difluoro-4-(2-oxo-2-((3-(3-(trifluoromethyl)bicyclo[1.1.1]pentan-1-yl)isoxazol-5-yl)amino)ethyl)phenyl)-1-isopropyl-1H-pyrazole-4-carboxamide | 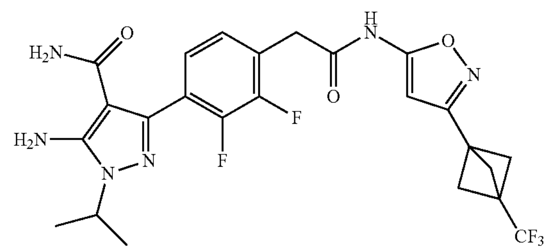 [SMILES: CC(C)n1nc(-c2ccc(CC(=O)Nc3cc(C45CC(C(F)(F)F)(C4)C5)no3)c(F)c2F)c(C(N)=O)c1N] | 539.4 |
| 157 | 5-Amino-3-[3-chloro-4-[2-[[3-(2,4-dichlorophenyl)isoxazol-5-yl]amino]-2-oxo-ethyl]phenyl]-1-isopropyl-pyrazole-4-carboxamide | 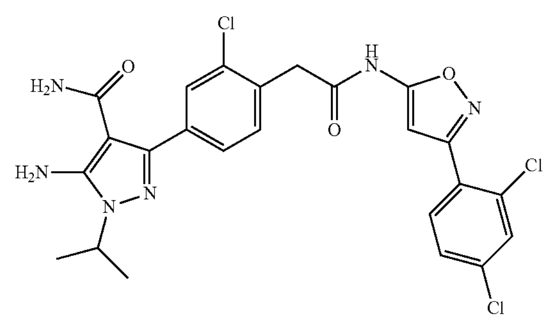 [SMILES: CC(C)n1nc(-c2ccc(CC(=O)Nc3cc(-c4ccc(Cl)cc4Cl)no3)c(Cl)c2)c(C(N)=O)c1N] | 547.1 |
| 158 | 5-Amino-3-[4-[2-[[3-[2,4-dichloro-5-[(dimethylamino)methyl]phenyl]isoxazol-5-yl]amino]-2-oxo-ethyl]phenyl]-1-isopropyl-pyrazole-4-carboxamide | 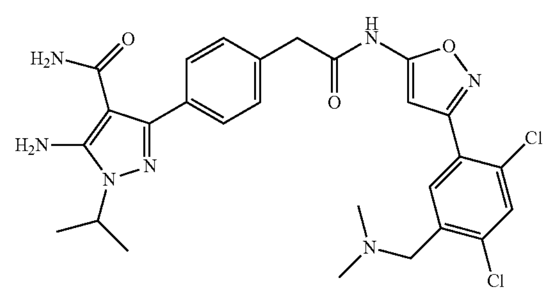 [SMILES: CC(C)n1nc(-c2ccc(CC(=O)Nc3cc(-c4cc(CN(C)C)c(Cl)cc4Cl)no3)cc2)c(C(N)=O)c1N] | 570.8 |

TABLE 30-continued

| Prep. No. | Chemical name | Structure | ES/MS m/z (M + H) |
|---|---|---|---|
| 159 | 5-Amino-1-(azetidin-3-yl)-3-(4-(2-((3-neopentylisoxazol-5-yl)amino)-2-oxoethyl)phenyl)-1H-pyrazole-4-carboxamide | 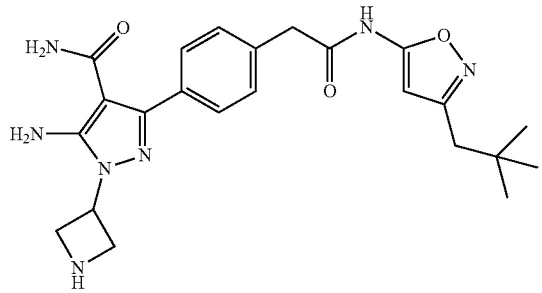 [SMILES: CC(C)(C)Cc1cc(NC(=O)Cc2ccc(-c3nn(C4CNC4)c(N)c3C(N)=O)cc2)on1] | 452.2 |
| 160 | 5-Amino-3-[4-[2-[[3-(2,2-dimethylcyclopropyl)isoxazol-5-yl]amino]-2-oxo-ethyl]phenyl]-1-isopropyl-pyrazole-4-carboxamide | 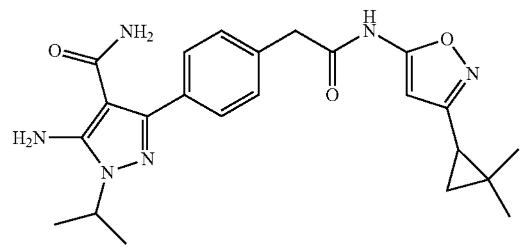 [SMILES: CC(C)n1nc(-c2ccc(CC(=O)Nc3cc(C4CC4(C)C)no3)cc2)c(C(N)=O)c1N] | 437 |
| 161 | 5-Amino-1-isopropyl-3-[4-[2-oxo-2-[(3-spiro[2.2]pentan-2-ylisoxazol-5-yl)amino]ethyl]phenyl]pyrazole-4-carboxamide | 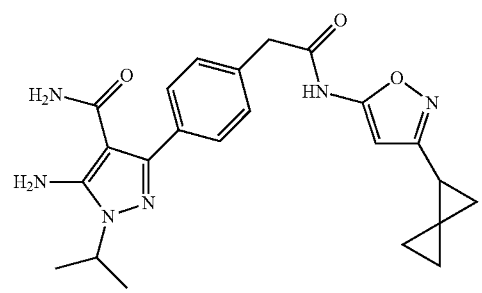 [SMILES: CC(C)n1nc(-c2ccc(CC(=O)Nc3cc(C4CC45CC5)no3)cc2)c(C(N)=O)c1N] | 435.1 |
| 162 | 5-Amino-3-[4-[2-[[3-[(2,2-difluorocyclopropyl)methyl]isoxazol-5-yl]amino]-2-oxo-ethyl]phenyl]-1-isopropyl-pyrazole-4-carboxamide | 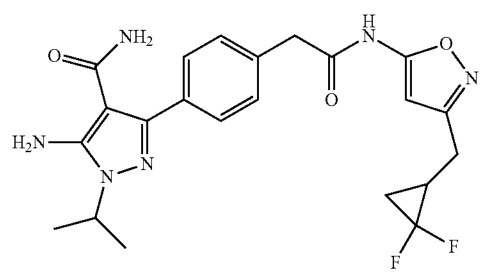 [SMILES: CC(C)n1nc(-c2ccc(CC(=O)Nc3cc(CC4CC4(F)F)no3)cc2)c(C(N)=O)c1N] | 459 |
| 163 | 5-Amino-3-[4-[2-[[3-(3,3-difluorocyclopentyl)isoxazol-5-yl]amino]-2-oxo-ethyl]phenyl]-1-isopropyl-pyrazole-4-carboxamide | 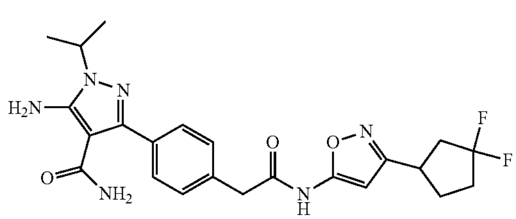 [SMILES: CC(C)n1nc(-c2ccc(CC(=O)Nc3cc(C4CCC(F)(F)C4)no3)cc2)c(C(N)=O)c1N] | 473 |

TABLE 30-continued

| Prep. No. | Chemical name | Structure | ES/MS m/z (M + H) |
|---|---|---|---|
| 164 | 5-Amino-1-isopropyl-3-[4-[2-oxo-2-[(3-spiro[2.3]hexan-2-ylisoxazol-5-yl)amino]ethyl]phenyl]pyrazole-4-carboxamide | 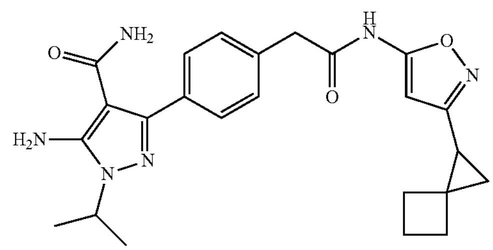 [SMILES: CC(C)n1nc(-c2ccc(CC(=O)Nc3cc(C4CC45CCC5)no3)cc2)c(C(N)=O)c1N] | 449.3 |
| 165 | 5-Amino-1-isopropyl-3-[4-[2-oxo-2-[(5-spiro[2.3]hexan-2-ylisoxazol-3-yl)amino]ethyl]phenyl]pyrazole-4-carboxamide | 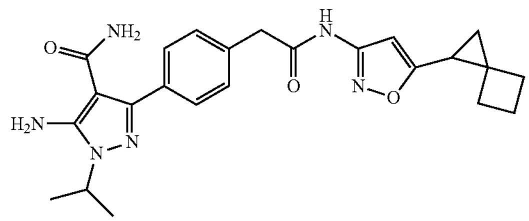 [SMILES: CC(C)n1nc(-c2ccc(CC(=O)Nc3cc(C4CC45CCC5)on3)cc2)c(C(N)=O)c1N] | 449 |
| 166 | 5-Amino-3-[4-[2-[[5-(2,2-dimethylcyclobutyl)isoxazol-3-yl]amino]-2-oxo-ethyl]phenyl]-1-isopropyl-pyrazole-4-carboxamide | 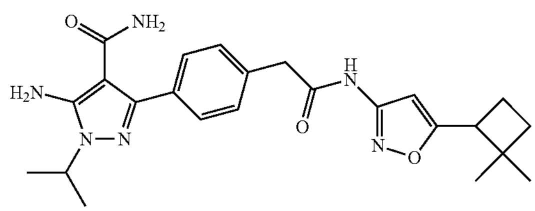 [SMILES: CC(C)n1nc(-c2ccc(CC(=O)Nc3cc(C4CCC4(C)C)on3)cc2)c(C(N)=O)c1N] | 451.1 |
| 167 | 5-Amino-3-[4-[2-[[3-(2,2-dimethylcyclobutyl)isoxazol-5-yl]amino]-2-oxo-ethyl]phenyl]-1-isopropyl-pyrazole-4-carboxamide | 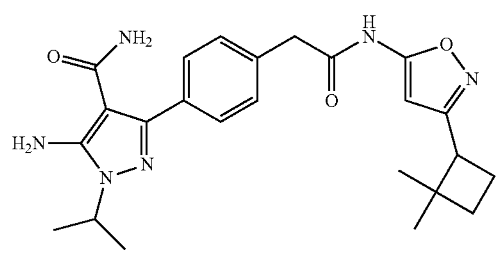 [SMILES: CC(C)n1nc(-c2ccc(CC(=O)Nc3cc(C4CCC4(C)C)no3)cc2)c(C(N)=O)c1N] | 451.1 |
| 168 | 5-Amino-1-isopropyl-3-[3-methoxy-4-[2-[[5-(1-methylcyclopentyl)isoxazol-3-yl]amino]-2-oxo-ethyl]phenyl]pyrazole-4-carboxamide | 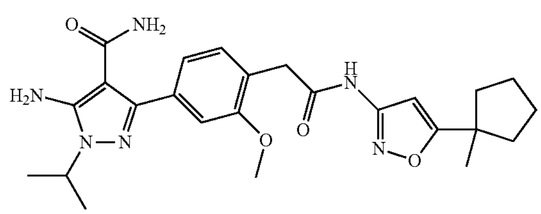 [SMILES: COc1cc(-c2nn(C(C)C)c(N)c2C(N)=O)ccc1CC(=O)Nc1cc(C2(C)CCCC2)on1] | 481 |
| 169 | 5-Amino-3-[3,5-difluoro-4-[2-oxo-2-[[5-(2,2,2-trifluoro-1,1-dimethyl-ethyl)isoxazol-3-yl]amino]ethyl]phenyl]-1-isopropyl-pyrazole-4-carboxamide | 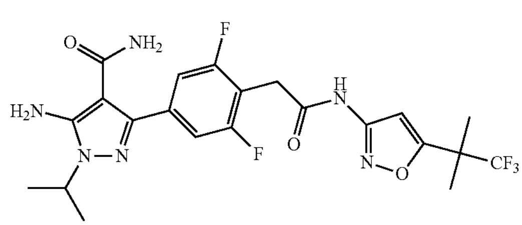 [SMILES: CC(C)n1nc(-c2cc(F)c(CC(=O)Nc3cc(C(C)(C)C(F)(F)F)on3)c(F)c2)c(C(N)=O)c1N] | 515.4 |

TABLE 30-continued

| Prep. No. | Chemical name | Structure | ES/MS m/z (M + H) |
|---|---|---|---|
| 170 | 5-Amino-3-[2-(hydroxymethyl)-4-[2-[[5-(1-methylcyclopentyl)isoxazol-3-yl]amino]-2-oxo-ethyl]phenyl]-1-isopropyl-pyrazole-4-carboxamide | 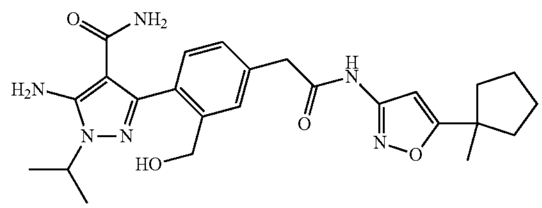 [SMILES: CC(C)n1nc(-c2ccc(CC(=O)Nc3cc(C4(C)CCCC4)on3)cc2CO)c(C(N)=O)c1N] | 481 |
| 171 | 5-Amino-3-[4-[2-[[3-(2,4-dichlorophenyl)isoxazol-5-yl]amino]-2-oxo-ethyl]-3-methoxy-phenyl]-1-isopropyl-pyrazole-4-carboxamide | 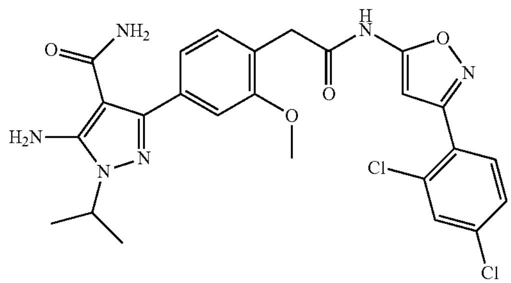 [SMILES: COc1cc(-c2nn(C(C)C)c(N)c2C(N)=O)ccc1CC(=O)Nc1cc(-c2ccc(Cl)cc2Cl)no1] | 543.2 |
| 172 | 5-Amino-3-[4-[2-[[3-(2,2-dimethylpropyl)isoxazol-5-yl]amino]-2-oxo-ethyl]-2-fluoro-phenyl]-1-isopropyl-pyrazole-4-carboxamide | 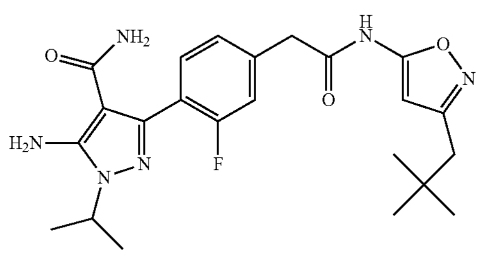 [SMILES: CC(C)n1nc(-c2ccc(CC(=O)Nc3cc(CC(C)(C)C)no3)cc2F)c(C(N)=O)c1N] | 457.2 |
| 173 | 5-Amino-3-[3-chloro-4-[2-[[3-(2,2-dimethylpropyl)isoxazol-5-yl]amino]-2-oxo-ethyl]-2-fluoro-phenyl]-1-isopropyl-pyrazole-4-carboxamide | 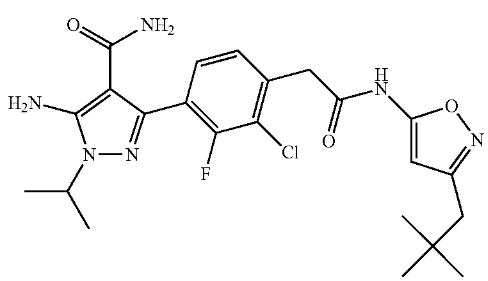 [SMILES: CC(C)n1nc(-c2ccc(CC(=O)Nc3cc(CC(C)(C)C)no3)c(Cl)c2F)c(C(N)=O)c1N] | 491.1 |
| 174 | 5-Amino-3-[2-chloro-4-[2-[[3-(2,2-dimethylpropyl)isoxazol-5-yl]amino]-2-oxo-ethyl]-3-fluoro-phenyl]-1-isopropyl-pyrazole-4-carboxamide | 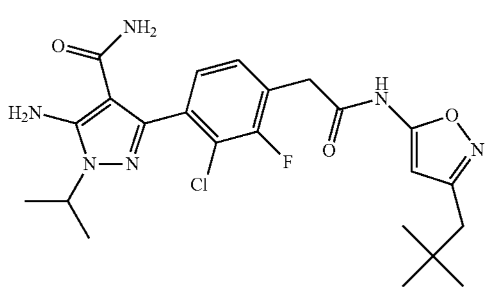 [SMILES: CC(C)n1nc(-c2ccc(CC(=O)Nc3cc(CC(C)(C)C)no3)c(F)c2Cl)c(C(N)=O)c1N] | 491.1 |

TABLE 30-continued

| Prep. No. | Chemical name | Structure | ES/MS m/z (M + H) |
|---|---|---|---|
| 175 | 5-Amino-3-[4-[2-[[3-(2,2-dimethylpropyl)isoxazol-5-yl]amino]-2-oxo-ethyl]-2-methyl-phenyl]-1-isopropyl-pyrazole-4-carboxamide | 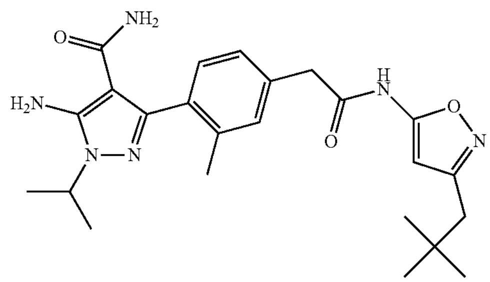 [SMILES: Cc1cc(CC(=O)Nc2cc(CC(C)(C)C)no2)ccc1-c1nn(C(C)C)c(N)c1C(N)=O] | 453.1 |
| 176 | 5-Amino-3-[4-[2-[[3-(cyclobutylmethyl)isoxazol-5-yl]amino]-2-oxo-ethyl]phenyl]-1-isopropyl-pyrazole-4-carboxamide | 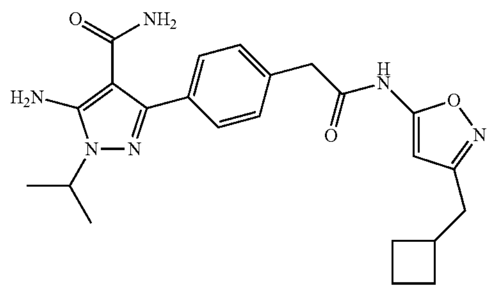 [SMILES: CC(C)n1nc(-c2ccc(CC(=O)Nc3cc(CC4CCC4)no3)cc2)c(C(N)=O)c1N] | 437 |
| 177 | 5-Amino-3-[2-chloro-4-[2-[[3-(2,2-dimethylpropyl)isoxazol-5-yl]amino]-2-oxo-ethyl]phenyl]-1-isopropyl-pyrazole-4-carboxamide | 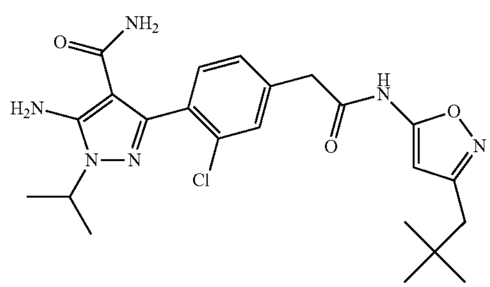 [SMILES: CC(C)n1nc(-c2ccc(CC(=O)Nc3cc(CC(C)(C)C)no3)cc2Cl)c(C(N)=O)c1N] | 473 |
| 178 | 5-Amino-1-isopropyl-3-[4-[2-[[3-[(1-methylcyclobutyl)methyl]isoxazol-5-yl]amino]-2-oxo-ethyl]phenyl]pyrazole-4-carboxamide | 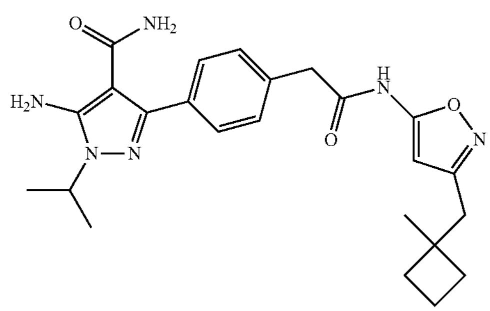 [SMILES: CC(C)n1nc(-c2ccc(CC(=O)Nc3cc(CC4(C)CCC4)no3)cc2)c(C(N)=O)c1N] | 451.2 |
| 179 | 5-Amino-3-[4-[2-[[3-(3,3-difluoro-1-methyl-cyclobutyl)isoxazol-5-yl]amino]-2-oxo-ethyl]phenyl]-1-isopropyl-pyrazole-4-carboxamide | 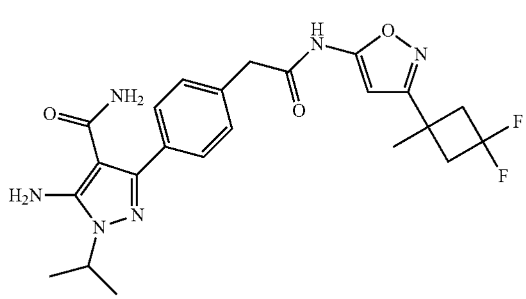 [SMILES: CC(C)n1nc(-c2ccc(CC(=O)Nc3cc(C4(C)CC(F)(F)C4)no3)cc2)c(C(N)=O)c1N] | 473.1 |

TABLE 30-continued

| Prep. No. | Chemical name | Structure | ES/MS m/z (M + H) |
|---|---|---|---|
| 180 | 5-Amino-3-[4-[2-[[3-(3,3-dimethylcyclobutyl)isoxazol-5-yl]amino]-2-oxo-ethyl]-2-fluoro-phenyl]-1-isopropyl-pyrazole-4-carboxamide | 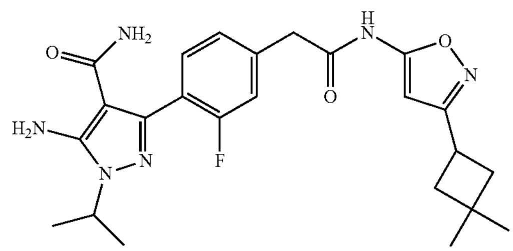 [SMILES: CC(C)n1nc(-c2ccc(CC(=O)Nc3cc(C4CC(C)(C)C4)no3)cc2F)c(C(N)=O)c1N] | 469.2 |
| 181 | 5-Amino-3-[2-chloro-4-[2-[[3-(3,3-dimethylcyclobutyl)isoxazol-5-yl]amino]-2-oxo-ethyl]phenyl]-1-isopropyl-pyrazole-4-carboxamide | 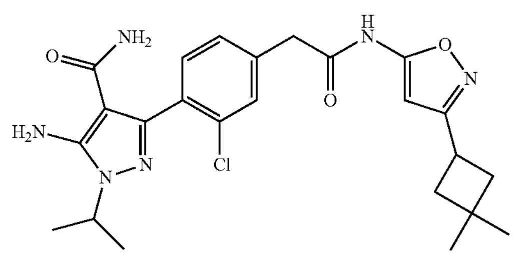 [SMILES: CC(C)n1nc(-c2ccc(CC(=O)Nc3cc(C4CC(C)(C)C4)no3)cc2Cl)c(C(N)=O)c1N] | 485.1 |
| 182 | 5-Amino-3-[2-chloro-4-[2-[[3-(3,3-dimethylcyclobutyl)isoxazol-5-yl]amino]-2-oxo-ethyl]-3-fluoro-phenyl]-1-isopropyl-pyrazole-4-carboxamide | 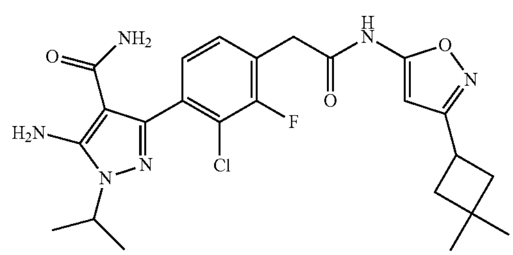 [SMILES: CC(C)n1nc(-c2ccc(CC(=O)Nc3cc(C4CC(C)(C)C4)no3)c(F)c2Cl)c(C(N)=O)c1N] | 503.1 |
| 183 | 5-Amino-3-[4-[2-[[3-(1,1-difluoro-2,2-dimethyl-propyl)isoxazol-5-yl]amino]-2-oxo-ethyl]phenyl]-1-isopropyl-pyrazole-4-carboxamide | 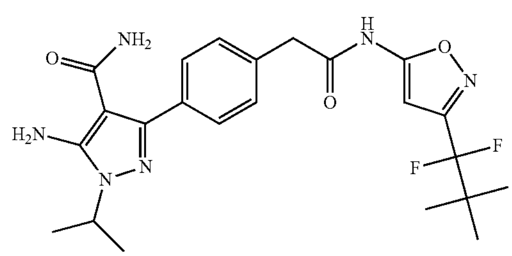 [SMILES: CC(C)n1nc(-c2ccc(CC(=O)Nc3cc(C(F)(F)C(C)(C)C)no3)cc2)c(C(N)=O)c1N] | 475 |
| 184 | 5-Amino-3-[2-fluoro-4-[2-[[3-(3-methyl-1-bicyclo[1.1.1]pentanyl)isoxazol-5-yl]amino]-2-oxo-ethyl]phenyl]-1-isopropyl-pyrazole-4-carboxamide | 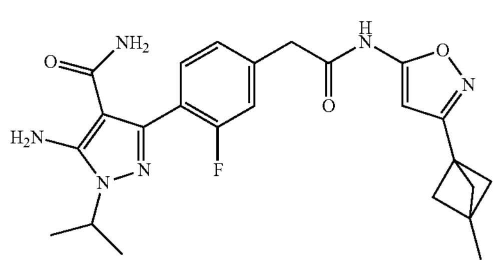 [SMILES: CC(C)n1nc(-c2ccc(CC(=O)Nc3cc(C45CC(C)(C4)C5)no3)cc2F)c(C(N)=O)c1N] | 467 |

TABLE 30-continued

| Prep. No. | Chemical name | Structure | ES/MS m/z (M + H) |
|---|---|---|---|
| 185 | 5-Amino-3-[4-[2-[[3-(3,3-dimethylcyclobutyl)isoxazol-5-yl]amino]-2-oxo-ethyl]-2,3-difluoro-phenyl]-1-isopropyl-pyrazole-4-carboxamide | 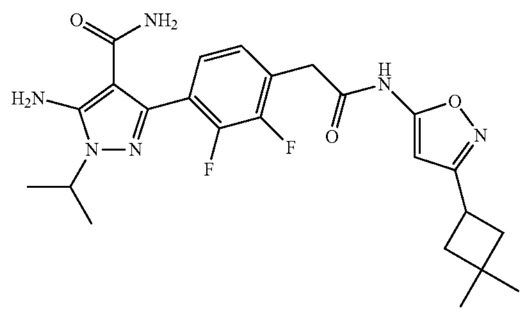 [SMILES: CC(C)n1nc(-c2ccc(CC(=O)Nc3cc(C4CC(C)(C)C4)no3)c(F)c2F)c(C(N)=O)c1N] | 487 |
| 186 | 5-Amino-3-[4-[2-[[3-(2,2-dimethylpropyl)isoxazol-5-yl]amino]-2-oxo-ethyl]-2,5-difluoro-phenyl]-1-isopropyl-pyrazole-4-carboxamide | 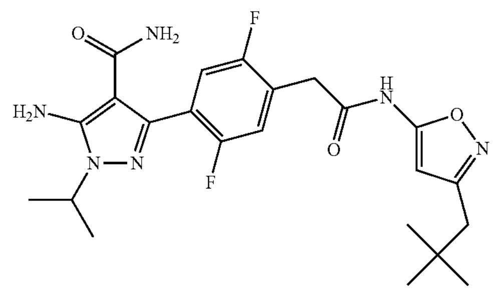 [SMILES: CC(C)n1nc(-c2cc(F)c(CC(=O)Nc3cc(CC(C)(C)C)no3)cc2F)c(C(N)=O)c1N] | 475.1 |
| 187 | 5-Amino-3-[4-[2-[[5-(3,3-dimethylcyclobutyl)isoxazol-3-yl]amino]-2-oxo-ethyl]phenyl]-1-isopropyl-pyrazole-4-carboxamide | 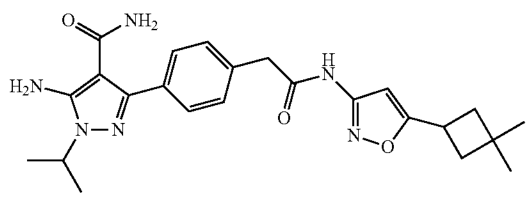 [SMILES: CC(C)n1nc(-c2ccc(CC(=O)Nc3cc(C4CC(C)(C)C4)on3)cc2)c(C(N)=O)c1N] | 451 |
| 188 | 5-Amino-3-[4-[2-[[3-(2,2-dimethylpropyl)isoxazol-5-yl]amino]-2-oxo-ethyl]-3,5-difluoro-phenyl]-1-isopropyl-pyrazole-4-carboxamide | 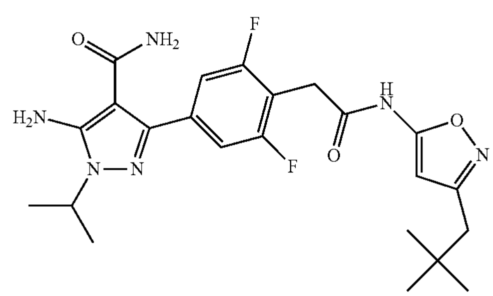 [SMILES: CC(C)n1nc(-c2cc(F)c(CC(=O)Nc3cc(CC(C)(C)C)no3)c(F)c2)c(C(N)=O)c1N] | 475.1 |
| 189 | 5-Amino-3-[2-chloro-4-[2-[[3-(3-methyl-1-bicyclo[1.1.1]pentanyl)isoxazol-5-yl]amino]-2-oxo-ethyl]phenyl]-1-isopropyl-pyrazole-4-carboxamide | 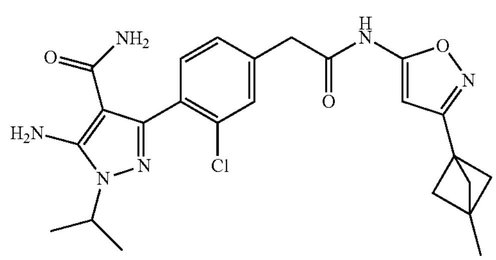 [SMILES: CC(C)n1nc(-c2ccc(CC(=O)Nc3cc(C45CC(C)(C4)C5)no3)cc2Cl)c(C(N)=O)c1N] | 483.1 |

TABLE 30-continued

| Prep. No. | Chemical name | Structure | ES/MS m/z (M + H) |
|---|---|---|---|
| 190 | 5-Amino-3-[2-chloro-3-fluoro-4-[2-[[3-(3-methyl-1-bicyclo[1.1.1]pentanyl)isoxazol-5-yl]amino]-2-oxo-ethyl]phenyl]-1-isopropyl-pyrazole-4-carboxamide | 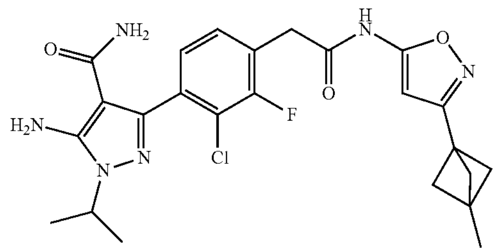 [SMILES: CC(C)n1nc(-c2ccc(CC(=O)Nc3cc(C45CC(C)(C4)C5)no3)c(F)c2Cl)c(C(N)=O)c1N] | 501 |
| 191 | 5-Amino-3-[4-[2-[[3-(3,3-dimethylcyclobutyl)-4-fluoro-isoxazol-5-yl]amino]-2-oxo-ethyl]phenyl]-1-isopropyl-pyrazole-4-carboxamide | 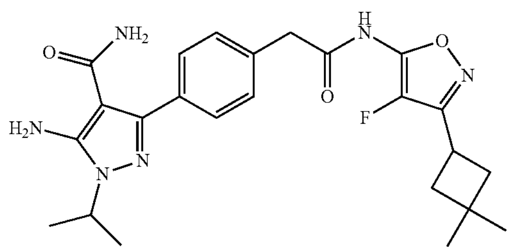 [SMILES: CC(C)n1nc(-c2ccc(CC(=O)Nc3onc(C4CC(C)(C)C4)c3F)cc2)c(C(N)=O)c1N] | 469.1 |
| 192 | 5-Amino-3-[3,5-difluoro-4-[2-[[3-(3-methyl-1-bicyclo[1.1.1]pentanyl)isoxazol-5-yl]amino]-2-oxo-ethyl]phenyl]-1-isopropyl-pyrazole-4-carboxamide | 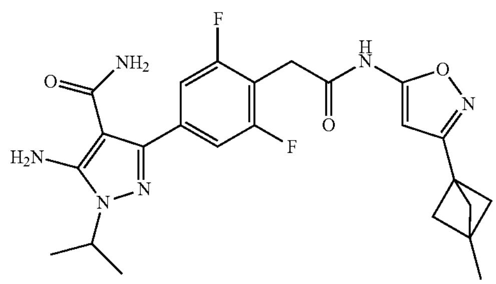 [SMILES: CC(C)n1nc(-c2cc(F)c(CC(=O)Nc3cc(C45CC(C)(C4)C5)no3)c(F)c2)c(C(N)=O)c1N] | 485 |
| 193 | 5-Amino-3-[4-[2-[[3-(2,2-dimethylpropyl)-4-fluoro-isoxazol-5-yl]amino]-2-oxo-ethyl]phenyl]-1-isopropyl-pyrazole-4-carboxamide | 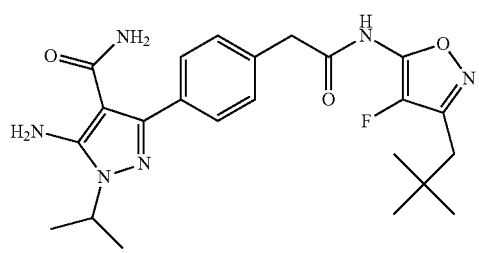 [SMILES: CC(C)n1nc(-c2ccc(CC(=O)Nc3onc(CC(C)(C)C)c3F)cc2)c(C(N)=O)c1N] | 457.1 |
| 194 | 5-Amino-3-[4-[2-[[4-fluoro-3-(3-methyl-1-bicyclo[1.1.1]pentanyl)isoxazol-5-yl]amino]-2-oxo-ethyl]phenyl]-1-isopropyl-pyrazole-4-carboxamide | 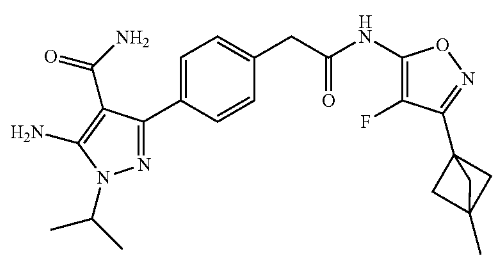 [SMILES: CC(C)n1nc(-c2ccc(CC(=O)Nc3onc(C45CC(C)(C4)C5)c3F)cc2)c(C(N)=O)c1N] | 467 |
| 195 | 5-Amino-1-isopropyl-3-[4-[2-oxo-2-[[5-[1-(trifluoromethyl)cyclopropyl]isoxazol-3-yl]amino]ethyl]phenyl]pyrazole-4-carboxamide | 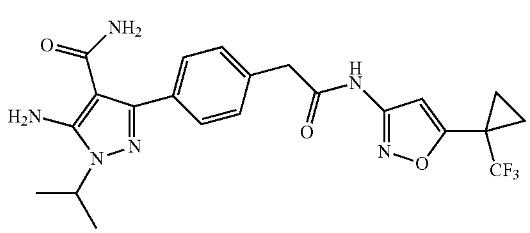 [SMILES: CC(C)n1nc(-c2ccc(CC(=O)Nc3cc(C4(C(F)(F)F)CC4)on3)cc2)c(C(N)=O)c1N] | 477.4 |

Example 196

5-Amino-1-isopropyl-3-[2-(methoxymethyl)-4-[2-[[5-(1-methylcyclopentyl)isoxazol-3-yl]amino]-2-oxo-ethyl]phenyl]pyrazole-4-carboxamide

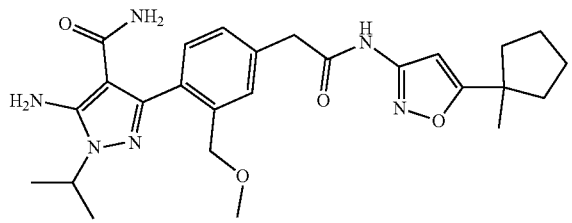 [SMILES: COCc1cc(CC(=O)Nc2cc(C3(C)CCCC3)on2)ccc1-c1nn(C(C)C)c(N)c1C(N)=O]

To 2-[4-bromo-3-(methoxymethyl)phenyl]-N-[5-(1-methylcyclopentyl)isoxazol-3-yl]acetamide (0.130 g, 0.319 mmol) in THF (3 mL) is added bis(pinacolato)diboron (89 mg, 0.350 mmol) and KOAc (95 mg, 0.968 mmol). The reaction mixture is degassed with Ar for 10 min, Pd(dppf)Cl$_2$·CH$_2$Cl$_2$ (27 mg, 0.032 mmol) is added, the mixture is stirred at 50° C. overnight, and cooled to RT. 5-Amino-3-bromo-1-isopropyl-pyrazole-4-carboxamide (95 mg, 0.384 mmol) in THF (1.2 mL) is added followed by K$_3$PO$_4$ (0.206 g, 0.970 mmol) in H$_2$O (1.2 mL). The mixture is degassed with Ar for 10 min and XantPhos Pd G3 (95%, 16 mg, 0.016 mmol) is added. The mixture is heated to 50° C. for 20 hr, cooled to RT, and filtered through talcum powder. The filtrate is diluted with EtOAc/H$_2$O and the aqueous layer is extracted with EtOAc (2×). The combined organic extracts are washed with brine, dried over Na$_2$SO$_4$, filtered, and concentrated under reduced pressure. The crude material is purified by silica gel chromatography, eluting with a gradient of 1% to 10% MeOH in DCM, followed by a second chromatography, eluting with a gradient of 90% to 100% EtOAc in DCM and by reversed-phase chromatography (C18Aq column), eluting with a gradient of 0% to 100% ACN (0.1% HOAc) in H$_2$O to give the title compound. The residue is dissolved in DCM and added dropwise to pentane. The suspension is stirred at RT for 2 hr and filtered. The solid is dried under vacuum at 38° C. for 3 days to give the title compound (35 mg, 22%). ES/MS (m/z) 495 (M+H).

The following compounds in Table 31 are prepared essentially as described for, 5-amino-1-isopropyl-3-[2-(methoxymethyl)-4-[2-[[5-(1-methylcyclopentyl)isoxazol-3-yl]amino]-2-oxo-ethyl]phenyl]pyrazole-4-carboxamide adjusting reaction time to determine completion of the reaction and using appropriate chromatography conditions for purification. The reaction temperature can range from about 50-55° C.

TABLE 31

| Ex No. | Chemical name | Structure | ES/MS m/z (M + H) |
|---|---|---|---|
| 197 | 5-Amino-1-isopropyl-3-[3-(methoxymethyl)-4-[2-[[5-(1-methylcyclopentyl)isoxazol-3-yl]amino]-2-oxo-ethyl]phenyl]pyrazole-4-carboxamide | 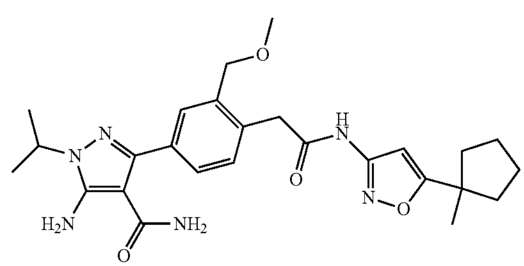 [SMILES: COCc1cc(-c2nn(C(C)C)c(N)c2C(N)=O)ccc1CC(=O)Nc1cc(C2(C)CCCC2)on1] | 495 |
| 198 | 5-Amino-3-[3-(hydroxymethyl)-4-[2-[[5-(1-methylcyclopentyl)isoxazol-3-yl]amino]-2-oxo-ethyl]phenyl]-1-isopropyl-pyrazole-4-carboxamide | 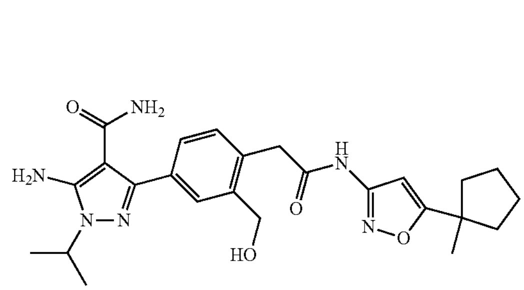 [SMILES: CC(C)n1nc(-c2ccc(CC(=O)Nc3cc(C4(C)CCCC4)on3)c(CO)c2)c(C(N)=O)c1N] | 481 |

Example 199

5-Amino-3-(4-(2-((3-(2-chloro-4-fluorophenyl)isoxazol-5-yl)amino)-2-oxoethyl)phenyl)-1-(1-methylcyclopropyl)-1H-pyrazole-4-carboxamide

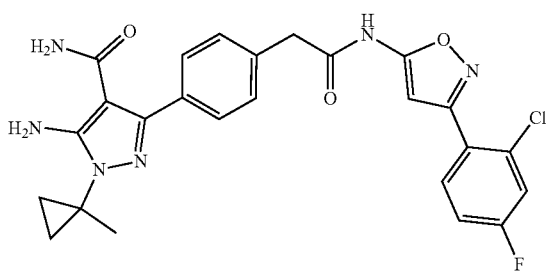 [SMILES: CC1(n2nc(-c3ccc(CC(=O)Nc4cc(-c5ccc(F)cc5Cl)no4)cc3)c(C(N)=O)c2N)CC1]

2-(4-(5-Amino-4-cyano-1-(1-methylcyclopropyl)-1H-pyrazol-3-yl)phenyl)-N-(3-(2-chloro-4-fluorophenyl)isoxazol-5-yl)acetamide (66 mg, 0.134 mmol) and Parkins catalyst (69.2 mg, 0.161 mmol) are stirred in EtOH (1.0 mL) and $H_2O$ (1.0 mL) at 60° C. for 4 hr, then 50° C. for 4 hrs and RT overnight. The reaction mixture and extracted with EtOAc and washed with $H_2O$ (3×). The combined organic extracts are concentrated, and purified by silica gel chromatography, eluting with a gradient of 0% to 100% EtOAc in hexanes followed by 0% to 20% MeOH (with 1% $NH_4OH$) in EtOAc to give the title compound (35 mg, 51% E). ES/MS (m/z) 509.1

The following compounds in Table 32 are prepared essentially as described for 5-amino-3-(4-(2-((3-(2-chloro-4-fluorophenyl)isoxazol-5-yl)amino)-2-oxoethyl)phenyl)-1-(1-methylcyclopropyl)-1H-pyrazole-4-carboxamide adjusting reaction time to determine completion of the reaction and using appropriate chromatography conditions for purification.

TABLE 32

| Ex. No. | Chemical name | Structure | ES/MS m/z (M + H) |
|---|---|---|---|
| 200 | 5-Amino-1-(1-cyclopropylethyl)-3-(4-(2-((3-neopentylisoxazol-5-yl)amino)-2-oxoethyl)phenyl)-1H-pyrazole-4-carboxamide | 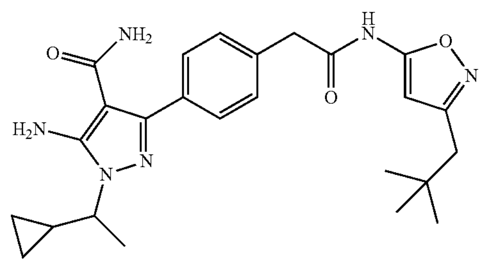 [SMILES: CC(C1CC1)n1nc(-c2ccc(CC(=O)Nc3cc(CC(C)(C)C)no3)cc2)c(C(N)=O)c1N] | 465.2 |
| 201 | 5-Amino-3-(4-(2-((3-neopentylisoxazol-5-yl)amino)-2-oxoethyl)phenyl)-1-(tetrahydrofuran-3-yl)-1H-pyrazole-4-carboxamide, | 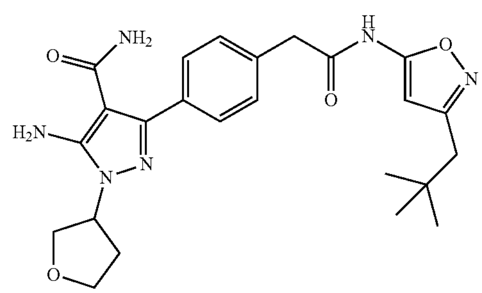 [SMILES: CC(C)(C)Cc1cc(NC(=O)Cc2ccc(-c3nn(C4CCOC4)c(N)c3C(N)=O)cc2)on1] | 467.2 |
| 202 | 5-Amino-1-cyclopentyl-3-(4-(2-((3-neopentylisoxazol-5-yl)amino)-2-oxoethyl)phenyl)-1H-pyrazole-4-carboxamide | 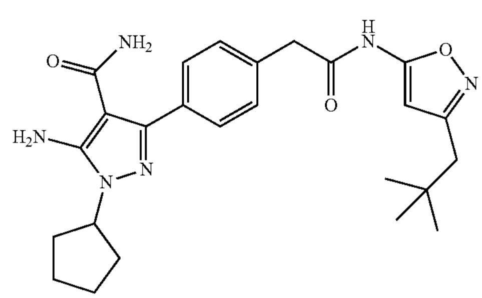 [SMILES: CC(C)(C)Cc1cc(NC(=O)Cc2ccc(-c3nn(C4CCCC4)c(N)c3C(N)=O)cc2)on1] | 465.2 |

TABLE 32-continued

| Ex. No. | Chemical name | Structure | ES/MS m/z (M + H) |
|---|---|---|---|
| 203 | 5-Amino-3-(4-(2-((3-neopentylisoxazol-5-yl)amino)-2-oxoethyl)phenyl)-1-(tetrahydro-2H-pyran-3-yl)-1H-pyrazole-4-carboxamide, | 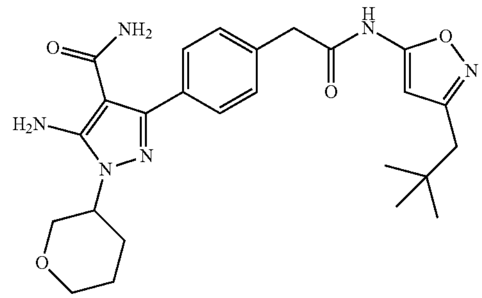 [SMILES: CC(C)(C)Cc1cc(NC(=O)Cc2ccc(-c3nn(C4CCCOC4)c(N)c3C(N)=O)cc2)on1] | 481.4 |
| 204 | 5-Amino-3-[4-[2-[[3-(2,4-dichlorophenyl)isoxazol-5-yl]amino]-2-oxo-ethyl]phenyl]-1-(1-methylcyclopropyl)pyrazole-4-carboxamide | 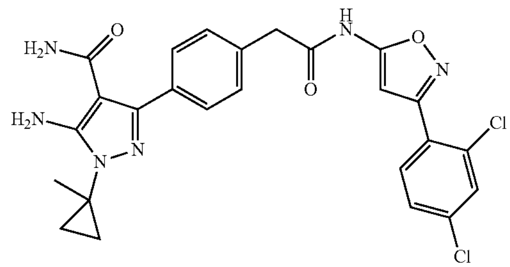 [SMILES: CC1(n2nc(-c3ccc(CC(=O)Nc4cc(-c5ccc(Cl)cc5Cl)no4)cc3)c(C(N)=O)c2N)CC1] | 525.1 |
| 205 | 5-Amino-3-(4-(2-((3-neopentylisoxazol-5-yl)amino)-2-oxoethyl)phenyl)-1-(tetrahydro-2H-pyran-4-yl)-1H-pyrazole-4-carboxamide | 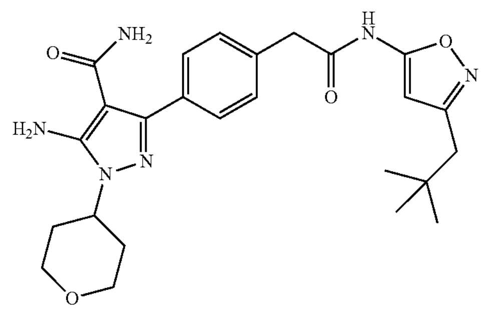 [SMILES: CC(C)(C)Cc1cc(NC(=O)Cc2ccc(-c3nn(C4CCOCC4)c(N)c3C(N)=O)cc2)on1] | 481.2 |
| 206 | 5-Amino-1-(3-ethoxycyclobutyl)-3-(4-(2-((3-neopentylisoxazol-5-yl)amino)-2-oxoethyl)phenyl)-1H-pyrazole-4-carboxamide | 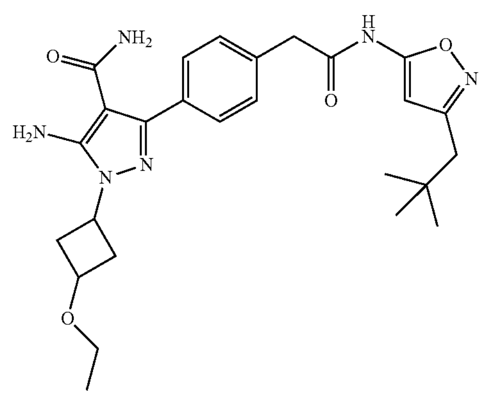 [SMILES: CCOC1CC(n2nc(-c3ccc(CC(=O)Nc4cc(CC(C)(C)C)no4)cc3)c(C(N)=O)c2N)C1] | 495.2 |
| 207 | 5-Amino-1-(1-hydroxypropan-2-yl)-3-(4-(2-((3-neopentylisoxazol-5-yl)amino)-2-oxoethyl)phenyl)-1H-pyrazole-4-carboxamide, | 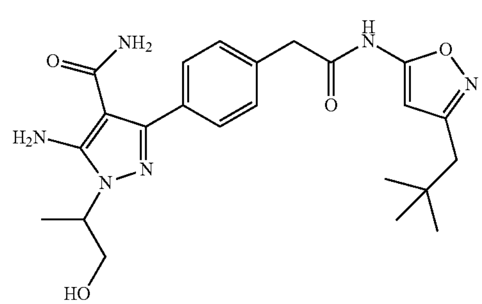 [SMILES: CC(CO)n1nc(-c2ccc(CC(=O)Nc3cc(CC(C)(C)C)no3)cc2)c(C(N)=O)c1N] | 455.2 |

TABLE 32-continued

| Ex. No. | Chemical name | Structure | ES/MS m/z (M + H) |
|---|---|---|---|
| 208 | 5-Amino-1-(1-hydroxy-2-methylpropan-2-yl)-3-(4-(2-((3-neopentylisoxazol-5-yl)amino)-2-oxoethyl)phenyl)-1H-pyrazole-4-carboxamide | 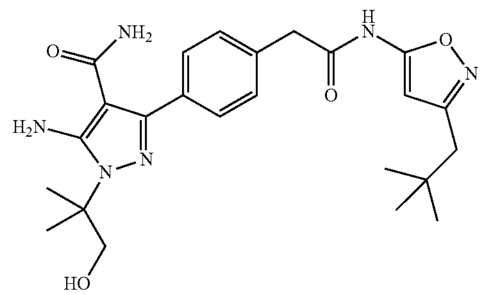 [SMILES: CC(C)(C)Cc1cc(NC(=O)Cc2ccc(-c3nn(C(C)(C)CO)c(N)c3C(N)=O)cc2)on1] | 469.2 |
| 209 | 5-Amino-1-isopropyl-3-[4-[2-oxo-2-[[3-(3,3,3-trifluoro-2,2-dimethyl-propyl)isoxazol-5-yl]amino]ethyl]phenyl]pyrazole-4-carboxamide | 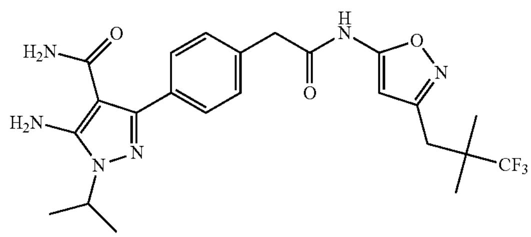 [SMILES: CC(C)n1nc(-c2ccc(CC(=O)Nc3cc(CC(C)(C)C(F)(F)F)no3)cc2)c(C(N)=O)c1N] | 492.2 |
| 210 | 5-Amino-3-(4-(2-((3-(4-fluorobicyclo[2.2.2]octan-1-yl)isoxazol-5-yl)amino)-2-oxoethyl)phenyl)-1-isopropyl-1H-pyrazole-4-carboxamide | 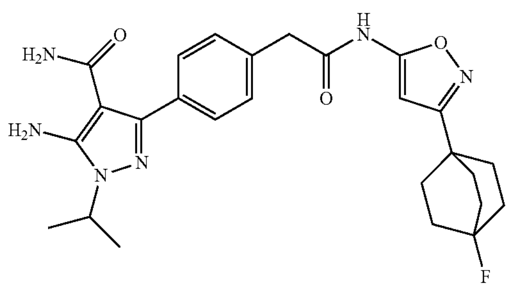 [SMILES: CC(C)n1nc(-c2ccc(CC(=O)Nc3cc(C45CCC(F)(CC4)CC5)no3)cc2)c(C(N)=O)c1N] | 495.4 |
| 211 | 5-Amino-1-cyclobutyl-3-(4-(2-((3-neopentylisoxazol-5-yl)amino)-2-oxoethyl)phenyl)-1H-pyrazole-4-carboxamide | 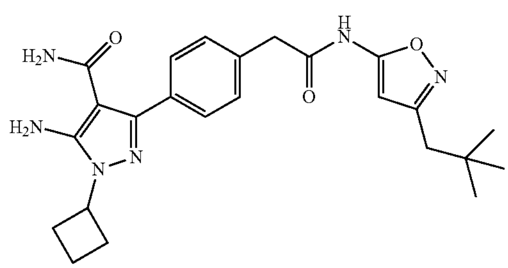 [SMILES: CC(C)(C)Cc1cc(NC(=O)Cc2ccc(-c3nn(C4CCC4)c(N)c3C(N)=O)cc2)on1] | 451.2 |
| 212 | 5-Amino-3-(4-(2-((3-neopentylisoxazol-5-yl)amino)-2-oxoethyl)phenyl)-1-(2,2,2-trifluoroethyl)-1H-pyrazole-4-carboxamide | 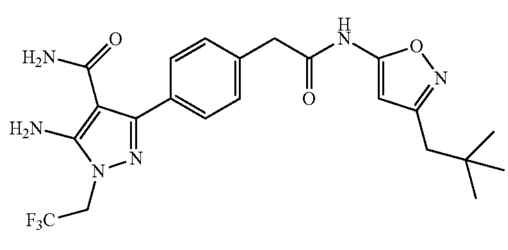 [SMILES: CC(C)(C)Cc1cc(NC(=O)Cc2ccc(-c3nn(CC(F)(F)F)c(N)c3C(N)=O)cc2)on1] | 479.2 |

TABLE 32-continued

| Ex. No. | Chemical name | Structure | ES/MS m/z (M + H) |
|---|---|---|---|
| 213 | 5-Amino-3-(4-(2-((3-neopentylisoxazol-5-yl)amino)-2-oxoethyl)phenyl)-1-((tetrahydrofuran-3-yl)methyl)-1H-pyrazole-4-carboxamide | 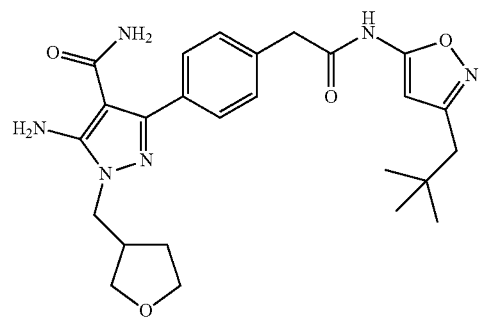 [SMILES: CC(C)(C)Cc1cc(NC(=O)Cc2ccc(-c3nn(CC4CCOC4)c(N)c3C(N)=O)cc2)on1] | 481.4 |
| 214 | 5-Amino-1-(tert-butyl)-3-(4-(2-((3-neopentylisoxazol-5-yl)amino)-2-oxoethyl)phenyl)-1H-pyrazole-4-carboxamide | 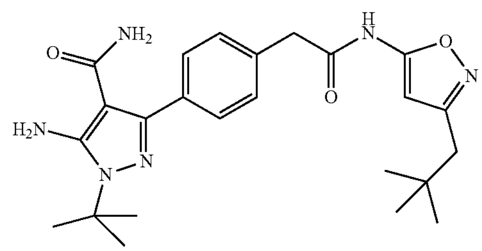 [SMILES: CC(C)(C)Cc1cc(NC(=O)Cc2ccc(-c3nn(C(C)(C)C)c(N)c3C(N)=O)cc2)on1] | 453.2 |
| 215 | 5-Amino-1-cyclopropyl-3-[4-[2-[[3-(2,2-dimethylpropyl)isoxazol-5-yl]amino]-2-oxo-ethyl]phenyl]pyrazole-4-carboxamide | 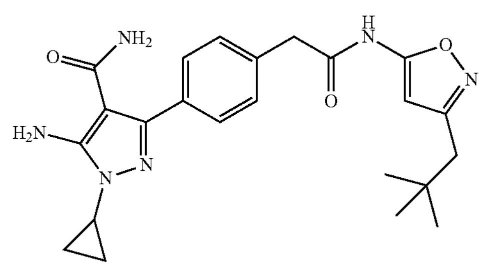 [SMILES: CC(C)(C)Cc1cc(NC(=O)Cc2ccc(-c3nn(C4CC4)c(N)c3C(N)=O)cc2)on1] | 437.2 |
| 216 | 5-Amino-3-[4-[2-[(3-benzylisoxazol-5-yl)amino]-2-oxo-ethyl]phenyl]-1-isopropyl-pyrazole-4-carboxamide | 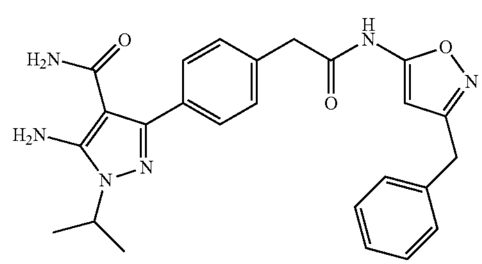 [SMILES: CC(C)n1nc(-c2ccc(CC(=O)Nc3cc(Cc4ccccc4)no3)cc2)c(C(N)=O)c1N] | 459.2 |
| 217 | 5-Amino-1-(bicyclo[1.1.1]pentan-1-yl)-3-(4-(2-((3-neopentylisoxazol-5-yl)amino)-2-oxoethyl)phenyl)-1H-pyrazole-4-carboxamide | 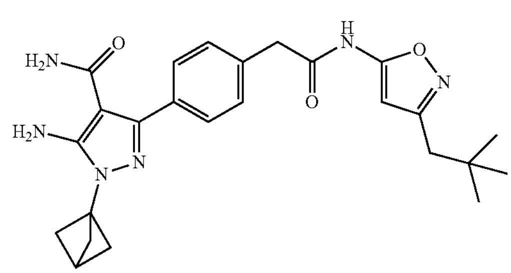 [SMILES: CC(C)(C)Cc1cc(NC(=O)Cc2ccc(-c3nn(C45CC(C4)C5)c(N)c3C(N)=O)cc2)on1] | 463.2 |

TABLE 32-continued

| Ex. No. | Chemical name | Structure | ES/MS m/z (M + H) |
|---|---|---|---|
| 218 | 5-Amino-3-[4-[2-[[3-(3-bicyclo[1.1.1]pentanylmethyl)isoxazol-5-yl]amino]-2-oxo-ethyl]phenyl]-1-isopropyl-pyrazole-4-carboxamide | 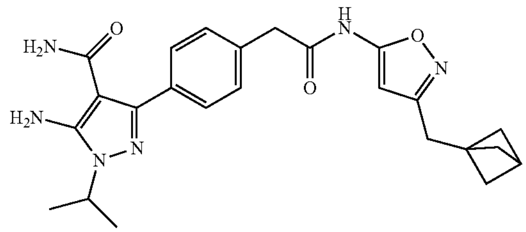 [SMILES: CC(C)n1nc(-c2ccc(CC(=O)Nc3cc(CC45CC(C4)C5)no3)cc2)c(C(N)=O)c1N] | 449.2 |
| 219 | 5-Amino-3-[4-[2-[[3-(2,2-dimethylpropyl)isoxazol-5-yl]amino]-2-oxo-ethyl]phenyl]-1-(1-methylcyclopropyl)pyrazole-4-carboxamide | 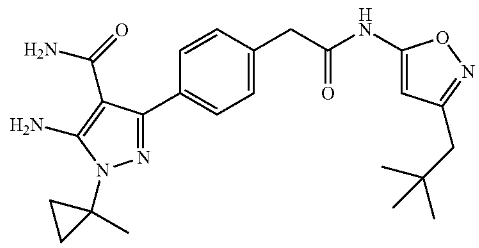 [SMILES: CC(C)(C)Cc1cc(NC(=O)Cc2ccc(-c3nn(C4(C)CC4)c(N)c3C(N)=O)cc2)on1] | 451.2 |
| 220 | 5-Amino-1-(3-hydroxypropyl)-3-(4-(2-((3-neopentylisoxazol-5-yl)amino)-2-oxoethyl)phenyl)-1H-pyrazole-4-carboxamide | 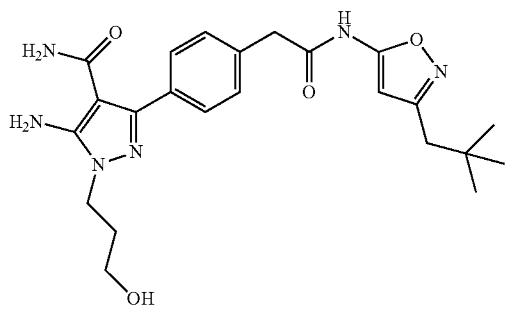 [SMILES: CC(C)(C)Cc1cc(NC(=O)Cc2ccc(-c3nn(CCCO)c(N)c3C(N)=O)cc2)on1] | 455.2 |

Example 221

5-Amino-3-[2,3-difluoro-4-[2-[[3-(3-fluoro-1-bicyclo[1.1.1]pentanyl)isoxazol-5-yl]amino]-2-oxo-ethyl]phenyl]-1-(1-methylcyclopropyl)pyrazole-4-carboxamide

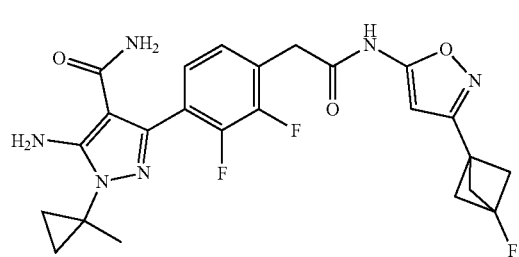 [SMILES: CC1(n2nc(-c3ccc(CC(=O)Nc4cc(C56CC(F)(C5)C6)no4)c(F)c3F)c(C(N)=O)c2N)CC1]

2-[4-[5-Amino-4-cyano-1-(1-methylcyclopropyl)pyrazol-3-yl]-2,3-difluorophenyl]-N-(3-[3-fluorobicyclo[1.1.1]pentan-1-yl]-1,2-oxazol-5-yl)acetamide (60 mg, 0.124 mmol), NaOH (25 mg, 0.625 mmol) in EtOH:DMSO (6 mL, 5:1), and H$_2$O$_2$ (0.38 mL, 3.72 mmol, 30% in H$_2$O) are added together and stirred for 1 hr at 50° C. The solution is allowed to cool to RT, quenched with saturated aq. Na$_2$SO$_3$ (10 mL) and extracted with EtOAc (3×20 mL). The organic extracts are dried over anhydrous Na$_2$SO$_4$, filtered, and concentrated under reduced pressure. The residue is purified by reversed-phase chromatography (C18 column), eluting with a gradient of 40% to 60% ACN in H$_2$O (0.1% FA) to give the title compound (45 mg, 73%). ES/MS (m/z) 501.2 (M+H).

Example 222

5-Amino-3-(2,3-difluoro-4-[[(3-[3-methylbicyclo[1.1.1]pentan-1-yl]-1,2-oxazol-5-yl)carbamoyl]methyl]phenyl)-1-(1-methylcyclopropyl)pyrazole-4-carboxamide

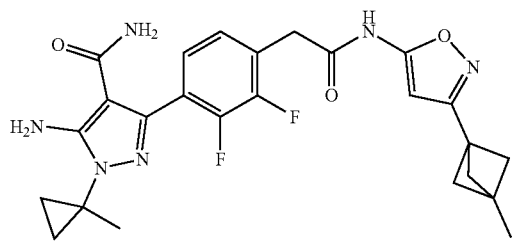 [SMILES: CC12CC(c3cc(NC(=O)Cc4ccc(-c5nn(C6(C)CC6)c(N)c5C(N)=O)c(F)c4F)on3)(C1)C2]

To a solution of 2-[4-[5-amino-4-cyano-1-(1-methylcyclopropyl)pyrazol-3-yl]-2,3-difluorophenyl]-N-(3-[3-methylbicyclo[1.1.1]pentan-1-yl]-1,2-oxazol-5-yl)acetamide (70 mg, 0.146 mmol) and NaOH (29 mg, 0.725 mmol) in EtOH (3 mL) and DMSO (0.60 mL) is added H$_2$O$_2$ (0.22 mL, 2.15 mmol, 30% in H$_2$O). The reaction is stirred for 1 hr at 50° C. The mixture is allowed to cool to RT and quenched with saturated aq. Na$_2$SO$_3$ (10 mL) at 0° C. The aqueous layer is extracted with EtOAc (2×30 mL). The combined organic extracts are washed with brine (2×20 mL), dried over anhydrous Na$_2$SO$_4$, filtered, and concentrated under reduced pressure. The residue is purified by reversed-phase chromatography (C18 column), eluting with a gradient of 40% to 60% ACN in H$_2$O (0.1% NH$_4$HCO$_3$) to give the title compound (36 mg, 50%) as a white solid. ES/MS (m/z) 497.3 (M+H).

Example 223

5-Amino-1-isopropyl-3-[4-([[3-(pyridin-2-yl)-1,2-oxazol-5-yl]carbamoyl]methyl)phenyl]pyrazole-4-carboxamide

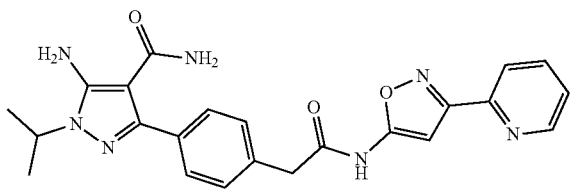 [SMILES: CC(C)n1nc(-c2ccc(CC(=O)Nc3cc(-c4ccccn4)no3)cc2)c(C(N)=O)c1N]

To a stirred solution of 2-[4-(5-amino-4-cyano-1-isopropylpyrazol-3-yl)phenyl]-N-[3-(pyridin-2-yl)-1,2-oxazol-5-yl]acetamide (60 mg, 0.140 mmol) and NaOH (28 mg, 0.700 mmol) in EtOH (1.5 mL), DMSO (0.30 mL), and H$_2$O (0.60 mL) is added H$_2$O$_2$ (0.22 mL, 2.15 mmol, 30% in H$_2$O) at RT. The mixture is stirred for 3 hr at 40° C. The reaction is quenched with saturated aq. Na$_2$SO$_3$ (10 mL). The mixture is extracted with EtOAc (3×100 mL). The combined organic extracts are washed with brine (100 mL), dried over anhydrous Na$_2$SO$_4$, filtered, and the filtrate is concentrated under reduced pressure. The residue is purified by reversed-phase chromatography, eluting with a gradient of 10% to 30% ACN in H$_2$O (0.1% NH$_3$H$_2$O) to give the title compound (26 mg, 40%) as a white solid. ES/MS (m/z) 446.2 (M+H).

The following compounds in Table 33 are prepared essentially as described 5-amino-1-isopropyl-3-[4-([[3-(pyridin-2-yl)-1,2-oxazol-5-yl]carbamoyl]methyl)phenyl]pyrazole-4-carboxamide, 0.3 formic acid, using the appropriate reagents, adjusting reaction time to determine completion of the reaction and using appropriate chromatography conditions for purification. The salt formation depends on purification conditions. H$_2$O$_2$ (about 15-30 equiv) can be added dropwise or portionwise, H$_2$O can be added if necessary, and temperature can range from about RT to 50°.

TABLE 33

| Ex. No. | Chemical name | Structure | ES/MS m/z (M + H) |
|---|---|---|---|
| 224 | 5-Amino-1-isopropyl-3-[4-([[5-(2-methylbutan-2-yl)-1,2-oxazol-3-yl]carbamoyl]methyl)phenyl]pyrazole-4-carboxamide | 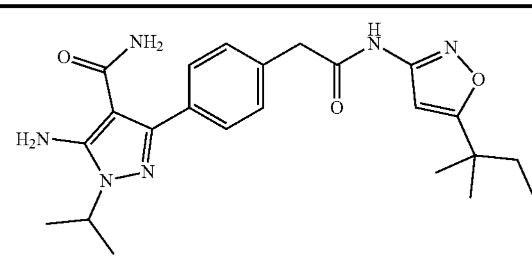 | 439.4 |
| 225 | 5-Amino-3-[4-([[3-(3,5-dichloropyridin-2-yl)-1,2-oxazol-5-yl]carbamoyl]methyl)phenyl]-1-isopropylpyrazole-4-carboxamide | 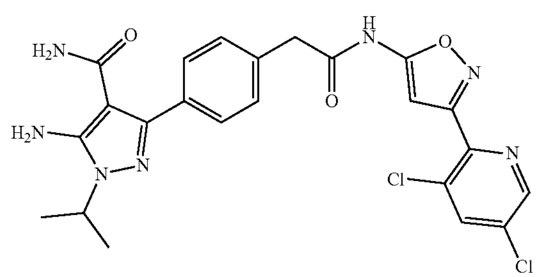 [SMILES: CC(C)n1nc(-c2ccc(CC(=O)Nc3cc(-c4ncc(Cl)cc4Cl)no3)cc2)c(C(N)=O)c1N] | 514.1 |
| 226 | 5-Amino-3-[4-([[5-(2,2-dimethylpropyl)-1,2-thiazol-3-yl]carbamoyl]methyl)phenyl]-1-isopropylpyrazole-4-carboxamide | 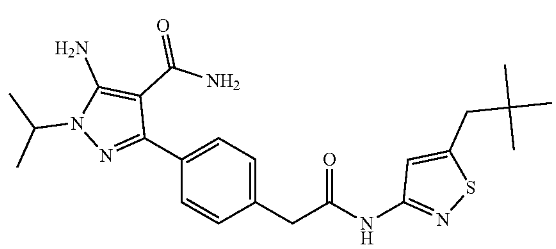 [SMILES: CC(C)n1nc(-c2ccc(CC(=O)Nc3cc(CC(C)(C)C)sn3)cc2)c(C(N)=O)c1N] | 455.3 |

TABLE 33-continued

| Ex. No. | Chemical name | Structure | ES/MS m/z (M + H) |
|---|---|---|---|
| 227 | 5-Amino-3-[4-([[5-(2,2-dimethylpropyl)-1,3-thiazol-2-yl]carbamoyl]methyl)phenyl]-1-isopropylpyrazole-4-carboxamide | 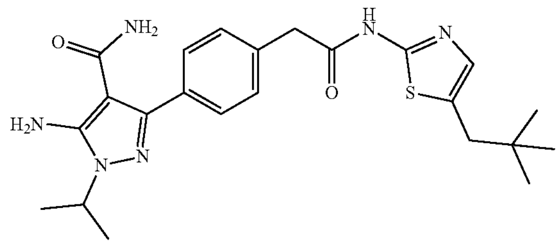 [SMILES: CC(C)n1nc(-c2ccc(CC(=O)Nc3ncc(CC(C)(C)C)s3)cc2)c(C(N)=O)c1N] | 455.4 |
| 228 | 5-Amino-3-[4-([[3-(2,2-dimethylpropyl)-1,2-oxazol-5-yl]carbamoyl]methyl)phenyl]-1-(1,1,1-trifluoro-2-methylpropan-2-yl)pyrazole-4-carboxamide | 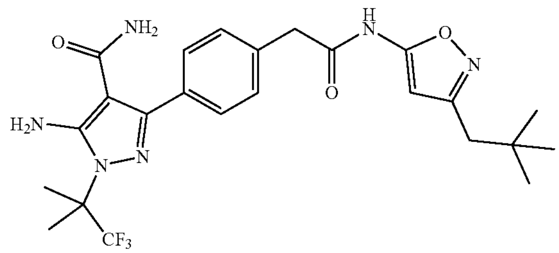 [SMILES: CC(C)(C)Cc1cc(NC(=O)Cc2ccc(-c3nn(C(C)(C)C(F)(F)F)c(N)c3C(N)=O)cc2)on1] | 507.3 |
| 229 | 5-Amino-3-[4-([[3-(3,3-dimethylcyclobutyl)-1,2-oxazol-5-yl]carbamoyl]methyl)phenyl]-1-(1-methylcyclopropyl)pyrazole-4-carboxamide | 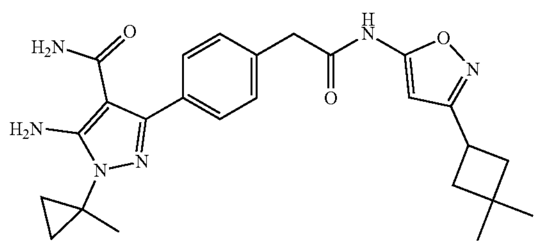 [SMILES: CC1(C)CC(c2cc(NC(=O)Cc3ccc(-c4nn(C5(C)CC5)c(N)c4C(N)=O)cc3)on2)C1] | 485.4 M + Na |
| 230 | 5-Amino-1-(1-methylcyclopropyl)-3-(4-(2-((5-neopentylisoxazol-3-yl)amino)-2-oxoethyl)phenyl)-1H-pyrazole-4-carboxamide | 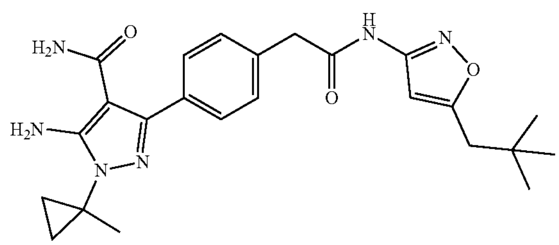 [SMILES: CC(C)(C)Cc1cc(NC(=O)Cc2ccc(-c3nn(C4(C)CC4)c(N)c3C(N)=O)cc2)no1] | 451.4 |
| 231 | 5-Amino-3-[4-([[3-(2,2-dimethylpropyl)-1,2-oxazol-5-yl]carbamoyl]methyl)phenyl]-1-(1-methoxy-2-methylpropan-2-yl)pyrazole-4-carboxamide | 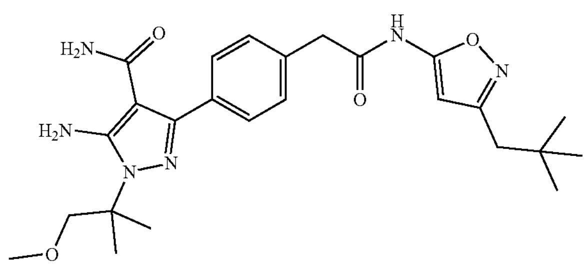 [SMILES: COCC(C)(C)n1nc(-c2ccc(CC(=O)Nc3cc(CC(C)(C)C)no3)cc2)c(C(N)=O)c1N] | 483.2 |
| 232 | 5-Amino-1-(1-methylcyclopropyl)-3-[4-[([3-[3-(trifluoromethyl)bicyclo[1.1.1]pentan-1-yl]-1,2-oxazol-5-yl]carbamoyl)methyl]phenyl]pyrazole-4-carboxamide | 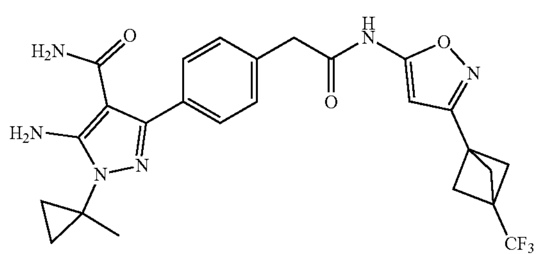 [SMILES: CC1(n2nc(-c3ccc(CC(=O)Nc4cc(C56CC(C(F)(F)F)(C5)C6)no4)cc3)c(C(N)=O)c2N)CC1] | 515.5 |

TABLE 33-continued

| Ex. No. | Chemical name | Structure | ES/MS m/z (M + H) |
|---|---|---|---|
| 233 | 5-Amino-3-[4-[([3-[3-(trifluoromethyl)bicyclo[1.1.1]pentan-1-yl]-1,2-oxazol-5-yl]carbamoyl)methyl]phenyl]-1-[1,1,1-trifluoropropan-2-yl]pyrazole-4-carboxamide | 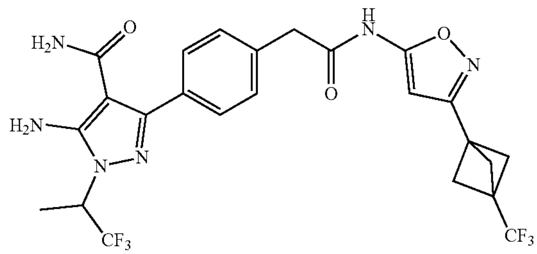 [SMILES: CC(n1nc(-c2ccc(CC(=O)Nc3cc(C45CC(C(F)(F)F)(C4)C5)no3)cc2)c(C(N)=O)c1N)C(F)(F)F] | 557.2 |
| 234 | 5-Amino-3-(4-(2-oxo-2-((3-(3-(trifluoromethyl)bicyclo[1.1.1]pentan-1-yl)isoxazol-5-yl)amino)ethyl)phenyl)-1-(2,2,2-trifluoroethyl)-1H-pyrazole-4-carboxamide | 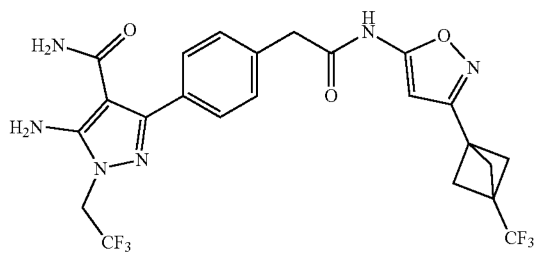 [SMILES: NC(=O)c1c(-c2ccc(CC(=O)Nc3cc(C45CC(C(F)(F)F)(C4)C5)no3)cc2)nn(CC(F)(F)F)c1N] | 543.3 |
| 235 | 5-Amino-1-cyclobutyl-3-[4-[([3-[3-(trifluoromethyl)bicyclo[1.1.1]pentan-1-yl]-1,2-oxazol-5-yl]carbamoyl)methyl]phenyl]pyrazole-4-carboxamide | 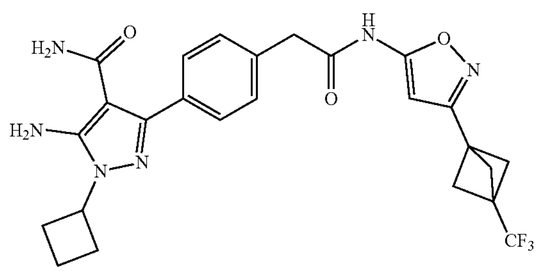 [SMILES: NC(=O)c1c(-c2ccc(CC(=O)Nc3cc(C45CC(C(F)(F)F)(C4)C5)no3)cc2)nn(C2CCC2)c1N] | 515.3 |
| 236 | 5-Amino-1-[1-hydroxypropan-2-yl]-3-(4-[[(3-[3-methylbicyclo[1.1.1]pentan-1-yl]-1,2-oxazol-5-yl)carbamoyl]methyl]phenyl)pyrazole-4-carboxamide | 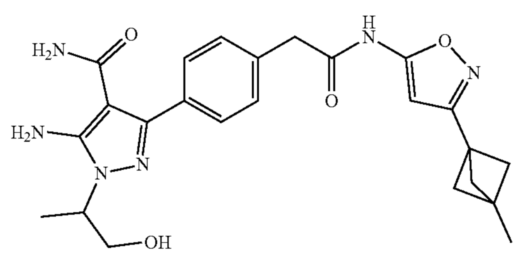 [SMILES: CC(CO)n1nc(-c2ccc(CC(=O)Nc3cc(C45CC(C)(C4)C5)no3)cc2)c(C(N)=O)c1N] | 465.2 |
| 237 | 5-Amino-1-(1-hydroxy-2-methylpropan-2-yl)-3-(4-[[(3-[3-methylbicyclo[1.1.1]pentan-1-yl]-1,2-oxazol-5-yl)carbamoyl]methyl]phenyl)pyrazole-4-carboxamide | 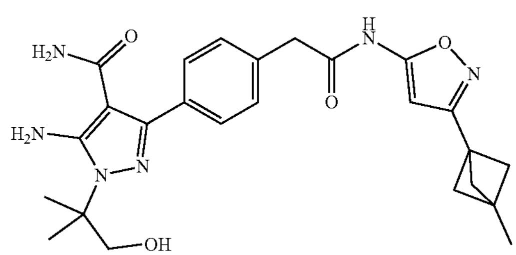 [SMILES: CC12CC(c3cc(NC(=O)Cc4ccc(-c5nn(C(C)(C)CO)c(N)c5C(N)=O)cc4)on3)(C1)C2] | 479.2 |
| 238 | 5-Amino-3-(4-[[(3-[3-methylbicyclo[1.1.1]pentan-1-yl]-1,2-oxazol-5-yl)carbamoyl]methyl]phenyl)-1-(1,1,1-trifluoro-2-methylpropan-2-yl)pyrazole-4-carboxamide | 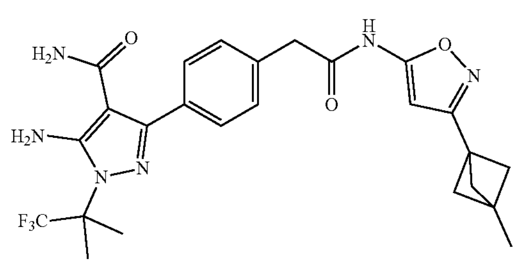 [SMILES: CC12CC(c3cc(NC(=O)Cc4ccc(-c5nn(C(C)(C)C(F)(F)F)c(N)c5C(N)=O)cc4)on3)(C1)C2] | 517.3 |

TABLE 33-continued

| Ex. No. | Chemical name | Structure | ES/MS m/z (M + H) |
|---|---|---|---|
| 239 | 5-Amino-1-tert-butyl-3-(4-[[(3-[3-methylbicyclo[1.1.1]pentan-1-yl]-1,2-oxazol-5-yl)carbamoyl]methyl]phenyl)pyrazole-4-carboxamide | 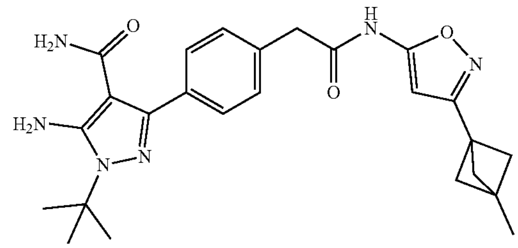 [SMILES: CC12CC(c3cc(NC(=O)Cc4ccc(-c5nn(C(C)(C)C)c(N)c5C(N)=O)cc4)on3)(C1)C2] | 463.3 |
| 240 | 5-Amino-3-[4-([[3-(2-chloro-4-fluorophenyl)-1,2-oxazol-5-yl]carbamoyl]methyl)phenyl]-1-(1-hydroxypropan-2-yl)pyrazole-4-carboxamide | 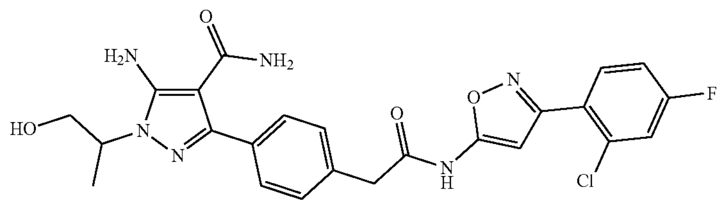 [SMILES: CC(CO)n1nc(-c2ccc(CC(=O)Nc3cc(-c4ccc(F)cc4Cl)no3)cc2)c(C(N)=O)c1N] | 513.1 |
| 241 | 5-Amino-3-[4-([[3-(2-chloro-4-fluorophenyl)-1,2-oxazol-5-yl]carbamoyl]methyl)phenyl]-1-(1-hydroxy-2-methylpropan-2-yl)pyrazole-4-carboxamide | 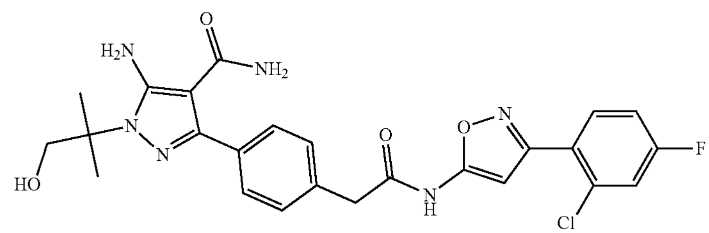 [SMILES: CC(C)(CO)n1nc(-c2ccc(CC(=O)Nc3cc(-c4ccc(F)cc4Cl)no3)cc2)c(C(N)=O)c1N] | 527.2 |
| 242 | 5-Amino-1-(1-hydroxypropan-2-yl)-3-[4-[([3-[4-(trifluoromethyl)bicyclo[2.2.1]heptan-1-yl]-1,2-oxazol-5-yl]carbamoyl)methyl]phenyl]pyrazole-4-carboxamide | 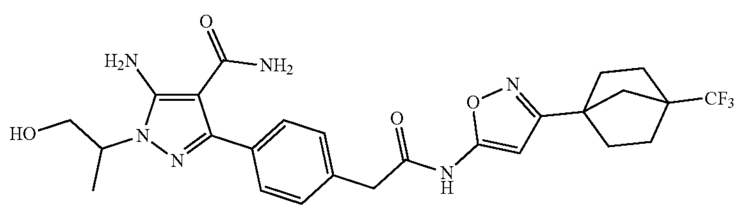 [SMILES: CC(CO)n1nc(-c2ccc(CC(=O)Nc3cc(C45CCC(C(F)(F)F)(CC4)C5)no3)cc2)c(C(N)=O)c1N] | 547.3 |
| 243 | 5-Amino-1-(1-methylcyclopropyl)-3-[4-[([3-[4-(trifluoromethyl)bicyclo[2.2.1]heptan-1-yl]-1,2-oxazol-5-yl]carbamoyl)methyl]phenyl]pyrazole-4-carboxamide | 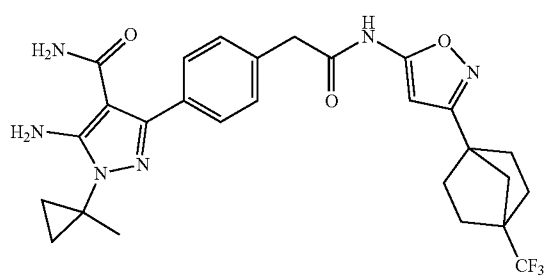 [SMILES: CC1(n2nc(-c3ccc(CC(=O)Nc4cc(C56CCC(C(F)(F)F)(CC5)C6)no4)cc3)c(C(N)=O)c2N)CC1] | 543.2 |
| 244 | 5-Amino-1-(1,1,1-trifluoro-2-methylpropan-2-yl)-3-[4-[([3-[4-(trifluoromethyl)bicyclo[2.2.1]heptan-1-yl]-1,2-oxazol-5-yl]carbamoyl)methyl]phenyl]pyrazole-4-carboxamide | 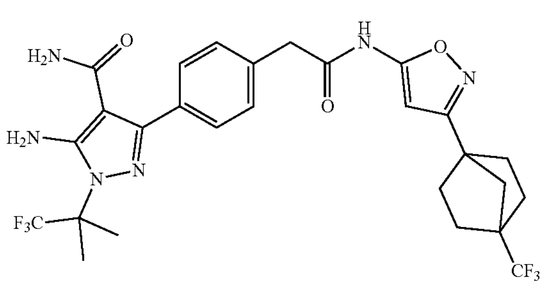 [SMILES: CC(C)(n1nc(-c2ccc(CC(=O)Nc3cc(C45CCC(C(F)(F)F)(CC4)C5)no3)cc2)c(C(N)=O)c1N)C(F)(F)F] | 599.1 |

TABLE 33-continued

| Ex. No. | Chemical name | Structure | ES/MS m/z (M + H) |
|---|---|---|---|
| 245 | 5-Amino-1-tert-butyl-3-[4-[([3-[4-(trifluoromethyl)bicyclo[2.2.1]heptan-1-yl]-1,2-oxazol-5-yl]carbamoyl)methyl]phenyl]pyrazole-4-carboxamide | 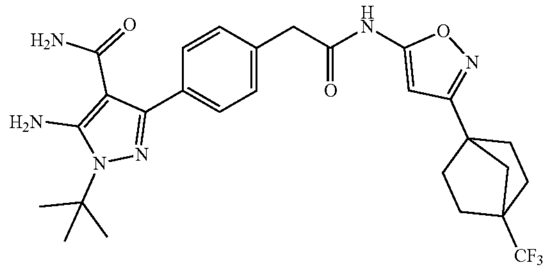 [SMILES: CC(C)(C)n1nc(-c2ccc(CC(=O)Nc3cc(C45CCC(C(F)(F)F)(CC4)C5)no3)cc2)c(C(N)=O)c1N] | 545.0 |
| 246 | 5-Amino-1-(1-hydroxy-2-methylpropan-2-yl)-3-[4-[([3-[4-(trifluoromethyl)bicyclo[2.2.1]heptan-1-yl]-1,2-oxazol-5-yl]carbamoyl)methyl]phenyl]pyrazole-4-carboxamide | 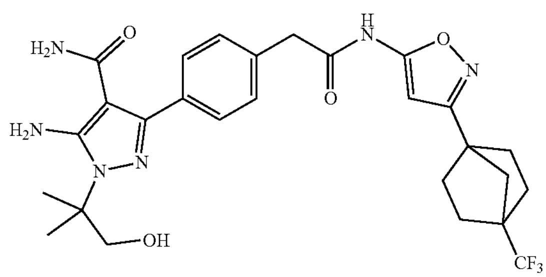 [SMILES: CC(C)(CO)n1nc(-c2ccc(CC(=O)Nc3cc(C45CCC(C(F)(F)F)(CC4)C5)no3)cc2)c(C(N)=O)c1N] | 561.1 |
| 247 | 5-Amino-3-(2-fluoro-4-(2-((3-(3-methylbicyclo[1.1.1]pentan-1-yl)isoxazol-5-yl)amino)-2-oxoethyl)phenyl)-1-(1-methylcyclopropyl)-1H-pyrazole-4-carboxamide | 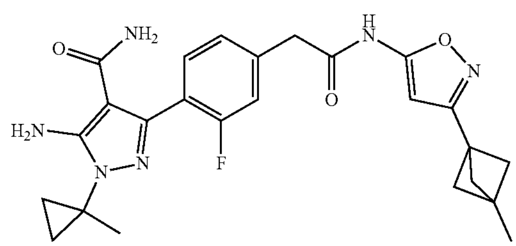 [SMILES: CC12CC(c3cc(NC(=O)Cc4ccc(-c5nn(C6(C)CC6)c(N)c5C(N)=O)c(F)c4)on3)(C1)C2] | 479.1 |
| 248 | 5-Amino-3-(2-fluoro-4-(2-oxo-2-((3-(3-(trifluoromethyl)bicyclo[1.1.1]pentan-1-yl)isoxazol-5-yl)amino)ethyl)phenyl)-1-(1-methylcyclopropyl)-1H-pyrazole-4-carboxamide | 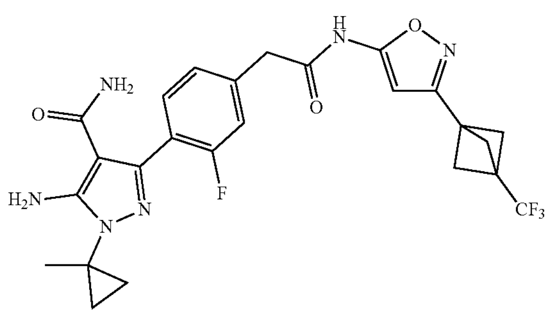 [SMILES: CC1(n2nc(-c3ccc(CC(=O)Nc4cc(C56CC(C(F)(F)F)(C5)C6)no4)cc3F)c(C(N)=O)c2N)CC1] | 533 |
| 249 | 5-Amino-3-[2,3-difluoro-4-[([3-[3-(trifluoromethyl)bicyclo[1.1.1]pentan-1-yl]-1,2-oxazol-5-yl]carbamoyl)methyl]phenyl]-1-(1-methylcyclopropyl)pyrazole-4-carboxamide | 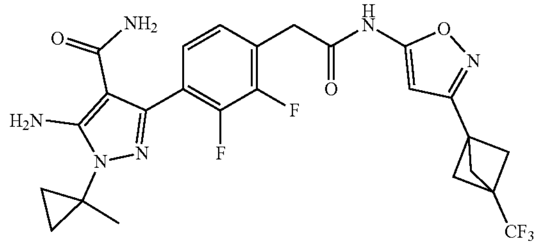 [SMILES: CC1(n2nc(-c3ccc(CC(=O)Nc4cc(C56CC(C(F)(F)F)(C5)C6)no4)c(F)c3F)c(C(N)=O)c2N)CC1] | 551.1 |

TABLE 33-continued

| Ex. No. | Chemical name | Structure | ES/MS m/z (M + H) |
|---|---|---|---|
| 250 | 5-Amino-3-[2,3-difluoro-4-[([3-[4-(trifluoromethyl)bicyclo[2.2.1]heptan-1-yl]-1,2-oxazol-5-yl]carbamoyl)methyl]phenyl]-1-(1-methylcyclopropyl)pyrazole-4-carboxamide | 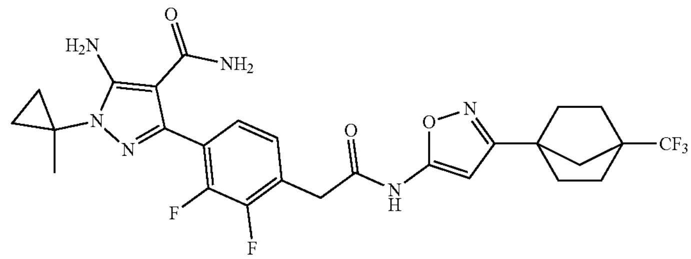 [SMILES: CC1(n2nc(-c3ccc(CC(=O)Nc4cc(C56CCC(C(F)(F)F)(CC5)C6)no4)c(F)c3F)c(C(N)=O)c2N)CC1] | 579.2 |
| 251 | 5-Amino-3-(2-fluoro-4-(2-oxo-2-((3-(4-(trifluoromethyl)bicyclo[2.2.1]heptan-1-yl)isoxazol-5-yl)amino)ethyl)phenyl)-1-(1-methylcyclopropyl)-1H-pyrazole-4-carboxamide | 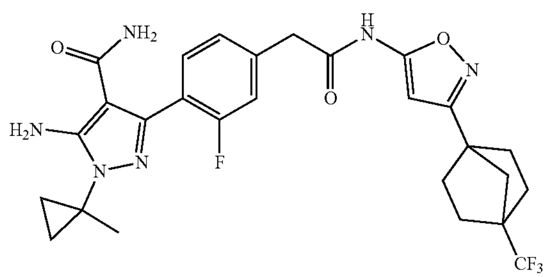 [SMILES: CC1(n2nc(-c3ccc(CC(=O)Nc4cc(C56CCC(C(F)(F)F)(CC5)C6)no4)cc3F)c(C(N)=O)c2N)CC1] | 561.2 |
| 252 | 5-Amino-3-[2,3-difluoro-4-[([3-[4-(trifluoromethyl)bicyclo[2.2.1]heptan-1-yl]-1,2-oxazol-5-yl]carbamoyl)methyl]phenyl]-1-isopropylpyrazole-4-carboxamide | 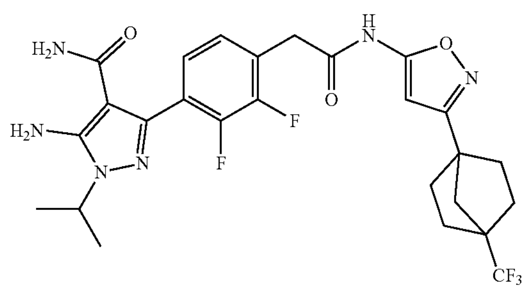 [SMILES: CC(C)n1nc(-c2ccc(CC(=O)Nc3cc(C45CCC(C(F)(F)F)(CC4)C5)no3)c(F)c2F)c(C(N)=O)c1N] | 567.3 |
| 253 | 5-Amino-3-[2,3-difluoro-4-[([3-[4-(trifluoromethyl)bicyclo[2.2.1]heptan-1-yl]-1,2-oxazol-5-yl]carbamoyl)methyl]phenyl]-1-isopropylpyrazole-4-carboxamide | 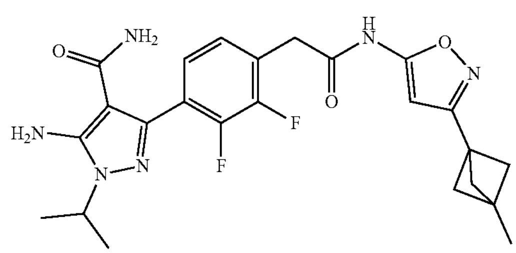 [SMILES: CC(C)n1nc(-c2ccc(CC(=O)Nc3cc(C45CC(C)(C4)C5)no3)c(F)c2F)c(C(N)=O)c1N] | 485.2 |
| 254 | 5-Amino-3-(4-(2-((3-(1,1-difluoroethyl)isoxazol-5-yl)amino)-2-oxoethyl)phenyl)-1-isopropyl-1H-pyrazole-4-carboxamide | 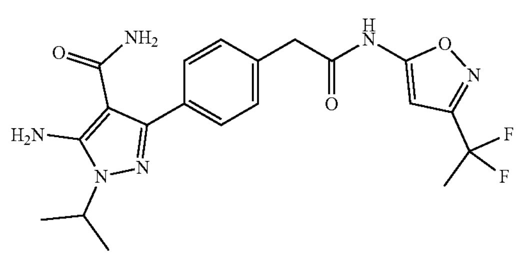 [SMILES: CC(C)n1nc(-c2ccc(CC(=O)Nc3cc(C(C)(F)F)no3)cc2)c(C(N)=O)c1N] | 433.5 |

TABLE 33-continued

| Ex. No. | Chemical name | Structure | ES/MS m/z (M + H) |
|---|---|---|---|
| 255 | 5-Amino-3-[4-([[5-(2,2-dimethylpropyl)-4-methyl-1,3-thiazol-2-yl]carbamoyl]methyl)phenyl]-1-isopropylpyrazole-4-carboxamide | 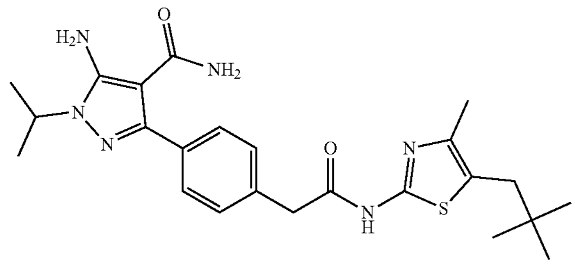 [SMILES: Cc1nc(NC(=O)Cc2ccc(-c3nn(C(C)C)c(N)c3C(N)=O)cc2)sc1CC(C)(C)C] | 491.4 M + Na |
| 256 | 5-Amino-3-(4-[[(3-[3-methylbicyclo[1.1.1]pentan-1-yl]-1,2-oxazol-5-yl)carbamoyl]methyl]phenyl)-1-(1-methylcyclopropyl)pyrazole-4-carboxamide | 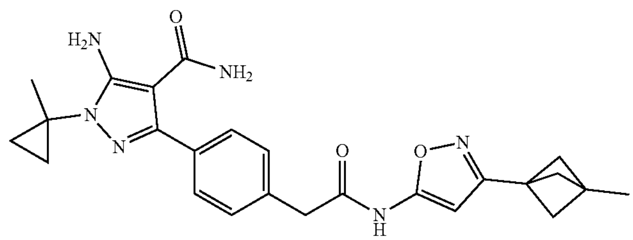 [SMILES: CC12CC(c3cc(NC(=O)Cc4ccc(-c5nn(C6(C)CC6)c(N)c5C(N)=O)cc4)on3)(C1)C2] | 461.2 |
| 257 | 5-Amino-3-[4-([[3-(2,2-dimethylpropyl)-1,2-oxazol-5-yl]carbamoyl]methyl)phenyl]-1-isopropylpyrazole-4-carboxamide | 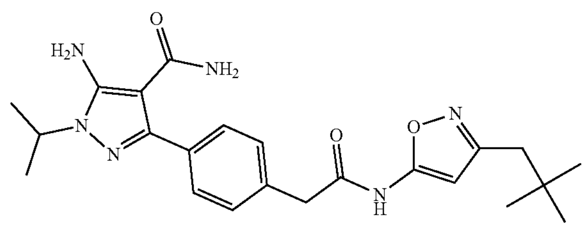 [SMILES: CC(C)n1nc(-c2ccc(CC(=O)Nc3cc(CC(C)(C)C)no3)cc2)c(C(N)=O)c1N] | 439.4 |

Example 258

5-Amino-3-[4-[([3-[3-(trifluoromethyl)bicyclo[1.1.1]pentan-1-yl]-1,2-oxazol-5-yl]carbamoyl)methyl]phenyl]-1-[1,1,1-trifluoropropan-2-yl]pyrazole-4-carboxamide, Isomer

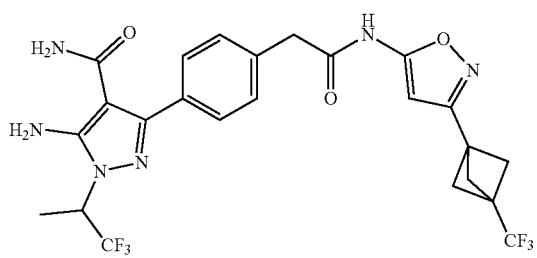 [SMILES: CC(n1nc(-c2ccc(CC(=O)Nc3cc(C45CC(C(F)(F)F)(C4)C5)no3)cc2)c(C(N)=O)c1N)C(F)(F)F]

Example 259

5-Amino-3-[4-[([3-[3-(trifluoromethyl)bicyclo[1.1.1]pentan-1-yl]-1,2-oxazol-5-yl]carbamoyl)methyl]phenyl]-1-[1,1,1-trifluoropropan-2-yl]pyrazole-4-carboxamide, Isomer 2

5-Amino-3-[4-[([3-[3-(trifluoromethyl)bicyclo[1.1.1]pentan-1-yl]-1,2-oxazol-5-yl]carbamoyl)methyl]phenyl]-1-[1,1,1-trifluoropropan-2-yl]pyrazole-4-carboxamide (70 mg) is purified by Prep-CHIRAL-HPLC with the following conditions: Column: Lux 5μ Cellulose-4, AXIA Packed, 2.12*25 cm, 5 μm eluting with 80% hexanes (0.1% TFA) and 20% IPA; flow rate 20 mL/min in 37 min 205/250 nm to give the title compound of Isomer 1 $t_{(R)}$ 18.6 min (15.4 mg, 22.0%, ee=100%) as a light brown solid, ES/MS (m/z) 557.2 (M+H) and the title compound of Isomer 2 $t_{(R)}$ 29.8 min (14.9 mg, 21.2%, ee=99.5%) as a light brown solid, ES/MS (m/z) 557.2 (M+H).

The following compounds in Table 34 are prepared essentially as described 5-amino-3-[4-[([3-[3-(trifluoromethyl)bicyclo[1.1.1]pentan-1-yl]-1,2-oxazol-5-yl]carbamoyl)methyl]phenyl]-1-[1,1,1-trifluoropropan-2-yl]pyrazole-4-carboxamide, Isomer 1 and Isomer 2 and adjusting the purification system as appropriate.

TABLE 34

| Ex. No. | Chemical name | Structure | ES/MS m/z (M + H) | t(R) min |
|---|---|---|---|---|
| [1]260 | 5-Amino-1-[1-hydroxypropan-2-yl]-3-(4-[[(3-[3-methylbicyclo[1.1.1]pentan-1-yl]-1,2-oxazol-5-yl)carbamoyl]methyl]phenyl)pyrazole-4-carboxamide, Isomer 1 | 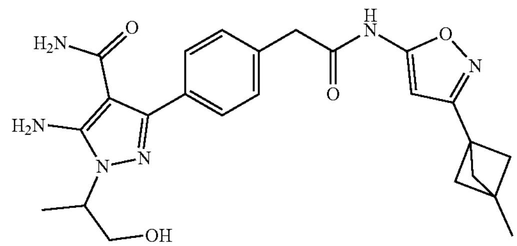 [SMILES: CC(CO)n1nc(-c2ccc(CC(=O)Nc3cc(C45CC(C)(C4)C5)no3)cc2)c(C(N)=O)c1N] | 465.1 | 5.25 |
| [1]261 | 5-Amino-1-[1-hydroxypropan-2-yl]-3-(4-[[(3-[3-methylbicyclo[1.1.1]pentan-1-yl]-1,2-oxazol-5-yl)carbamoyl]methyl]phenyl)pyrazole-4-carboxamide, Isomer 2 | 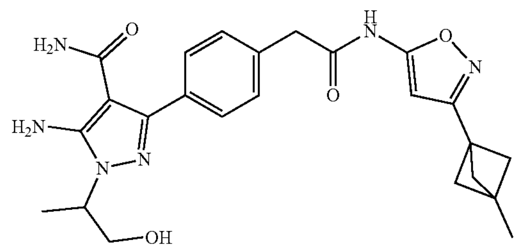 [SMILES: CC(CO)n1nc(-c2ccc(CC(=O)Nc3cc(C45CC(C)(C4)C5)no3)cc2)c(C(N)=O)c1N] | 465.1 | 11.5 |
| [1]262 | 5-Amino-3-[4-([[3-(2-chloro-4-fluorophenyl)-1,2-oxazol-5-yl]carbamoyl]methyl)phenyl]-1-(1-hydroxypropan-2-yl)pyrazole-4-carboxamide, Isomer 1 | 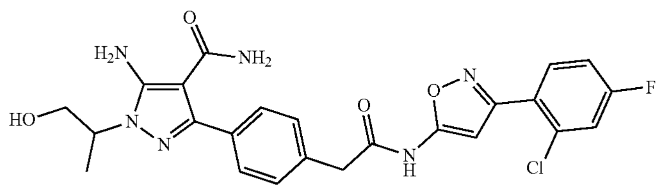 [SMILES: CC(CO)n1nc(-c2ccc(CC(=O)Nc3cc(-c4ccc(F)cc4Cl)no3)cc2)c(C(N)=O)c1N] | | 8.12 |
| [1]263 | 5-Amino-3-[4-([[3-(2-chloro-4-fluorophenyl)-1,2-oxazol-5-yl]carbamoyl]methyl)phenyl]-1-(1-hydroxypropan-2-yl)pyrazole-4-carboxamide, Isomer 2 | 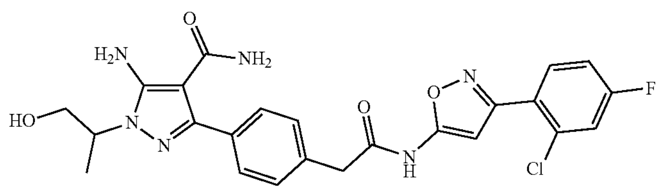 [SMILES: CC(CO)n1nc(-c2ccc(CC(=O)Nc3cc(-c4ccc(F)cc4Cl)no3)cc2)c(C(N)=O)c1N] | | 16.3 |
| [2]264 | 5-Amino-1-[1-hydroxypropan-2-yl]-3-[4-[([3-[4-(trifluoromethyl)bicyclo[2.2.1]heptan-1-yl]-1,2-oxazol-5-yl]carbamoyl)methyl]phenyl]pyrazole-4-carboxamide, Isomer 1 | 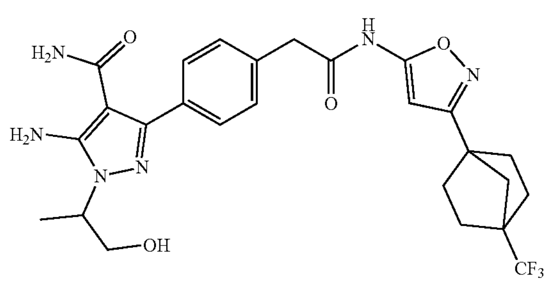 [SMILES: CC(CO)n1nc(-c2ccc(CC(=O)Nc3cc(C45CCC(C(F)(F)F)(CC4)C5)no3)cc2)c(C(N)=O)c1N] | 547.2 | 11.43 |
| [2]265 | 5-Amino-1-[1-hydroxypropan-2-yl]-3-[4-[([3-[4-(trifluoromethyl)bicyclo[2.2.1]heptan-1-yl]-1,2-oxazol-5-yl]carbamoyl)methyl]phenyl]pyrazole-4-carboxamide, Isomer 2 | 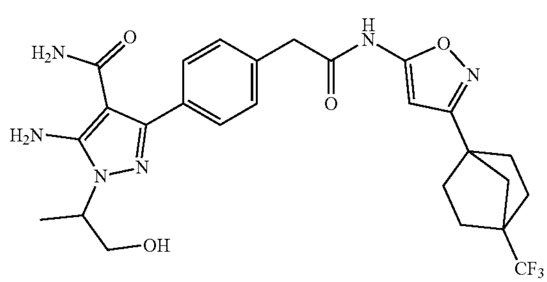 [SMILES: CC(CO)n1nc(-c2ccc(CC(=O)Nc3cc(C45CCC(C(F)(F)F)(CC4)C5)no3)cc2)c(C(N)=O)c1N] | 547.3 | 18.05 |

TABLE 34-continued

| Ex. No. | Chemical name | Structure | ES/MS m/z (M + H) | t(R) min |
|---|---|---|---|---|
| 3266 | 5-Amino-1-isopropyl-3-[4-[2-oxo-2-[[3-[2,2-dimethylcyclopropyl]isoxazol-5-yl]amino]ethyl]phenyl]pyrazole-4-carboxamide, Isomer 1 | | 437 | 8.70 |
| 3267 | 5-Amino-1-isopropyl-3-[4-[2-oxo-2-[[3-[2,2-dimethylcyclopropyl]isoxazol-5-yl]amino]ethyl]phenyl]pyrazole-4-carboxamide, Isomer 2 | | 437 | 12.8 |
| 4268 | 5-Amino-1-isopropyl-3-[4-[2-oxo-2-[[3-[spiro[2.2]pentan-2-yl]isoxazol-5-yl]amino]ethyl]phenyl]pyrazole-4-carboxamide, Isomer 1 | | 435.1 | 8.29 |
| 4269 | 5-Amino-1-isopropyl-3-[4-[2-oxo-2-[[3-[spiro[2.2]pentan-2-yl]isoxazol-5-yl]amino]ethyl]phenyl]pyrazole-4-carboxamide, Isomer 2 | | 435.1 | 10.15 |
| 5270 | 5-Amino-1-isopropyl-3-[4-[2-oxo-2-[[3-[[2,2-difluorocyclopropyl]methyl]isoxazol-5-yl]amino]ethyl]phenyl]pyrazole-4-carboxamide, Isomer 1 | | 459 | 5.35 |

TABLE 34-continued

| Ex. No. | Chemical name | Structure | ES/MS m/z (M + H) | t(R) min |
|---|---|---|---|---|
| 5271 | 5-Amino-1-isopropyl-3-[4-[2-oxo-2-[[3-[[2,2-difluorocyclopropyl]methyl]isoxazol-5-yl]amino]ethyl]phenyl]pyrazole-4-carboxamide, Isomer 2 | | 459.1 | 6.35 |
| 272 | 5-Amino-3-[4-[2-[[3-[3,3-difluorocyclopentyl]isoxazol-5-yl]amino]-2-oxo-ethyl]phenyl]-1-isopropyl-pyrazole-4-carboxamide, Isomer 1 | | 473 | 28.5 |
| 273 | 5-Amino-3-[4-[2-[[3-[3,3-difluorocyclopentyl]isoxazol-5-yl]amino]-2-oxo-ethyl]phenyl]-1-isopropyl-pyrazole-4-carboxamide, Isomer 2 | | 473 | 32.84 |
| 4274 | 5-Amino-1-isopropyl-3-[4-[2-oxo-2-[[3-[spiro[2.3]hexan-2-yl]isoxazol-5-yl]amino]ethyl]phenyl]pyrazole-4-carboxamide, Isomer 1 | | 449 | 10.6 |
| 4275 | 5-Amino-1-isopropyl-3-[4-[2-oxo-2-[[3-[spiro[2.3]hexan-2-yl]isoxazol-5-yl]amino]ethyl]phenyl]pyrazole-4-carboxamide, Isomer 2 | | 449 | 13.54 |
| 6276 | 5-Amino-1-isopropyl-3-[4-[2-oxo-2-[[5-[spiro[2.3]hexan-2-yl]isoxazol-3-yl]amino]ethyl]phenyl]pyrazole-4-carboxamide, Isomer 1 | | 449.1 | 2.22 |

TABLE 34-continued

| Ex. No. | Chemical name | Structure | ES/MS m/z (M + H) | $t_{(R)}$ min |
|---|---|---|---|---|
| 277 | 5-Amino-1-isopropyl-3-[4-[2-oxo-2-[[5-[spiro[2.3]hexan-2-yl]isoxazol-3-yl]amino]ethyl]phenyl]pyrazole-4-carboxamide, Isomer 2 | 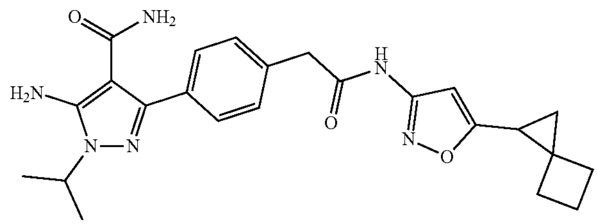 [SMILES: CC(C)n1nc(-c2ccc(CC(=O)Nc3cc(C4CC45CCC5)on3)cc2)c(C(N)=O)c1N] | 449.1 | 3.79 |
| 278 | 5-Amino-1-isopropyl-3-[4-[2-oxo-2-[[5-[2,2-dimethylcyclobutyl]isoxazol-3-yl]amino]ethyl]phenyl]pyrazole-4-carboxamide, Isomer 1 | 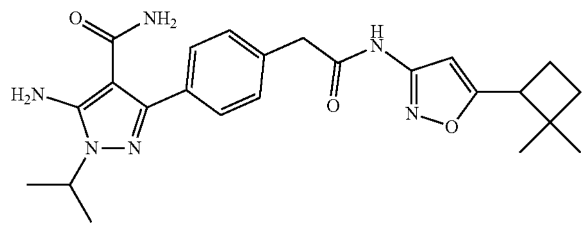 [SMILES: CC(C)n1nc(-c2ccc(CC(=O)Nc3cc(C4CCC4(C)C)on3)cc2)c(C(N)=O)c1N] | 451.1 | 20.95 |
| 279 | 5-Amino-1-isopropyl-3-[4-[2-oxo-2-[[5-[2,2-dimethylcyclobutyl]isoxazol-3-yl]amino]ethyl]phenyl]pyrazole-4-carboxamide, Isomer 2 | 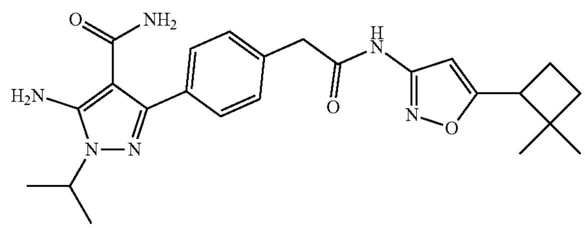 [SMILES: CC(C)n1nc(-c2ccc(CC(=O)Nc3cc(C4CCC4(C)C)on3)cc2)c(C(N)=O)c1N] | 451 | 21.94 |
| 280 | 5-Amino-1-isopropyl-3-[4-[2-oxo-2-[[3-[2,2-dimethylcyclobutyl]isoxazol-5-yl]amino]ethyl]phenyl]pyrazole-4-carboxamide, Isomer 1 | 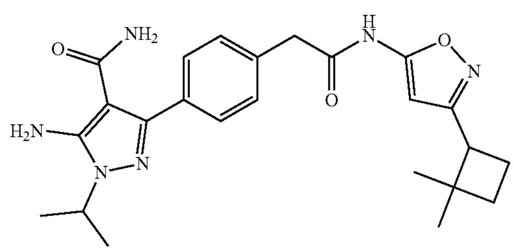 [SMILES: CC(C)n1nc(-c2ccc(CC(=O)Nc3cc(C4CCC4(C)C)no3)cc2)c(C(N)=O)c1N] | 451.1 | 5.27 |
| [7]281 | 5-Amino-1-isopropyl-3-[4-[2-oxo-2-[[3-[2,2-dimethylcyclobutyl]isoxazol-5-yl]amino]ethyl]phenyl]pyrazole-4-carboxamide, Isomer 2 | 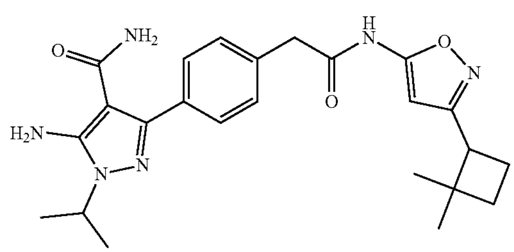 [SMILES: CC(C)n1nc(-c2ccc(CC(=O)Nc3cc(C4CCC4(C)C)no3)cc2)c(C(N)=O)c1N] | 451.4 | 5.76 |
| [8]282 | 5-Amino-1-(1-cyclopropylethyl)-3-(4-(2-((3-neopentylisoxazol-5-yl)amino)-2-oxoethyl)phenyl)-1H-pyrazole-4-carboxamide, Isomer 1 | 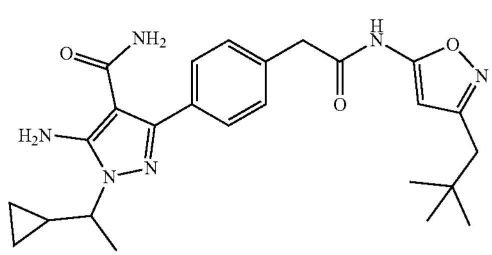 [SMILES: CC(C1CC1)n1nc(-c2ccc(CC(=O)Nc3cc(CC(C)(C)C)no3)cc2)c(C(N)=O)c1N] | 465.2 | 2.37 |

TABLE 34-continued

| Ex. No. | Chemical name | Structure | ES/MS m/z (M + H) | $t_{(R)}$ min |
|---|---|---|---|---|
| [8]283 | 5-Amino-1-(1-cyclopropylethyl)-3-(4-(2-((3-neopentylisoxazol-5-yl)amino)-2-oxoethyl)phenyl)-1H-pyrazole-4-carboxamide, Isomer 2 | | 465.2 | 2.96 |
| [9]284 | 5-Amino-3-(4-(2-((3-neopentylisoxazol-5-yl)amino)-2-oxoethyl)phenyl)-1-(tetrahydrofuran-3-yl)-1H-pyrazole-4-carboxamide, Isomer 1 | | 467.2 | 1.7 |
| [9]285 | 5-Amino-3-(4-(2-((3-neopentylisoxazol-5-yl)amino)-2-oxoethyl)phenyl)-1-(tetrahydrofuran-3-yl)-1H-pyrazole-4-carboxamide, Isomer 2 | | 467.2 | 2.2 |
| 286 | 5-Amino-3-(4-(2-((3-neopentylisoxazol-5-yl)amino)-2-oxoethyl)phenyl)-1-(tetrahydro-2H-pyran-3-yl)-1H-pyrazole-4-carboxamide, Isomer 1 | | 481.4 | 4.9 |
| 287 | 5-Amino-3-(4-(2-((3-neopentylisoxazol-5-yl)amino)-2-oxoethyl)phenyl)-1-(tetrahydro-2H-pyran-3-yl)-1H-pyrazole-4-carboxamide, Isomer 2 | | 481.4 | 7.1 |

TABLE 34-continued

| Ex. No. | Chemical name | Structure | ES/MS m/z (M + H) | $t_{(R)}$ min |
|---|---|---|---|---|
| [10]288 | 5-Amino-1-(1-hydroxypropan-2-yl)-3-(4-(2-((3-neopentylisoxazol-5-yl)amino)-2-oxoethyl)phenyl)-1H-pyrazole-4-carboxamide, Isomer 1 | 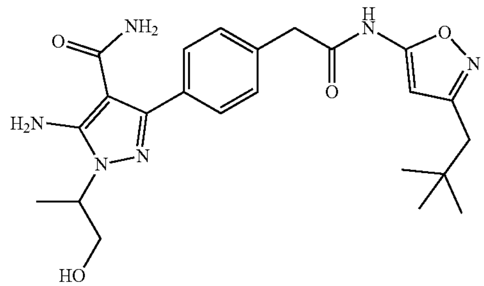 [SMILES: CC(CO)n1nc(-c2ccc(CC(=O)Nc3cc(CC(C)(C)C)no3)cc2)c(C(N)=O)c1N] | 455.2 | 1.11 |
| [10]289 | 5-Amino-1-(1-hydroxypropan-2-yl)-3-(4-(2-((3-neopentylisoxazol-5-yl)amino)-2-oxoethyl)phenyl)-1H-pyrazole-4-carboxamide, Isomer 2 | 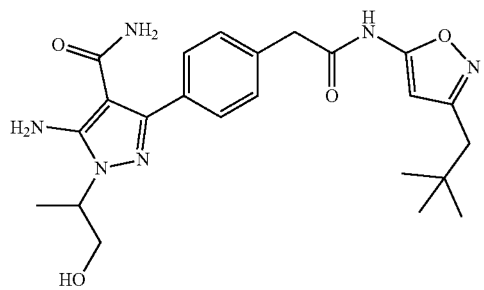 [SMILES: CC(CO)n1nc(-c2ccc(CC(=O)Nc3cc(CC(C)(C)C)no3)cc2)c(C(N)=O)c1N] | 455.2 | 1.46 |
| [11]290 | 5-Amino-3-(4-(2-((3-neopentylisoxazol-5-yl)amino)-2-oxoethyl)phenyl)-1-((tetrahydrofuran-3-yl)methyl)-1H-pyrazole-4-carboxamide, Isomer 1 | 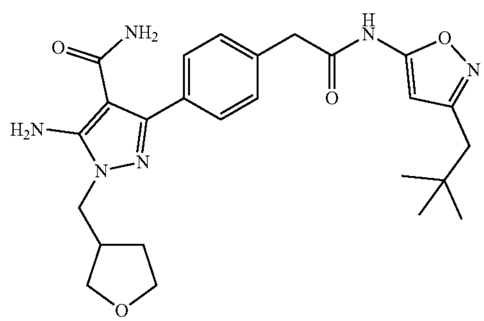 [SMILES: CC(C)(C)Cc1cc(NC(=O)Cc2ccc(-c3nn(CC4CCOC4)c(N)c3C(N)=O)cc2)on1] | 481.4 | 1.71 |
| [11]291 | 5-Amino-3-(4-(2-((3-neopentylisoxazol-5-yl)amino)-2-oxoethyl)phenyl)-1-((tetrahydrofuran-3-yl)methyl)-1H-pyrazole-4-carboxamide, Isomer 2 | 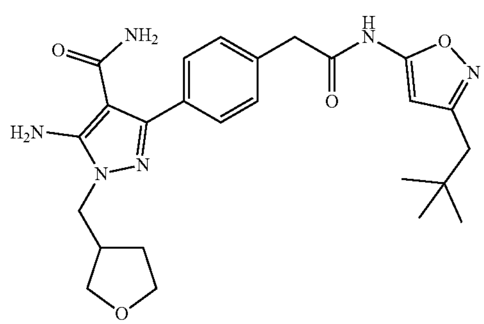 [SMILES: CC(C)(C)Cc1cc(NC(=O)Cc2ccc(-c3nn(CC4CCOC4)c(N)c3C(N)=O)cc2)on1] | 481.4 | 2.38 |

[1]CHIRAL ART Amylose-SA, 2 * 25 cm, 5 μm, 70% hexanes (10 mM $NH_3$ in MeOH and 30% EtOH.
[2]CHIRALPAK IA 2 * 25 cm, 5 μm, 70% hexanes (10 mM $NH_3$ in MeOH) and 30% EtOH.
[3]CHIRALPAK AD 250 mm × 4.6, 5 μm, 70% to 30% $CO_2$ with EtOH (0.5% IPAm).
[4]Waters Prep SFC200 Chiralpak AD-H 5 μm, 250 × 30 mm 70 30 $CO_2$/EtOH (0.5% IPAm).
[5]CHIRALPAK AD-H 5 μm, 250 × 30 mm, 78% $CO_2$/MeOH (0.5% IPAm).
[6]Chiralcel OD 500 × 76.5 mm, 20 μm, 100% ACN (0.05% IPA).
[7]Waters Prep SFC80 (Pirkle (R,R) Whelk-01 5 μm, 250 × 21.1 mm, 70% $CO_2$/MeOH (0.5% IPAm).
[8]ChiralPak IC, 4.6 × 150 mm, 30% MeOH/$CO_2$.
[9]ChiralPak AD-H, 4.6 × 150 mm, 35% EtOH/$CO_2$.
[10]ChiralCel OJ-H, 4.6 × 150 mm, 15% MeOH/$CO_2$.
[11]ChiralPak IA, 4.6 × 150 mm, 30% EtOH/$CO_2$.

Example 292

5-Amino-1-isopropyl-3-[5-[2-oxo-2-[3-(trifluoromethyl)anilino]ethyl]-2-pyridyl]pyrazole-4-carboxamide

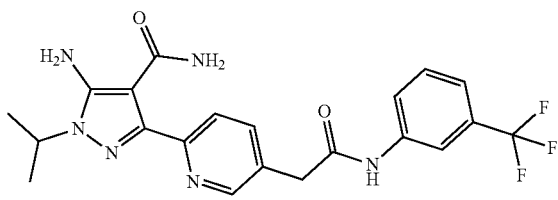 [SMILES: CC(C)n1nc(-c2ccc(CC(=O)Nc3cccc(C(F)(F)F)c3)cn2)c(C(N)=O)c1N]

To a stirred solution of 2-[6-(5-amino-4-cyano-1-isopropyl-pyrazol-3-yl)-3-pyridyl]acetic acid (0.070 g, 0.24 mmol), 3-(trifluoromethyl)aniline (0.047 g, 0.29 mmol), and DIPEA (0.16 g, 1.22 mmol) in DMF (2 mL) is added T3P® (0.46 g, 0.73 mmol, 50% in DMF). The mixture is stirred for 2 hr at RT under $N_2$ then concentrated under reduced pressure. The residue is purified by reversed-phase chromatography (C18 gel column), eluting with a gradient of 40% to 60% ACN in $H_2O$ (0.1% FA) to give 2-[6-(5-amino-4-cyano-1-isopropyl-pyrazol-3-yl)-3-pyridyl]-N-[3-(trifluoromethyl)phenyl]acetamide (0.050 g, 45%) as a white solid. ES/MS (m/z) 429.1 (M+H).

To a stirred solution of 2-[6-(5-amino-4-cyano-1-isopropyl-pyrazol-3-yl)-3-pyridyl]-N-[3-(trifluoromethyl)phenyl] acetamide (0.050 g, 0.11 mmol) and NaOH (0.13 g, 0.58 mmol) in EtOH:DMSO (1.2 mL, 5:1) at 0° C. is added $H_2O_2$ (0.13 g, 1.16 mmol, 30% in $H_2O$). The mixture is stirred for 4 hr at 40° C. The solution is cooled to 0° C., quenched with saturated aq. $Na_2SO_3$, and extracted with EtOAc (2×10 mL). The combined organic extracts are washed with brine (2×30 mL), dried over anhydrous $Na_2SO_4$, filtered, and concentrated under reduced pressure. The residue is purified by reversed-phase chromatography (C18 gel column), eluting with a gradient of 35% to 45% ACN in $H_2O$ (0.1% $NH_3H_2O$) to give the title compound (0.021 g, 40%) as a white solid. ES/MS (m/z) 447.1 (M+H).

The compounds in Table 35 are prepared essentially as described for 5-amino-1-isopropyl-3-[5-[2-oxo-2-[3-(trifluoromethyl)anilino]ethyl]-2-pyridyl]pyrazole-4-carboxamide, using the appropriate amine and carboxylic acid (or lithium salt) and adjusting the reaction time as needed to complete the reaction.

TABLE 35

| Ex. No. | Chemical name | Structure | ES/MS m/z (M + H) |
|---|---|---|---|
| 293 | 5-Amino-1-isopropyl-3-[5-[2-oxo-2-[[5-(2,2,2-trifluoro-1,1-dimethyl-ethyl)isoxazol-3-yl]amino]ethyl]-2-pyridyl]pyrazole-4-carboxamide | 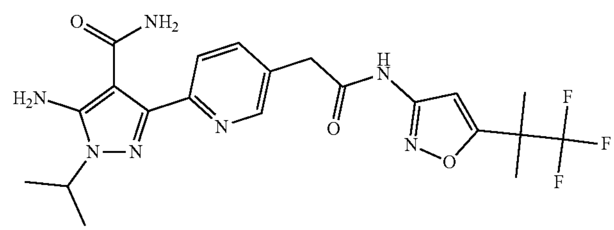 [SMILES: CC(C)n1nc(-c2ccc(CC(=O)Nc3cc(C(C)(C)C(F)(F)F)on3)cn2)c(C(N)=O)c1N] | 480.2 |
| 294 | 5-Amino-1-isopropyl-3-[5-[2-[[3-(1-methylcyclopentyl)isoxazol-5-yl]amino]-2-oxo-ethyl]-2-pyridyl]pyrazole-4-carboxamide | 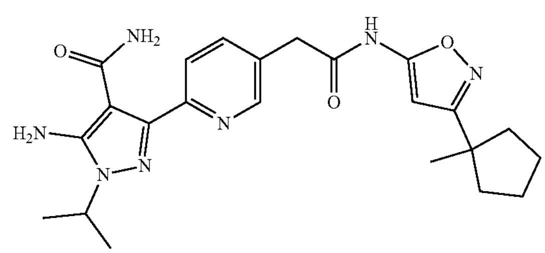 [SMILES: CC(C)n1nc(-c2ccc(CC(=O)Nc3cc(C4(C)CCCC4)no3)cn2)c(C(N)=O)c1N] | 452 |
| 295 | 5-Amino-1-isopropyl-3-[5-[2-[[5-(1-methylcyclopentyl)isoxazol-3-yl]amino]-2-oxo-ethyl]-2-pyridyl]pyrazole-4-carboxamide | 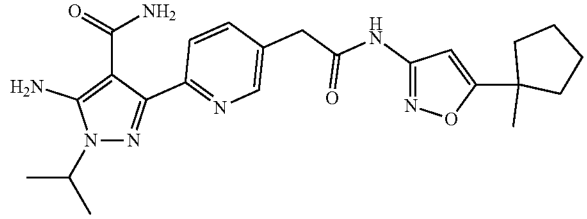 [SMILES: CC(C)n1nc(-c2ccc(CC(=O)Nc3cc(C4(C)CCCC4)on3)cn2)c(C(N)=O)c1N] | 452.2 |

TABLE 35-continued

| Ex. No. | Chemical name | Structure | ES/MS m/z (M + H) |
|---|---|---|---|
| 296 | 5-Amino-3-[5-[2-[[3-(2-chlorophenyl)isoxazol-5-yl]amino]-2-oxo-ethyl]-2-pyridyl]-1-isopropyl-pyrazole-4-carboxamide | 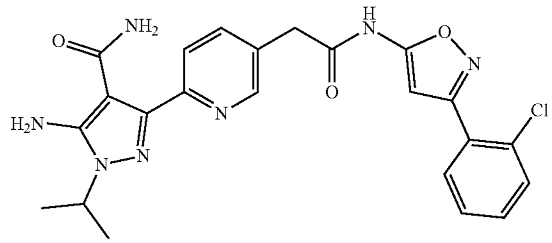 [SMILES: CC(C)n1nc(-c2ccc(CC(=O)Nc3cc(-c4ccccc4Cl)no3)cn2)c(C(N)=O)c1N] | 480 |
| 297 | 5-Amino-3-[5-[2-[(5-tert-butylisoxazol-3-yl)amino]-2-oxo-ethyl]-2-pyridyl]-1-isopropyl-pyrazole-4-carboxamide | 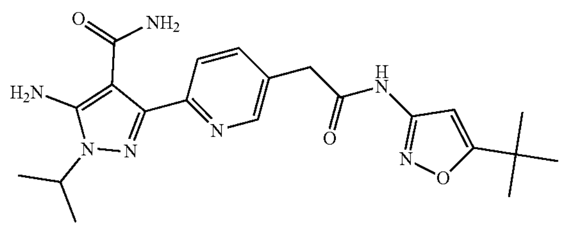 [SMILES: CC(C)n1nc(-c2ccc(CC(=O)Nc3cc(C(C)(C)C)on3)cn2)c(C(N)=O)c1N] | 426 |
| 298 | 5-Amino-1-isopropyl-3-[5-[2-oxo-2-[(5-phenylisoxazol-3-yl)amino]ethyl]-2-pyridyl]pyrazole-4-carboxamide | 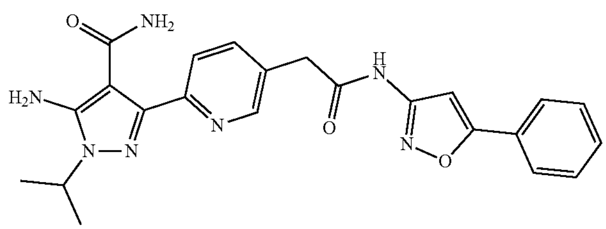 [SMILES: CC(C)n1nc(-c2ccc(CC(=O)Nc3cc(-c4ccccc4)on3)cn2)c(C(N)=O)c1N] | 446 |
| 299 | 5-Amino-1-isopropyl-3-[5-[2-oxo-2-[(3-phenylisoxazol-5-yl)amino]ethyl]-2-pyridyl]pyrazole-4-carboxamide | 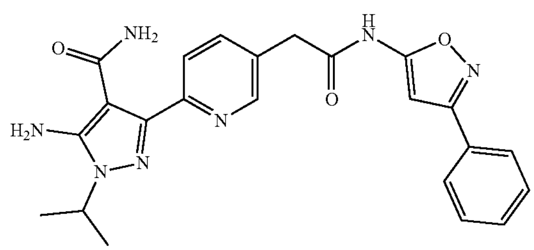 [SMILES: CC(C)n1nc(-c2ccc(CC(=O)Nc3cc(-c4ccccc4)no3)cn2)c(C(N)=O)c1N] | 446 |
| 300 | 5-Amino-3-[5-[2-[[3-(2,4-dichlorophenyl)isoxazol-5-yl]amino]-2-oxo-ethyl]-2-pyridyl]-1-isopropyl-pyrazole-4-carboxamide | 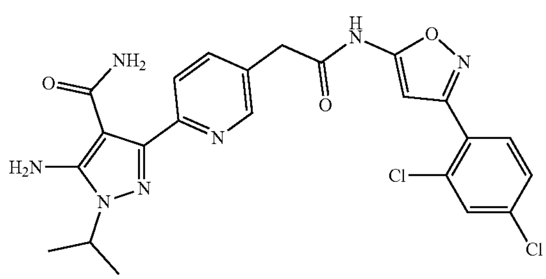 | 514.1 |
| 301 | 5-Amino-3-[5-[2-[(3-cyclohexylisoxazol-5-yl)amino]-2-oxo-ethyl]-2-pyridyl]-1-isopropyl-pyrazole-4-carboxamide | 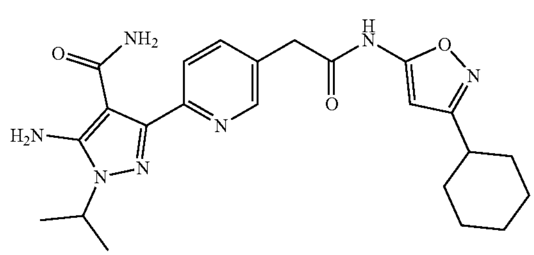 [SMILES: CC(C)n1nc(-c2ccc(CC(=O)Nc3cc(C4CCCCC4)no3)cn2)c(C(N)=O)c1N] | 452.4 |

TABLE 35-continued

| Ex. No. | Chemical name | Structure | ES/MS m/z (M + H) |
|---|---|---|---|
| 302 | 5-Amino-3-[5-[2-[[3-(2-chloro-4-fluoro-phenyl)isoxazol-5-yl]amino]-2-oxo-ethyl]-2-pyridyl]-1-isopropyl-pyrazole-4-carboxamide | 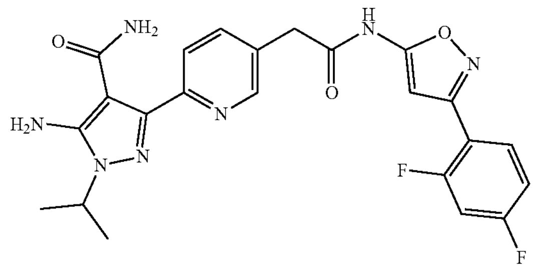 | 498 |
| 303 | 5-Amino-3-[5-[2-[[3-(1,1-dimethylpropyl)isoxazol-5-yl]amino]-2-oxo-ethyl]-2-pyridyl]-1-isopropyl-pyrazole-4-carboxamide | 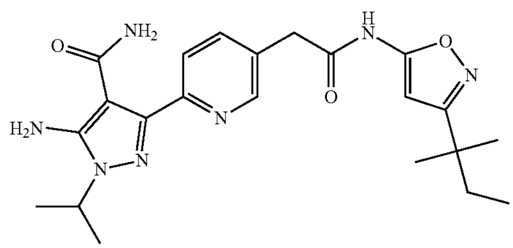 [SMILES: CCC(C)(C)c1cc(NC(=O)Cc2ccc(-c3nn(C(C)C)c(N)c3C(N)=O)nc2)on1] | 440 |
| 304 | 5-Amino-1-isopropyl-3-[5-[2-[[3-(1-methylcyclopropyl)isoxazol-5-yl]amino]-2-oxo-ethyl]-2-pyridyl]pyrazole-4-carboxamide | 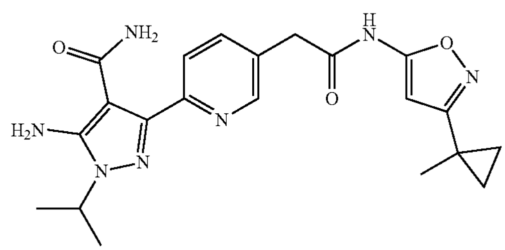 [SMILES: CC(C)n1nc(-c2ccc(CC(=O)Nc3cc(C4(C)CC4)no3)cn2)c(C(N)=O)c1N] | 424 |
| 305 | 5-Amino-3-[5-[2-[(5-tert-butylisothiazol-3-yl)amino]-2-oxo-ethyl]-2-pyridyl]-1-isopropyl-pyrazole-4-carboxamide | 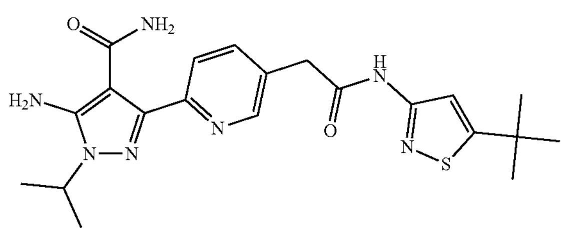 [SMILES: CC(C)n1nc(-c2ccc(CC(=O)Nc3cc(C(C)(C)C)sn3)cn2)c(C(N)=O)c1N] | 442 |
| 306 | 5-Amino-3-[5-[2-[[3-(1,1-difluoroethyl)isoxazol-5-yl]amino]-2-oxo-ethyl]-2-pyridyl]-1-isopropyl-pyrazole-4-carboxamide | 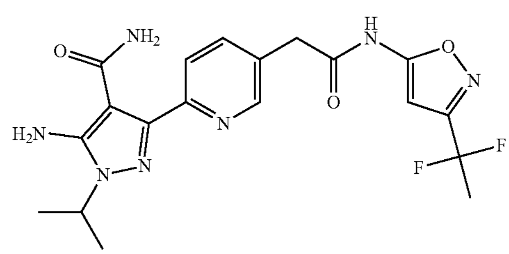 [SMILES: CC(C)n1nc(-c2ccc(CC(=O)Nc3cc(C(C)(F)F)no3)cn2)c(C(N)=O)c1N] | 434 |
| 307 | 5-Amino-1-isopropyl-3-[5-[2-oxo-2-[[5-(2,2,2-trifluoro-1,1-dimethyl-ethyl)isoxazol-3-yl]amino]ethyl]pyrazin-2-yl]pyrazole-4-carboxamide | 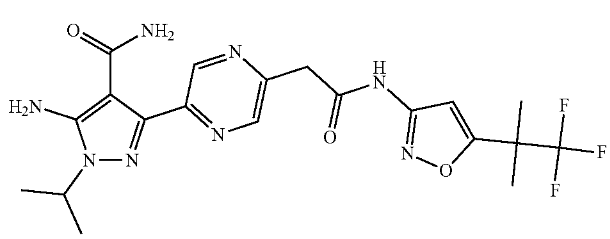 [SMILES: CC(C)n1nc(-c2cnc(CC(=O)Nc3cc(C(C)(C)C(F)(F)F)on3)cn2)c(C(N)=O)c1N] | 481.1 |

TABLE 35-continued

| Ex. No. | Chemical name | Structure | ES/MS m/z (M + H) |
|---|---|---|---|
| 308 | 5-Amino-3-[5-[2-[[3-(2,4-dichlorophenyl)isoxazol-5-yl]amino]-2-oxo-ethyl]pyrazin-2-yl]-1-isopropyl-pyrazole-4-carboxamide | 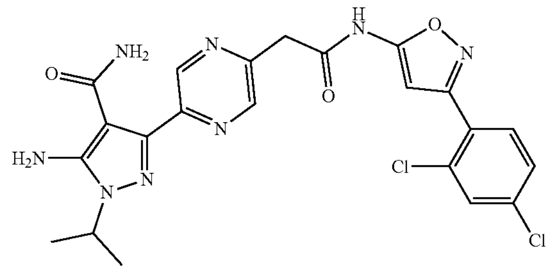 [SMILES: CC(C)n1nc(-c2cnc(CC(=O)Nc3cc(-c4ccc(Cl)cc4Cl)no3)cn2)c(C(N)=O)c1N] | 515.1 |
| 309 | 5-Amino-1-isopropyl-3-[5-[2-[[5-(1-methylcyclopentyl)isoxazol-3-yl]amino]-2-oxo-ethyl]pyrazin-2-yl]pyrazole-4-carboxamide | 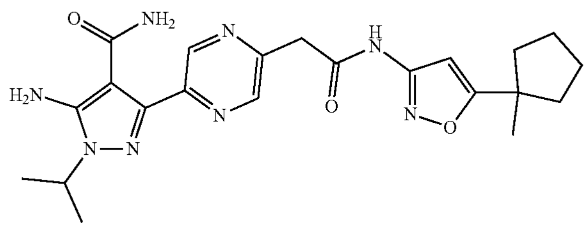 [SMILES: CC(C)n1nc(-c2cnc(CC(=O)Nc3cc(C4(C)CCCC4)on3)cn2)c(C(N)=O)c1N] | 453.2 |
| 310 | 5-Amino-3-[5-[2-[[3-(1,1-dimethylpropyl)isoxazol-5-yl]amino]-2-oxo-ethyl]pyrazin-2-yl]-1-isopropyl-pyrazole-4-carboxamide | 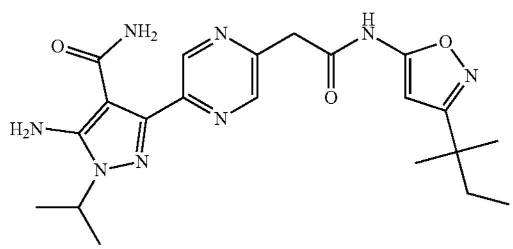 [SMILES: CCC(C)(C)c1cc(NC(=O)Cc2cnc(-c3nn(C(C)C)c(N)c3C(N)=O)cn2)on1] | 441.3 |
| 311 | 5-Amino-3-[5-[2-[(5-tert-butylisoxazol-3-yl)amino]-2-oxo-ethyl]pyrazin-2-yl]-1-isopropyl-pyrazole-4-carboxamide | 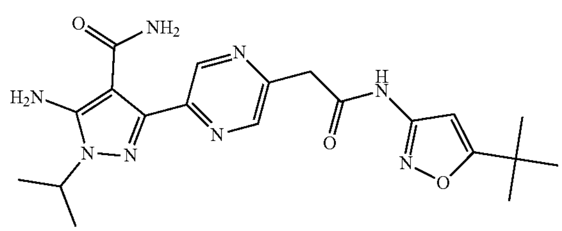 [SMILES: CC(C)n1nc(-c2cnc(CC(=O)Nc3cc(C(C)(C)C)on3)cn2)c(C(N)=O)c1N] | 425.3 (M − H) |
| 312 | 5-Amino-1-isopropyl-3-[6-[2-oxo-2-[[5-(2,2,2-trifluoro-1,1-dimethyl-ethyl)isoxazol-3-yl]amino]ethyl]-3-pyridyl]pyrazole-4-carboxamide | 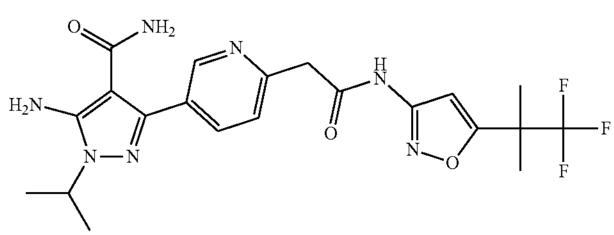 [SMILES: CC(C)n1nc(-c2ccc(CC(=O)Nc3cc(C(C)(C)C(F)(F)F)on3)nc2)c(C(N)=O)c1N] | 480.3 |
| 313 | 5-Amino-1-isopropyl-3-[6-[2-oxo-2-[(3-phenylisoxazol-5-yl)amino]ethyl]-3-pyridyl]pyrazole-4-carboxamide | 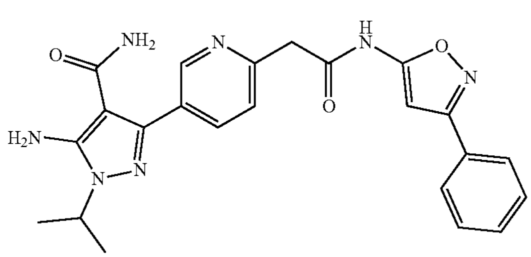 [SMILES: CC(C)n1nc(-c2ccc(CC(=O)Nc3cc(-c4ccccc4)no3)nc2)c(C(N)=O)c1N] | 446 |

TABLE 35-continued

| Ex. No. | Chemical name | Structure | ES/MS m/z (M + H) |
|---|---|---|---|
| 314 | 5-Amino-1-isopropyl-3-[6-[2-[[5-(1-methylcyclopentyl)isoxazol-3-yl]amino]-2-oxo-ethyl]-3-pyridyl]pyrazole-4-carboxamide | 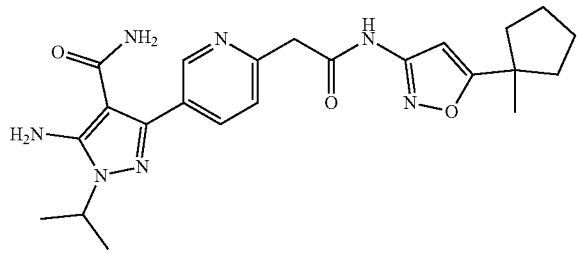 [SMILES: CC(C)n1nc(-c2ccc(CC(=O)Nc3cc(C4(C)CCCC4)on3)nc2)c(C(N)=O)c1N] | 452 |
| 315 | 5-Amino-3-[6-[2-[[3-(1,1-difluoroethyl)isoxazol-5-yl]amino]-2-oxo-ethyl]-3-pyridyl]-1-isopropyl-pyrazole-4-carboxamide | 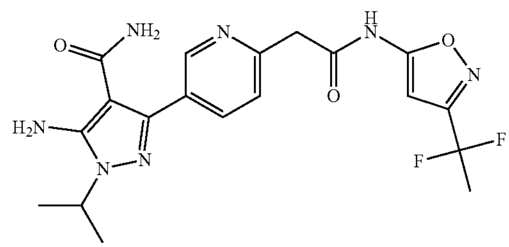 [SMILES: CC(C)n1nc(-c2ccc(CC(=O)Nc3cc(C(C)(F)F)no3)nc2)c(C(N)=O)c1N] | 434 |
| 316 | 5-Amino-3-[6-[2-[[3-(2,4-dichlorophenyl)isoxazol-5-yl]amino]-2-oxo-ethyl]-3-pyridyl]-1-isopropyl-pyrazole-4-carboxamide | 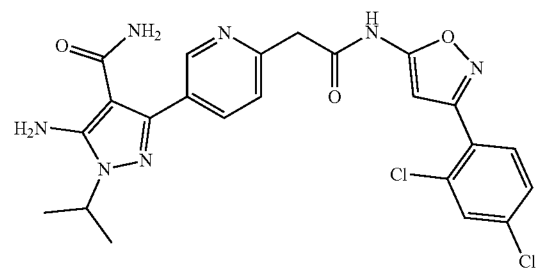 | 514 |
| 317 | 5-Amino-3-[6-[2-[[3-(2-chlorophenyl)isoxazol-5-yl]amino]-2-oxo-ethyl]-3-pyridyl]-1-isopropyl-pyrazole-4-carboxamide | 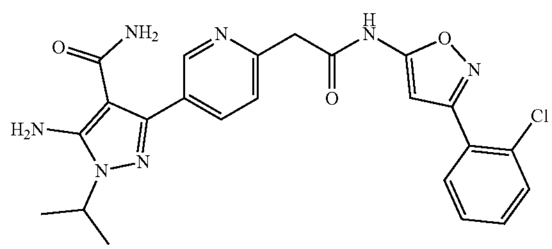 [SMILES: CC(C)n1nc(-c2ccc(CC(=O)Nc3cc(-c4ccccc4Cl)no3)nc2)c(C(N)=O)c1N] | 480.2 |
| 318 | 5-Amino-3-[6-[2-[(5-tert-butylisoxazol-3-yl)amino]-2-oxo-ethyl]-3-pyridyl]-1-isopropyl-pyrazole-4-carboxamide | 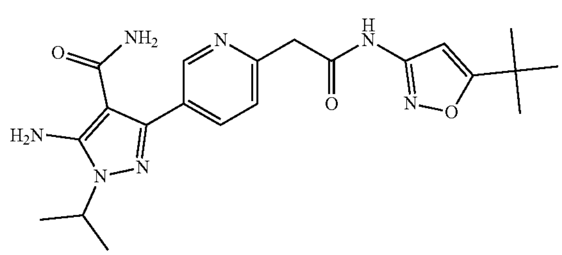 [SMILES: CC(C)n1nc(-c2ccc(CC(=O)Nc3cc(C(C)(C)C)on3)nc2)c(C(N)=O)c1N] | 426.4 |
| 319 | 5-Amino-1-isopropyl-3-[6-[2-[[3-(1-methylcyclopropyl)isoxazol-5-yl]amino]-2-oxo-ethyl]-3-pyridyl]pyrazole-4-carboxamide | 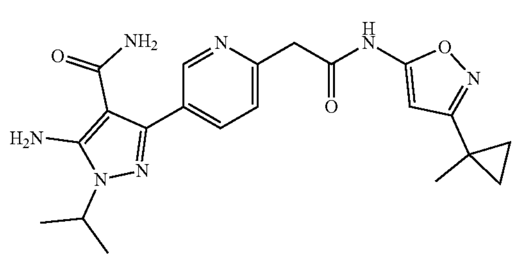 [SMILES: CC(C)n1nc(-c2ccc(CC(=O)Nc3cc(C4(C)CC4)no3)nc2)c(C(N)=O)c1N] | 424 |

TABLE 35-continued

| Ex. No. | Chemical name | Structure | ES/MS m/z (M + H) |
|---|---|---|---|
| 320 | 5-Amino-3-[6-[2-[[3-(4-chloro-3-fluoro-phenyl)isoxazol-5-yl]amino]-2-oxo-ethyl]-3-pyridyl]-1-isopropyl-pyrazole-4-carboxamide | 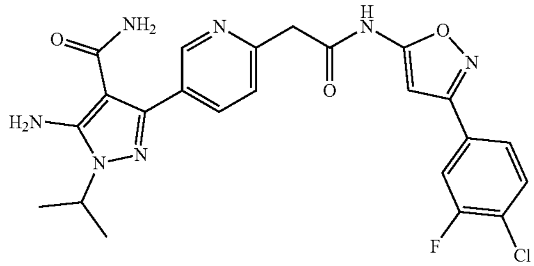 [SMILES: CC(C)n1nc(-c2ccc(CC(=O)Nc3cc(-c4ccc(Cl)c(F)c4)no3)nc2)c(C(N)=O)c1N] | 498.2 |
| 321 | 5-Amino-3-[6-[2-[[3-(4-chloro-2-fluoro-phenyl)isoxazol-5-yl]amino]-2-oxo-ethyl]-3-pyridyl]-1-isopropyl-pyrazole-4-carboxamide | 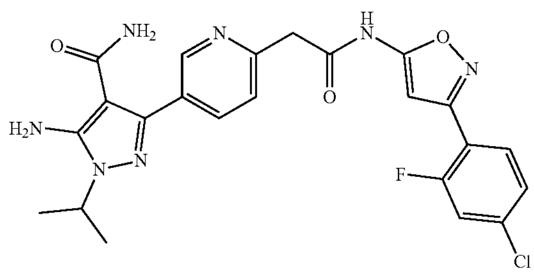 [SMILES: CC(C)n1nc(-c2ccc(CC(=O)Nc3cc(-c4ccc(Cl)cc4F)no3)nc2)c(C(N)=O)c1N] | 498.2 |
| 322 | 5-Amino-3-[6-[2-[[3-(4-chloro-2-methoxy-phenyl)isoxazol-5-yl]amino]-2-oxo-ethyl]-3-pyridyl]-1-isopropyl-pyrazole-4-carboxamide | 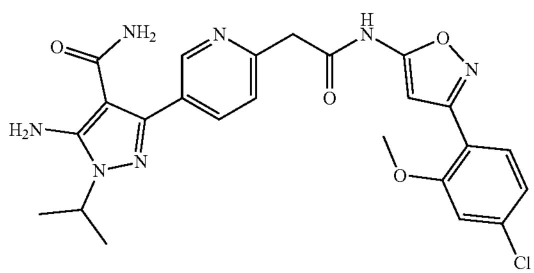 [SMILES: COc1cc(Cl)ccc1-c1cc(NC(=O)Cc2ccc(-c3nn(C(C)C)c(N)c3C(N)=O)cn2)on1] | 510.2 |
| 323 | 5-Amino-3-[6-[2-[[3-(2-chloro-4-fluoro-phenyl)isoxazol-5-yl]amino]-2-oxo-ethyl]-3-pyridyl]-1-isopropyl-pyrazole-4-carboxamide | 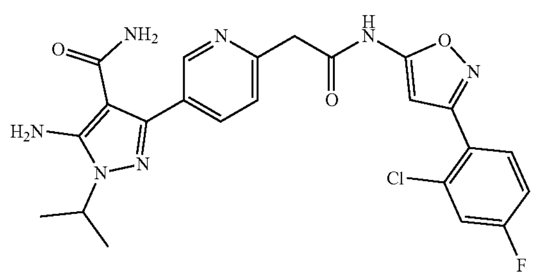 | 498 |
| 324 | 5-Amino-3-[6-[2-[[3-(2-chloro-4-methyl-phenyl)isoxazol-5-yl]amino]-2-oxo-ethyl]-3-pyridyl]-1-isopropyl-pyrazole-4-carboxamide | 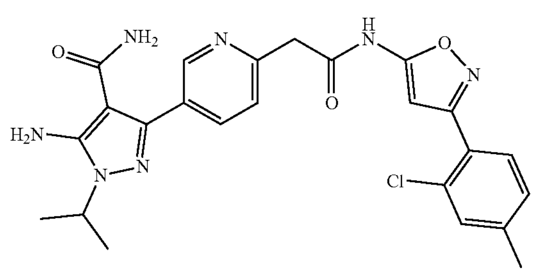 [SMILES: Cc1ccc(-c2cc(NC(=O)Cc3ccc(-c4nn(C(C)C)c(N)c4C(N)=O)cn3)on2)c(Cl)c1] | 494.2 |

TABLE 35-continued

| Ex. No. | Chemical name | Structure | ES/MS m/z (M + H) |
|---|---|---|---|
| 325 | 5-Amino-3-[6-[2-[[3-[2-chloro-4-(trifluoromethyl)phenyl]isoxazol-5-yl]amino]-2-oxo-ethyl]-3-pyridyl]-1-isopropyl-pyrazole-4-carboxamide | 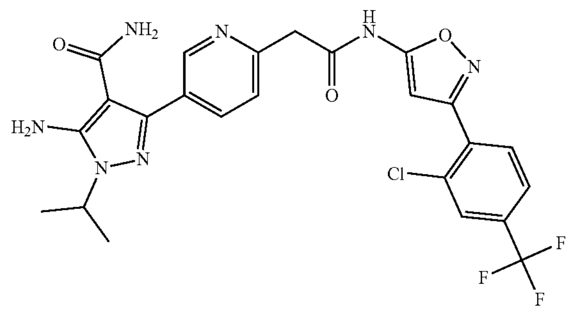 [SMILES: CC(C)n1nc(-c2ccc(CC(=O)Nc3cc(-c4ccc(C(F)(F)F)cc4Cl)no3)nc2)c(C(N)=O)c1N] | 548.1 |
| 326 | 5-Amino-3-[6-[2-[[5-(2,4-dichlorophenyl)-1H-pyrazol-3-yl]amino]-2-oxo-ethyl]-3-pyridyl]-1-isopropyl-pyrazole-4-carboxamide | 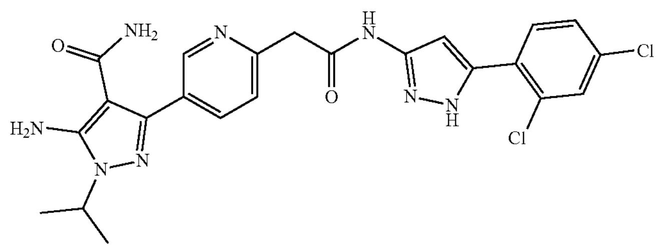 [SMILES: CC(C)n1nc(-c2ccc(CC(=O)Nc3cc(-c4ccc(Cl)cc4Cl)[nH]n3)nc2)c(C(N)=O)c1N] | 513.2 |
| 327 | 5-Amino-3-[6-[2-[[3-(1,1-dimethylpropyl)isoxazol-5-yl]amino]-2-oxo-ethyl]-3-pyridyl]-1-isopropyl-pyrazole-4-carboxamide | 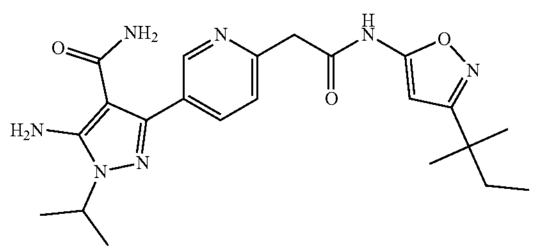 [SMILES: CCC(C)(C)c1cc(NC(=O)Cc2ccc(-c3nn(C(C)C)c(N)c3C(N)=O)cn2)on1] | 440.4 |
| 328 | 5-Amino-3-[6-[2-[[3-(3,5-dichloro-2-pyridyl)isoxazol-5-yl]amino]-2-oxo-ethyl]-3-pyridyl]-1-isopropyl-pyrazole-4-carboxamide | 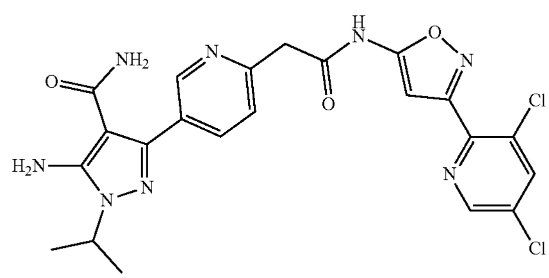 [SMILES: CC(C)n1nc(-c2ccc(CC(=O)Nc3cc(-c4ncc(Cl)cc4Cl)no3)nc2)c(C(N)=O)c1N] | 515.0 |
| 329 | 5-Amino-1-isopropyl-3-[6-[2-[4-[(4-methylpiperazin-1-yl)methyl]-3-(trifluoromethyl)anilino]-2-oxo-ethyl]-3-pyridyl]pyrazole-4-carboxamide | 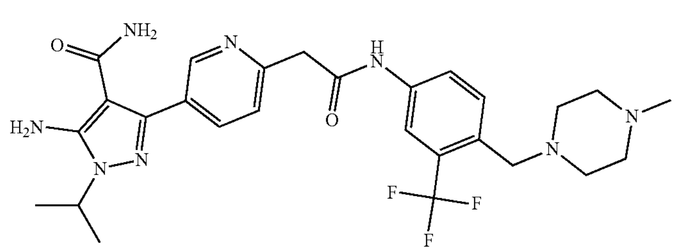 [SMILES: CC(C)n1nc(-c2ccc(CC(=O)Nc3ccc(CN4CCN(C)CC4)c(C(F)(F)F)c3)nc2)c(C(N)=O)c1N] | 559.3 |

TABLE 35-continued

| Ex. No. | Chemical name | Structure | ES/MS m/z (M + H) |
|---|---|---|---|
| 330 | 5-Amino-3-[6-[2-[[3-(2,4-dichloro-3-fluoro-phenyl)isoxazol-5-yl]amino]-2-oxo-ethyl]-3-pyridyl]-1-isopropyl-pyrazole-4-carboxamide | 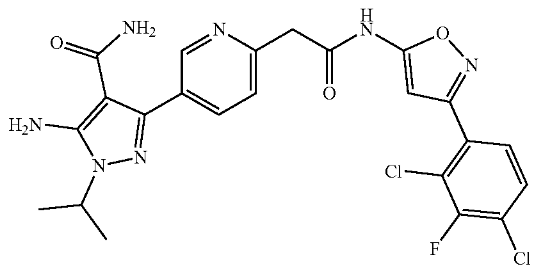 [SMILES: CC(C)n1nc(-c2ccc(CC(=O)Nc3cc(-c4ccc(Cl)c(F)c4Cl)no3)nc2)c(C(N)=O)c1N] | 532.1 |
| 331 | 5-Amino-3-[6-[2-[[3-(4-chloro-2-methyl-phenyl)isoxazol-5-yl]amino]-2-oxo-ethyl]-3-pyridyl]-1-isopropyl-pyrazole-4-carboxamide | 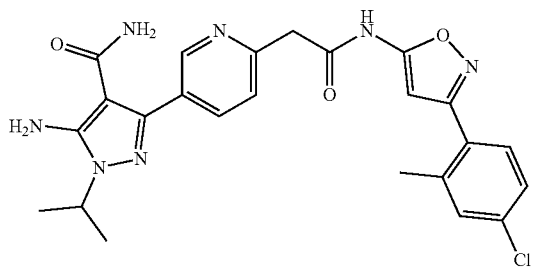 [SMILES: Cc1cc(Cl)ccc1-c1cc(NC(=O)Cc2ccc(-c3nn(C(C)C)c(N)c3C(N)=O)cn2)on1] | 494.1 |
| 332 | 5-Amino-3-[6-[2-[[3-(2,2-dimethylpropyl)isoxazol-5-yl]amino]-2-oxo-ethyl]-3-pyridyl]-1-isopropyl-pyrazole-4-carboxamide | 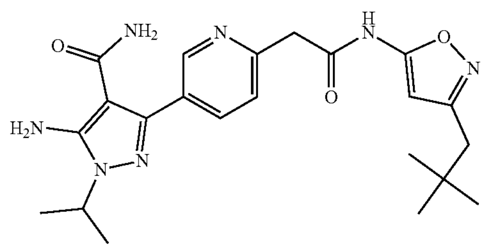 [SMILES: CC(C)n1nc(-c2ccc(CC(=O)Nc3cc(CC(C)(C)C)no3)nc2)c(C(N)=O)c1N] | 440.2 |
| 333 | 5-Amino-3-[6-[2-[[5-(2,4-dichlorophenyl)-1-methyl-pyrazol-3-yl]amino]-2-oxo-ethyl]-3-pyridyl]-1-isopropyl-pyrazole-4-carboxamide | 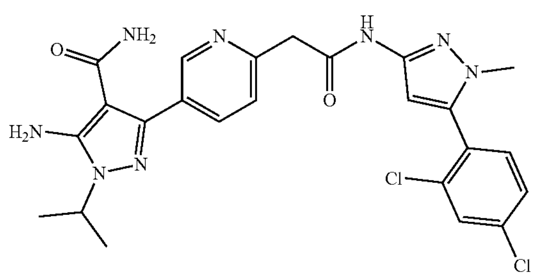 [SMILES: CC(C)n1nc(-c2ccc(CC(=O)Nc3cc(-c4ccc(Cl)cc4Cl)n(C)n3)nc2)c(C(N)=O)c1N] | 527.1 |
| 334 | 5-Amino-3-[6-[2-[[3-(2-chloro-4-methoxy-phenyl)isoxazol-5-yl]amino]-2-oxo-ethyl]-3-pyridyl]-1-isopropyl-pyrazole-4-carboxamide | 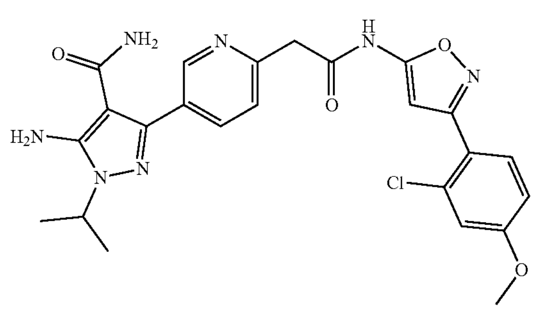 [SMILES: COc1ccc(-c2cc(NC(=O)Cc3ccc(-c4nn(C(C)C)c(N)c4C(N)=O)cn3)on2)c(Cl)c1] | 510.1 |

TABLE 35-continued

| Ex. No. | Chemical name | Structure | ES/MS m/z (M + H) |
|---|---|---|---|
| 335 | 5-Amino-1-isopropyl-3-[6-[2-oxo-2-[[5-(3,3,3-trifluoro-1,1-dimethyl-propyl)isoxazol-3-yl]amino]ethyl]-3-pyridyl]pyrazole-4-carboxamide | 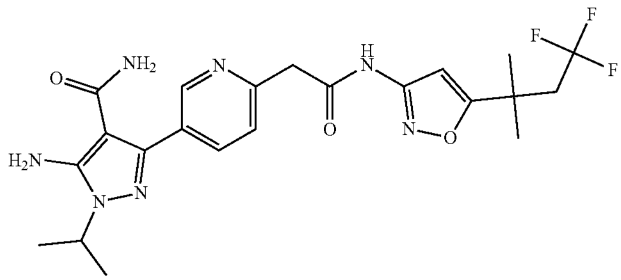 [SMILES: CC(C)n1nc(-c2ccc(CC(=O)Nc3cc(C(C)(C)CC(F)(F)F)on3)nc2)c(C(N)=O)c1N] | 494.2 |
| 336 | 5-Amino-3-[6-[2-[[5-(2,2-dimethylpropyl)isoxazol-3-yl]amino]-2-oxo-ethyl]-3-pyridyl]-1-isopropyl-pyrazole-4-carboxamide | 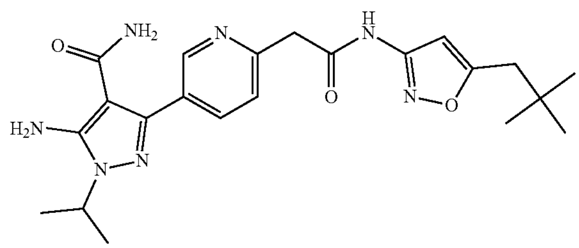 [SMILES: CC(C)n1nc(-c2ccc(CC(=O)Nc3cc(CC(C)(C)C)on3)nc2)c(C(N)=O)c1N] | 440.1 |
| 337 | 5-Amino-1-ethyl-3-[6-[2-oxo-2-[[5-(2,2,2-trifluoro-1,1-dimethyl-ethyl)isoxazol-3-yl]amino]ethyl]-3-pyridyl]pyrazole-4-carboxamide | 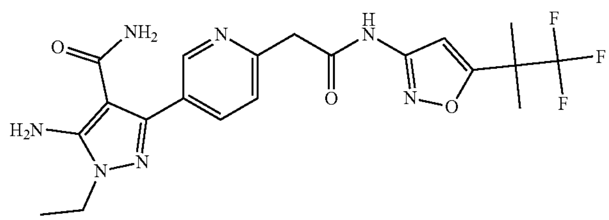 [SMILES: CCn1nc(-c2ccc(CC(=O)Nc3cc(C(C)(C)C(F)(F)F)on3)nc2)c(C(N)=O)c1N] | 466.1 |
| 338 | 5-Amino-1-isopropyl-3-[2-[2-oxo-2-[[5-(2,2,2-trifluoro-1,1-dimethyl-ethyl)isoxazol-3-yl]amino]ethyl]pyrimidin-5-yl]pyrazole-4-carboxamide | 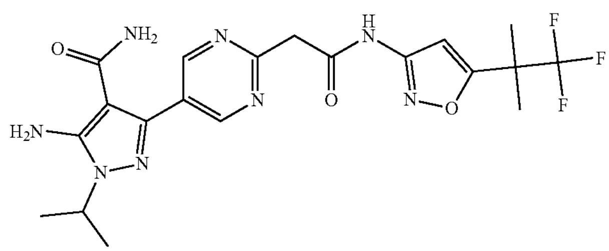 [SMILES: CC(C)n1nc(-c2cnc(CC(=O)Nc3cc(C(C)(C)C(F)(F)F)on3)nc2)c(C(N)=O)c1N] | 481.3 |
| 339 | 5-Amino-3-[2-[2-[[3-(2,4-dichlorophenyl)isoxazol-5-yl]amino]-2-oxo-ethyl]pyrimidin-5-yl]-1-isopropyl-pyrazole-4-carboxamide | 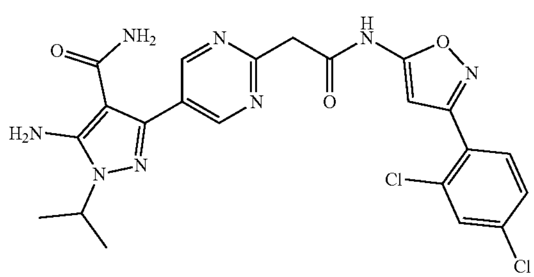 [SMILES: CC(C)n1nc(-c2cnc(CC(=O)Nc3cc(-c4ccc(Cl)cc4Cl)no3)nc2)c(C(N)=O)c1N] | 515.1 |
| 340 | 5-Amino-1-isopropyl-3-[5-[2-oxo-2-[[5-(2,2,2-trifluoro-1,1-dimethyl-ethyl)isoxazol-3-yl]amino]ethyl]pyrimidin-2-yl]pyrazole-4-carboxamide | 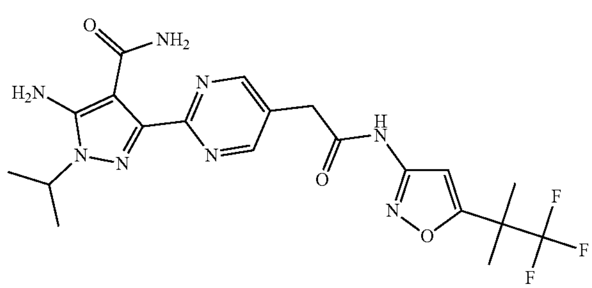 [SMILES: CC(C)n1nc(-c2ncc(CC(=O)Nc3cc(C(C)(C)C(F)(F)F)on3)cn2)c(C(N)=O)c1N] | 481.1 |

Biological Assays

The following assays demonstrate that the compounds described herein are RET kinase inhibitors

Assay A: RET Enzyme Assay

Compounds of formulas I, Ia to Ix, IIa to Ix, and/or IIIa to IIIx are screened for their ability to inhibit wildtype, V804 M, and G810S mutant RET kinase using CisBio's HTRF® KinEASE™-TK assay technology. N-terminal GST tagged recombinant human RET cytoplasmic domain (aa 658-end) from Eurofins (1.25 nM RET; Catalog No. 14-570 M) or N-terminal GST tagged recombinant human V804 M mutant RET cytoplasmic domain (aa 658-end) from Millipore (1.25 nM enzyme; Catalog No. 14-760) or N-Terminal GST-tagged recombinant human G810S (aa-658-end) (1.25 nM Enzyme; produced in insect cells) is incubated with 62.5 nM TK-substrate biotin (CisBio, part of Catalog No. 62TK0PEC) and 1 mM ATP along with test compound (0.4% final DMSO in the assay) in a 1× Cisbuio enzymatic buffer consisting of 1 nM DTT, 5 mM MgCl$_2$, 0.04% BSA and 0.05% Tween20 in a volume of 10 μL. Compounds are typically prepared in a threefold serial dilution in DMSO and added to the assay to give the appropriate final concentration. After a 40-60 min (40 min for V804 M, 60 min for WT and G810S) incubation at 22° C., the reaction is quenched by adding quench solution (10 μL) containing 7.8 nM Streptavidine-XL665 and 0.5× TK-ab-Cryptate in HTRF detection buffer (all from CisBio, part of Cat. No. 62TK0PEC). After a 60-80 min incubation (60 minutes for WT, 80 minutes for V804 M and G810S) at 22° C., the extent of reaction is determined using a PHERastar plate reader via HTRF detection at excitation/emission 337/665 nm. Percent of inhibition is calculated with 0% inhibition referring to control conditions containing no compound (0.4% DMSO only) and 100% inhibition represented by conditions containing no enzyme. The % inhibition values are fit to a 4 parameter logistic curve, and the determined IC$_{50}$ value is defined as the estimated concentration of inhibitor at the inflexion point of the fitted curve. The compounds of Examples 1, 2, 3, 4, 5, 6, 7, 8, 9, 10, 153, 154, 199, 221, 222, 292, 293, 294, 299, 300, 301, 302, 303, 306, 308, 310, 311, 316, 317, 318, 321, 324, 329, 330, and 335 all exhibited IC$_{50}$ values of less than 150 nM in at least one of wildtype, V804 M, and G810S mutant RET kinases in these assays. This data demonstrates these compounds are RET inhibitors, as are the other compounds disclosed herein.

Assay B: RET Cell Assay

Compounds of formulas I, Ia to Ix, IIa to Ix, and/or IIIa to IIIx are screened for their ability to inhibit the intracellular autophosphorylation of RET at tyrosine 1062 as detected by In-Cell Western. HEK293 cells containing a doxycycline-inducible plasmid for inducible expression of KIF5B-RET WT and RET mutant forms V804 M and G810S are seeded at 25,000 cells/well into black poly-D-lysine pre-coated 384-well plates (Corning, Catalog No. 356697). Expression of KIF5B-RET is induced with doxycycline at 1 μg/mL and cells are incubated at 37° C. overnight. Compounds are prepared in a threefold serial dilution in DMSO before further diluting 1:100 in media prior to the addition to the cells (0.1% final DMSO concentration). Compound treatment is performed for 1 hr at 37° C. followed by fixation of cells with 4% formaldehyde for 20 min at RT and cell permeabilisation with ice-cold MeOH for 10 min at RT. Cells are incubated with Intercept® blocking buffer (Li—COR, Catalogue No. 927-70010) for 1 hr at RT. Incubation with primary antibodies against human phospho-RET (Y1062) (R&D, Catalogue No. AF5009, 1/250 dilution) and human glyceraldehyde-3-phosphate dehydrogenase (clone 6C5, Merck, Catalog No. MAB374, 1/1000 dilution) are performed overnight at 4° C. Incubation with secondary antibodies IRDye® 800 CW goat anti-rabbit IgG (Li—COR, Catalogue No. 926-32211, 1/1000 dilution) and IRDye® 680 CW goat anti-mouse IgG (Li—COR, Catalogue No. 926-68070, 1/1000 dilution) are performed for 1 hr at RT. All antibody dilutions are done in Intercept® blocking buffer containing 0.05% Tween20. After washing cells with PBS-T (Cell Signaling technology, Catalogue No. 9809), the images are acquired on a Li—COR Odyssey LCx at 700 and 800 nm. Percent of DMSO control is calculated with 100% signal referring to control conditions containing no compound (0.4% DMSO only) and 0% signal represented by conditions containing control compound. The % of DMSO control values are fit to a 4 parameter logistic curve, and the determined EC$_{50}$ value is defined as the estimated concentration of inhibitor at the inflexion point of the fitted curve. The compounds of Examples 1, 2, 3, 4, 5, 6, 7, 8, 9, 10, 153, 154, 199, 221, 222, 292, 293, 294, 299, 300, 301, 302, 303, 306, 308, 310, 311, 316, 317, 318, 321, 324, 329, 330, and 335 all inhibited the intracellular autophosphorylation of RET at tyrosine 1062 with EC$_{50}$ values of less than 150 nM in at least one of wildtype, V804 M, and G810S RET mutant cell assays. This data demonstrates these compounds are RET inhibitors, as are the other compounds disclosed herein.

The invention claimed is:

1. A compound of the formula:

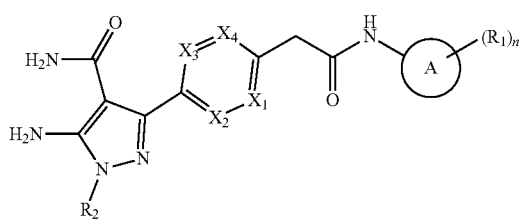

wherein

A is $C_6$-$C_{10}$ aryl or $C_5$-$C_6$ heteroaryl;

each $R_1$ is independently hydrogen, halogen, $C_1$-$C_6$ alkyl, $C_1$-$C_6$ heteroalkyl, —($C_1$-$C_4$ alkyl)($C_5$-$C_6$ heteroalkyl), —($C_0$-$C_4$ alkyl)($C_3$-$C_7$ cycloalkyl), —($C_0$-$C_4$ heteroalkyl)($C_3$-$C_7$ cycloalkyl), —($C_0$-$C_4$ alkyl)($C_3$-$C_7$ cycloheteroalkyl), —($C_0$-$C_4$ heteroalkyl)($C_3$-$C_7$ cycloheteroalkyl), —($C_0$-$C_4$ alkyl)($C_4$-$C_{10}$ bicyclyl), —($C_0$-$C_4$ alkyl)($C_5$-$C_6$ aryl), —($C_0$-$C_4$ alkyl)($C_5$-$C_6$ heteroaryl), —($C_0$-$C_4$ alkyl)($C_4$-$C_{10}$ heterobicyclyl), $C_5$-$C_{12}$ spiranyl, $C_5$-$C_{12}$ heterospiranyl, dimethylphosphoryl, adamantyl, $C_1$-$C_6$ alkoxy, —($C_1$-$C_4$ alkyl)-$SO_2$—($C_1$-$C_4$ alkyl), difluoromethylsulfanyl, or pentafluorosulfanyl, wherein each $R_1$ is unsubstituted or when it is capable of being substituted, it is substituted with one or more substituents that are independently selected from the group consisting of halogen, cyano, hydroxyl, oxo, methyl, methoxy, hydroxymethyl, ethyl, ethoxy, hydroxyethyl, methylamine, N,N-dimethylmethylamine, mono-, di, or trihalomethoxy, mono-, di-, or trihalomethyl, and $C_0$-$C_3$ alkyl-pyrrolidinyl, where the pyrrolidinyl group is unsubstituted or substituted with one, two or 3 independently selected halogen atoms, and wherein two $R_1$ groups can fuse to form a ring structure that includes a portion of A and is optionally aromatic, and n is 1, 2, 3, 4, 5, or 6;

$X_1$, $X_2$, $X_3$, and $X_4$ are each independently N, CH, C—$CH_3$, C—$CH_2$—OH, C—$OCH_3$, C—$CH_2$—$OCH_3$, or C-halogen; wherein at least one of $X_1$, $X_2$, $X_3$, and $X_4$ is N, and $R_2$ is $C_1$-$C_6$ alkyl, —($C_0$-$C_4$ alkyl)($C_3$-$C_7$ cycloalkyl), —($C_0$-$C_4$ alkyl)($C_4$-$C_7$ heterocycloalkyl), —($C_0$-$C_4$ alkyl)($C_4$-$C_{10}$ bicyclic) each optionally substituted with one or more of halogen, cyano, hydroxyl, oxo, methyl, methoxy, hydroxymethyl, ethyl, ethoxy, hydroxyethyl, cyclopropyl, or mono-, di-, or tri-halomethyl;

or a pharmaceutically acceptable salt thereof.

2. The compounds or a pharmaceutically acceptable salts thereof according to claim 1, wherein A-$(R_1)_n$ is

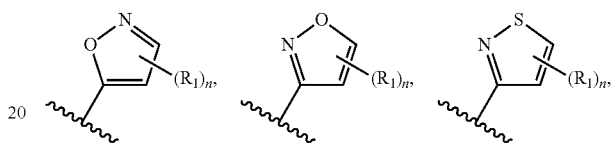

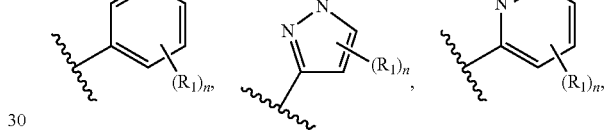

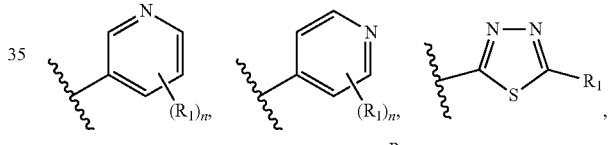

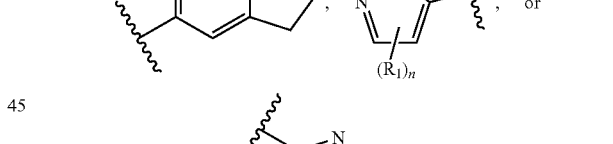

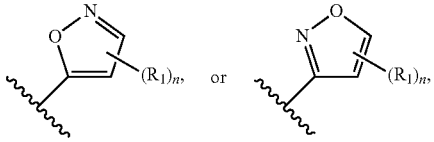

wherein a wavy line indicates connection to the backbone and the maximum value of n depends on the number of substitutable positions on the A-ring.

3. The compound or a pharmaceutically acceptable salt thereof according to claim 1, wherein A-$(R_1)_n$ is and the maximum value of n depends on the number of substitutable positions on the A-ring.

4. The compound or a pharmaceutically acceptable salts thereof according to claim 1, wherein A-(R₁)ₙ is

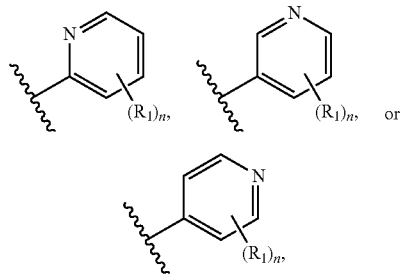

and the maximum value of n depends on the number of substitutable positions on the A-ring.

5. The compound or a pharmaceutically acceptable salt thereof according to claim 1, wherein A-(R₁)ₙ is

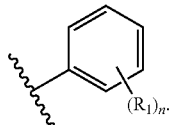

6. The compound or a pharmaceutically acceptable salts thereof according to claim 1, wherein A-(R₁)ₙ is

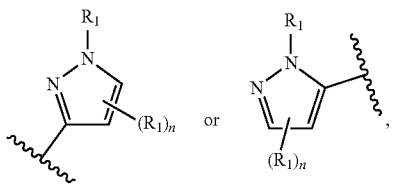

and the maximum value of n depends on the number of substitutable positions on the A-ring.

7. The compound or a pharmaceutically acceptable salt thereof according to claim 1, wherein the compound is selected from the group consisting of

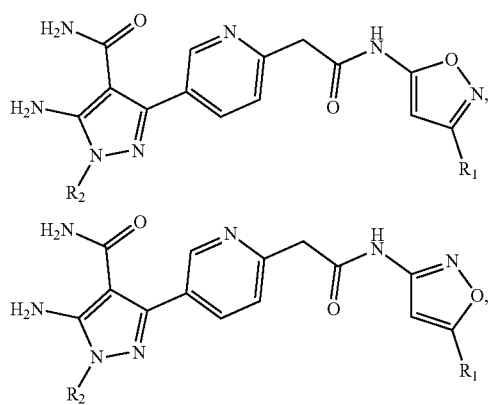

-continued

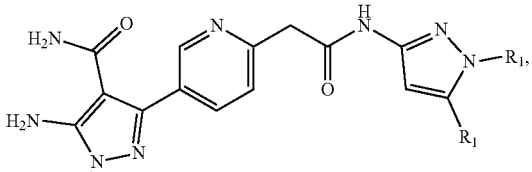

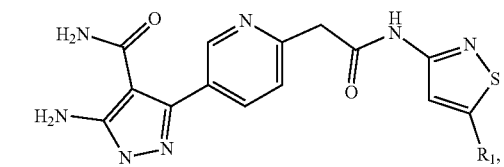

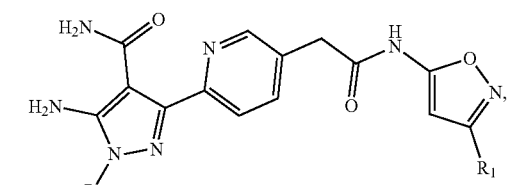

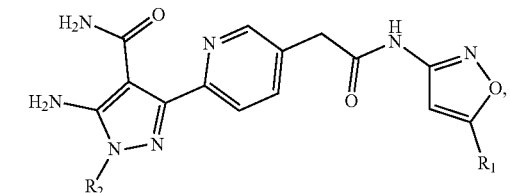

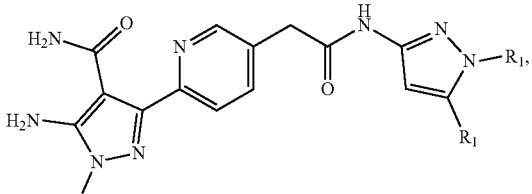

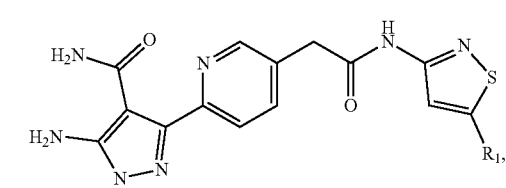

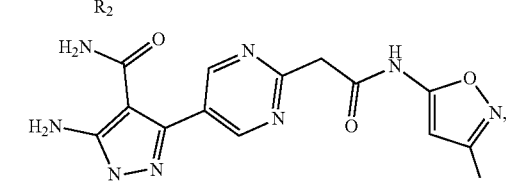

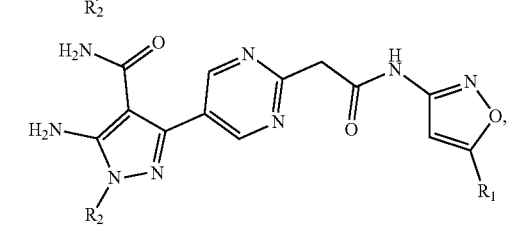

317
-continued

318
-continued

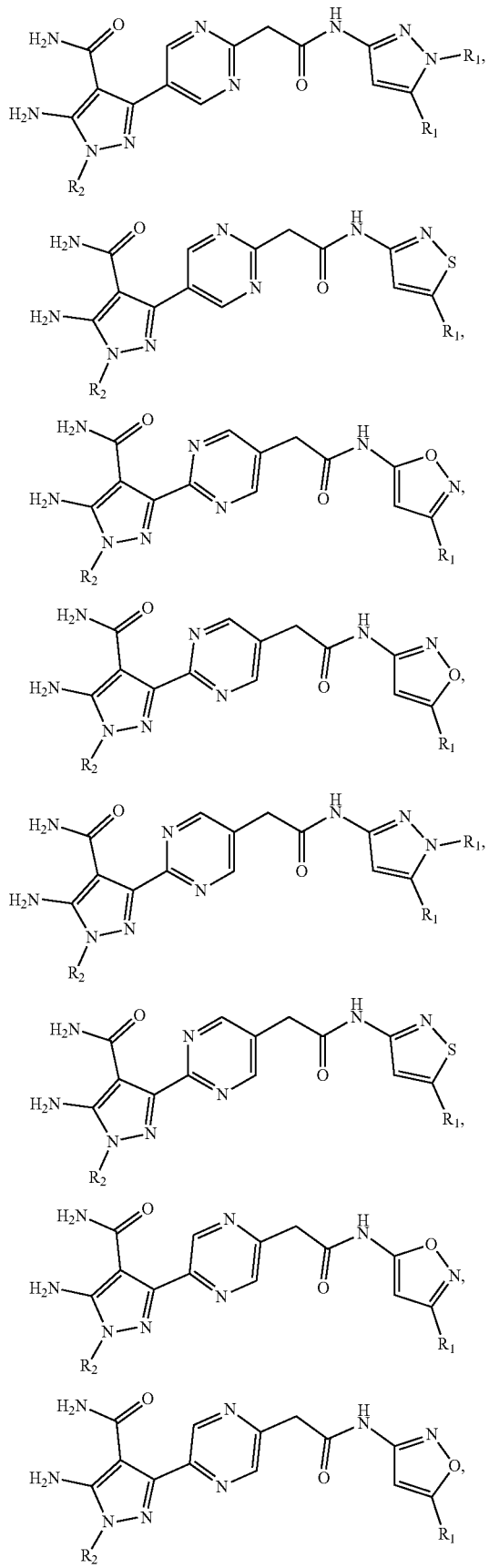

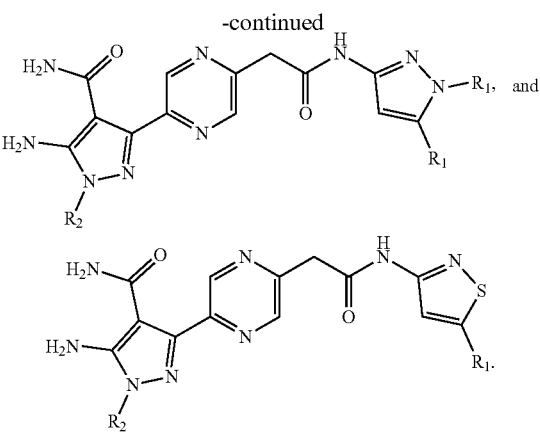

8. The compound according to claim 7, wherein each $R_1$ is independently selected from the group consisting of hydrogen, $C_1$-$C_6$ alkyl, $C_4$-$C_{10}$ bicyclyl and $C_5$-$C_{12}$ spiranyl, wherein the $C_4$-$C_{10}$ bicyclyl is a $C_4$-$C_8$ bridged bicycloalkyl, and wherein each $R_1$ is optionally substituted with one or more of halogen, cyano, hydroxyl, oxo, methyl, methoxy, hydroxymethyl, ethyl, ethoxy, hydroxyethyl, methylamine, N,N-dimethylmethylamine, or mono-, di-, or tri-halomethyl.

9. The compound or a pharmaceutically acceptable salt thereof according to claim 7, wherein each $R_1$ is independently 2,2-dimethylpropyl; 2-chloro-4-fluoro-phenyl; 2,4-dichlorophenyl; 1,1-dimethyl-2,2,2-trifluoroethyl; 1,1-dimethylethyl; 1,1-dimethylpropyl; trifluoromethyl; 1,1-dimethyl-2,2-difluoropropyl; 1,1-dimethyl-3,3,3-trifluoropropyl; 1-methylcyclopropyl; (1-methylcyclopropyl)methyl; 3-methylbicyclo[1.1.1]pentan-1-yl; 3-(trifluoromethyl)bicyclo[1.1.1]pentan-1-yl; or (3,3-dimethylcyclobutyl)methyl.

10. The compound or a pharmaceutically acceptable salt thereof according to claim 7, wherein each $R_1$ is a $C_4$-$C_8$ bridged bicycloalkyl that is unsubstituted or substituted with 1 or 2 groups independently selected from the group consisting of methyl, ethyl, $CF_3$, halo, and CN.

11. The compound or a pharmaceutically acceptable salt thereof according to claim 7, wherein each $R_1$ is independently

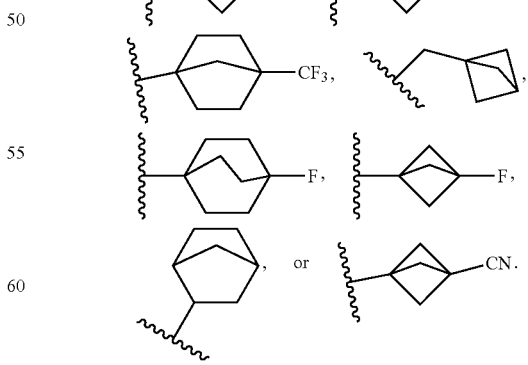

12. The compound or a pharmaceutically acceptable salt thereof according to claim 7, wherein each $R_1$ is independently —$CH_2C(CH_3)_3$, —$CH(CH_2CH_3)_2$, —$CF_2CH_3$, —CH$_2$CH$_2$CF$_3$, —C(CH$_3$)$_2$F, —C(CH$_3$)$_2$CF$_3$, —CH$_2$-cyclopentyl, —CH$_2$-cyclohexyl, —CH$_2$-cyclopropyl, —CH$_2$-cyclobutyl, —CH$_2$-morpholinyl, —CH$_2$-pyrrolidinyl, phenyl, naphthyl, pyran-4-yl, 4-methylphenyl, 4-methoxyphenyl, 2-fluorophenyl, 2-fluoro-4-chlorophenyl, 3-trifluoromethylphenyl, 3-fluoro-5-trifluoromethylphenyl, cyclopropyl, cyclobutyl, cyclopentyl, cyclohexyl, cycloheptyl, 2,4-dimethylphenyl, 4-chlorophenyl, 2-methylphenyl, 3-fluorophenyl, 3-chlorophenyl, 2-methoxyphenyl, 4-difluoromethoxyphenyl, —C(CH$_3$)$_2$SO$_2$CH$_3$, 4-fluorophenyl, 2,4-difluorophenyl, 2,4-dichlorophenyl, 3-chlorophenyl, methyl, ethyl, tert-butyl, isopropyl, trifluoromethyl, 3-methoxyphenyl, 3-bromophenyl, 4-bromophenyl, 2,4,6-trifluoromethylphenyl, 3-tetrahydrofuranyl, —C(CH$_3$)$_2$CH$_2$CH$_3$, —C(CH$_3$)$_2$OH, 3,3-dimethylcyclobut-1-yl, 2,3-dichlorobenzyl, 3,3-difluoromethylcyclobutyl, 2,2-dimethylcycloprop-1-yl, 2,2-difluorocyclopropyl, N-methylimidazolyl, 2-methyl-4-chlorophenyl, 2,4-dichloro-3-fluorophenyl, —CH$_2$OCH$_3$, —CH$_2$CF$_3$, —CF$_2$CH$_3$, —CF$_2$C(CH$_3$)$_3$, —CH(CH$_3$)cyclopropyl, 2,6-difluorophenyl, pyrid-2-yl, pyrid-3-yl, pyrid-4-yl, 3-chloropyrid-2-yl, 2-methylpyrid-3-yl, 4-methylpyrid-3-yl, 3,5-dichloropyrid-2-yl, 3,3-difluorocyclopentyl, fluoro, chloro, bromo, 2-methoxy-4-chloro-phenyl, 2-fluoro-4-chlorophenyl, 3-fluoro-4-chlorophenyl, benzyl, piperidinyl, 4-methyl-piperidinyl, 4-methoxy-piperidinyl, N-methylpyrazol-3-yl, —C(O)-piperidinyl, —OCHF$_2$,

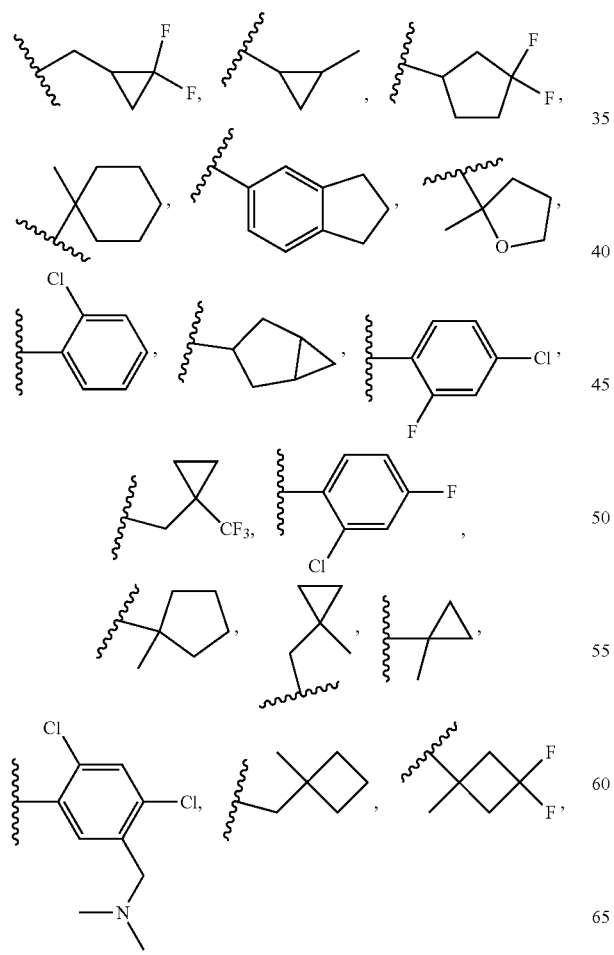

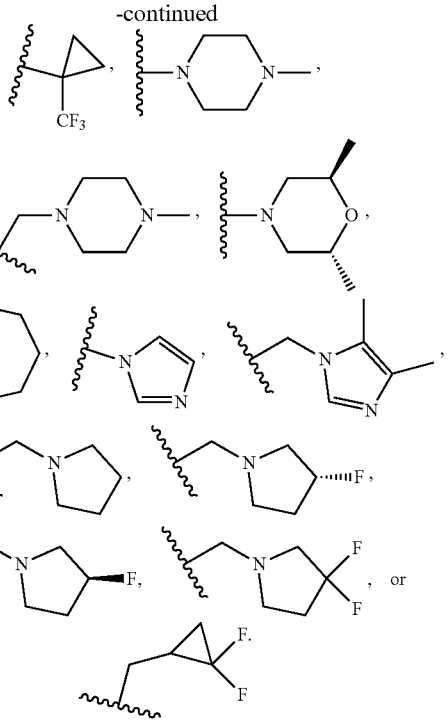

13. The compound or a pharmaceutically acceptable salt thereof according to claim 7, wherein n is 1 and R$_1$ is 2,2-dimethylpropyl or

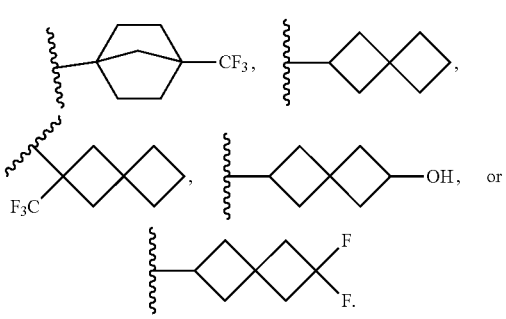

14. The compound or a pharmaceutically acceptable salt thereof according to claim 7, wherein R$_1$ is independently 15. The compound or a pharmaceutically acceptable salt thereof according to claim 7, wherein R$_2$ is —C$_1$-C$_6$ alkyl, —C$_1$-C$_4$ alkyl-tetrahydrofuranyl, C$_3$-C$_6$ cycloalkyl, tetrahydrofuranyl, pyranyl, —C$_1$-C$_4$ alkyl-tetrahydropyranyl, —C$_1$-C$_4$ alkyl —C$_3$-C$_6$ cycloalkyl, and azetidinyl, wherein each is unsubstituted or substituted with one or two groups that are independently selected from the group consisting of halogen, cyano, hydroxyl, oxo, methyl, methoxy, hydroxymethyl, ethyl, ethoxy, hydroxyethyl, cyclopropyl, or mono-, di-, or tri-halomethyl.

16. The compound or a pharmaceutically acceptable salt thereof according to claim 7, wherein R$_2$ is of tert-butyl, —CH(CH₃)-cyclopropyl, -2-tetrahydrofuranyl, -3-tetrahydrofuranyl, -3-pyranyl, -4-pyranyl, —CH(CH₃)CH₂OH, —C(CH₃)₂CH₂OH, —CH₂-(2-tetrahydrofuranyl), —CH₂-(3-tetrahydrofuranyl), —(CH₂)₃OH, —C(CH₃)₂CH₂OCH₃, —CH(CH₃)CF₃, —CH₂CF₃, —C(CH₃)₂CH₂OCH₃, cyclopentyl,

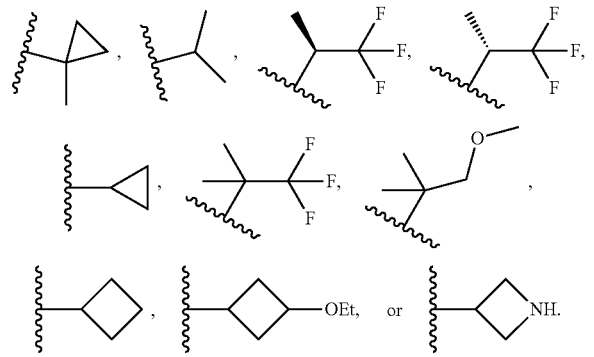

17. The compound or a pharmaceutically acceptable salt thereof according to claim 7, wherein R₂ is

18. The compound or a pharmaceutically acceptable salt thereof according to claim 7, wherein R₂ is

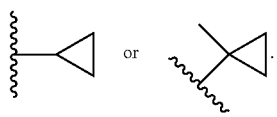

19. The compound or a pharmaceutically acceptable salt thereof, according to claim 1 that is

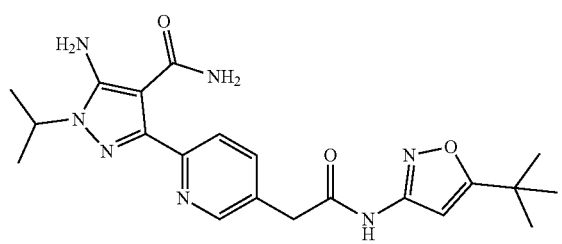

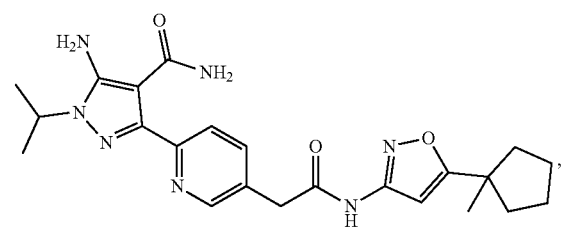

-continued

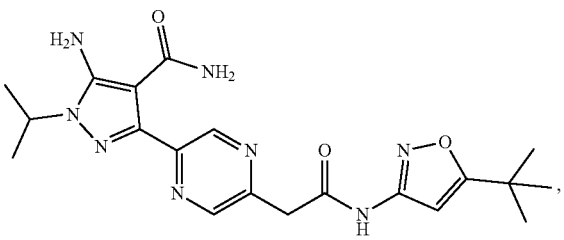

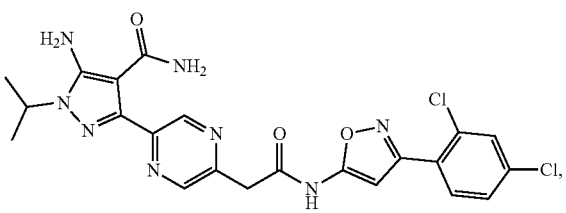

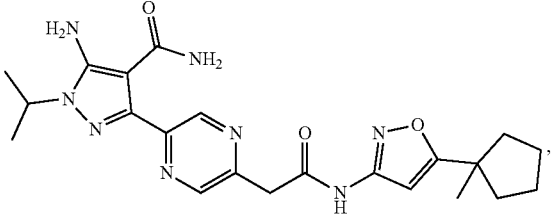

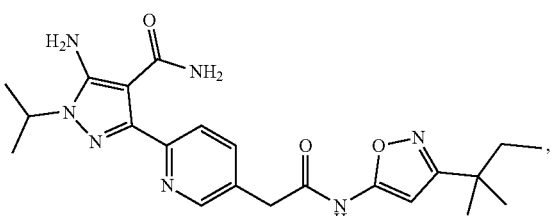

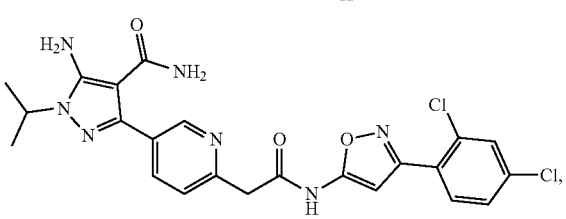

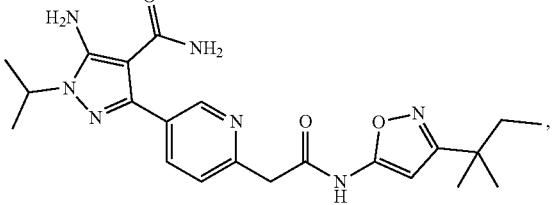

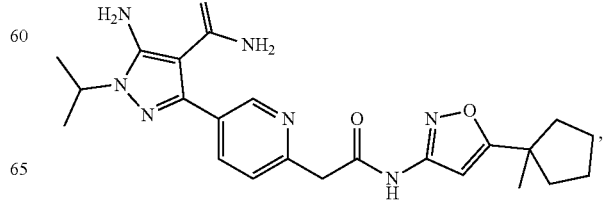

-continued

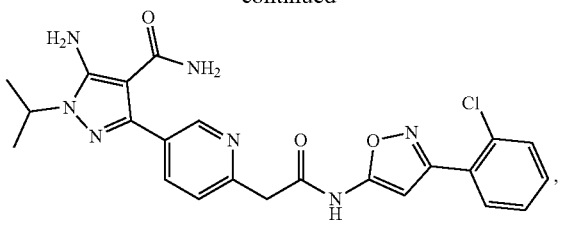

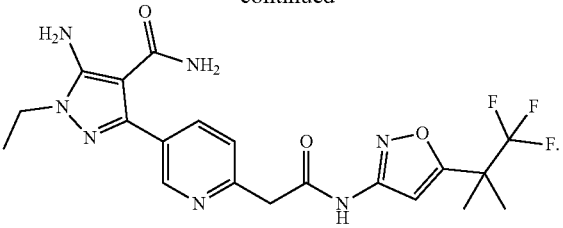

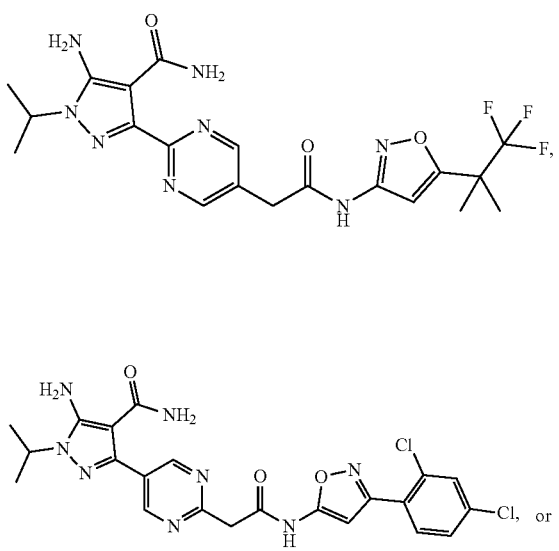

20. A method of treating cancer in a patient, comprising administering to a patient in need of such treatment an effective amount of a compound, or a pharmaceutically acceptable salt thereof, according to claim 1, wherein the cancer is a RET-associated cancer.

21. The method according to claim 20, wherein the cancer is selected from the group consisting of lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

22. The method of claim 21, wherein the cancer is medullary thyroid cancer.

23. The method of claim 21, wherein the lung cancer is small cell lung carcinoma, non-small cell lung cancer, bronchioles lung cell carcinoma, RET fusion lung cancer, or lung adenocarcinoma.

24. A pharmaceutical composition comprising a compound, or a pharmaceutically acceptable salt thereof, according to claim 1 and at least one pharmaceutically acceptable carrier, diluent, or excipient.

* * * * *

SEQUENCE LISTING

```
Sequence total quantity: 1
SEQ ID NO: 1         moltype = AA   length = 1114
FEATURE              Location/Qualifiers
source               1..1114
                     mol_type = protein
                     organism = Homo sapiens
SEQUENCE: 1
MAKATSGAAG LRLLLLLLLP LLGKVALGLY FSRDAYWEKL YVDQAAGTPL LYVHALRDAP  60
EEVPSFRLGQ HLYGTYRTRL HENNWICIQE DTGLLYLNRS LDHSSWEKLS VRNRGFPLLT 120
VYLKVFLSPT SLREGECQWP GCARVYFSFF NTSFPACSSL KPRELCFPET RPSFRIRENR 180
PPGTFHQFRL LPVQFLCPNI SVAYRLLEGE GLPFRCAPDS LEVSTRWALD REQREKYELV 240
AVCTVHAGAR EEVVMVPFPV TVYDEDDSAP TFPAGVDTAS AVVEFKRKED TVVATLRVFD 300
ADVVPASGEL VRRYTSTLLP GDTWAQQTFR VEHWPNETSV QANGSFVRAT VHDYRLVLNR 360
NLSISENRTM QLAVLVNDSD FQGPGAGVLL LHFNVSVLPV SLHLPSTYSL SVSRRARRFA 420
QIGKVCVENC QAFSGINVQY KLHSSGANCS TLGVVTSAED TSGILFVNDT KALRRPKCAE 480
LHYMVVATDQ QTSRQAQAQL LVTVEGSYVA EEAGCPLSCA VSKRRLECEE CGGLGSPTGR 540
CEWRQGDGKG ITRNFSTCSP STKTCPDGHC DVVETQDINI CPQDCLRGSI VGGHEPGEPR 600
```

-continued

```
GIKAGYGTCN CFPEEEKCFC EPEDIQDPLC DELCRTVIAA AVLFSFIVSV LLSAFCIHCY   660
HKFAHKPPIS SAEMTFRRPA QAFPVSYSSS GARRPSLDSM ENQVSVDAFK ILEDPKWEFP   720
RKNLVLGKTL GEGEFGKVVK ATAPHLKGRA GYTTVAVKML KENASPSELR DLLSEFNVLK   780
QVNHPHVIKL YGACSQDGPL LLIVEYAKYG SLRGFLRESR KVGPGYLGSG GSRNSSSLDH   840
PDERALTMGD LISFAWQISQ GMQYLAEMKL VHRDLAARNI LVAEGRKMKI SDFGLSRDVY   900
EEDSYVKRSQ GRIPVKWMAI ESLFDHIYTT QSDVWSFGVL LWEIVTLGGN PYPGIPPERL   960
FNLLKTGHRM ERPDNCSEEM YRLMLQCWKQ EPDKRPVFAD ISKDLEKMMV KRRDYLDLAA  1020
STPSDSLIYD DGLSEEETPL VDCNNAPLPR ALPSTWIENK LYGMSDPNWP GESPVPLTRA  1080
DGTNTGFPRY PNDSVYANWM LSPSAAKLMD TFDS                              1114
```